US011504382B2

(12) United States Patent
De Francesco et al.

(10) Patent No.: US 11,504,382 B2
(45) Date of Patent: Nov. 22, 2022

(54) TRICYCLIC INHIBITORS OF HEPATITIS B VIRUS

(71) Applicant: Antios Therapeutics, Inc., Mendham, NJ (US)

(72) Inventors: Raffaele De Francesco, Milan (IT); Lorena Donnici, Milan (IT); Luca Guidotti, Milan (IT); Matteo Iannacone, Milan (IT); Romano Di Fabio, Pomezia (IT); Vincenzo Summa, Pomezia (IT); Adolfo Prandi, Milan (IT); Pietro Randazzo, Milan (IT); Davide Gornati, Milan (IT); Alessandro Grillo, Milan (IT); Luca Ferrante, Milan (IT); Leda Ivanova Bencheva, Milan (IT); Marilenia De Matteo, Milan (IT); Marco Ferrara, San Donato Milanese (IT)

(73) Assignee: Antios Therapeutics, Inc., Mendham, NJ (US)

( * ) Notice: Subject to any disclaimer, the term of this patent is extended or adjusted under 35 U.S.C. 154(b) by 0 days.

(21) Appl. No.: 17/267,693

(22) PCT Filed: Aug. 9, 2019

(86) PCT No.: PCT/EP2019/071408
§ 371 (c)(1),
(2) Date: Feb. 10, 2021

(87) PCT Pub. No.: WO2020/030781
PCT Pub. Date: Feb. 13, 2020

(65) Prior Publication Data
US 2022/0110943 A1    Apr. 14, 2022

(30) Foreign Application Priority Data
Aug. 10, 2018 (EP) .................................... 18188409

(51) Int. Cl.
| | |
|---|---|
| *A61P 31/20* | (2006.01) |
| *C07D 513/14* | (2006.01) |
| *C07D 515/08* | (2006.01) |
| *C07D 515/14* | (2006.01) |
| *C07D 519/00* | (2006.01) |
| *A61K 31/554* | (2006.01) |
| *A61K 31/407* | (2006.01) |

(52) U.S. Cl.
CPC .......... *A61K 31/554* (2013.01); *A61K 31/407* (2013.01); *A61P 31/20* (2018.01); *C07D 513/14* (2013.01); *C07D 515/08* (2013.01); *C07D 515/14* (2013.01); *C07D 519/00* (2013.01)

(58) Field of Classification Search
CPC ..... A61K 31/554; A61K 31/407; A61P 31/12; C07D 513/14; C07D 515/08; C07D 4515/14; C07D 519/00
See application file for complete search history.

(56) References Cited

FOREIGN PATENT DOCUMENTS

WO    2017/001655 A1    1/2017

OTHER PUBLICATIONS

ISA/EP, "PCT International Search Report and Written Opinion", issued in connection with PCT International Application No. PCT/EP2019/071408, dated Oct. 1, 2019 (9 pages).

*Primary Examiner* — Alicia L Otton
(74) *Attorney, Agent, or Firm* — Taft Stettinius & Hollister LLP; Joseph Bennett-Paris

(57) ABSTRACT

The present invention relates to compounds that are inhibitors of hepatitis B virus (HBV). Compounds of this invention are useful alone or in combination with other agents for treating, ameliorating, preventing or curing HBV infection and related conditions. The present invention also relates to pharmaceutical compositions containing the compounds.

15 Claims, No Drawings
Specification includes a Sequence Listing.

TRICYCLIC INHIBITORS OF HEPATITIS B VIRUS

CROSS-REFERENCE TO RELATED APPLICATIONS

This application is a 371 of PCT/EP2019/071408, filed Aug. 9, 2019, which claims the benefit of European Patent Application No. 18188409.9, filed Aug. 10, 2018.

FIELD OF THE INVENTION

The present invention relates to compounds that are inhibitors of hepatitis B virus (HBV). Compounds of this invention are useful alone or in combination with other agents for treating, ameliorating, preventing or curing HBV infection and related conditions. The present invention also relates to pharmaceutical compositions containing said compounds.

BACKGROUND OF THE INVENTION

The Hepatitis B virus (HBV) is an enveloped, partially double-stranded DNA (dsDNA) virus of the hepadnaviridae family that is spread by contact with infected blood and body fluids and causes acute and chronic necroinflammatory liver diseases of varying severity (Guidotti L G, Chisari F V. Annu Rev Pathol. 2006; 1:23-61). The HBV lipid envelope contains 3 in-frame viral envelope proteins (large, middle and small), each of which possesses the hepatitis B virus surface antigen (HBsAg) determinant (Seeger C, Mason W S. Virology. 2015 May; 479-480:672-86). This envelope encloses a protein shell, or capsid, that is composed of 240 monomers of the core protein and each monomer possesses the hepatitis B virus core antigen (HBcAg or Cp) determinant. The capsid in turn encloses a partially double-stranded, relaxed circular DNA (rcDNA) form of the viral genome as well as a molecule of the viral polymerase. Upon entry into susceptible cells (i.e. the hepatocytes) via the interaction of the large envelope protein with specific receptors on the hepatocellular membrane, the capsid is released into the cytoplasm and transported at the nuclear membrane. The rcDNA is then released into the nucleus and repaired by cellular polymerases into an episomal "minichromosome", termed covalently closed circular DNA (cccDNA), which represents the viral transcriptional template. The minus strand of the viral DNA encodes 3.5, 2.4, 2.1 and 0.7 kb mRNA species that are translated into structural (envelope and core) and nonstructural (polymerase, precore and X) proteins of the virus. Following transport into the cytoplasm, one of the 3.5 kb RNAs (termed pregenomic RNA) is selectively packaged into a nascent capsid by interacting with the core and polymerase proteins that have been translated from their respective mRNAs. Within these capsids, the viral polymerase reverse transcribes the pregenomic RNA into a single minus (−) strand DNA molecule that serves as template for the viral polymerase-mediated DNA plus (+) strand synthesis and the cohesive structure of the linear DNA intermediates converts them into a relaxed circular double stranded molecule. A fraction of these HBV DNA-containing "mature" capsids are transported back to the nucleus where second strand synthesis is completed and the ends of both strands are ligated, leading to amplification of the pool of cccDNA. Another fraction of the capsids binds to viral envelope proteins that have been independently translated and translocated to membranes of endoplasmic reticulum (ER)-like structures. Following binding, the enveloped capsids bud into the lumen of the ER and exit the cell as infectious virions to initiate new cycles of infection.

Thus, the HBV core protein and the related capsids are essential components and regulators of the HBV life cycle. The full-length core protein Cp183, or its N-terminal domain Cp149, predominantly assembles into a T=4 icosahedral capsids. Due to its critical roles in capsid assembly, pregenomic RNA packaging, and cccDNA maintenance, it is not surprising that the HBV core protein and the related capsids have been widely recognized as attractive antiviral targets (Durantel D, Zoulim F; J Hepatol. 2016 April; 64(1 Suppl):S117-S131).

According to World Health Organization (WHO) statistics, HBV infection is one of the major medical scourges of our time. As a sexually transmitted disease that is also transferred by intravenous drug abuse and from mother to infant at birth, over one third of the world's population has been infected by HBV at some point in their lives (Burns G S, Thompson A J; Cold Spring Harb Perspect Med. 2014 Oct. 30; 4(12)). While most of these people have successfully cleared the virus, more than 250 million people remain persistently infected and almost 900,000 of these individuals die annually from the complications of chronic infection (i.e. cirrhosis and/or hepatocellular carcinoma). HBV infection is highly endemic in sub-Saharan Africa, the Pacific, and particularly Asia. Regions with high rates of chronic HBV infection also include the Middle East, the Indian subcontinent, areas of South and Central America, and the southern parts of Eastern and Central Europe. In recent years the number of chronic carriers has increased steadily in the western world as well, mostly because of the influx of immigrants from endemic areas. Additionally, HBV acts as a helper virus to hepatitis delta virus (HDV) and it should be noted that the more than 15 million people co-infected with HBV and HDV have an increased risk of rapid progression to cirrhosis and hepatic decompensation (Hughes, S. A. et al. Lancet 2011, 378, 73-85).

Well-tolerated vaccines that elicit neutralizing antibodies to HBsAg efficiently prevent de novo HBV infection, but have no therapeutic potential for the millions of people that are already persistently infected (Zoulim, Durantel D; Cold Spring Harb Perspect Med. 2015 Apr. 1; 5(4)). Therapy for these individuals mainly relies on direct acting antiviral (DAA) drugs (e.g. tenofovir, lamivudine, adefovir, entecavir or telbivudine) that suppress virus production but do not eradicate HBV from the liver, requiring lifelong treatment. Cohorts of patients still receive a therapy based on pegylated interferon-α (PEG-IFN-α), which has the advantages of limited treatment duration and higher rates of HBsAg seroconversion but the relevant disadvantage of greater adverse effects. As such, the number of patients receiving PEG-IFN-α is progressively decreasing.

Different chemical classes of inhibitors targeting the encapsidation process of HBV (also termed capsid assembly modulators or CAMs) are under development, and they include heteroaryldihydropyrimidines (HAPs) and sulfamoylbenzamides (SBAs). For instance, Novira Therapeutics recently utilized a humanized mouse model of HBV infection to show that a combination of CAM and PEG-IFN-α has higher antiviral activity than that previously observed with DAAs. NVR3-778, the first member of this class of CAM, in Phase 1b proof-of-concept clinical studies showed both significant reduction in HBV DNA and serum HBV RNA. This compound was recently discontinued. The compound JNJ-56136379 (or JNJ-379), developed by Janssen, has recently demonstrated potent antiviral activity and is now entering into Phase 2 clinical trial.

WO2013/006394, published on Jan. 10, 2013, relates to a subclass of sulfamoyl-arylamides having general formula A, useful for the treatment of Hepatitis B virus (HBV) infection:

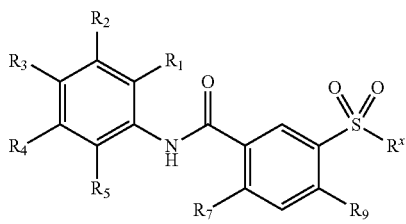

(A)

WO2013/096744, published on Jun. 26, 2013 relates to sulfamoyl-arylamides of formula B active against HBV:

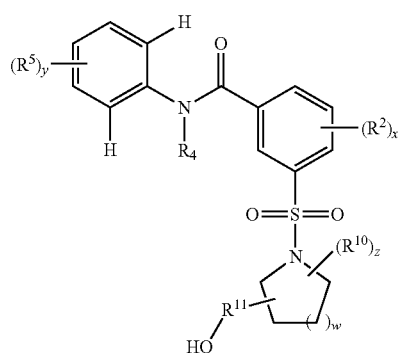

(B)

WO2014/106019, published on Jul. 3, 2014, relates to compounds of formula C, useful as nucleocapsid assembly inhibitors for the treatment of viruses, especially but not exclusively, including pregenomic RNA encapsidation inhibitors of HBV for the treatment of Hepatitis B virus (HBV) infection and related conditions:

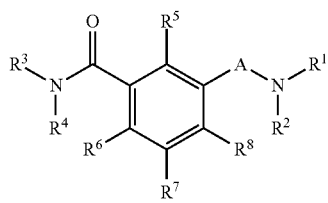

(C)

WO2014/165128, published on Oct. 9, 2014, WO2015/109130 published on Jul. 23, 2015, US2015274652, published on Oct. 1, 2015, all relate to sulfamoyl-arylamides compounds active against HBV.

WO2015/120178, published on Aug. 13, 2015, relates to sulfamoyl-arylamides compounds used in combination therapy with peginterferon alpha-2a, or another interferon analog for the treatment of HBV infection.

WO2016/089990, published on Jun. 9, 2016, relates to sulfide alkyl and pyridyl reverse sulphonamide compounds for HBV treatment.

US2016185748, published on Jun. 30, 2016, relates to pyridyl reverse sulfonamides for HBV treatment.

US2016151375, published on Jun. 2, 2016 relates to sulfide alkyl compounds for HBV treatment.

WO2017/001655A1, published on Jan. 5, 2017, relates to cyclized sulfamoylarylamide derivatives having structure:

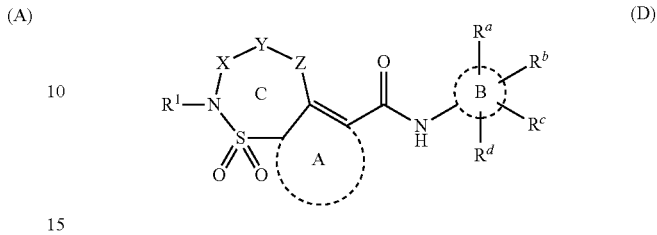

(D)

Amongst the problems which HBV direct antivirals may encounter are toxicity, mutagenicity, lack of selectivity, poor efficacy, poor bioavailability, low solubility and/or off-target activity, and until now there are no compounds in any of the structural classes identified above approved as drugs for the treatment of HBV patients.

There is a need for additional HBV inhibitors that may overcome at least one of these disadvantages or that have additional advantages such as increased potency, increased bioavailability or an increased safety window.

The present invention provides small molecule drugs obtained through chemical modification of the known sulfamoyl arylamides derivatives. In particular the compound of the invention are characterized by a fused tricyclic core structure comprising a pyrrole ring. The chemotype discovered in the present invention results in potent HBV inhibitors with improved pharmacokinetic properties, good kinetic solubility, stability in mouse and human hepatocytes, low in vivo clearance and positive liver-to-plasma concentration. Given the liver's key role in metabolic regulation and the fact that it is the principal tissue affected by hepatitis B disease, designing HBV inhibitors with hepatoselective distribution profiles is an important strategy in developing safe drug candidates (Tu M. et al., Current Topics in Medicinal Chemistry, 2013, 13, 857-866).

DESCRIPTION OF THE INVENTION

The compounds of this invention are inhibitors of hepatitis B virus (HBV).

It is therefore an object of the present invention a compound of general formula (I):

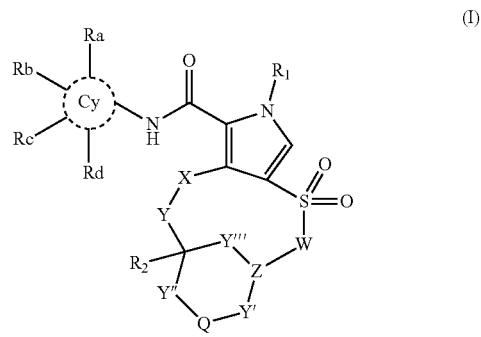

(I)

wherein:

Cy is aryl or heteroaryl;

X is O, NH, N—$C_{1-6}$alkyl, S, SO or $SO_2$;

Y, Y', Y" and Y'" are each independently a single bond or $C_{1-6}$alkanediyl optionally substituted with one or more $R_3$;

Z is $CR_4$ or N;

W is a single bond or $NR_5$, wherein if W is a single bond, Z is N, and if W is $NR_5$, Z is $CR_4$;

A is $NR_6$, O, S or $C_{1-6}$alkanediyl optionally substituted with one or more $R_3$;

$R_1$ is H or $C_{1-6}$alkyl;

$R_2$ is selected from H, OH and $C_{1-6}$alkyl;

$R_3$ is selected from H, OH, $C_{1-6}$alkyl, $C_{3-8}$cycloalkyl and halogen or two geminal $R_3$ form together with the atom to which they are attached a spiro-$C_{3-8}$cycloalkyl or a spiro-$C_{3-8}$heterocycloalkyl or $R_3$ is O forming together with the carbon atom to with it is bonded a C=O;

$R_4$ is H or $C_{1-6}$alkyl;

or when W is $NR_5$ and Z is $CR_4$, $R_2$ and $R_4$ may optionally form a $C_{1-6}$alkanediyl bridge;

$R_5$ is selected from H, $C_{1-6}$alkyl, $C_{1-6}$alkylaryl, $C_{1-6}$alkylheteroaryl and $C_{1-6}$alkyl-$C_{3-8}$cycloalkyl wherein each of said $C_{1-6}$alkyl, $C_{1-6}$alkylaryl, $C_{1-6}$alkylheteroaryl or $C_{1-6}$alkyl-$C_{3-8}$cycloalkyl is optionally substituted with one or more substituents each independently selected from: OH, halogen, halo$C_{1-6}$alkyl, cyano and $NH_2$;

$R_6$ is selected from:

hydrogen;

OH;

C(O)$R_7$;

C(O)O$R_7$;

C(O)NH$R_7$;

C(O)N($R_7$)$_2$;

SO$_2R_7$;

SO$_2$NH($R_7$);

SO$_2$N($R_7$)$_2$;

$C_{1-6}$alkyl optionally substituted with one or more substituents each independently selected from the group consisting of: OH, halogen, CN, $NH_2$, NH($R_7$), N($R_7$)$_2$, aryl, heteroaryl, 3-7 membered saturated ring and 5-7 membered unsaturated ring, each of said saturated or unsaturated ring optionally containing one or more heteroatoms selected from the group consisting of O, N and S and each of said aryl, heteroaryl, 3-7 membered saturated or 5-7 membered unsaturated ring being optionally substituted with one or more substituents each independently selected from OH, halogen, halo$C_{1-6}$alkyl, CN, halo$C_{1-6}$alkoxy and $C_{1-6}$alkoxy;

aryl or heteroaryl ring, each of said aryl or heteroaryl ring being optionally substituted with one or more substituents each independently selected from: OH, halogen, halo$C_{1-6}$alkyl, CN, halo$C_{1-6}$alkoxy, $C_{1-6}$alkoxy, $C_{1-6}$alkyl, and $NH_2$; and a 3-8 membered saturated or partially unsaturated cyclic or bicyclic ring optionally containing one or more heteroatoms each independently selected from the group consisting of: O, S and N, the 3-8 membered saturated or partially unsaturated cyclic or bicyclic ring being optionally substituted with one, two or more substituents each independently selected from the group consisting of: OH, halogen, CN, $C_{1-6}$alkyl, hydroxy$C_{1-6}$alkyl, C(O)O$R_7$, C(O)$R_7$, halo$C_{1-6}$alkyl, halo$C_{1-6}$alkoxy and $C_{1-6}$alkoxy;

$R_7$ is selected from the group consisting of: $C_{1-9}$alkyl, $C_{3-8}$cycloalkyl, aryl, heteroaryl and 3-8 membered saturated or partially saturated heterocyclic ring, wherein each of said $C_{1-9}$alkyl, $C_{3-8}$cycloalkyl, aryl, heteroaryl or 3-8 membered saturated or partially saturated heterocyclic ring is optionally substituted with one or more substituents each independently selected from the group consisting of: OH, halogen, CN, $C_{1-6}$alkyl, hydroxy$C_{1-6}$alkyl, halo$C_{1-6}$alkyl, halo$C_{1-6}$alkoxy, $C_{1-6}$alkoxy, $NH_2$, OC(=O)$C_{1-6}$alkyl, OP(=O)(OH)$_2$, aryl, heteroaryl and NHC(=O)$C_{1-6}$alkyl;

Ra, Rb, Rc and Rd are each independently selected from the group consisting of: hydrogen, halogen, CN, $C_{1-6}$alkyl, $C_{1-6}$alkoxy, halo$C_{1-6}$alkyl and halo$C_{1-6}$alkoxy;

and pharmaceutically acceptable salts, tautomers, isomers, stereoisomers thereof.

It is to be intended that any reference to the "compound(s) of the invention", or more simply "the compound(s)", includes compounds of formula (I) as well as pharmaceutically acceptable salts, tautomers, isomers, stereoisomers thereof.

It is also an object of the present invention a compound of general formula (I):

(I)

wherein:

Cy is aryl or heteroaryl;

X is O, NH or N—$C_{1-6}$alkyl;

Y, Y', Y" and Y'" are each independently a single bond or $C_{1-6}$alkanediyl optionally substituted with one or more $R_3$;

Z is $CR_4$ or N;

W is a single bond or $NR_5$, wherein if W is a single bond, Z is N, and if W is $NR_5$, Z is $CR_4$;

A is $NR_6$, O, S or $C_{1-6}$alkanediyl optionally substituted with one or more $R_3$;

$R_1$ is H or $C_{1-6}$alkyl;

$R_2$ is selected from H, OH and $C_{1-6}$alkyl;

$R_3$ is selected from H, OH, $C_{1-6}$alkyl, $C_{3-8}$cycloalkyl and halogen or two geminal $R_3$ form together with the atom to which they are attached a spiro-$C_{3-8}$cycloalkyl or a spiro-$C_{3-8}$heterocycloalkyl;

$R_4$ is H or $C_{1-6}$alkyl;

or when W is $NR_5$ and Z is $CR_4$, $R_2$ and $R_4$ may optionally form a $C_{1-6}$alkanediyl bridge;

$R_5$ is selected from H, $C_{1-6}$alkyl, $C_{1-6}$alkylaryl, $C_{1-6}$alkylheteroaryl and $C_{1-6}$alkyl-$C_{3-8}$cycloalkyl wherein each of said $C_{1-6}$alkyl, $C_{1-6}$alkylaryl, $C_{1-6}$alkylheteroaryl or $C_{1-6}$alkyl-$C_{3-8}$cycloalkyl is optionally substituted with one or more substituents each independently selected from: OH, halogen, halo$C_{1-6}$alkyl, cyano and $NH_2$;

$R_6$ is selected from:

hydrogen;

OH;

C(O)$R_7$;

C(O)O$R_7$;

C(O)NH$R_7$;

C(O)N($R_7$)$_2$;

SO$_2R_7$;

SO$_2$NH($R_7$);

SO$_2$N($R_7$)$_2$;

$C_{1-6}$alkyl optionally substituted with one or more substituents each independently selected from the group consisting of: OH, halogen, CN, $NH_2$, $NH(R_7)$, $N(R_7)_2$, aryl, heteroaryl, 3-7 membered saturated ring and 5-7 membered unsaturated ring, each of said saturated or unsaturated ring optionally containing one or more heteroatoms selected from the group consisting of O, N and S and each of said aryl, heteroaryl, 3-7 membered saturated or 5-7 membered unsaturated ring being optionally substituted with one or more substituents each independently selected from OH, halogen, halo$C_{1-6}$alkyl, CN, halo$C_{1-6}$alkoxy and $C_{1-6}$alkoxy;

aryl or heteroaryl ring, each of said aryl or heteroaryl ring being optionally substituted with one or more substituents each independently selected from: OH, halogen, halo$C_{1-6}$alkyl, CN, halo$C_{1-6}$alkoxy and $C_{1-6}$alkoxy; and a 3-8 membered saturated or partially unsaturated cyclic or bicyclic ring optionally containing one or more heteroatoms each independently selected from the group consisting of: O, S and N, the 3-8 membered saturated or partially unsaturated cyclic or bicyclic ring being optionally substituted with one, two or more substituents each independently selected from the group consisting of: OH, halogen, CN, $C_{1-6}$alkyl, hydroxy$C_{1-6}$alkyl, $C(O)OR_7$, $C(O)R_7$, halo$C_{1-6}$alkyl, halo$C_{1-6}$alkoxy and $C_{1-6}$alkoxy;

$R_7$ is selected from the group consisting of: $C_{1-6}$alkyl, $C_{3-8}$cycloalkyl, aryl, heteroaryl and 3-8 membered saturated or partially saturated heterocyclic ring, wherein each of said $C_{1-6}$alkyl, $C_{3-8}$cycloalkyl, aryl, heteroaryl or 3-8 membered saturated or partially saturated heterocyclic ring is optionally substituted with one or more substituents each independently selected from the group consisting of: OH, halogen, CN, $C_{1-6}$alkyl, hydroxy$C_{1-6}$alkyl, halo$C_{1-6}$alkyl, halo$C_{1-6}$alkoxy and $C_{1-6}$alkoxy;

Ra, Rb, Rc and Rd are each independently selected from the group consisting of: hydrogen, halogen, CN, $C_{1-6}$alkyl, $C_{1-6}$alkoxy, halo$C_{1-6}$alkyl and halo$C_{1-6}$alkoxy;

and pharmaceutically acceptable salts, tautomers, isomers, stereoisomers thereof.

Preferably, Cy is aryl. Still preferably, Cy is phenyl.

Preferably, X is O, NH, S, SO or $SO_2$. More preferably, X is O or NH. Still preferably, X is O.

Preferably, Y, Y' and Y'' are each independently a single bond or an unsubstituted $C_{1-4}$alkanediyl.

More preferably, Y, Y' and Y'' are each independently methanediyl. Preferably, Y''' is a single bond. Preferably, Y and Y'' are the same and are both a single bond or an unsubstituted $C_{1-4}$alkanediyl. More preferably, Y and Y'' are the same and are both methanediyl.

Preferably, Z is CH or N. Still preferably, Z is CH.

Preferably, W is a single bond or NH. More preferably, W is NH.

Preferably, A is $NR_6$, O or unsubstituted $C_{1-4}$alkanediyl. More preferably, A is $NR_6$ or methanediyl.

Also preferably, A is $NR_6$ or methanediyl and Y' and Y''' are the same and are both methanediyl.

Preferably, $R_1$ is $C_{1-6}$alkyl. More preferably, $R_1$ is methyl.

Preferably, $R_2$ is H, OH or methyl. More preferably, $R_2$ is H.

Preferably, $R_3$ is H. Preferably, $R_4$ is H. Preferably, $R_5$ is H.

Preferably, $R_6$ is selected from: hydrogen, $C(O)R_7$, $C(O)OR_7$, $C(O)NHR_7$, $SO_2R_7$, $SO_2NH(R_7)$, aryl, heteroaryl, $C_{1-6}$alkyl, said $C_{1-6}$alkyl being optionally substituted with one or more substituents each independently selected from the group consisting of: halogen, CN and phenyl. Still preferably, Re is selected from: hydrogen, C(O)OEt, C(O)OtBu, C(O)NHMe, $SO_2$iPr, $SO_2$Me, $SO_2$cyclopropyl, $SO_2$NHiPr and methyl.

Preferably, $R_7$ is $C_{1-6}$alkyl, $C_{3-8}$cycloalkyl, aryl, heteroaryl or a 3-8 membered saturated heterocyclic ring. More preferably, $R_7$ selected from: methyl, ethyl, i-propyl, methyl, cyclopropyl, t-butyl, the hexahydrofuro[2,3-b]furan system, 1,3-oxazole, 1,2,4-oxadiazole, 1,2,5-oxadiazole, 1,3,4-oxadiazole, 1,2-oxazole, pyridine, pyrazine, pyrazone, pyrazole, 1,3-thiazole, 1,3,4-thiadiazole, pyrimidine, pyrimidone, wherein any of said preferred $R_7$ group is optionally substituted with one or more substituents each independently selected from the group consisting of: $OP(=O)(OH)_2$, $NH_2$, $OC(=O)CH_3$, methyl, OH, fluorine and chlorine.

Preferably, Ra, Rb, Rc and Rd are each independently selected from the group consisting of: hydrogen, halogen, CN, $C_{1-6}$alkyl and halo$C_{1-6}$alkyl. More preferably, Ra, Rb, Rc and Rd are each independently selected from the group consisting of: hydrogen, fluorine, chlorine, methyl, CN and $CHF_2$.

Preferably at least one of Ra, Rb, Rc and Rd is halogen, more preferably fluorine, and the other(s) is/are hydrogen.

Preferably, at least two of Ra, Rb, Rc and Rd are each independently selected from the group consisting of: hydrogen, halogen, CN, $C_{1-6}$alkyl and halo$C_{1-6}$alkyl. More preferably, at least two of Ra, Rb, Rc and Rd are each independently selected from the group consisting of: hydrogen, fluorine, chlorine, methyl, CN and $CHF_2$.

Preferably, at least three of Ra, Rb, Rc and Rd are each independently selected from the group consisting of: hydrogen, halogen, CN, $C_{1-6}$alkyl and halo$C_{1-6}$alkyl. More preferably, at least three of Ra, Rb, Rc and Rd are each independently selected from the group consisting of: hydrogen, fluorine, chlorine, methyl, CN and $CHF_2$.

Preferably, two of Ra, Rb, Rc and Rd are halogen, more preferably fluorine.

Preferably, three of Ra, Rb, Rc and Rd are halogen, more preferably fluorine.

It is a further object of the invention a compound having general formula (Ia):

(Ia)

wherein Cy, Y, Y', Y'', A, $R_1$, $R_2$, Ra, Rb, Rc and Rd are as defined above and X is O, S, NH or N—$C_{1-6}$alkyl; and pharmaceutically acceptable salts, tautomers, isomers, stereoisomers thereof.

In a preferred embodiment, the invention provides a compound having general formula (I) or (Ia) as defined above, wherein Cy is phenyl, and/or X is O, S or NH, and/or A is $CH_2$, and/or $R_1$ is $CH_3$, and/or $R_2$ is hydrogen and/or $R_3$ is hydrogen and pharmaceutically acceptable salts, tautomers, isomers, stereoisomers thereof. Preferably, Cy is phenyl, X is O, NH or S, A is $CH_2$, $R_1$ is $CH_3$, $R_2$ and $R_3$ are hydrogen. More preferably, Cy is phenyl, X is O or NH, A is CH$_2$, R$_1$ is CH$_3$, R$_2$ and R$_3$ are hydrogen.

It is a further object of the invention a compound having general formula (Ib):

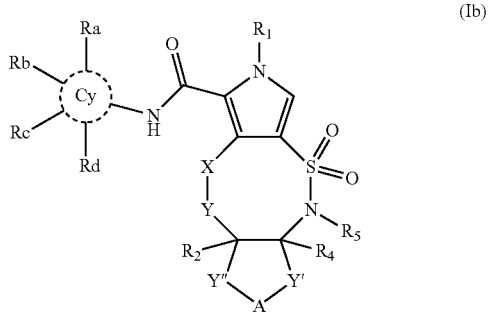
(Ib)

wherein Cy, Y, Y', Y", A, R$_1$, R$_2$, R$_4$, R$_5$, Ra, Rb, Re and Rd are as defined in claim 1 and X is O, S, NH or N—C$_{1-6}$alkyl; and pharmaceutically acceptable salts, tautomers, isomers, stereoisomers thereof.

In a preferred embodiment, the invention provides a compound having general formula (I) or (Ib) as defined above, wherein Cy is phenyl, and/or X is O or S and/or Y is CH$_2$, and/or Y' is CH$_2$, and/or Y" is CH$_2$, and/or A is CH$_2$, O or NR$_6$ and pharmaceutically acceptable salts, tautomers, isomers, stereoisomers thereof. Preferably, Cy is phenyl, X is O, NH or S, Y is CH$_2$, Y' is CH$_2$, Y" is CH$_2$, and A is CH$_2$, O or NR$_6$.

In a preferred aspect, the invention refers to a compound of formula (I), (Ia) or (Ib) as defined above, wherein Cy is phenyl; and/or X is O; and/or Y is a single bond or methanediyl; and/or R$_1$ is methyl; and/or R$_2$ is H.

Preferably, in a compound of formula (I), (Ia) or (Ib) as defined above, A is NR$_6$, O or C$_{1-4}$alkanediyl; R$_6$ is selected from the group consisting of: hydrogen, C(O)R$_7$, C(O)OR$_7$, C(O)NHR$_7$, SO$_2$R$_7$, SO$_2$NH(R$_7$), aryl, heteroaryl, C$_{1-6}$alkyl, said C$_{1-6}$alkyl being optionally substituted with one or more substituents each independently selected from the group consisting of: halogen, CN and phenyl; R$_7$ is C$_{1-6}$alkyl, C$_{3-8}$cycloalkyl, aryl, heteroaryl or a 3-8 membered saturated heterocyclic ring and R$_7$ is optionally substituted with one or more substituents each independently selected from the group consisting of: OP(=O)(OH)$_2$, NH$_2$, OC(=O)CH$_3$, methyl, OH, aryl, heteroaryl, NHC(=O)C$_{1-6}$alkyl and halogen such as fluorine, bromine and chlorine.

Also preferably, in a compound of formula (I), (Ia) or (Ib) as defined above, A is NR$_6$, R$_6$ is C(O)R$_7$ and R$_7$ is selected from the group consisting of: C$_{1-6}$alkyl, C$_{3-8}$cycloalkyl, aryl, heteroaryl and 3-8 membered saturated or partially saturated heterocyclic ring, wherein each of said C$_{1-6}$alkyl, C$_{3-8}$cycloalkyl, aryl, heteroaryl or 3-8 membered saturated or partially saturated heterocyclic ring is optionally substituted with one or more substituents each independently selected from the group consisting of: OH, halogen, CN, C$_{1-6}$alkyl, hydroxyC$_{1-6}$alkyl, haloC$_{1-6}$alkyl, haloC$_{1-6}$alkoxy, C$_{1-6}$alkoxy, NH$_2$, aryl, heteroaryl.

In a preferred embodiment, the invention relates to compounds of formula (I) wherein Cy is phenyl. Still preferably, the invention relates to compounds of formula (I) wherein X is O.

In a preferred embodiment, the compound of the invention has formula (Ia) wherein Cy is phenyl, X is O or NH, A is CH$_2$, R$_1$ is CH$_3$, R$_2$ and R$_3$ are hydrogen.

In a further preferred embodiment, the compound of the invention has formula (Ib) wherein Cy is phenyl, X is O, Y is a single bond, Y' is CH$_2$, Y" is CH$_2$ or a single bond and A is CH$_2$, O or N—R$_6$.

Still preferably, the invention relates to a compounds of formula (I), having in particular, Formula (Ib-I) or Formula (Ib-II):

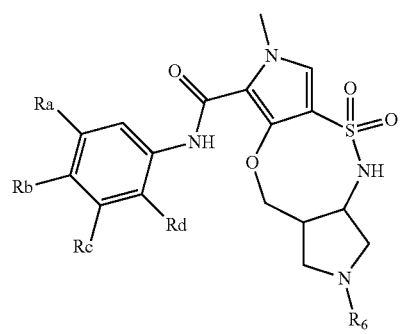
(Ib-I)

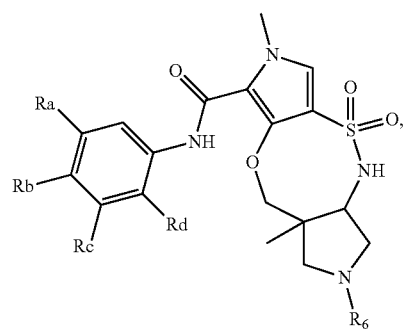
(Ib-II)

wherein
R$_6$ is selected from:
C(O)R$_7$;
C(O)OR$_7$;
C(O)NHR$_7$;
C(O)N(R$_7$)$_2$;
SO$_2$R$_7$;
SO$_2$NH(R$_7$);
SO$_2$N(R$_7$)$_2$;
R$_7$ is C$_{1-6}$alkyl, C$_{3-8}$cycloalkyl, aryl, heteroaryl or a 3-8 membered saturated heterocyclic ring and R$_7$ is optionally substituted with one or more substituents each independently selected from the group consisting of: OP(=O)(OH)$_2$, NH$_2$, OC(=O)CH$_3$, methyl, OH, aryl, heteroaryl, fluorine, bromine and chlorine;
Ra, Rb, Rc and Rd are as defined in claim 1;
and pharmaceutically acceptable salts, tautomers, isomers and stereoisomers thereof.

Still preferably, in compounds of formula (I), (Ia), (Ib), (Ib-I) or (Ib-II), R$_6$ is C(O)R$_7$ and R$_7$ is an heteroaromatic ring system selected from:

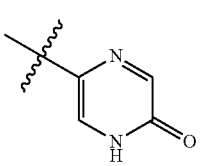 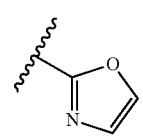 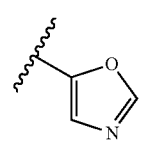

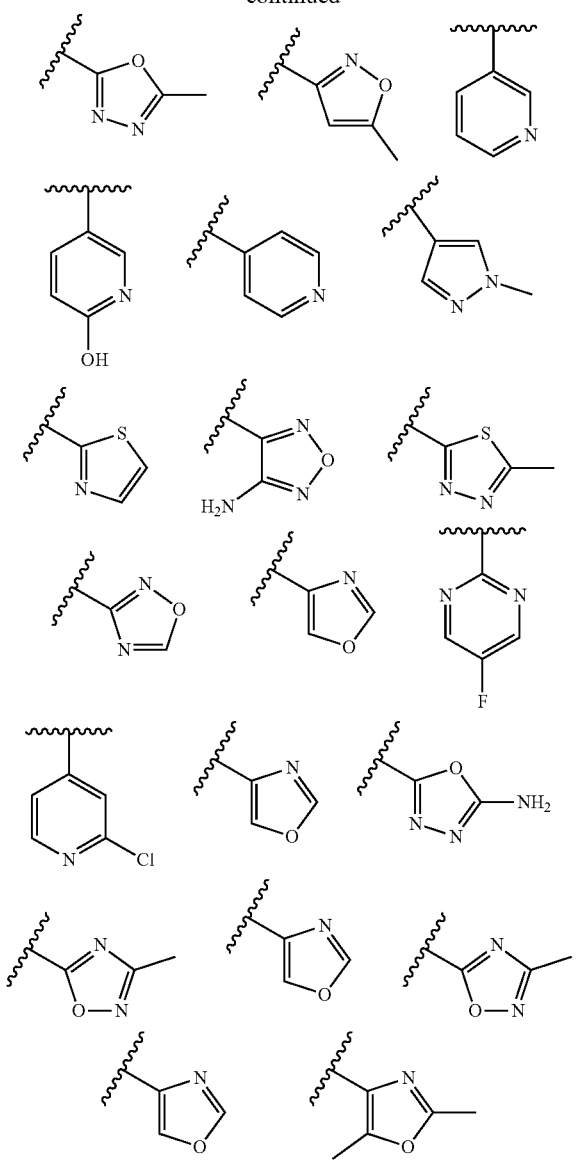

Still preferably, in compounds of formula (I), (Ia), (Ib), (Ib-I) or (Ib-II), $R_6$ is $C(O)R_7$ and $R_7$ is a 3-8 membered saturated heterocyclic ring system selected from:

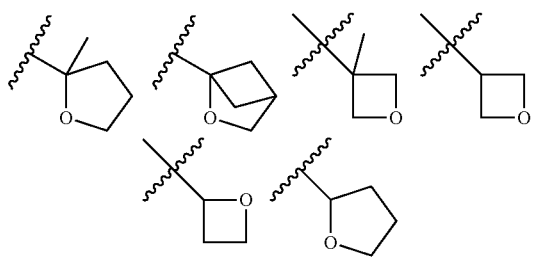

In a preferred embodiment, the compounds of the invention are pure stereochemical isomers. In a more preferred embodiment, the compounds have Formula (Ib-I') or Formula (Ib-I'')

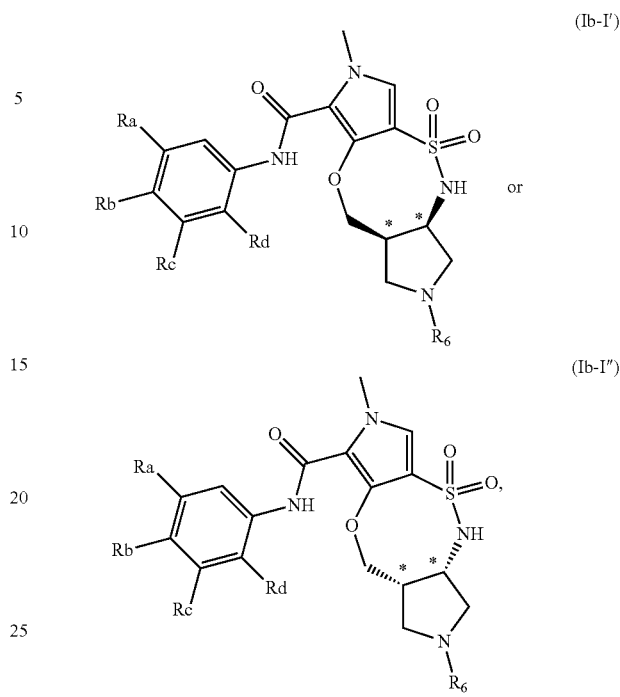

wherein the "*" indicates the chiral centers and the stereochemistry is (R,R) in compounds of formula (Ib-I') and (S,S) in compounds of formula (Ib-I'').

In a preferred embodiment compounds of the invention are selected from the following list:

N-(3,4-difluorophenyl)-2-methyl-6,7,8,9,9a,10-hexahydro-2H-pyrido[1,2-e]pyrrolo[3,4-b][1,4,5]oxathiazepine-1-carboxamide 4,4-dioxide;

N-(3,4-difluorophenyl)-2-methyl-2,6,7,8,9,9a,10,11-octahydropyrido[1,2-b]pyrrolo[3,4-f][1,2,5]thiadiazepine-1-carboxamide 4,4-dioxide;

N-(3,4-difluorophenyl)-2-methyl-6,7,7a,8-tetrahydro-2H-azeto[1,2-e]pyrrolo[3,4-b][1,4,5]oxathiazepine-1-carboxamide 4,4-dioxide;

trans-N-(3,4-difluorophenyl)-7-methyl-1,3a,4,9a-tetrahydro-3H,7H-furo[3,4-f]pyrrolo[3,4-b][1,4,5]oxathiazepine-8-carboxamide 5,5-dioxide;

cis-N-(3,4-difluorophenyl)-9-methyl-3,4,5,6-tetrahydro-2H,9H-3,5-methanopyrrolo[3,4-b][1,4,5]oxathiazoline-8-carboxamide 1,1-dioxide;

cis-N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide;

trans-7-methyl-N-(3,4,5-trifluorophenyl)-1,3a,4,9a-tetrahydro-3H,7H-furo[3,4-f]pyrrolo[3,4-b][1,4,5]oxathiazepine-8-carboxamide 5,5-dioxide;

(5aR,8aR)—N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide;

(5aS,8aS)—N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide;

cis-Ethyl 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;

cis-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2,7-dimethyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-Ethyl 8-((3,4-difluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

cis-Ethyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

cis-Ethyl 8-((3-chloro-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

cis-Ethyl 8-((3-(difluoromethyl)-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

cis-Ethyl 8-((3-cyano-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

cis-2-(isopropylsulfonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(methylsulfonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(cyclopropylsulfonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(N-isopropylsulfamoyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-(3R,3aS,6aR)-hexahydrofuro[2,3-b]furan-3-yl 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;

$N^2$,7-dimethyl-$N^8$-(3,4,5-trifluorophenyl)-3a,4,10,10a-tetrahydro-1H,7H-dipyrrolo[3,4-b:3',4'-f][1,4,5]oxathiazocine-2,8(3H)-dicarboxamide 5,5-dioxide;

tert-butyl 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;

(3aR,10aS)—N-(3,4-difluorophenyl)-7-methyl-2,3,3a,4,10,10a-hexahydro-1H,7H-dipyrrolo[3,4-b:3',2'-f][1,4,5]oxathiazocine-8-carboxamide 5,5-dioxide;

(3aR,10aS)—N8-(3,4-difluorophenyl)-N1,7-dimethyl-2,3,3a,4,10,10a-hexahydro-1H,7H-dipyrrolo[3,4-b:3',2'-f][1,4,5]oxathiazocine-1,8-dicarboxamide 5,5-dioxide;

ethyl (3aR,10aS)-8-((3,4-difluorophenyl)carbamoyl)-7-methyl-2,3,3a,4,10,10a-hexahydro-1H,7H-dipyrrolo[3,4-b:3',2'-f][1,4,5]oxathiazocine-1-carboxylate 5,5-dioxide;

cis-2-methyl-N-(3,4,5-trifluorophenyl)-5a,6,7,8,8a,9-hexahydro-2H,5H-cyclopenta[f]pyrrolo[3,4-b][1,4,5]oxathiazocine-1-carboxamide 4,4-dioxide;

N-(3,4-difluorophenyl)-2,8a-dimethyl-5a,6,7,8,8a,9-hexahydro-2H,5H-cyclopenta[f]pyrrolo[3,4-b][1,4,5]oxathiazocine-1-carboxamide 4,4-dioxide;

cis-N-(3,4-difluorophenyl)-8a-hydroxy-2-methyl-5a,6,7,8,8a,9-hexahydro-2H,5H-cyclopenta[f]pyrrolo[3,4-b][1,4,5]oxathiazocine-1-carboxamide 4,4-dioxide;

(3aS,10aS)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

ethyl (3aR,10aR)-7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;

ethyl (3aS,10aS)-7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;

tert-butyl (3aS,10aS)-7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;

tert-butyl (3aR,10aR)-7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;

(5aS,8aR) N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide;

(5aR,8aS) N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide;

(3aS,10aS) ethyl 8-((3,4-difluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3aR,10aR) ethyl 8-((3,4-difluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3aS,10aS) ethyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3aR,10aR) ethyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3aS,10aS) ethyl 8-((3-chloro-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3aR,10aR) ethyl 8-((3-chloro-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3aS,10aS) ethyl 8-((3-(difluoromethyl)-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3aR,10aR) ethyl 8-((3-(difluoromethyl)-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3aS,10aS) ethyl 8-((3-cyano-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3aR,10aR) ethyl 8-((3-cyano-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

cis-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7-methyl-2-(pyridin-3-yl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7-methyl-2-(1,3,4-oxadiazol-2-yl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(oxazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(5-methyl-1,3,4-oxadiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7-methyl-2-(5-methylisoxazole-3-carbonyl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-2-(6-hydroxynicotinoyl)-7-methyl-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7-methyl-2-nicotinoyl-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-2-isonicotinoyl-7-methyl-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(5-oxo-4,5-dihydropyrazine-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(1-methyl-1H-pyrazole-4-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(thiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(6-oxo-1,6-dihydropyrimidin-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(4-amino-1,2,5-oxadiazole-3-carbonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(4-amino-1,2,5-oxadiazole-3-carbonyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7-methyl-2-(5-methyl-1,3,4-thiadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7-methyl-2-(1,2,4-oxadiazole-3-carbonyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(oxazole-5-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(oxazole-4-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7-methyl-2-(3-methyloxetane-3-carbonyl)-2,3,3a,4,10,10a-hexahydro-1H,7H-dipyrrolo[3,4-b:3',4'-f][1,4,5]oxathiazocine-8-carboxamide 5,5-dioxide;

cis-2-(L-alanyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(L-seryl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(L-threonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(7-methyl-5,5-dioxido-8-((3,4,5-trifluorophenyl)carbamoyl)-3a,4,10,10a-tetrahydro-1H,7H-dipyrrolo[3,4-b:3',4'-f][1,4,5]oxathiazocin-2(3H)-yl)-2-oxoethyl acetate;

cis-2-(2-hydroxyacetyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(7-methyl-5,5-dioxido-8-((3,4,5-trifluorophenyl)carbamoyl)-3a,4,10,10a-tetrahydro-1H,7H-dipyrrolo[3,4-b:3',4'-f][1,4,5]oxathiazocin-2(3H)-yl)-2-oxoethyl dihydrogen phosphate;

cis-7-methyl-2-(2,2,2-trifluoroethyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(cyanomethyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(5-fluoropyrimidin-2-yl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(2-chloropyridin-4-yl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide;

ethyl (3R,6R)-10-methyl-9-((3,4,5-trifluorophenyl)carbamoyl)-3,4,6,7-tetrahydro-10H-3,6-methanopyrrolo[3,4-b][1,4,5,8]oxathiadiazecine-5(2H)-carboxylate 1,1-dioxide;

cis-7-methyl-2-(5-methyl-1,3,4-oxadiazol-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(cyanomethyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7-methyl-2-(2,2,2-trifluoroethyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(pyridin-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(pyrazin-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(3-methyl-1,2,4-oxadiazol-5-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(5-hydroxypyrimidin-2-yl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-(3aR,10aR)-7-methyl-2-(5-methyl-1,3,4-oxadiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7,10a-dimethyl-2-(5-methyl-1,3,4-oxadiazole-2-carbonyl)-2,3,3a,4,10,10a- hexahydro-1H,7H-dipyrrolo[3,4-b:3',4'-f][1,4,5]oxathiazocine-8-carboxamide 5,5-dioxide;

cis-N-(4-fluoro-3-methylphenyl)-7,10a-dimethyl-2-(5-methyloxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7,10a-dimethyl-2-(2-methyltetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7,10a-dimethyl-2-(3-methyloxetane-3-carbonyl)-2,3,3a,4,10,10a-hexahydro-1H,7H-dipyrrolo[3,4-b:3',4'-f][1,4,5]oxathiazocine-8-carboxamide 5,5-dioxide;

cis-2-(2-oxabicyclo[2.1.1]hexane-1-carbonyl)-N-(4-fluoro-3-methylphenyl)-7,10a-dimethyl-2,3,3a,4,10,10a-hexahydro-1H,7H-dipyrrolo[3,4-b:3',4'-f][1,4,5]oxathiazocine-8-carboxamide 5,5-dioxide;

(3aS,10aS) ethyl 7,10a-dimethyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;

(3aR,10aR) ethyl 7,10a-dimethyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;

(3aS,10aS) ethyl 8-((4-fluoro-3-methylphenyl)carbamoyl)-7,10a-dimethyl-3a,4,10,10a-tetrahydro-1H,7H-dipyrrolo[3,4-b:3',4'-f][1,4,5]oxathiazocine-2(3H)-carboxylate 5,5-dioxide;

(3aR,10aR) ethyl 8-((4-fluoro-3-methylphenyl)carbamoyl)-7,10a-dimethyl-3a,4,10,10a-tetrahydro-1H,7H-dipyrrolo[3,4-b:3',4'-f][1,4,5]oxathiazocine-2(3H)-carboxylate 5,5-dioxide;

(3aS,10aS) N-(4-fluoro-3-methylphenyl)-7,10a-dimethyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR) N-(4-fluoro-3-methylphenyl)-7,10a-dimethyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)-7-methyl-2-(5-methyl-1,3,4-oxadiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(3-chloro-4-fluorophenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-((R)-tetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-((S)-tetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)-2-(5-amino-1,3,4-oxadiazole-2-carbonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(3-methyl-1,2,4-oxadiazole-5-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(oxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(1,2,5-oxadiazole-3-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)-7-methyl-2-(oxazole-4-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(5-methyl-1,3,4-thiadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(oxetane-3-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)-2-(2-oxabicyclo[2.1.1]hexane-1-carbonyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(oxetane-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(2-methyltetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(2-methyloxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(5-methyloxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)-2-(2,5-dimethyloxazole-4-carbonyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(3-methyl-1,2,4-oxadiazol-5-yl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(3-chloro-4-fluorophenyl)-7-methyl-2-(3-methyl-1,2,4-oxadiazol-5-yl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)-7-methyl-2-(3-methyl-1,2,4-oxadiazol-5-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(5-methyl-1,3,4-oxadiazol-2-yl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(3-chloro-4-fluorophenyl)-7-methyl-2-(5-methyl-1,3,4-oxadiazol-2-yl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)-7-methyl-2-(5-methyl-1,3,4-oxadiazol-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

ethyl (3aR,10aR)-8-((4-fluoro-3-methylphenyl)carbamoyl)-7-methyl-3a,4,10,10a-tetrahydro-1H,7H-dipyrrolo[3,4-c:3',4'-g][1,6,2]dithiazocine-2(3H)-carboxylate 5,5-dioxide;

ethyl (3aR,10aR)-8-((4-fluoro-3-methylphenyl)carbamoyl)-7-methyl-3a,4,10,10a-tetrahydro-1H,7H-dipyrrolo[3,4-c:3',4'-g][1,6,2]dithiazocine-2(3H)-carboxylate 5,5,9-trioxide;

ethyl (3aR,10aR)-8-((4-fluoro-3-methylphenyl)carbamoyl)-7-methyl-3a,4,10,10a-tetrahydro-1H,7H-dipyrrolo[3,4-c:3',4'-g][1,6,2]dithiazocine-2(3H)-carboxylate 5,5,9,9-tetraoxide;

(3aR,10aR)—N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-c:3',4'-g][1,6,2]dithiazocine-8-carboxamide 5,5-dioxide;

cis-N-(4-fluoro-3-methylphenyl)-2-methyl-8-(5-methyl-1,3,4-oxadiazole-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

cis-N-(4-fluoro-3-methylphenyl)-2-methyl-8-(3-methyloxetane-3-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

cis-N-(4-fluoro-3-methylphenyl)-2-methyl-8-(2-methyltetrahydrofuran-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

cis-8-(2-oxabicyclo[2.1.1]hexane-1-carbonyl)-N-(4-fluoro-3-methylphenyl)-2-methyl-5,5a,6,7,8,9,9a,10-octahydro-2H-pyrido[4,3-f]pyrrolo[3,4-b][1,4,5]oxathiazocine-1-carboxamide 4,4-dioxide;

cis-N-(4-fluoro-3-methylphenyl)-2-methyl-8-(5-methyloxazole-4-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

trans-N-(4-fluoro-3-methylphenyl)-2-methyl-8-(5-methyl-1,3,4-oxadiazole-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

trans-N-(4-fluoro-3-methylphenyl)-2-methyl-8-(3-methyloxetane-3-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

trans-N-(4-fluoro-3-methylphenyl)-2-methyl-8-(2-methyltetrahydrofuran-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

trans-8-(2-oxabicyclo[2.1.1]hexane-1-carbonyl)-N-(4-fluoro-3-methylphenyl)-2-methyl-5,5a,6,7,8,9,9a,10-octahydro-2H-pyrido[4,3-f]pyrrolo[3,4-b][1,4,5]oxathiazocine-1-carboxamide 4,4-dioxide;

trans-N-(4-fluoro-3-methylphenyl)-2-methyl-8-(5-methyloxazole-4-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

cis-N-(4-fluoro-3-methylphenyl)-2-methyl-7-(5-methyl-1,3,4-oxadiazole-2-carbonyl)-5,5a,6,7,8,9,9a,10-octahydro-2H-pyrido[3,4-f]pyrrolo[3,4-b][1,4,5]oxathiazocine-1-carboxamide 4,4-dioxide;

cis-N-(4-fluoro-3-methylphenyl)-2-methyl-7-(3-methyloxetane-3-carbonyl)-5,5a,6,7,8,9,9a,10-octahydro-2H-pyrido[3,4-f]pyrrolo[3,4-b][1,4,5]oxathiazocine-1-carboxamide 4,4-dioxide;

cis-N-(4-fluoro-3-methylphenyl)-2-methyl-8-(2-methyltetrahydrofuran-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

cis-7-(2-oxabicyclo[2.1.1]hexane-1-carbonyl)-N-(4-fluoro-3-methylphenyl)-2-methyl-5,5a,6,7,8,9,9a,10-octahydro-2H-pyrido[3,4-f]pyrrolo[3,4-b][1,4,5]oxathiazocine-1-carboxamide 4,4-dioxide;

cis-N-(4-fluoro-3-methylphenyl)-2-methyl-7-(5-methyloxazole-4-carbonyl)-5,5a,6,7,8,9,9a,10-octahydro-2H-pyrido[3,4-f]pyrrolo[3,4-b][1,4,5]oxathiazocine-1-carboxamide 4,4-dioxide;

trans-N-(4-fluoro-3-methylphenyl)-2-methyl-7-(5-methyl-1,3,4-oxadiazole-2-carbonyl)-5,5a,6,7,8,9,9a,10-octahydro-2H-pyrido[3,4-f]pyrrolo[3,4-b][1,4,5]oxathiazocine-1-carboxamide 4,4-dioxide;

trans-N-(4-fluoro-3-methylphenyl)-2-methyl-7-(3-methyloxetane-3-carbonyl)-5,5a,6,7,8,9,9a,10-octahydro-2H-pyrido[3,4-f]pyrrolo[3,4-b][1,4,5]oxathiazocine-1-carboxamide 4,4-dioxide;

trans-N-(4-fluoro-3-methylphenyl)-2-methyl-8-(2-methyltetrahydrofuran-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

trans-7-(2-oxabicyclo[2.1.1]hexane-1-carbonyl)-N-(4-fluoro-3-methylphenyl)-2-methyl-5,5a,6,7,8,9,9a,10-octahydro-2H-pyrido[3,4-f]pyrrolo[3,4-b][1,4,5]oxathiazocine-1-carboxamide 4,4-dioxide;

trans-N-(4-fluoro-3-methylphenyl)-2-methyl-7-(5-methyloxazole-4-carbonyl)-5,5a,6,7,8,9,9a,10-octahydro-2H-pyrido[3,4-f]pyrrolo[3,4-b][1,4,5]oxathiazocine-1-carboxamide 4,4-dioxide;

trans-tert-butyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

trans-N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;

trans-N-(4-fluoro-3-methylphenyl)-7-methyl-2-(5-methyloxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide;

trans-N-(4-fluoro-3-methylphenyl)-7-methyl-2-(2-methyltetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide;

trans-N-(4-fluoro-3-methylphenyl)-7-methyl-2-(3-methyloxetane-3-carbonyl)-2,3,3a,4,10,10a-hexahydro-1H,7H-dipyrrolo[3,4-b:3',4'-f][1,4,5]oxathiazocine-8-carboxamide 5,5-dioxide;

trans-2-(2-oxabicyclo[2.1.1]hexane-1-carbonyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide;

tert-butyl (3aS,10aR)-8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

tert-butyl (3aR,10aS)-8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3aS,10aR)—N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aS)—N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;

cis 2-benzyl-N-(4-fluoro-3-methylphenyl)-7-methyl-3-oxo-2,3,3a,4,10,10a-hexahydro-1H,7H-dipyrrolo[3,4-b:3',4'-f][1,4,5]oxathiazocine-8-carboxamide 5,5-dioxide;

cis/trans ethyl 7-methyl-8-((3,4,5-trifluorophenyl)carbamoyl)-1,3a,4,10,11,11a-hexahydro-7H-dipyrrolo[3,4-b:3',4'-f][1,4,5]oxathiazoline-2(3H)-carboxylate 5,5-dioxide;

cis ethyl 8-((4-fluoro-3-methylphenyl)carbamoyl)-7-methyl-3a,4,7,9,10,10a-hexahydro-1H-dipyrrolo[3,4-c:3',4'-g][1,2,6]thiadiazocine-2(3H)-carboxylate 5,5-dioxide;

and pharmaceutically acceptable salts, tautomers, isomers, stereoisomers thereof.

Preferred compounds exhibit an HBV inhibition percentage activity, as defined hereinbelow, greater than 50% at the test concentration (preferably greater than 60%, even more preferably greater than 75%) and/or an $EC_{50}$, as defined hereinbelow, lower than 1 µM. HBV inhibition may indicate inhibition of HBV expression and/or replication. The inhibition activity of the compound of the invention can be measured as described hereinafter.

Preferably, the compounds as defined above are for medical use. Still preferably, the compounds as defined above are for use in the treatment and/or prevention of an HBV infection and/or a condition related to an HBV infection.

Even more preferably, the compounds of the invention are intended for use in treating, eradicating, reducing, slowing or inhibiting an HBV infection in an individual in need thereof, and/or in reducing the viral load associated with an HBV infection in an individual in need thereof, and/or in reducing reoccurrence of an HBV infection in an individual in need thereof, and/or in inducing remission of hepatic injury from an HBV infection in an individual in need thereof, and/or in prophylactically treating an HBV infection in an individual afflicted with a latent HBV infection.

Preferably, the compound as defined above is for use in combination with at least one further therapeutic agent. Preferably, said use in combination comprises the administration of at least one therapeutic agent.

It is an object of the invention a pharmaceutical composition comprising the compound as defined above, alone or in combination with at least one further therapeutic agent, and at least one pharmaceutically acceptable excipient.

Preferably, the at least one further therapeutic agent is selected from the group consisting of: a therapeutic vaccine; an RNA interference therapeutic/antisense oligonucleotide; an immunomodulator; a STING agonist; a RIG-I modulator; a NKT modulator; an IL agonist; an interleukin or another immune acting protein; a therapeutic and prophylactic vaccine; an immune checkpoint modulator/inhibitor; an HBV entry inhibitor; a cccDNA modulator; an inhibitor of HBV protein expression; an agent targeting HBV RNA; a capsid assembly inhibitor/modulator; a core or X protein targeting agent; a nucleotide analogue; a nucleoside analogue; an interferon or a modified interferon; an HBV antiviral of distinct or unknown mechanism; a cyclophilin inhibitor; a sAg release inhibitor; an HBV polymerase inhibitor; a dinucleotide; a SMAC inhibitor; a HDV targeting agent; a viral maturation inhibitor; a reverse transcriptase inhibitor and an HBV RNA destabilizer or another small-molecule inhibitor of HBV protein expression; or a combination thereof.

Preferably, the therapeutic vaccine is selected from: HBsAG-HBIG, HB-Vac, ABX203, NASVAC, GS-4774, GX-110 (HB-110E), CVI-HBV-002, RG7944 (INO-1800), TG-1050, FP-02 (Hepsyn-B), AIC649, VGX-6200, KW-2, TomegaVax-HBV, ISA-204, NU-500, INX-102-00557, HBV MVA and PepTcell.

Preferably, the RNA interference therapeutic is a siRNA, a ddRNA or a shRNA. Preferably, the RNA interference therapeutic is selected from: TKM-HBV (ARB-1467), ARB-1740, ARC-520, ARC-521, BB-HB-331, REP-2139, ALN-HBV, ALN-PDL, LUNAR-HBV, GS3228836 and GS3389404.

Preferably, the immunomodulator is a TLR agonist. Preferably the TLR agonist is a TLR7, TLR8 or TLR9 agonist. Preferably, the TLR7, TLR8 or TLR9 agonist is selected from: RG7795 (RO-6864018), GS-9620, SM360320 (9-benzyl-8-hydroxy-2-(2-methoxy-ethoxy)adenine), AZD 8848 (methyl [3-({[3-(6-amino-2-butoxy-8-oxo-7,8-dihydro-9H-pyrin-9-yl)propyl][3-(4-morpholinyl)propyl]amino}methyl)phenyl]acetate) and ARB-1598.

Preferably, the RIG-I modulator is SB-9200. Preferably, the IL agonist or other immune acting protein is INO-9112 or recombinant IL12. Preferably, the immune checkpoint modulator/inhibitor is BMS-936558 (Opdivo (nivolumab)) or pembrolizumab. Preferably, the HBV entry inhibitor is Myrcludex B, IVIG-Tonrol or GC-1102.

Preferably, the cccDNA modulator is selected from: a direct cccDNA inhibitor, an inhibitor of cccDNA formation or maintenance, a cccDNA epigenetic modifier and an inhibitor of cccDNA transcription.

Preferably, the capsid assembly inhibitor/modulator, core or X protein targeting agent, direct cccDNA inhibitor, inhibitor of cccDNA formation or maintenance, or cccDNA epigenetic modifier is selected from: BAY 41-4109, NVR 3-778, GLS-4, NZ-4 (W28F), Y101, ARB-423, ARB-199, ARB-596, AB-506, JNJ-56136379, ASMB-101 (AB-V102), ASMB-103, CHR-101, CC-31326, AT-130 and RO7049389.

Preferably, the interferon or modified interferon is selected from: interferon alpha (IFN-α), pegylated interferon alpha (PEG-IFN-α), interferon alpha-2a, recombinant interferon alpha-2a, peginterferon alpha-2a (Pegasys), interferon alpha-2b (Intron A), recombinant interferon alpha-2b, interferon alpha-2b XL, peginterferon alpha-2b, glycosylated interferon alpha-2b, interferon alpha-2c, recombinant interferon alpha-2c, interferon beta, interferon beta-1a, peginterferon beta-1a, interferon delta, interferon lambda (IFN-λ), peginterferon lambda-1, interferon omega, interferon tau, interferon gamma (IFN-γ), interferon alfacon-1, interferon alpha-n1, interferon alpha-n3, albinterferon alpha-2b, BLX-883, DA-3021, PI 101 (also known as AOP2014), PEG-infergen, Belerofon, INTEFEN-IFN, albumin/interferon alpha 2a fusion protein, rHSA-IFN alpha 2a, rHSA-IFN alpha 2b, PEG-IFN-SA and interferon alpha biobetter. Particularly preferred are: peginterferon alpha-2a, peginterferon alpha-2b, glycosylated interferon alpha-2b, peginterferon beta-1a, and peginterferon lambda-1. More particularly preferred is peginterferon alpha-2a.

Preferably, the HBV antiviral of distinct or unknown mechanism is selected from: AT-61 ((E)-N-(1-chloro-3-oxo-1-phenyl-3-(piperidin-1-yl)prop-1-en-2-yl)benzamide), AT130 ((E)-N-(1-bromo-1-(2-methoxyphenyl)-3-oxo-3-(piperidin-1-yl)prop-1-en-2-yl)-4-nitrobenzamide), analogues thereof, REP-9AC (REP-2055), REP-9AC' (REP-2139), REP-2165 and HBV-0259.

Preferably, the cyclophilin inhibitor is selected from: OCB-030 (NVP-018), SCY-635, SCY-575 and CPI-431-32.

Preferably, said HBV polymerase inhibitor is selected from: entecavir (Baraclude, Entavir), lamivudine (3TC, Zeffix, Heptovir, Epivir, and Epivir-HBV), telbivudine (Tyzeka, Sebivo), clevudine, besifovir, adefovir (hepsera), tenofovir. Preferably, tenofovir is in a salt form.

Preferably, tenofovir is in a salt form selected from: tenofovir disoproxil fumarate (Viread), tenofovir alafenamide fumarate (TAF), tenofovir disoproxil orotate (DA-2802), tenofovir disoproxil aspartate (CKD-390), AGX-1009, and CMX157.

Preferably, the dinucleotide is SB9200. Preferably, the SMAC inhibitor is Birinapant. Preferably, the HDV targeting agent is Lonafamib.

Preferably, the HBV RNA destabilizer or other small-molecule inhibitor of HBV protein expression is RG7834 or AB-452.

Preferably, the at least one further therapeutic agent is an agent useful in the treatment and prevention of hepatitis B. Preferably, the at least one further therapeutic agent is an anti-HDV agent, an anti-HCV agent and/or an anti-HIV agent.

Preferably, the at least one further therapeutic agent is selected from the group consisting of: HBV polymerase inhibitor, interferon, viral entry inhibitor, BAY 41-4109, reverse transcriptase inhibitor, a TLR-agonist, AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl)prop-1-en-2-yl)-4-nitrobenzamide), and a combination thereof, wherein the HBV polymerase inhibitor is preferably at least one of Lamivudine, Entecavir, Tenofovir, Adefovir, Telbivudine, Clevudine; and wherein the TLR agonist is preferably selected from the group consisting of SM360320 (9-benzyl-8-hydroxy-2-(2-methoxy-ethoxy)adenine), AZD 8848 (methyl [3-({[3-(6-amino-2-butoxy-8-oxo-7,8-dihydro-9H-purin-9-yl)propyl][3-(4-morpholinyl)propyl]amino}methyl) phenyl] acetate) and a combination thereof.

Preferably, the compound of the invention is for use in combination with one, two or more further therapeutic agent(s) as defined above.

Preferably, the pharmaceutical composition of the invention comprises one, two or more further therapeutic agent(s) as defined above.

Preferably, said pharmaceutical composition is for use in the treatment and/or prevention of an HBV infection and/or a condition related to an HBV infection. Even more preferably, said pharmaceutical composition is for use in treating, eradicating, reducing, slowing or inhibiting an HBV infection in an individual in need thereof, and/or in reducing the viral load associated with an HBV infection in an individual in need thereof, and/or in reducing reoccurrence of an HBV infection in an individual in need thereof, and/or in inducing remission of hepatic injury from an HBV infection in an individual in need thereof, and/or in prophylactically treating an HBV infection in an individual afflicted with a latent HBV infection.

In an embodiment, the invention provides a kit comprising at least one pharmaceutically acceptable vial or container containing one or more doses of a compound of the invention or of a pharmaceutical composition of the invention and optionally a) instructions for use thereof in mammals and/or b) an infusion bag or container containing a pharmaceutically acceptable diluent.

It is a further object of the invention a process for the synthesis of a compound of general formula (I), (Ia) or (Ib) according to the synthetic Schemes included in the description of the invention.

In particular, it is an object of the present invention a process for the synthesis of the compound of formula I or the pharmaceutically acceptable salt, tautomer, solvate, isomer or stereoisomer thereof as defined hereinabove, said process comprising at least one of the following steps:

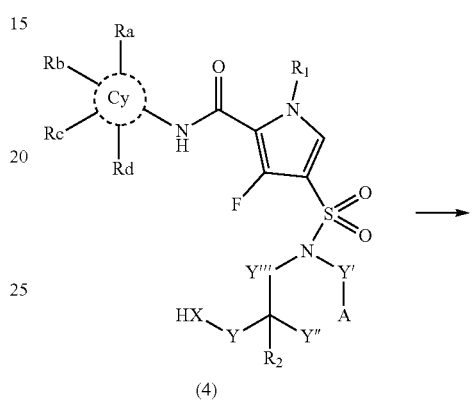

(4)

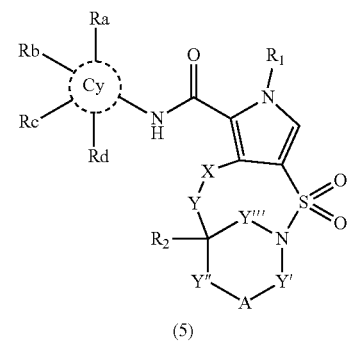

(5)

cyclisation of a compound of formula (4) in the presence of an appropriate base such as $Cs_2CO_3$ to obtain a compound of formula (5), wherein Cy, X, Y, Y', Y", Y''', A, $R_1$, $R_2$, Ra, Rb, Rc and Rd are as defined above; or

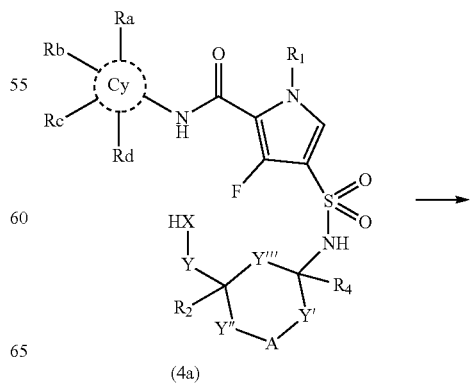

(4a)

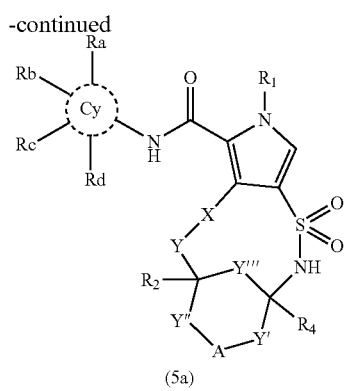

(5a)

cyclisation of a compound of formula (4a) in the presence of an appropriate base such as $Cs_2CO_3$ to obtain a compound of formula (5a), wherein Cy, X, Y, Y', Y", Y'", A, $R_1$, $R_2$, $R_4$, Ra, Rb, Rc and Rd are as defined above.

It is a further object of the invention a pharmaceutical composition comprising an effective amount of one or more compounds as defined above or a pharmaceutically acceptable prodrug thereof, alone or in combination with other active compounds, and at least one pharmaceutically acceptable excipient.

The present invention includes within its scope prodrugs of the compounds of formula (I), (Ia) or (Ib) above. In general, such prodrugs will be functional derivatives of the compounds of formula (I), (Ia), (Ib) which are readily convertible in vivo into the required compound of formula (I), (Ia), (Ib). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The invention also includes all suitable isotopic variations of a compound of the disclosure. Examples of isotopes that can be incorporated into compounds of the disclosure include isotopes such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the disclosure, for example, those in which a radioactive isotope such as $^3H$ or $^{14}C$ is incorporated, are useful in drug and/or substrate tissue distribution studies. Further, substitution with isotopes such as deuterium $^2H$, may afford certain therapeutic advantages resulting from greater metabolic stability. Isotopic variations of the compounds of the disclosure can generally be prepared by conventional procedures such as by the illustrative methods or by the preparations described in the examples hereafter using appropriate isotopic variations of suitable reagents.

The present invention includes within its scope solvates of the compounds of (I), (Ia) or (Ib) or of the relative salts, for example, hydrates, alcoholates and the like.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

In addition, the compounds disclosed herein may exist as tautomers and both tautomeric forms are intended to be encompassed by the scope of the invention, even though only one tautomeric structure is depicted.

The compounds may exist in different isomeric forms, including geometric isomers, stereoisomers, tautomers, all of which are encompassed by the present invention.

Pure stereoisomeric forms of the compounds and intermediates of this invention may be obtained by the application of art-known procedures and are intended to be encompassed by the scope of the invention. In particular, "pure stereoisomeric form" or "stereoisomerically pure" indicate a compound having stereoisomeric excess of at least 80%, preferably of at least 85%. For instance, enantiomers may be separated from each other by the selective crystallization of their diastereomeric salts or by chromatographic techniques using chiral stationary phases. Pure stereochemically isomeric forms may also be derived from the corresponding pure stereochemically isomeric forms of the appropriate starting materials, provided that the reaction occurs stereospecifically. The term "enantiomerically pure" shall be interpreted in a similar way, having regard to the enantiomeric ratio.

When any variable (e.g. $R_1$ and $R_2$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" should be taken to be equivalent to the phrase "unsubstituted or substituted with one or more substituents" and in such cases the preferred embodiment will have from zero to three substituents. More particularly, there are zero to two substituents.

The expressions "one or more substituents" and "one, two or more substituents" refer to in particular to 1, 2, 3, 4 or more substituents, in particular to 1, 2, 3 or 4 substituents, more in particular 1, 2 or 3 substituents.

As used herein "Y is a single bond" indicates that, in the general formula (I), X is directly linked via a single bond to the carbon atom bearing $R_2$; "Y' is a single bond" indicates that, in the general formula (I), A is directly linked via a single bond to Z; "Y" is a single bond" indicates that, in the general formula (I), A is directly linked via a single bond to the carbon atom bearing $R_2$; "Y'" is a single bond" indicates that Z, in the general formula (I), is directly linked via a single bond to the carbon atom bearing $R_2$.

As used herein, "alkyl" is intended to include both branched and straight-chain saturated aliphatic hydrocarbon groups having the specified number of carbon atoms. For example, "$C_{1-6}$alkyl" is defined to include groups having 1, 2, 3, 4, 5 or 6 carbons in a linear or branched arrangement. For example, "$C_{1-6}$ alkyl" specifically includes methyl, ethyl, n-propyl, i-propyl, n-butyl, t-butyl, i-butyl, pentyl, hexyl, and so on. "$C_{1-4}$alkyl" is defined to include groups having 1, 2, 3 or 4 carbons in a linear or branched arrangement. For example, "$C_{1-4}$ alkyl" specifically includes methyl, ethyl, n-propyl, i-propyl, n-butyl, t-butyl, i-butyl, and so on. "$C_{1-3}$alkyl" is defined to include groups having 1, 2, or 3 carbons in a linear or branched arrangement. For example, "$C_{1-3}$ alkyl" specifically includes methyl, ethyl, n-propyl, i-propyl, and so on. Preferred alkyl groups are methyl, ethyl, i-propyl or t-butyl.

As used herein, "alkoxy" represents an alkyl group of indicated number of carbon atoms attached through an oxygen bridge. "Alkoxy" therefore encompasses the definitions of alkyl above. $C_{1-6}$ alkoxy group is preferably a linear or branched $C_{1-4}$ alkoxy group, more preferably a $C_{1-3}$alkoxy group, still more preferably a $C_{1-2}$ alkoxy group. Examples of suitable alkoxy groups include, but are not limited to methoxy, ethoxy, n-propoxy, i-propoxy, n-butoxy, s-butoxy or t-butoxy.

Preferred alkoxy groups include methoxy, ethoxy and t-butoxy.

As used herein, the terms "halo$C_{1-6}$alkyl" and "halo$C_{1-6}$alkoxy" mean a $C_{1-6}$alkyl or $C_{1-6}$alkoxy group in which one or more (in particular, 1 to 3) hydrogen atoms have been replaced by halogen atoms, especially fluorine or chlorine atoms. Halo$C_{1-6}$alkoxy group is preferably a linear or branched halo$C_{1-4}$alkoxy group, more preferably a halo$C_{1-3}$alkoxy group, still more preferably a halo$C_{1-2}$alkoxy group, for example $OCF_3$, $OCHF_2$, $OCH_2F$, $OCH_2CH_2F$, $OCH_2CHF_2$ or $OCH_2CF_3$, and most especially $OCF_3$ or $OCHF_2$. Halo$C_{1-6}$alkyl group is preferably a linear or branched halo$C_{1-3}$alkyl group, more preferably a halo$C_{1-2}$alkyl group for example, $CF_3$, $CHF_2$, $CH_2F$, $CH_2CH_2F$, $CH_2CHF_2$, $CH_2CF_3$ or $CH(CH_3)CF_3$, and most especially $CF_3$, $CHF_2$ or $CH(CH_3)CF_3$.

As used herein, the term "hydroxy$C_{1-6}$alkyl" means a $C_{1-6}$alkyl group in which one or more (in particular, 1 to 3) hydrogen atoms have been replaced by hydroxy groups. Similarly, the term "hydroxy$C_{1-4}$alkyl" means a $C_{1-4}$alkyl group in which one or more (in particular, 1 to 2) hydrogen atoms have been replaced by hydroxy groups. Illustrative examples include, but are not limited to $CH_2OH$, $CH_2CH_2OH$, $CH(CH_3)OH$ and $CHOHCH_2OH$.

As used herein, the term "aryl" means a monocyclic or polycyclic aromatic ring comprising carbon atoms and hydrogen atoms. If indicated, such aromatic ring may include one or more heteroatoms, then also referred to as "heteroaryl", preferably, 1 to 3 heteroatoms, independently selected from nitrogen, oxygen, and sulfur, preferably nitrogen. As is well known to those skilled in the art, heteroaryl rings have less aromatic character than their all-carbon counter parts. Thus, for the purposes of the present invention, a heteroaryl group need only have some degree of aromatic character. Illustrative examples of aryl groups are optionally substituted phenyl. Illustrative examples of heteroaryl groups according to the invention include optionally substituted thiophene, oxazole, 1,3,4-oxadiazole, 1,2,4-oxadiazole, thiazole, thiadiazole, imidazole, pyrazole, pyrimidine, pyrazine and pyridine. Thus, examples of monocyclic aryl optionally containing one or more heteroatoms, for example one or two heteroatoms, are a 5- or 6-membered aryl or heteroaryl group such as, but not limited to, phenyl, pyridyl, pyrimidinyl, pyrazinyl, pyridazinyl, pyrrolyl, thienyl, thiazolyl, thiadiazolyl, pyrazolyl, imidazolyl, triazolyl, tetrazolyl, furyl, isoxazolyl, oxadiazolyl and oxazolyl. Examples of polycyclic aromatic ring, optionally containing one or more heteroatoms, for example one or two heteroatoms, are a 8-10 membered aryl or heteroaryl group such as, but not limited to, benzimidazolyl, benzofurandionyl, benzofuranyl, benzofurazanyl, benzopyrazolyl, benzotriazolyl, benzothienyl, benzoxazolyl, benzoxazolonyl, benzothiazolyl, benzothiadiazolyl, benzodioxolyl, benzoxadiazolyl, benzoisoxazolyl, benzoisothiazolyl, indolyl, indolizinyl, isoindolinyl, indazolyl, isobenzofuranyl, isoindolyl, isoquinolyl, quinazolinyl, quinolyl, quinoxalinyl, quinolizinyl, naphtyl, naphthyridinyl and phthalazinyl. A preferred aromatic ring according to the present invention is phenyl. Preferred heteroaromatic rings according to the present invention include pyridyl, 1,3-oxazole, 1,2-oxazole, 1,2,4-oxadiazole, 1,2,5-oxadiazole, 1,3,4-oxadiazole, pyrazine, pyrazone, pyrazole, 1,3-thiazole, 1,3,4-thiadiazole, pyrimidine, pyrimidone, 1,2,4-thiadiazole, imidazole, and the like.

Heterocycle, heterocyclic compound or ring structure is a cyclic compound that has atoms of at least two different elements as members of its ring(s).

As used herein, the term "heterocyclic ring" is a saturated or partially saturated non aromatic monocyclic or bicyclic ring system, of 4 to 10 members which contains one or more heteroatoms selected from N, O or S. Examples include, but are not limited to azetidinyl, piperazinyl, piperidinyl, morpholinyl, thiomorpholinyl, thiazolidinyl, pyrrolidinyl, azepanyl, diazepanyl, oxazepanyl, thiazepanyl, azocanyl, oxazocanyl, 2-oxabicyclo[2.1.1]hexane, 3-oxabicyclo[3.1.0]hexane, tetrahydrofurane, oxetane, octahydrocyclopenta[b]pyrrole and the hexahydrofuro[2,3-b]furan system. Preferred heterocyclic rings according to the present invention include oxetane, tetrahydrofurane, 2-oxabicyclo[2.1.1]hexane, the hexahydrofuro[2,3-b]furan system A substituent on a saturated, partially saturated or unsaturated heterocycle can be attached at any substitutable position.

As used herein, the term "$C_{1-6}$ alkanediyl" as group or part of a group defines bivalent straight or branched chained saturated hydrocarbon radicals having from 1 to 4 carbon atoms. $C_{1-6}$ alkanediyl group, is preferably a $C_{1-4}$ alkanediyl group, a $C_{1-3}$ alkanediyl or more preferably a $C_{1-2}$ alkanediyl. Examples include, but are not limited to methanediyl, ethanediyl, propanediyl, butanediyl, pentanediyl and hexanediyl. Preferably, "$C_{1-6}$ alkanediyl" refers to methanediyl, ethanediyl and propanediyl.

As used herein, the term "3-7 membered saturated ring" means saturated cyclic hydrocarbon (cycloalkyl) with 3, 4, 5, 6 or 7 carbon atoms and is generic to cyclopropyl, cyclobutyl, cyclopentyl, cyclohexyl or cycloheptyl. Said saturated ring optionally contains one or more heteroatoms (also referred to as heterocyclyl or heterocyclic ring), such that at least one carbon atom is replaced by a heteroatom selected from N, O and S, in particular from N and O. Depending on the dimension of the ring, it can be of a cyclic or bicyclic structure. Examples include, but are not limited to oxetanyl, azetidinyl, tetrahydro-2H-pyranyl, piperazinyl, piperidinyl, tetrahydrofuranyl, morpholinyl, thiomorpholinyl, thiazolidinyl, thiolane 1,1-dioxide, pyrrolidinyl, azepanyl, diazepanyl, oxazepanyl, thiazepanyl, azocanyl or oxazocanyl. Preferred are saturated cyclic hydrocarbons with 3, 4 or 5 carbon atoms and 1 oxygen or 1 nitrogen atom. Examples include oxetanyl, tetrahydrofuranyl, tetrahydro-2H-pyranyl, piperidinyl or pyrrolidinyl.

It should be noted that different isomers of the various heterocycles may exist within the definitions as used throughout the specification. For example, pyrrolyl may be 1H-pyrrolyl or 2H-pyrrolyl.

It should also be noted that the radical positions on any molecular moiety used in the definitions may be anywhere on such moiety as long as it is chemically stable. For example, pyridyl includes 2-pyridyl, 3-pyridyl, 4-pyridyl.

As used herein, the term "halogen" includes fluorine, chlorine, bromine and iodine, of which fluorine, chlorine and bromine are preferred.

The term "heteroatom" refers to an atom other than carbon or hydrogen in a ring structure or a saturated backbone as defined herein. Typical heteroatoms include N(H), O, S.

As used herein, the term "$C_{3-8}$ cycloalkyl" means saturated cyclic hydrocarbon (cycloalkyl) with 3 or 4, 5, 6, 7 or 8 carbon atoms and is generic to cyclopropyl, cyclobutyl, cyclopentyl, cyclohexyl, cycloheptyl or cyclooctyl.

The term "$C_{1-6}$alkylaryl" as used herein indicates one or more aryl groups appended to a $C_{1-6}$alkyl radical. As used herein, the term "$C_{1-6}$alkylheteroaryl" indicates one or more heteroaryl groups appended to a $C_{1-6}$alkyl radical.

As used herein, the term "$C_{1-6}$alkyl-$C_{3-8}$cycloalkyl" indicates one or more $C_{3-8}$cycloalkyl groups appended to a $C_{1-6}$alkyl radical.

The terms "spiro-$C_{3-8}$cycloalkyl" or "spiro-$C_{3-8}$heterocycloalkyl" indicate respectively a $C_{3-8}$cycloalkyl or a $C_{3-8}$heterocycloalkyl forming a bicyclic organic compound with rings connected through just one atom. The rings can be different in nature or identical. The connecting atom is also called the spiroatom, most often a quaternary carbon ("spiro carbon").

Included in the instant invention is the free base of compounds of formula (I), (Ia) or (Ib) as well as the pharmaceutically acceptable salts and stereoisomers thereof. Some of the specific compounds exemplified herein are the protonated salts of amine compounds. Compounds of formula (I), (Ia) or (Ib) containing one or more N atoms may be protonated on any one, some or all of the N atoms. The term "free base" refers to the amine compounds in non-salt form. The encompassed pharmaceutically acceptable salts not only include the salts exemplified for the specific compounds described herein, but also all the typical pharmaceutically acceptable salts of the free form of compounds of formula (I), (Ia) or (Ib). The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base. In a preferred embodiment, the compounds of the invention have at least one acidic proton and the corresponding sodium or potassium salt can be formed, for example, by reaction with the appropriate base.

Thus, pharmaceutically acceptable salts of the compounds of this invention include the conventional non-toxic salts of the compounds of this invention as formed by reacting a basic instant compound with an inorganic or organic acid or an acid compound with an inorganic or organic base. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. Conventional non-toxic salts further include those derived from an inorganic base, such as potassium, sodium hydroxide, magnesium or calcium hydroxide, as well as salts prepared from organic bases, such as ethylene diamine, lysine, tromethamine, meglumine and the like. Preferably, a pharmaceutically acceptable salt of this invention contains one equivalent of a compound of formula (I), (Ia) or (Ib) and 1, 2 or 3 equivalent of an inorganic or organic acid or base. More particularly, pharmaceutically acceptable salts of this invention are the tartrate, trifluoroacetate or the chloride salts.

When the compound of the present invention is acidic, suitable "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," J. Pharm. Sci., 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of the present invention find use in a variety of applications for human and animal health. The compounds of the present invention are inhibitors of hepatitis B virus (HBV).

In the context of the present invention, HBV may be any known isolate, genotype, strain, etc. of HBV.

In particular, the hepatitis B virus has been classified into eight main genotypes (designated A-H), and two additional genotypes (I and J) were tentatively proposed. HBV genotypes have been further separated into several subgenotypes that differ by 4.0 to 7.5% in the whole nucleotide sequence. HBV genotypes differ substantially in many virological and probably some clinical parameters; however, the precise role of HBV genotypes in the evolution of the infection remains controversial. Due to geographical distribution, only two or three HBV genotypes co-circulate in most regions of the world, thereby limiting genotype comparisons.

The compounds of the present invention are inhibitors of hepatitis B virus (HBV) useful for the treatment and/or prevention of an HBV infection. In particular the compounds of the present invention are inhibitors of hepatitis B virus (HBV) core (HBc) protein useful for the treatment and/or prevention of an HBV infection.

The compounds, compositions and methods provided herein are particularly deemed useful for treating, ameliorating or preventing HBV infection and related conditions, including chronic hepatitis B, HBV/HDV co-infection, HBV/HCV co-infection, HBV/HIV co-infection, inflammation, necrosis, cirrhosis, hepatocellular carcinoma, hepatic decompensation and hepatic injury from an HBV infection.

In the present invention, the expression "HBV infection" comprises any and all conditions deriving from infection with HBV, including but not limited to hepatitis B, preferably chronic hepatitis B, HBV/HDV co-infection, HBV/HCV coinfection, HBV/HIV coinfection.

HBV infection leads to a wide spectrum of hepatic complications, all of these are intended as conditions related to an HBV infection. As used herein, "condition related to an HBV infection" is preferably selected from the group consisting of: chronic hepatitis B, HBV/HDV co-infection, HBV/HCV co-infection, HBV/HIV co-infection, inflammation, necrosis, cirrhosis, hepatocellular carcinoma, hepatic decompensation and hepatic injury from an HBV infection.

Expressions like "treating, eradicating, reducing, slowing or inhibiting an HBV infection" are used to indicate the application or administration of a therapeutic agent, i.e., a compound of the invention (alone or in combination with another pharmaceutical agent), to a patient or application or administration of a therapeutic agent to an isolated tissue or cell line from a patient (e.g., for diagnosis or ex vivo applications), who has an HBV infection, a symptom of HBV infection or the potential to develop an HBV infection, with the purpose to cure, heal, alleviate, relieve, alter, remedy, ameliorate, improve or affect the HBV infection, the symptoms of HBV infection, or the potential to develop an HBV infection. Such treatments may be specifically tailored or modified, based on knowledge obtained from the field of pharmacogenomics.

Efficacy of treatment may be determined using quantification of viral load or other evidence of infection, such as through measurement of HBeAg, HBsAg, HBV DNA levels, ALT activity levels, serum HBV levels, and the like, thereby allowing adjustment of treatment dose, treatment frequency, and treatment length.

HBeAg stands for hepatitis B e-antigen. This antigen is a protein from the hepatitis B virus that circulates in infected blood when the virus is actively replicating.

ALT stands for Alanine Transaminase and is an enzyme involved in the transfer of an amino group from the amino-acid alanine to alpha-ketoglutaric acid to produce glutamate and pyruvate. ALT is located primarily in liver and kidney, with lesser amounts in heart and skeletal muscle. ALT is commonly measured clinically as part of liver function tests.

The compounds of the invention can reduce viral load in an individual suffering from an HBV infection. In a non limiting embodiment, the compounds of the invention result in viral load reduction during therapy in an individual in need thereof from a minimum of one- or two-log decrease to a maximum of about eight-log decrease.

As used herein, the expression "remission of hepatic injury from an HBV infection" means that the chronic necroinflammatory liver disease has been halted by the fact that the viral antigens have disappeared from the organ (and the immune system no longer attacks the liver cells).

As used herein, the term "prophylactically treating" means no disorder or disease development if none had occurred, or no further disorder or disease development if there had already been development of the disorder or disease. Also considered is the ability to prevent some or all of the symptoms associated with the disorder or disease. An example of prophylactic treatment might also indicate the necessity of reducing the risk of infecting a liver graft (in case of liver transplant in chronically infected patients) or infecting newborns (in case of chronically infected mothers that pass the virus at time of delivery).

As used herein, "reducing reoccurrence of an HBV infection" indicates that patients may have reactivation of HBV replication and exacerbation of a condition related to an HBV infection, e.g. hepatitis, after years of quiescence. These patients may still be at risk of developing a condition related to an HBV infection, e.g. hepatocellular carcinoma development. Antiviral therapy is also recommended as prophylaxis for patients who are HBsAg-positive as well as patients who are HBsAg-negative and hepatitis B core antibody-positive who require treatment with immunosuppressive therapies that are predicted to have a moderate to high risk of HBV reactivation.

The compounds of this invention may be administered to mammals, preferably humans, either alone or in combination with pharmaceutically acceptable carriers, excipients or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal and topical routes of administration.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium croscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin.

The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula (I), (Ia) or (Ib) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of formula (I), (Ia) or (Ib) are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The compounds of the invention may be presented in a liposome or other micro particulate or other nanoparticle designed to target the compound. Acceptable liposomes can be neutral, negatively, or positively charged, the charge being a function of the charge of the liposome components and pH of the liposome solution. Liposomes can be normally prepared using a mixture of phospholipids and cholesterol. Suitable phospholipids include phosphatidylcholine, phosphatidylethanolamine, phosphatidic acid, phosphatidylglycerol, phosphatidylinositol. Polyethylene glycol can be added to improve the blood circulation time of liposomes. Acceptable nanoparticles include albumin nanoparticles and gold nanoparticles.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing anti HBV treatment. Administration generally occurs in an amount between about: 0.01 mg/kg of body weight to about 100 mg/kg of body weight per day, preferably between about 0.01 mg/kg of body weight to about 60 mg/kg of body weight per day, preferably between about 0.1 mg/kg of body weight to about 50 mg/kg of body weight per day, preferably between about 0.5 mg/kg of body weight to about 40 mg/kg of body weight per day.

The instant compounds are also useful in combination with known therapeutic agents for simultaneous, separate or sequential administration.

In an embodiment, the compounds of the present invention may be used in combination with at least one or more additional therapeutic agents, in particular anti-HBV agents.

The indication that compounds of the invention are for use in the treatment and/or prevention of an HBV infection indicates that the compounds are efficacious for treating, eradicating, reducing, slowing or inhibiting an HBV infection.

The therapeutic agent is any agent commonly used in the treatment and/or prevention and/or amelioration of an HBV infection or a condition related to an HBV infection. The therapeutic agent is known in the art.

The term "anti-HBV agent", or more simply "HBV antiviral(s)" also includes compounds that are therapeutic nucleic acids, antibodies or proteins either in their natural form or chemically modified and/or stabilized. The term therapeutic nucleic acid includes but is not limited to nucleotides and nucleosides, oligonucleotides, polynucleotides, of which non limiting examples are antisense oligonucleotides, miRNA, siRNA, shRNA, therapeutic vectors and DNA/RNA editing components.

The term anti-HBV agent also includes compounds capable of treating HBV infection via immunomodulation, i.e. immunomodulators or immunomodulating compounds. Examples of immunomodulators are interferon-α (IFN-α), pegylated interferon-α or stimulants of the innate immune system such as Toll-like receptor 7 and/or 8 agonists and therapeutic or prophylactic vaccines. One embodiment of the present invention relates to combinations of a compound of formula (I) or (Ia) or any subgroup thereof, as specified herein, with an immunomodulating compound, more specifically a Toll-like receptor 7 and/or 8 agonist.

The additional HBV antiviral(s) can be selected for example, from therapeutic vaccines; RNA interference therapeutic/antisense oligonucleotides (e.g. siRNA, ddRNA, shRNA); immunomodulators (such as TLR agonists (e.g. TLR7, TLR8 or TLR9 agonists); STING agonists; RIG-I modulators; NKT modulators; IL agonists; Interleukin or other immune active proteins, therapeutic and prophylactic vaccines and immune checkpoint modulators; HBV entry inhibitors; cccDNA modulators (such as for example direct cccDNA inhibitors, inhibitors of cccDNA formation or maintenance, cccDNA epigenetic modifiers, inhibitors of cccDNA transcription); inhibitors of HBV protein expression; agents targeting HBV RNA; capsid assembly inhibitors/modulators; core or X protein targeting agents; nucleotide analogues; nucleoside analogues; interferons or modified interferons; HBV antivirals of distinct or unknown mechanism; cyclophilin inhibitors; sAg release inhibitors; HBV polymerase inhibitors; dinucleotides; SMAC inhibitors; HDV targeting agents; viral maturation inhibitors; reverse transcriptase inhibitors and HBV RNA destabilizers and other small-molecule inhibitors of HBV protein expression.

In particular, the combination of previously known anti-HBV agents, such as interferon-α (IFN-α), pegylated interferon-α, 3TC, tenofovir, lamivudine, entecavir, telbivudine, and adefovir or a combination thereof, and a compound of formula (I) or (Ia) or any subgroup thereof can be used as a medicine in a combination therapy. Additional examples of further therapeutic agents that may be combined with the compounds of the present invention include: Zidovudine, Didanosine, Zalcitabine, Stavudine, Abacavir, ddA Emtricitabine, Apricitabine, Atevirapine, ribavirin, acyclovir, valacyclovir, famciclovir, ganciclovir, valganciclovir, cidofovir, Efavirenz, Nevirapine, Delavirdine and Etravirine.

Particular examples of such HBV antiviral(s) include, but are not limited to:
  RNA interference (RNAi) therapeutics: TKM-HBV (also known as ARB-1467), ARB-1740, ARC-520, ARC-521, BB-HB-331, REP-2139, ALN-HBV, ALN-PDL, LUNAR-HBV, GS3228836, and GS3389404;
  HBV entry inhibitors: Myrcludex B, IVIG-Tonrol, GC-1102;
  HBV capsid inhibitor/modulators, core or X protein targeting agents, direct cccDNA inhibitors, inhibitors of cccDNA formation or maintenance, or cccDNA epigenetic modifiers: BAY 41-4109, NVR 3-778, GLS-4, NZ-4 (also known as W28F), Y101, ARB-423, ARB-199, ARB-596, AB-506, JNJ-56136379, ASMB-101 (also known as AB-V102), ASMB-103, CHR-101, CC-31326, AT-130, RO7049389.
  HBV polymerase inhibitors: entecavir (Baraclude, Entavir), lamivudine (3TC, Zeffix, Heptovir, Epivir, and Epivir-HBV), telbivudine (Tyzeka, Sebivo), clevudine, besifovir, adefovir (hepsera), tenofovir (in particular tenofovir disoproxil fumarate (Viread), tenofovir alafenamide fumarate (TAF)), tenofovir disoproxil orotate (also known as DA-2802), tenofovir disoproxil aspartate (also known as CKD-390), AGX-1009, and CMX157);
  HBV RNA destabilizers and other small-molecule inhibitors of HBV protein expression: RG7834, AB-452;
  cyclophilin inhibitors: OCB-030 (also known as NVP-018), SCY-635, SCY-575, and CPI-431-32;
  dinucleotides: SB9200;
  compounds of distinct or unknown mechanism, such as but not limited to AT-61 ((E)-N-(1-chloro-3-oxo-1-phenyl-3-(piperidin-1-yl)prop-1-en-2-yl)benzamide), AT130 ((E)-N-(1-bromo-1-(2-methoxyphenyl)-3-oxo-3-(piperidin-1-yl)prop-1-en-2-yl)-4-nitrobenzamide), and similar analogs; REP-9AC (also known as REP-2055), REP-9AC' (also known as REP-2139), REP-2165 and HBV-0259;

TLR agonists (TLR7, 8 and/or 9): RG7795 (also known as RO-6864018), GS-9620, SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-pyrin-9-yl)propyl][3-(4-morpholinyl)propyl]amino}methyl)phenyl]acetate); ARB-1598;

RIG-I modulators: SB-9200;

SMAC inhibitor: Birinapant

Immune Check Point inhibitors: BMS-936558 (Opdivo (nivolumab)), KEYTRUDA® (pembrolizumab);

therapeutic vaccines: HBsAG-HBIG, HB-Vac, ABX203, NASVAC, GS-4774, GX-110 (also known as HB-110E), CVI-HBV-002, RG7944 (also known as INO-1800), TG-1050, FP-02 (Hepsyn-B), AIC649, VGX-6200, KW-2, TomegaVax-HBV, ISA-204, NU-500, INX-102-00557 HBV MVA, PepTcell;

IL agonists and immune acting proteins: INO-9112; recombinant IL12;

interferons: interferon alpha (IFN-α), interferon alpha-2a, recombinant interferon alpha-2a, peginterferon alpha-2a (Pegasys), interferon alpha-2b (Intron A), recombinant interferon alpha-2b, interferon alpha-2b XL, peginterferon alpha-2b, glycosylated interferon alpha-2b, interferon alpha-2c, recombinant interferon alpha-2c, interferon beta, interferon beta-1a, peginterferon beta-1a, interferon delta, interferon lambda (IFN-λ), peginterferon lambda-1, interferon omega, interferon tau, interferon gamma (IFN-γ), interferon alfacon-1, interferon alpha-n1, interferon alpha-n3, albinterferon alpha-2b, BLX-883, DA-3021, PI 101 (also known as AOP2014), PEG-infergen, Belerofon, INTEFEN-IFN, albumin/interferon alpha 2a fusion protein, rHSA-IFN alpha 2a, rHSA-IFN alpha 2b, PEG-IFN-SA, interferon alpha biobetter; in particular, peginterferon alpha-2a, peginterferon alpha-2b, glycosylated interferon alpha-2b, peginterferon beta-1a, and peginterferon lambda-1; more in particular, peginterferon alpha-2a;

HDV targeting agent: Lonafamib.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In some embodiments, pulsed administration is more effective than continuous treatment because total pulsed doses are often lower than would be expected from continuous administration of the same composition. Each pulse dose can be reduced and the total amount of drug administered over the course of treatment is minimized. Individual pulses can be delivered to the patient continuously over a period of several hours, such as about 2, 4, 6, 8, 10, 12, 14 or 16 hours, or several days, such as 2, 3, 4, 5, 6 or 7 days.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The present invention will be described by means of the following non-limiting examples and biological data are presented.

Materials and Methods

Chemistry

General

Unless otherwise indicated, commercially available reagents and solvents (HPLC grade) were used without further purification.

Specifically, the following abbreviations may have been used in the descriptions of the experimental methods:

NMR: Nuclear Magnetic Resonance; $^1$H: proton; MHz: Megahertz; Hz: Hertz; HPLC: High Performance Liquid Chromatography; LC-MS: Liquid Chromatography Mass Chromatography Spectrum; s: second(s); min: minute(s); h: hour(s); mg: milligram(s); g: gram(s); Ml: microliter(s); mL: millilitre(s); mmol: millimole(s); nm: nanometer(s) μM: micromolar; M: molarity or molar concentration; Rt: retention time in minutes; MW: microwave; Boc: tert-butyloxycarbonyl protecting group; DMF: dimethylformamide; DMSO: dimethylsulfoxide; MeOH: methanol; EtOH: ethanol; EtOAc: ethyl acetate; DCM: dichloromethane; MeCN or ACN: acetonitrile; PE: Petroleum Ether; TFA: trifluoroacetic acid; DEE: diethyl ether; (g): gas; eq.: equivalent(s); RT: room temperature; DIPEA: N,N-diisopropylethylamine; DIAD: diisopropyl azodicarboxylate; sat.aq.: saturated aqueous solution; sat. sol. or s.s.: saturated solution; aq: aqueous; anh: anhydrous; TEA: triethylamine; THF: tetrahydrofuran; IPA: isopropylamine; pTSA: para toluene sulfonic acid; TBDMS: tert-butyldimethylsilyl; LiHMDS: Lithium bis(trimethylsilyl)amide; TBTU: 2-(1H-Benzotriazole-1-yl)-1,1,3,3-tetramethylaminium tetrafluoroborate; y: yield; FC: flash chromatography.

Except where indicated otherwise, all temperatures are expressed in ° C. (degrees centigrade) or K (Kelvin).

The $^1$H-NMR spectra were acquired with an Avance II 300 MHz Bruker spectrometer. The chemical shifts are expressed in parts per million (ppm, δ units). The coupling constants are expressed in Hertz (Hz) and the splitting patterns are described as s (singlet), bs (broad signal), d (doublet), t (triplet), q (quartet), quint (quintet), m (multiplet).

The LC-MS analyses were performed by means of an UPLC Acquity Waters System equipped with the SQD spectrometer, single quadrupole mass detector, and a TUV detector, using column 1: ACQUITY UPLC BEH SHIELD, $RP_{18}$ (2.1×50 mm, id=1.7 μm); column2: ACQUITY UPLC HSS T3, $RP_{18}$ (2.1×50 mm, id=1.8 μm) and column3: ACQUITY UPLC BEH SHIELD, $RP_{18}$ (2.1×100 mm, id=1.7 μm). Column temperature 40° C. Sample temperature 25° C. Phase A was composed by water (HiPerSolv Chromanorm Water VWR for HPLC-MS)+0.05% Trifluoroacetic Acid; Phase B by $CH_3CN$ (HiPerSolv Chromanorm Acetonitrile SuperGradient VWR, suitable for UPLC/UHPLC instruments)+0,05% Trifluoroacetic Acid; flow rate: 0.5 mL/min; UV detection (DIODE array) 200 nm; ESI+ and ESI– detection in the 100-1000 m/z range.

Method 1: column 1, run time: 3 minutes, run gradient: 5% B to 100% B in 2.80 min+100% B for 0.2 min, equilibration time: 0.8 min, ionization mode: ESI$^+$.

Method 2: column 2, run time: 4 minutes, run gradient: 0% B to 45% B in 3.5 min+45% B to 100% B in 0.05 min+100% B for 0.45 min, equilibration time: 0.8 min, ionization mode: ESI+.

Method 3: column 3, run time: 6 minutes, run gradient: 5% B to 100% B in 5 min+100% B for 1 min, equilibration time: 2 min.

Method 4: column 3, run time: 6 minutes, run gradient: 5% B to 50% B in 5 min+50% B to 100% B in 0.2 min 100% B for 0.8 min, equilibration time: 2 min, ionization mode: ESI+.

Method 5: column 1, run time: 3 minutes, run gradient: 5% B to 100% B in 2.80 min+100% B for 0.2 min, equilibration time: 0.8 min, ionization mode: ESI+.

Method 6: column 2, run time: 4 minutes. run gradient: 0% B to 45% B in 3.5 min+45% B to 100% B in 0.05 min+100% B for 0.45 min. Equilibration time: 0.8 min, ionization mode: ESI+.

Method 7: column 3, run time: 6 minutes, run gradient: 5% B to 100% B in 5 min+100% B for 1 min, equilibration time: 2 min, ionization mode: ESI+.

Method 8: column 3, run time: 6 minutes, run gradient: 5% B to 50% B in 5 min+50% B to 100% B in 0.2 min 100% B for 0.8 min, Equilibration time: 2 min, ionization mode: ESI+.

Method 9: column 1. run time: 4 minutes, column 1, run time: 4 minutes, run gradient:5% B to 100% B in 3.00 min+100% B for 1 min, equilibration time: 0.8 min, ionization mode: ESI+.

Method 10: column 1. run time: 4 minutes, run gradient: 5% B to 100% B in 3.00 min+100% B for 1 min, equilibration time: 0.8 min, Ionization Mode: ESI−.

Method 11: column 1, run time: 3 minutes, run gradient: 40% B to 100% B in 2.80 min+100% B for 0.2 min, equilibration time: 0.8 min. Ionization Mode: ESI+.

Method 12: column 3, run time: 6 minutes, run gradient: 25% B to 70% B in 5 min+100% B for 1 min, equilibration time: 2 min, Flow: 0.5 mL/min, ionization mode: ESI+.

Method 13: column 1, run time: 4 minutes, run gradient: 10% B to 60% B in 3.00 min+100% B for 1.00 min, equilibration time: 0.8 min, ionization mode: ESI+.

Method 14: column 1, run time: 3 minutes, run gradient: 30% B to 70% B in 2.80 min+100% B for 0.2 min, equilibration time: 0.8 min, ionization mode: ESI+.

Synthesis

According to a further aspect of the invention there is provided a process for the preparation of compounds of formula (I), (Ia) or (Ib) or salts thereof. The following schemes are examples of synthetic schemes that may be used to synthesise the compounds of the invention. In the following schemes reactive groups can be protected with protecting groups and deprotected according to well established techniques. In the following schemes unless otherwise indicated $R_1$, $R_2$, $R_4$, A, X, Y, Y', Y'', Y''', Cy, Ra, Rb, Rc, Rd are as defined herein above in formula (I), (Ia) or (Ib).

It will be understood by those skilled in the art that certain compounds of the invention can be converted into other compounds of the invention according to standard chemical methods.

Compounds of the invention may be prepared according to the general routes indicated in the following Scheme 1 and Scheme 2:

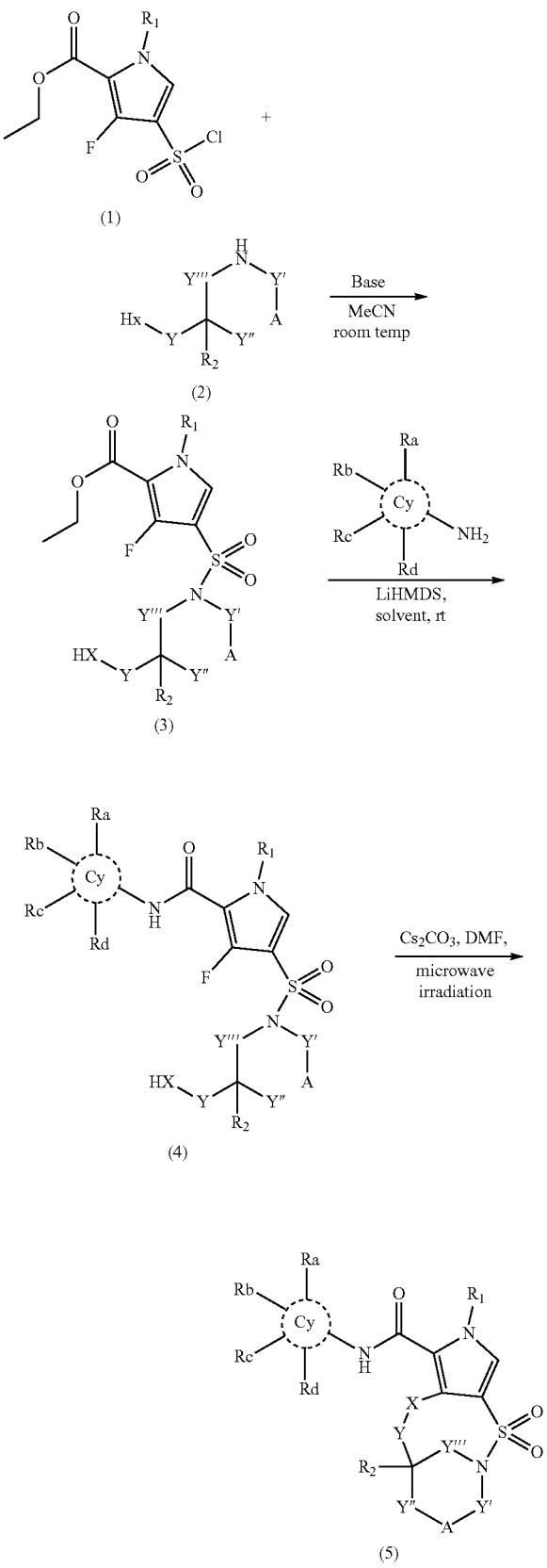

Scheme 2

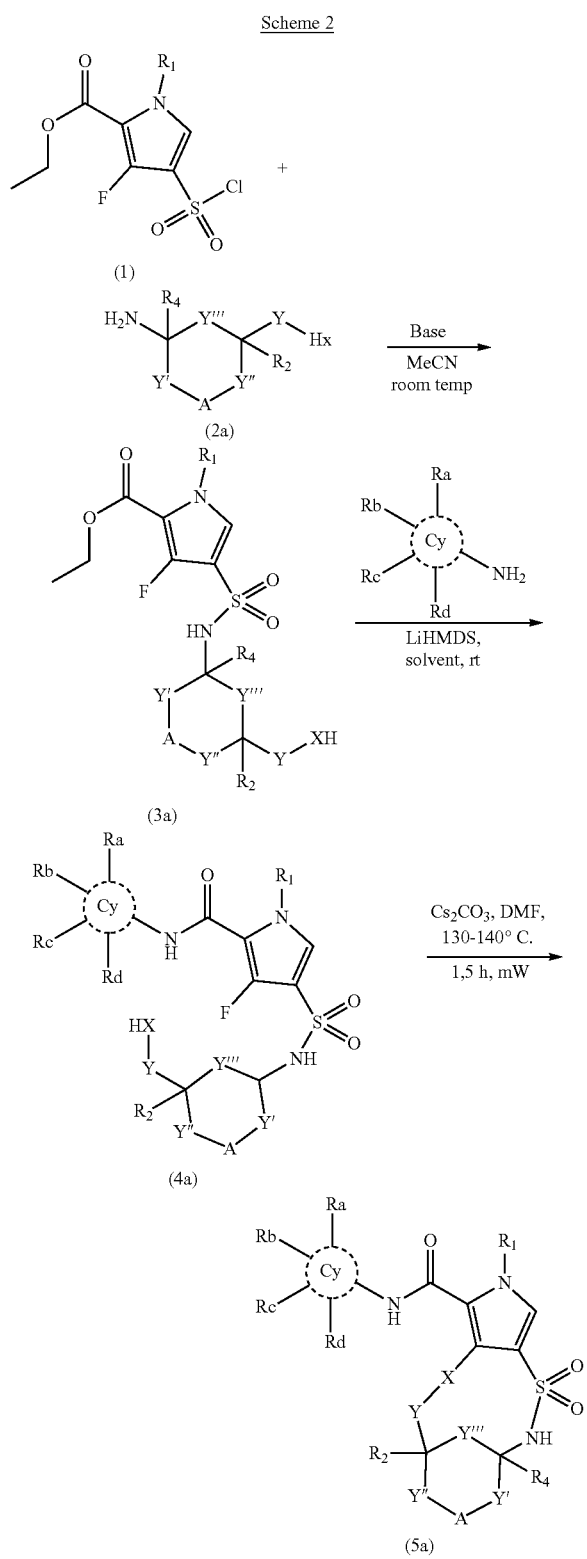

Ethyl 4-(chlorosulfonyl)-3-fluoro-1-methyl-1H-pyrrole-2-carboxylate, indicated as compound (1) in Scheme 1 and Scheme 2, was prepared according to the procedure described in WO2017/001655. According to Scheme 1, a cyclic amine derivative bearing a nucleophilic —XH substituent is reacted with the compound (1) in the presence of the appropriate base, such as trimethylamine or N,N-diisopropylethylamine, to give the corresponding sulphonamide product (3). Reaction of (3) with an arylamine in the presence of a strong non-nucleophilic base such as lithium bis(trimethylsilyl)amide LiHMDS in a solvent like tetrahydrofuran, converts the ethyl carboxylate into an arylamide derivative (4). A subsequent cyclization step through intramolecular nucleophilic attack of the XH on the fluorine gives the tricyclic core of compound (5). The synthetic pathway outlined in Scheme 2 is very similar to the one in Scheme (1), but uses a primary amine of structure (2a). Depending on the specific nature of A in compounds (5) or (5a), the product can be further elaborated through protection, deprotection or further functionalization steps. In particular, when A is a nitrogen derivative it can be protected as the N-Boc derivative. The Boc can be removed by acidic treatment and the resulting NH can be further converted for example into a carbamate, urea, sulphonamide, sulphonyl urea derivative or can be alkylated through, for example, reductive amination chemistry.

Where not otherwise indicated, starting materials and/or intermediates were obtained from commercial sources or can be obtained through synthetic procedures known in the chemistry literature. The indication of the commercial source of certain compounds in the description of the experimental procedure, when provided, is only for easy reference to skilled chemist and should not be interpreted as the indication to use only that particular commercial compound.

In the following paragraphs, the Descriptions 1 to 102 illustrate the preparation of intermediates used to make compounds of formula (I), (Ia) or (Ib) and salts thereof. The Descriptions 103 to 118 and the Examples illustrate the preparation of the compounds of the invention and salts thereof.

Where the compounds have more than one chiral center, it is understood that they might exist as mixtures of diastereoisomers or as single isomers. Both racemic and chiral compounds are within the scope of the present invention. The indicated procedures are provided merely for assistance to the skilled chemist. The starting material may not necessarily have been prepared from the batch of the Description or the Example referred to.

Synthesis of Amine Derivatives of General Formula (2) as Indicated in Scheme 1 or of General Formula (2a) as Indicated in Scheme 2

Amine derivatives (2) of Scheme 1 and (2a) of Scheme 2 were prepared according to the synthetic strategies outlined in Schemes 3-11. The procedures in the schemes can be used for the synthesis of the compounds indicated below and can be used as well for the synthesis of the compounds as single diastereoisomers and/or enantiomers by choosing the appropriate starting materials.

Synthesis of cis-(2-aminocyclopentyl)methanol (D2)

Scheme 3

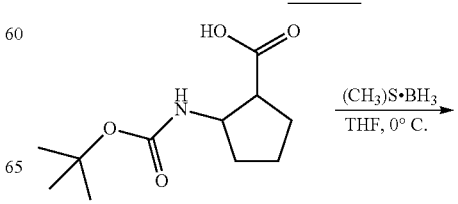

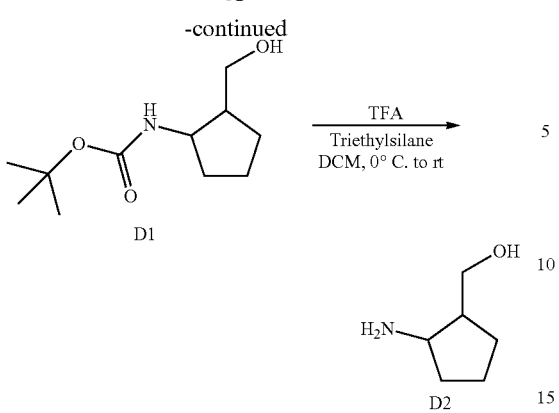

Scheme 3 refers to the synthesis of D2 and applies also to the synthesis of D4 and D6. Synthetic steps are described below.

Description 1: Tert-Butyl cis-(2-(hydroxymethyl)cyclopentyl)carbamate (D1)

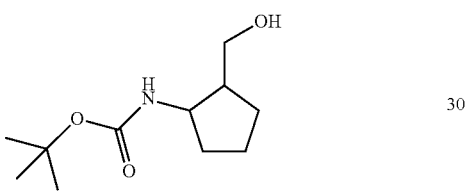

To a solution of cis-2-Boc-amino-cyclopentanecarboxylic acid (200 mg, 0.87 mmol) in dry THF (4 mL), borane dimethylsulfide complex (0.4 mL, 4.33 mmol) was added at 0° C. After 10 min mixture was allowed to warm at room temperature. After 1 h a further aliquot of borane dimethylsulfide (0.4 mL, 4.33 mmol) was added and after 2.5 h conversion was completed. Mixture was quenched by slow addition of methanol at 0° C., and then solvent was removed under reduced pressure to afford D1 as a white solid (195 mg, y>100%) that was used without purification. Method 1: Rt=1.54 min, m/z=216 (M+H)$^+$.

Description 2: cis-(2-aminocyclopentyl)methanol (D2)

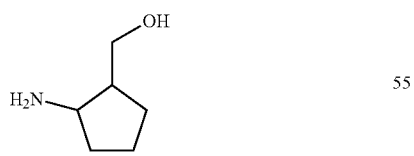

To a stirred solution of D1 (195 mg, 0.9 mmol) in DCM (5 mL), trifluoroacetic acid (0.350 mL, 4.6 mmol) and triethylsilane (0.160 ml) were added at 0° C. After 5 min, the reaction mixture was allowed to warm at room temperature. After 2 h additional aliquots of trifluoroacetic acid (0.150 mL, 1.96 mmol) and triethylsilane (0.080 mL) were added. Reaction went to completion after 2.5 h and mixture evaporated under reduced pressure to afford D2 trifluoracetate as a white solid (429 mg, y>100%) that was used in next step without purification. m/z=116 (M+H)$^+$.

Description 3: Tert-Butyl ((1R,2R)-2-(hydroxymethyl)cyclopentyl)carbamate (D3)

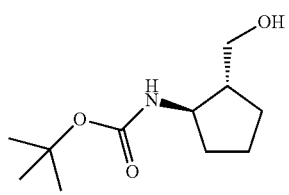

To a stirred solution of (1R,2R)-2-((tert-Butoxycarbonyl)amino)cyclopentanecarboxylic acid (113 mg, 0.49 mmol) in THF (2 mL), borane dimethylsulfide complex 2M in THF (1.2 mL, 2.4 mmol) was added at 0° C. After 5 min mixture was allowed to warm at rt. After 1 h mixture was quenched with slow addition of MeOH at 0° C., diluted with DCM and washed with HCl 1N and water. Organic layer was dried over Na$_2$SO$_4$, filtered and solvent removed under reduced pressure to afford D3 as a white solid (101 mg). Method 1: Rt=1.50 min, m/z=216 (M+H)$^+$.

Description 4: ((1R,2R)-2-aminocyclopentyl)methanol (D4)

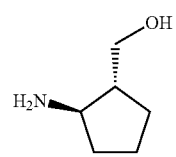

To a stirred solution of D3 (101 mg, 0.469 mmol) in DCM (3 mL), trifluoroacetic acid (0.180 mL, 2.3457 mmol) and triethylsilane (0.085 mL, 0.532 mmol) were added at 0° C. After 5 min the reaction mixture was allowed to warm up to room temperature. After 3.5 h the reaction mixture was quenched with NaOH 5M (1.5 mL) and stirred for 5 minutes. Mixture was evaporated under reduced pressure, then suspended in acetonitrile and filtered over Na$_2$SO$_4$ pad to remove part of salts and water to afford D4 as a white sticky solid (746 mg) that was used in the next step without purification. Method 1: Rt=0.36 min, m/z=116 (M+H)$^+$.

Description 5: Tert-Butyl ((1S,2S)-2-(hydroxymethyl)cyclopentyl)carbamate (D5)

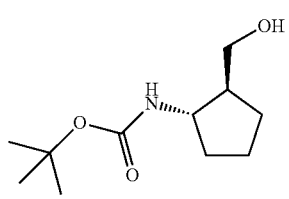

Prepared similarly as described for compound D3 starting from (1S,2S)-2-((tert-butoxycarbonyl)amino)cyclopentanecarboxylic acid to give D5. Method 1: Rt=1.50 min, m/z=216 (M+H)$^+$.

Description 6: ((1S,2S)-2-aminocyclopentyl)methanol (D6)

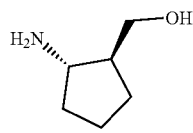

Prepared from D5, following same procedure as described for compound D4. Method 1: Rt=0.36 min, m/z=116 (M+H)+.

Synthesis of Tert-Butyl cis-3-amino-4-(hydroxymethyl)pyrrolidine-1-carboxylate (D10)

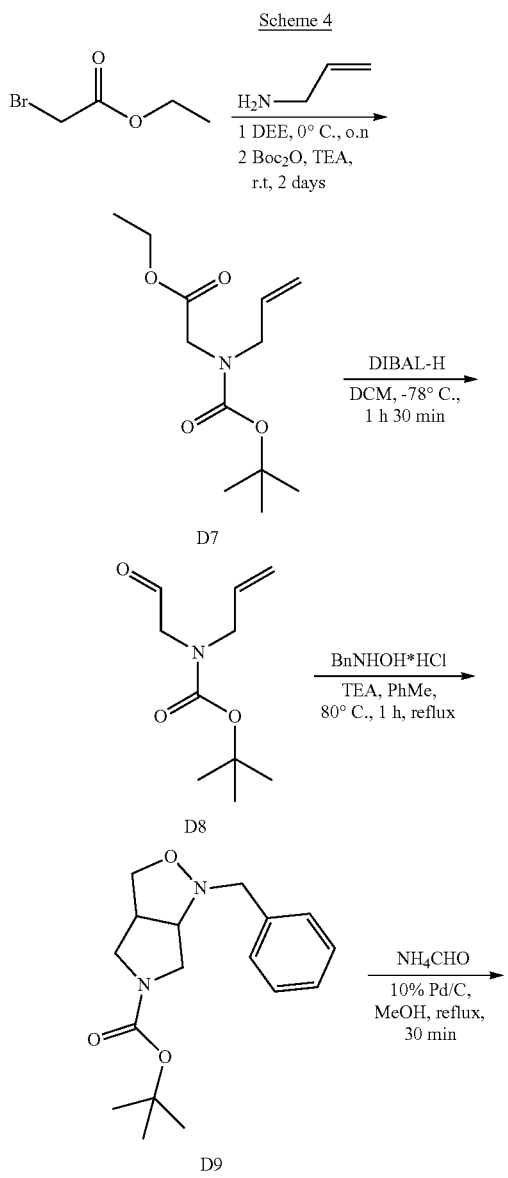

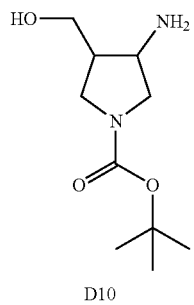

Scheme 4 refers to the synthesis of tert-butyl cis-3-amino-4-(hydroxymethyl)pyrrolidine-1-carboxylate D10. Synthetic steps are described below.

Description 7: Ethyl N-allyl-N-(tert-butoxycarbonyl)glycinate (D7)

The compound was prepared according to US2006148722. A solution of prop-2-en-1-amine (2.92 mL, 38.92 mmol) in diethylether (17 mL) was cooled at 0° C. in a dry ice/acetone bath in a sealed 20 mL vial. Ethyl 2-bromoacetate (3.74 mL, 19.46 mmol) was added in 200-300 uL portions over 10 min. A white precipitate was formed. After one night at room temperature, the mixture was filtered and the filtrate was evaporated at reduced pressure (200 mmbar). The residue (6 g) was dissolved in DCM (200 mL), treated with triethylamine (2.7 mL, 19.46 mmol) and cooled to 0° C. with ice bath. The resulting solution was treated with di-tert-butyl dicarbonate (4.25 g, 19.46 mmol) and stirred for 2 days at room temperature. Solvent was removed under reduced pressure and partitioned between water and EtOAc. The organic layer was washed with brine (×2) and 5% citric acid acq. solution, dried over $Na_2SO_4$ (anh.), filtered and evaporated. The residue (yellowish mobile oil) was purified by flash chromatography (direct phase, eluent 95/5 PE/DCM), giving about 5 g of ethyl N-allyl-N-(tert-butoxycarbonyl)glycinate (D7) as colourless oil. $^1H$ NMR (300 MHz, $CDCl_3$) δ ppm 1.04-1.29 (m, 3H) 1.29-1.50 (m, 9H) 3.54-3.99 (m, 4H) 4.12 (q, J=7.09 Hz, 2H) 4.92-5.19 (m, 2H) 5.45-6.01 (m, 1H); Method 1, Rt=2.06 min. m/z=143.07 (M+H)+.

Description 8: tert-Butyl allyl(2-oxoethyl)carbamate (D8)

The compound was prepared according to procedure described in WO2010/016005. A solution of D7 (1 g, 4.11 mmol) in DCM (11 mL) was cooled to −78° C. with acetone/dry ice bath under nitrogen atmosphere. 1M DIBAL-H in DCM (8.22 mL, 8.22 mmol) was added over 1 hr with a syringe pump. The reaction mixture was stirred at −78° C. for 30 min. The reaction was stopped by addition of $NH_4Cl$ sat. solution (1.2 mL) and 2N HCl (4 mL) in a single portion, then the reaction was magnetically stirred giving a white mixture. The reaction mixture was partitioned between water and DCM, treated with potassium sodium tartrate tetrahydrate (Rochelle's salt) until saturation, magnetically stirred for 15 min then further extracted with DCM. The combined organic extracts were dried over $MgSO_4$ (anh.), filtered and finally evaporated giving D8 (0.8 g, 4.015 mmol) as a white sticky oil. Method 1, Rt=1.58 min. m/z=200 (M+H)+.

Description 9: Cis-Tert-Butyl 1-benzyltetrahydro-1H-pyrrolo[3,4-c]isoxazole-5(3H)-carboxylate (D9)

A solution of N-(phenylmethyl)hydroxylamine hydrochloride (Fluorochem, cat no 091512) (10.5 g, 65.79 mmol) in water (54 mL) was treated with NaHCO$_3$ (10.5 g, 124.99 mmol) and extracted with DCM (100 mL×3). The water phase was further basified with 2N NaOH until pH=10 (by paper) and extracted with EtOAc. The combined organic extracts were dried over Na$_2$SO$_4$ (anh.), filtered and evaporated giving N-benzylhydroxylamine (8.10 g, 65.79 mmol, yield quantitative) as a low melting white solid. Method 1; Rt: 0.66 m/z: 124.00 (M+H)$^+$.

D8 (0.8 g, 4.02 mmol) and N-benzylhydroxylamine, 0.99 g, 8.03 mmol) were suspended in toluene (32 mL) and triethylamine (0.61 mL, 4.42 mmol). The mixture was heated at 80° C. for about 1 hr and at room temperature overnight. The reaction was poured into a separating funnel, diluted with EtOAc, washed with NaHCO$_3$ (sat. solution), 5% citric acid acq. solution and brine then evaporated. The crude residue (1 g) was purified by flash chromatography over silica gel (eluent: EtOAc/PE) to obtain D9 (0.6 g, 1.97 mmol) as a colorless oil. Method 1, Rt=1.94 min. m/z=305.29 (M+H)$^+$.

Description 10: Tert-Butyl cis-3-amino-4-(hydroxymethyl)pyrrolidine-1-carboxylate (D10)

A solution of D9 (0.55 g, 1.81 mmol) in methanol (30 mL) was treated with a single portion of ammonium formate (0.57 mg, 9.03 mmol) and 10% Pd/C (50 mg). The mixture was refluxed for 30 min, then cooled to room temperature and filtered on celite, washing with methanol. Solvent was removed in vacuo, affording D10 tert-butyl cis-3-amino-4-(hydroxymethyl)pyrrolidine-1-carboxylate (0.4 g, 1.85 mmol) as colourless oil. Method 1, Rt=0.86 min. m/z=217.26 (M+H)$^+$. $^1$H NMR (300 MHz, DMSO-d6+TFA) δ ppm 1.51 (s, 9H) 2.65-2.73 (m, 1H) 3.19-3.39 (m, 1H) 3.43-3.79 (m, 5H) 3.82-4.01 (m, 1H) 8.03 (brs, 3H).

Synthesis of Tert-Butyl (2S,3R)-3-amino-2-(hydroxymethyl)pyrrolidine-1-carboxylate (D11)

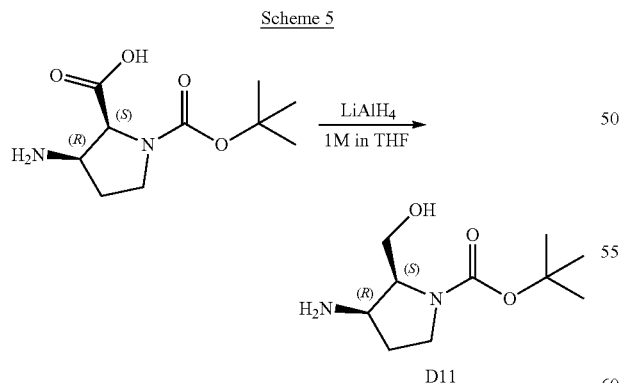

Scheme 5

Description 11: Tert-Butyl (2S,3R)-3-amino-2-(hydroxymethyl)pyrrolidine-1-carboxylate (D11)

2-Methyl 1-(2-methyl-2-propanyl) (2S,3R)-3-amino-1,2-pyrrolidinedicarboxylate hydrochloride (Fluorochem, cat no 515165) (1:1) (200 mg, 0.712 mmol, 1 eq) was suspended in dry THF (5.5 mL), the mixture was cooled to 0° C., 1M solution of lithium aluminium hydride in THF (3 mL, 3 mmol, 4.2 eq) was added in 10 min and then reaction mixture was stirred at the same temperature. Reaction was quenched after 1 h. Saturated Rochelle salt solution (1.5 mL) was added to reaction mixture at 0° C., it was allowed to warm up to rt, it was filtered to remove salts. Then, DCM was added, organic layer was washed once with brine, dried over sodium sulfate, filtered and solvent was removed under reduced pressure affording D11 a colourless oil (134 mg). Method 4: Rt=1.14 min, MH+=217 m/z (M+H)$^+$. Stereochemistry cis, single enantiomer.

Synthesis of Cis-Ethyl 4-amino-3-(hydroxymethyl)-3-methylpyrrolidine-1-carboxylate (D15)

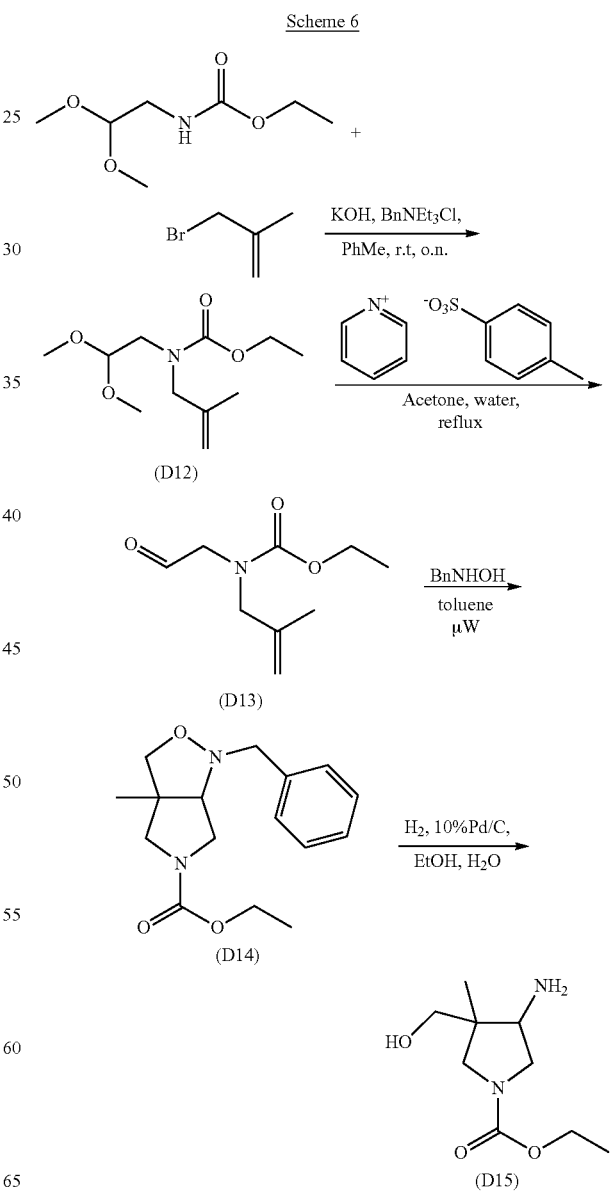

Scheme 6

Scheme 6 refers to the synthesis of cis-ethyl 4-amino-3-(hydroxymethyl)-3-methylpyrrolidine-1-carboxylate (D15) Synthetic steps are described below.

Description 12: Ethyl (2,2-dimethoxyethyl)(2-methylallyl)carbamate (D12)

Under nitrogen atmosphere, a solution of ethyl 2,2-dimethoxyethylcarbamate (Fluorochem, cat no 334125) (15 g, 84.65 mmol) in toluene (75 mL) was treated with a single portion of potassium hydroxide (24.19 g, 431.1 mmol) and N-benzyl-N,N-diethylethanaminium chloride (437.1 mg, 1.92 mmol). The mixture was stirred at room temperature for 5 min, then a solution of 3-bromo-2-methylprop-1-ene (067665 Fluorochem) (10.84 mL, 104.34 mmol) in toluene (25 mL) was added dropwise and the reaction mixture was additionally stirred overnight at room temperature. The resulting milky suspension was treated with water (50 mL) dropwise, over 10 min, then transferred into a separating funnel and extracted with toluene. The combined organic extracts were washed with brine and 5% citric acid acq. solution, dried over $Na_2SO_4$ (anh.), filtered and finally evaporated giving D12 as yellow mobile oil. $^1$H NMR (300 MHz, DMSO-$d_6$) δ ppm 1.07-1.28 (m, 3H) 1.62 (s, 3H) 3.19 (br s, 2H) 3.28 (s, 6H) 3.77-3.88 (m, 2H) 3.97-4.16 (m, 2H) 4.41-4.55 (m, 1H) 4.71 (br s, 1H) 4.77-4.92 (m, 1H). Method 1; Rt: 1.64. m/z: 232.25 $(M+H)^+$.

Description 13: Ethyl (2-methylallyl)(2-oxoethyl)carbamate (D13)

A solution of D12 (5 g, 21.62 mmol) in acetone (50.8 mL) and water (38.1 mL) was refluxed for 12 hrs in the presence of pyridine 4-methylbenzenesulfonate (5.2 g, 20.67 mmol). Acetone was removed in vacuo and the reaction solution (water) was extracted with DCM, washed with brine and 5% $NaHCO_3$ aqueous solution, dried over $Na_2SO_4$, filtered and evaporated, giving D13 (3 g, 16.2 mmol, y: 75%). $^1$H NMR (300 MHz, DMSO-$d_6$) δ ppm 1.11-1.23 (m, 3H) 1.56-1.71 (m, 3H) 3.81 (s, 2H) 3.91-4.11 (m, 4H) 4.78 (br d, J=4.03 Hz, 1H) 4.85 (s, 1H) 9.48 (d, J=4.77 Hz, 1H). Method 1; Rt: 1.44 min. m/z: 186.17 $(M+H)^+$.

Description 14: Cis-Ethyl 1-benzyl-3a-methyltetrahydro-1H-pyrrolo[3,4-c]isoxazole-5(3H)-carboxylate (D14)

A solution of N-(phenylmethyl)hydroxylamine hydrochloride (Fluorochem, cat no 091512) (10.5 g, 65.79 mmol) in water (54 mL) was treated with $NaHCO_3$ (10.5 g, 124.99 mmol) and extracted with DCM (100 mL×3). The water phase was further basified with 2N NaOH until pH=10 (by paper) and extracted with EtOAc. The combined organic extracts were dried over $Na_2SO_4$ (anh.), filtered and evaporated giving N-benzylhydroxylamine (8.10 g, 65.79 mmol, yield quantitative) as a low melting white solid. Method 1; Rt: 0.66 m/z: 124.00 $(M+H)^+$.

D13 (3 g, 16.2 mmol) was dissolved in toluene (25 mL) and charged into a round bottom flask equipped with Dean-Stark apparatus and a rubber septa. A toluene (12 mL) solution of N-benzylhydroxylamine (2.1 g, 17.05 mmol), as previously obtained, was added under reflux, with a syringe over 1 h 30 min. The reaction solution was refluxed for 1 h, then it was cooled to room temperature. Solvent was removed in vacuo and the residue purified by FC (direct phase, eluent EtOAc/PE). The fractions containing the pure product were combined giving a yellow oil (3 g). All the fractions containing the product and impurities were collected and evaporated, dissolved in PhMe (30 mL) and extracted with 10% HCl (30×4). The acq. layer was washed with PhMe (10 mL), basified with solid $NaHCO_3$ giving a milky suspension and further basified with 2N NaOH (pH=10 by paper) then extracted with PhMe (30 mL×4). The combined organic extracts were washed with brine (30 mL), dried over $Na_2SO_4$ (anh.), filtered and finally evaporated giving a second crop of the title product (0.35 g). The two residues were combined giving D14 (3.35 g, 11.54 mmol, y: 71%) as a colourless oil. $^1$H NMR (300 MHz, DMSO-$d_6$) δ ppm 1.17 (t, J=7.06 Hz, 3H) 1.27 (s, 3H) 3.07 (br d, J=1.65 Hz, 2H) 3.35 (br s, 2H) 3.45 (d, J=10.60 Hz, 1H) 3.58-3.68 (m, 1H) 3.69-3.80 (m, 1H) 3.86-4.09 (m, 4H) 7.14-7.41 (m, 5H). Method 1; Rt: 1.76 min. m/z: 291.23 $(M+H)^+$.

Description 15: Cis-Ethyl 4-amino-3-(hydroxymethyl)-3-methylpyrrolidine-1-carboxylate (D15)

D14 ethyl 3a-methyl-1-(phenylmethyl)-3,4,6,6a-tetrahydropyrrolo[3,4-c][1,2]oxazole-5-carboxylate (2.75 g, 9.47 mmol) was dissolved in ethanol (301 mL) and water (48 mL), then hydrogenated with a continuous flow hydrogenator (H-Cube (ThalesNano) equipped with 10% Pd/C cartridge (flow 0.7 mL/min, pressure $P_{H2}$=10 barr, T=85° C.) in three runs. Solvent was removed in vacuo, giving D15 ethyl 4-azanyl-3-(hydroxymethyl)-3-methyl-pyrrolidine-1-carboxylate (1.915 g, 9.47 mmol, quantitative yield) as colourless oil. $^1$H NMR (300 MHz, DMSO-$d_6$) δ ppm 0.94 (s, 3H) 1.17 (t, J=7.06 Hz, 3H) 1.55 (br s, 2H) 2.88 (dd, J=10.50, 6.10 Hz, 1H) 2.95-3.10 (m, 2H) 3.25-3.43 (m, 4H) 3.43-3.55 (m, 1H) 4.00 (q, J=7.06 Hz, 2H). Method 1; Rt: 0.67 min. m/z: 203.20 $(M+H)^+$.

Synthesis of Ethyl (3R,4R)-3-amino-4-(hydroxymethyl)pyrrolidine-1-carboxylate Hydrochloride (D17)

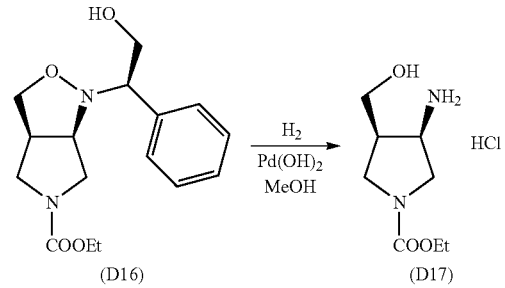

Scheme 7

Description 16: Ethyl (3aR,6aR)-1-((R)-2-hydroxy-1-phenylethyl)tetrahydro-1H-pyrrolo[3,4-c]isoxazole-5(3H)-carboxylate (D16)

Prepared following the procedure reported in J. Org. Chem. 2003, 68, 8739-8741, starting from ethyl allyl(2-oxoethyl)carbamate (prepared as reported in US2018/0222918) and (R)-2-(hydroxyamino)-2-phenylethan-1-ol (prepared as reported in WO2010/016005). $^1$H NMR (300 MHz, Chloroform-d) δ ppm 1.15 (t, J=7.11 Hz, 3H) 2.87 (dd, J=8.89, 4.40 Hz, 1H) 3.06-3.56 (m, 5H) 3.57-3.75 (m, 3H) 3.75-3.83 (m, 1H) 3.94-4.11 (m, 3H) 4.27 (brt, J=8.12 Hz, 1H) 7.22-7.36 (m, 5H). Method 3; Rt=2.18 min. m/z=307 (M+H)+.

Description 17: Ethyl (3R,4R)-3-amino-4-(hydroxymethyl)pyrrolidine-1-carboxylate Hydrochloride (D17)

D16 (2.9 g, 9.47 mmol) was dissolved in methanol (150 mL, 3.703 mol), palladium(II) hydroxide (3.06 g, 4.35 mmol) was added and the suspension was hydrogenated at 1 atm at room temperature for 16 hrs. Acetic acid (15.16 mL, 265.05 mmol) was added and the reaction stirred for 15 min then filtered over paper, washing with methanol (approx 70 mL). The solution was evaporated (30° C.), the residue treated with 1M HCl (20 mL) then further evaporated. The residue was dissolved in water (10 mL), pH was adjusted with 1M HCl (3 mL), washed with DCM and the aqueous layer was further evaporated and co-evaporated with toluene, in order to remove acetic acid traces, giving title compound D17 (1.6 g, 7.12 mmol) as off-white powder (Yield=75%). $^1$H NMR (300 MHz, DMSO-d6+TFA) δ ppm 1.18 (t, J=7.06 Hz, 3H), 2.54-2.66 (m, 1H), 3.17-3.66 (m, 6H), 3.72-3.88 (m, 1H), 3.93-4.14 (m, 2H), 8.10 (br s, 3H). Method 13; Rt=1.02 min; m/z=189 (M+H)+.

Synthesis of cis-1-(tert-butyl) 3-ethyl 4-aminopiperidine-1,3-dicarboxylate (D20) and trans-1-(tert-butyl) 3-ethyl 4-aminopiperidine-1,3-dicarboxylate (D22)

Scheme 8

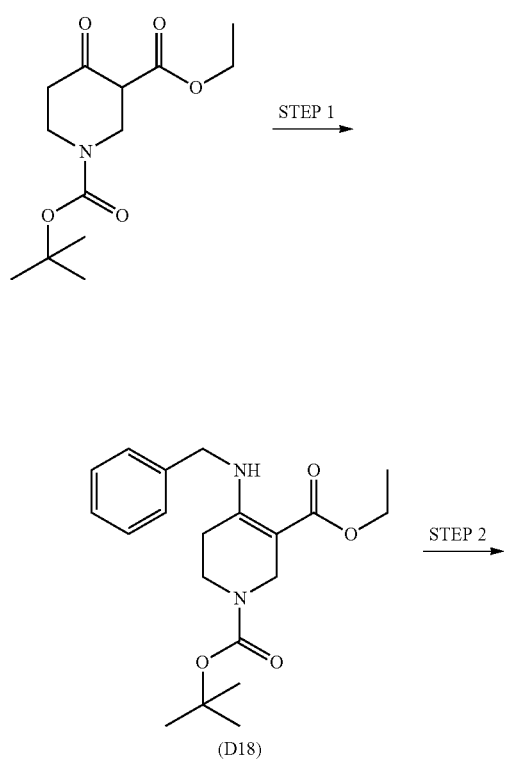

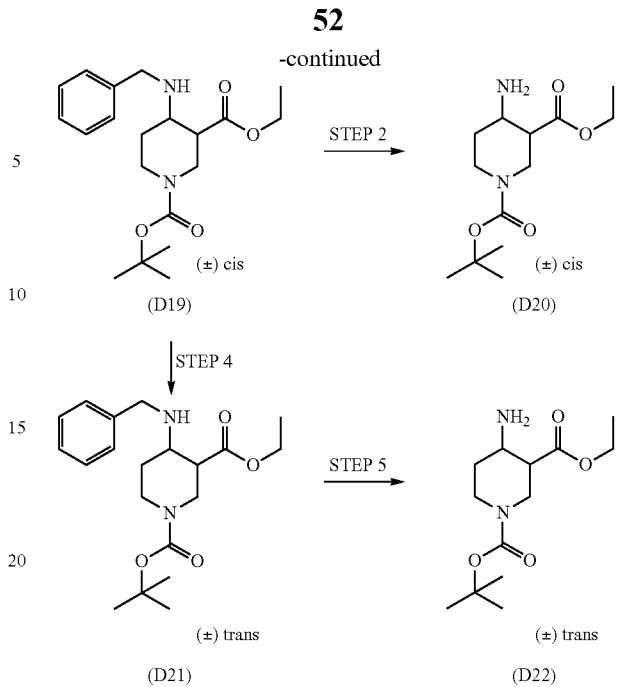

STEP 1) BnNH$_2$, toluene, 130° C., 16 hrs; STEP 2) NaBH(OAc)$_3$, AcOH, MeCN, 0° C. to RT, 24 hrs; STEP 3) H$_2$, Pd/C (10%w), HCube®, EtOH, 10bar, 50° C.; STEP 4) $^t$BuOK, EtOH, 90° C., 2 hrs; STEP 4) H$_2$, Pd/C (10%w), HCube®, EtOH, 10bar, 50° C.

Scheme 8 refers to the synthesis of D20 and D22. Synthetic steps are described below.

Description 18: 1-(tert-butyl) 3-ethyl 4-(benzylamino)-5,6-dihydropyridine-1,3(2H)-dicarboxylate (D18)

A solution of N-Boc-3-carboethoxy-4-piperidone (2.0 g, 7.37 mmol) and benzylamine (0.9 mL, 8.24 mmol) in toluene (25 mL) was heated under reflux in a Dean Stark apparatus for 16 hrs, then cooled to RT and then evaporated to dryness to give a pale yellow oil (2.66 g) used without further purification. Method 1; Rt: 2.47 min. m/z: 361 (M+H)+.

Description 19: Cis-1-(tert-butyl) 3-ethyl 4-(benzylamino)piperidine-1,3-dicarboxylate (D19)

Sodium triacetoxyhydroboronhydride (7.0 g, 33.2 mmol) was added over 6 hrs (three equal portions each 2 hrs) to a solution of D18 (2.66 g, 7.38 mmol) in dry MeCN (30 mL) and acetic acid (2.5 mL) cooled to 0° C. After the third addition the suspension was stirred at RT for 16 hrs then diluted with EtOAc and slowly quenched with sat NaHCO$_3$. The two phases were separated and the organic phase concentrated and the organic phase washed with in sat Na$_2$CO$_3$, dried over Na$_2$SO$_4$ filtered and concentrated. Purification by FC (direct phase, eluent cyclohexane/EtOAc) afford D19 as a colourless oil (1.95 g, 60%). Method 1; Rt: 1.43 min. m/z: 363 (M+H)+.

Description 20: Cis 1-(tert-butyl) 3-ethyl 4-aminopiperidine-1,3-dicarboxylate (D20)

A solution of D19 (739 mg, 2.04 mmol) in EtOH (50 mL) was hydrogenated with a H-Cube continuous flow hydrogenator (flow 1 mL/min, pressure H$_2$=10 barr, T=50° C.). After complete conversion the solvent was removed under reduce pressure to afford D20 as a colourless oil (525 mg) that was used without further purification. Method 1; Rt: 1.11 min. m/z: 273 (M+H)$^+$.

Description 21: Trans-1-(tert-butyl) 3-ethyl 4-(benzylamino)piperidine-1,3-dicarboxylate (D21)

A solution of D19 (1.04 g, 2.87 mmol) in ethanol (28 mL) was treated with potassium tert-butoxide (64.33 mg, 0.570 mmol). The reaction mixture was stirred at 90° C. for two hours then quenched with AcOH (100 uL) and then concentrated. Crude was purified by reverse phase chromatography using H$_2$O/MeCN+0.1% TFA. Fractions containing the title product were combined, basified with NaHCO$_3$ (10 g) and extracted with AcOEt (200 ml). The organic layer was dried over Na$_2$SO$_4$ filtered and concentrated to afford D21 (541 mg) in 90% purity. Method 1; Rt: 1.48. m/z: 363 (M+H)$^+$.

Description 22: Trans-1-(tert-butyl) 3-ethyl 4-aminopiperidine-1,3-dicarboxylate (D22)

A solution of D21 (541 mg, 1.49 mmol) in EtOH (40 mL) was hydrogenated with a H-Cube continuous flow hydrogenator (flow 1 mL/min, pressure H$_2$=10 barr, T=50° C.). The reaction was followed by UPLC-MS and after complete conversion the solvent was removed under reduce pressure to afford D22 as a pale yellow oil (406 mg) in 90% purity. Method 1; Rt: 1.16 min. m/z: 273 (M+H)$^+$.

Synthesis of cis-1-(tert-butyl) 4-ethyl 3-aminopiperidine-1,4-dicarboxylate (D25) and trans-1-(tert-butyl) 4-ethyl 3-aminopiperidine-1,4-dicarboxylate (D27)

Scheme 9 refers to the synthesis of D25 and D27. Synthetic steps are described below.

Scheme 9

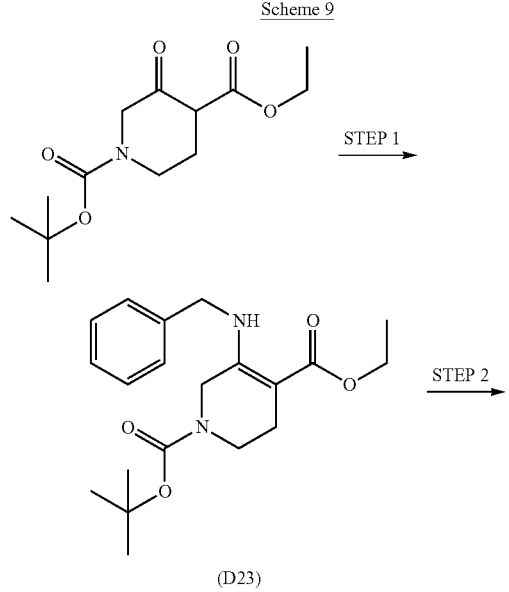

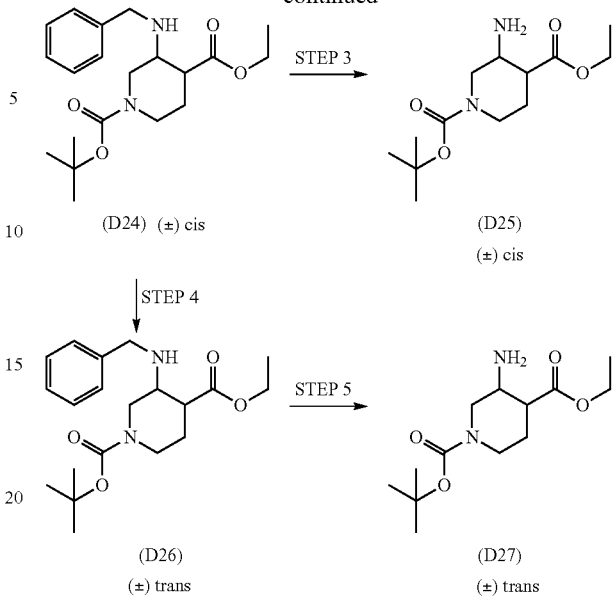

STEP 1) BnNH$_2$, toluene, 130° C., 48 hrs; STEP 2) NaBH$_4$, AcOH, MeCN, RT, 2 hrs; STEP 3) H$_2$, Pd/C (10%w), HCube®, EtOH, 10bar, 50° C.; STEP 4) $^t$BuOK, EtOH, 90° C., 2 hrs; STEP 5) H$_2$, Pd/C (10%w), HCube®, EtOH, 10bar, 50° C.

Description 23: 1-(tert-butyl) 4-ethyl 5-(benzylamino)-3,6-dihydropyridine-1,4(2H)-dicarboxylate (D23)

A solution of 1-tert-butyl 4-ethyl 3-oxopiperidine-1,4-dicarboxylate (1.3 g, 4.79 mmol) and benzylamine (0.63 mL, 5.75 mmol) in toluene (17 mL) was heated under reflux in a Dean Stark apparatus for 48 hrs, then cooled to RT and then evaporated to dryness to give a pale yellow oil (1.72 g) used without further purification. Method 1; Rt: 2.54 min. m/z: 361 (M+H)$^+$.

Description 24: Cis-1-(tert-butyl) 4-ethyl 3-(benzylamino)piperidine-1,4-dicarboxylate (D24)

Sodium tetrahydroborate (218 mg, 5.75 mmol) was added to a solution of D23 (1.73 g, 4.79 mmol) in dry MeCN (20 mL) and acetic acid (2.2 mL) cooled to 0° C. The resulting mixture was stirred at RT for 2 hrs then diluted with EtOAc and slowly quenched with sat NaHCO$_3$. The two phases were separated and the organic phase concentrated and the organic phase washed with in sat Na$_2$CO$_3$, dried over Na$_2$SO$_4$ filtered and concentrated. Purification by FC (direct phase, eluent cyclohexane/EtOAc) afford D24 as a colourless oil (1.17 g, 67%). $^1$H NMR (300 MHz, DMSO-d$_6$) δ ppm 1.14 (t, J=7.11 Hz, 3H) 1.40 (s, 9H) 1.48-1.63 (m, 1H) 1.63-1.90 (m, 2H) 2.62-2.92 (m, 3H) 2.93-3.07 (m, 1H) 3.52-3.70 (m, 1H) 3.73-3.96 (m, 2H) 3.98-4.16 (m, 3H) 7.11-7.44 (m, 5H). Method 1; Rt: 1.46 min. m/z: 363 (M+H)$^+$.

Description 25: Cis-1-(tert-butyl) 4-ethyl 3-aminopiperidine-1,4-dicarboxylate (D25)

A solution of D24 (742 mg, 2.05 mmol) in EtOH (50 mL) was hydrogenated with a H-Cube continuous flow hydrogenator (flow 1 mL/min, pressure H$_2$=10 barr, T=50° C.). After complete conversion the solvent was removed under reduce pressure to afford D25 as a colourless oil (559 mg) that was used without further purification. Method 1; Rt: 1.09 min. m/z: 273 (M+H)+.

Description 26: Trans-1-(tert-butyl) 4-ethyl 3-(benzylamino)piperidine-1,4-dicarboxylate (D26)

A solution of D24 (1.18 g, 3.26 mmol) in ethanol (32 mL) was treated with potassium tert-butoxide (73 mg, 0.65 mmol). The reaction mixture was stirred at 90° C. for two hours then quenched with AcOH (100 uL) and then concentrated. Crude was purified by reverse phase chromatography using H$_2$O/MeCN+0.1% TFA. Fractions containing the title product were combined, basified with NaHCO$_3$ (10 g) and extracted with AcOEt (200 ml). The organic layer was dried over Na$_2$SO$_4$ filtered and concentrated to afford D26 (500 mg). Method 1; Rt: 1.51 min. m/z: 363 (M+H)$^+$.

Description 27: Trans-1-(tert-butyl) 4-ethyl 3-aminopiperidine-1,4-dicarboxylate (D27)

D27 (96 mg, 0.353 mmol) was prepared as D25 starting from D26 (174 mg). Method 1; Rt: 1.45 min. m/z: 273 (M+H)$^+$.

Synthesis of Ethyl (2R,4R)-4-amino-2-(hydroxymethyl)pyrrolidine-1-carboxylate Hydrochloride (D31)

Scheme 10

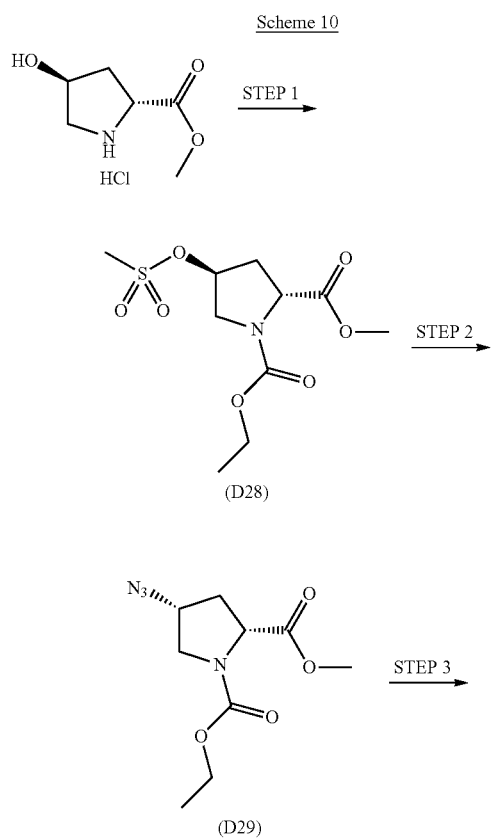

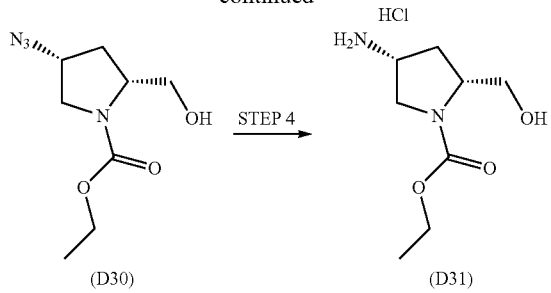

STEP 1) i) EtOCOCl, TEA, DCM 0° C., 30 min; ii) MsCl, TEA, 0° C. to RT 2 hrs; STEP 2) NaN$_3$, DMF, 70° C., 16 hrs; STEP 3) LiBH$_4$, THF, Et$_2$O, 0° C., 2 hrs; STEP 4) HCO$_2$H, Pd/C (10%w), EtOH, 30° C., 2 hrs Scheme 10 refers to the synthesis of D31. Synthetic steps are described below.

Description 28: 1-ethyl 2-methyl (2R,4S)-4-((methylsulfonyl)oxy)pyrrolidine-1,2-dicarboxylate (D28)

Ethyl chloroformate (0.15 mL, 1.51 mmol) was added drop wise to a 0° C. cooled solution of methyl (2R,4S)-4-hydroxypyrrolidine-2-carboxylate (Fluorochem, cat no 223289) (250 mg, 1.38 mmol) and triethylamine (0.48 mL, 3.44 mmol) in dry DCM (7 mL). The reaction was stirred at the same temperature for 30 min then a solution of methane sulfonylchloride (0.14 mL, 1.79 mmol) in dry DCM (3 mL) was slowly added. The reaction was allowed to slowly warm up and stirred at RT for further 2 hrs then was diluted with DCM and washed with 5% citric acid solution, water and brine. The organic layer was dried over Na$_2$SO$_4$ filtered and concentrated to afford the D28 (406 mg) as a pale yellow oil that was used without further purification. $^1$H NMR (300 MHz, DMSO-d$_6$) δ ppm $^1$H NMR (300 MHz, DMSO-d$_6$) δ ppm 1.06-1.26 (m, 3H) 2.09-2.36 (m, 1H) 2.52-2.65 (m, 1H) 3.27 (s, 3H) 3.61-3.76 (m, 5H) 3.92-4.15 (m, 2H) 4.24-4.50 (m, 1H) 5.29 (br s, 1H). Method 1; Rt: 1.32 min. m/z: 296 (M+H)$^+$.

Description 29: 1-ethyl 2-methyl (2R,4R)-4-azidopyrrolidine-1,2-dicarboxylate (D29)

Sodium azide (268.5 mg, 4.13 mmol) was added to a solution of D28 (403 mg, 1.32 mmol) in dry DMF (7 mL). The reaction mixture was stirred at 70° C. for 16 hrs then cooled to RT, diluted with EtOAc and water, and stirred for 15 min. The two phases were separated and the organic phase washed with water and brine, dried over Na$_2$SO$_4$ filtered and concentrated to afford D29 (281 mg, 84%) as a pale yellow foam that was used without further purification. $^1$H NMR (300 MHz, DMSO-d$_6$+TFA) δ ppm 1.10-1.23 (m, 3H) 1.95-2.11 (m, 1H) 2.56 (m, 1H) 3.28-3.35 (m, 1H) 3.64-3.72 (m, 5H) 3.97-4.08 (m, 2H) 4.38 (br s, 1H). Method 1; Rt: 1.45 min. m/z: 243.20 (M+H)$^+$.

Description 30: ethyl (2R,4R)-4-azido-2-(hydroxymethyl)pyrrolidine-1-carboxylate (D30)

A 2M solution of lithium borohydride in THF (1.3 M, 2.6 mmol) was added at 0° C., over 30 minutes to a solution of D29 (280 mg, 1.25 mmol) in Et$_2$O (7 mL) and dry THF (1.5 mL). The reaction was stirred at the same temperature for further 90 minutes then quenched with sat. NaHCO$_3$ solution and extracted with EtOAc. The organic phase was washed with brine, dried over Na$_2$SO$_4$ filtered and concentrated to afford D30 (214 mg) as a yellow oil that was used without further purification. $^1$H NMR (300 MHz, DMSO-d$_6$) δ ppm 1.18 (t, J=7.11 Hz, 3H) 1.82-2.12 (m, 1H) 2.12-2.36 (m, 1H) 2.19-2.31 (m, 1H) 3.14 (br d, J=10.64 Hz, 1H) 3.33-3.42 (m, 1H) 3.57-3.71 (m, 1H) 3.77 (tt, J=8.15, 3.91 Hz, 1H) 3.99-4.10 (m, 2H) 4.28-4.38 (m, 1H) 4.81 (br t, J=5.18 Hz, 1H). Rt: 1.25 min. m/z: 215.23 (M+H)$^+$.

Description 31: Ethyl (2R,4R)-4-amino-2-(hydroxymethyl)pyrrolidine-1-carboxylate Hydrochloride (D31)

In a closed vessel, Pd/C (10% weight, 30 mg) was added to solution of D30 (214 mg, 1.16 mmol) in degassed EtOH (9 mL). Then formic acid (0.6 mL, 11 mmol) was added and the reaction was stirred at 30° C. for 2 hrs. Then the reaction was filtered and filter was washed with EtOH several times. A solution of HCl in dioxane was added to the filtrate and D31 (200 mg) was obtained after solvent concentration as a colourless oil. Rt: 0.57 min. m/z: 189 (M+H)$^+$.

Synthesis of cis-3-amino-1-benzyl-4-(hydroxymethyl)pyrrolidin-2-one (D37)

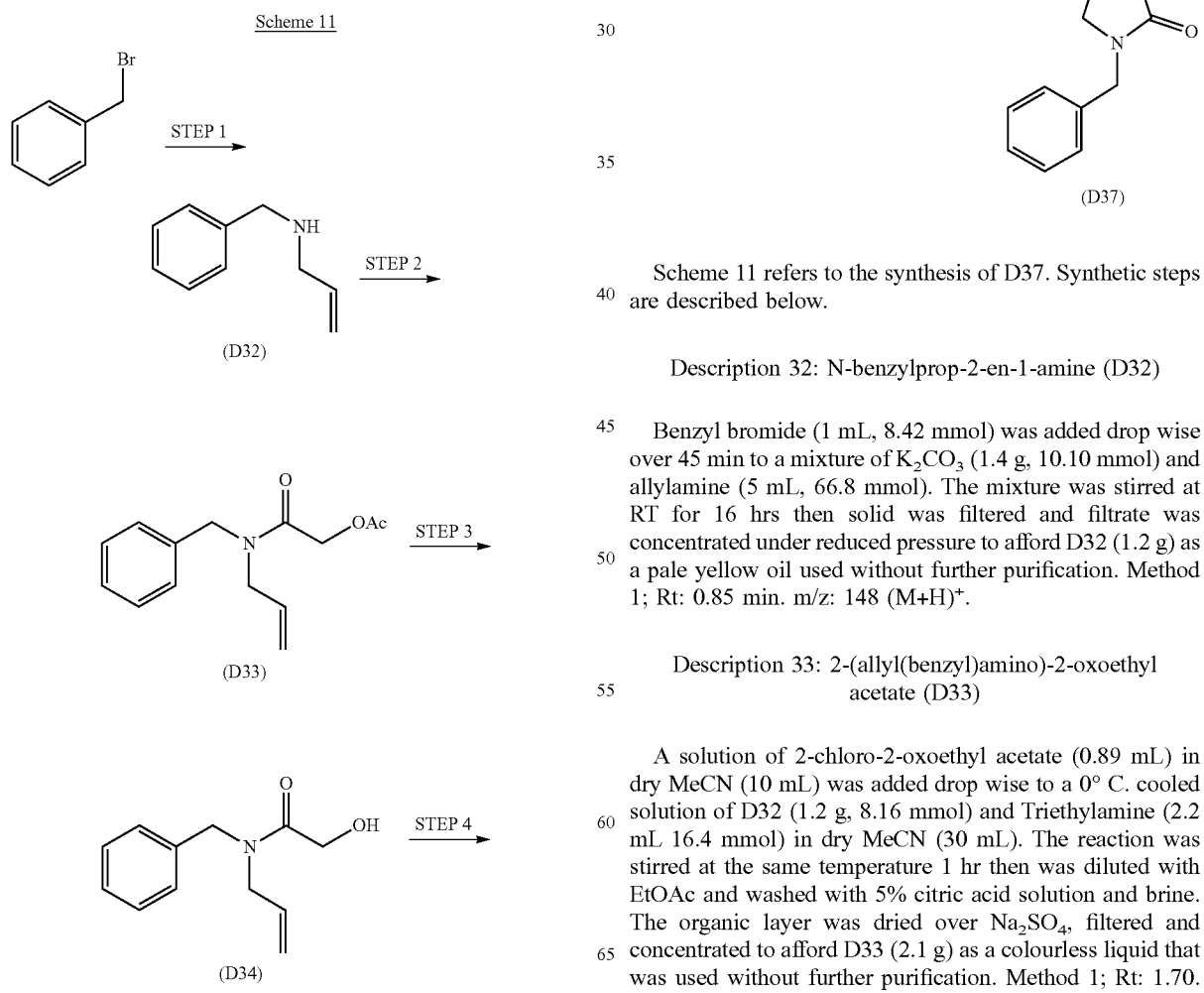

Scheme 11 refers to the synthesis of D37. Synthetic steps are described below.

Description 32: N-benzylprop-2-en-1-amine (D32)

Benzyl bromide (1 mL, 8.42 mmol) was added drop wise over 45 min to a mixture of K$_2$CO$_3$ (1.4 g, 10.10 mmol) and allylamine (5 mL, 66.8 mmol). The mixture was stirred at RT for 16 hrs then solid was filtered and filtrate was concentrated under reduced pressure to afford D32 (1.2 g) as a pale yellow oil used without further purification. Method 1; Rt: 0.85 min. m/z: 148 (M+H)$^+$.

Description 33: 2-(allyl(benzyl)amino)-2-oxoethyl acetate (D33)

A solution of 2-chloro-2-oxoethyl acetate (0.89 mL) in dry MeCN (10 mL) was added drop wise to a 0° C. cooled solution of D32 (1.2 g, 8.16 mmol) and Triethylamine (2.2 mL 16.4 mmol) in dry MeCN (30 mL). The reaction was stirred at the same temperature 1 hr then was diluted with EtOAc and washed with 5% citric acid solution and brine. The organic layer was dried over Na$_2$SO$_4$, filtered and concentrated to afford D33 (2.1 g) as a colourless liquid that was used without further purification. Method 1; Rt: 1.70. m/z: 248.27 (M+H)$^+$.

Description 34: N-allyl-N-benzyl-2-hydroxyacetamide (D34)

Sodium methoxide (463 mg, 8.58 mmol) was added to a solution of D33 (2.1 g, 8.16 mmol) in dry MeOH (60 mL) and the reaction was stirred at RT for 4 hrs. Then the reaction was quenched by using methanolic HCl (3M, 2.85 mL) and concentrated under reduce pressure. Crude was diluted in EtOAc and filtered to remove salt, and concentrated under reduce pressure. Purification by FC (direct phase, eluent ETP/EtOAc) afford D34 (1.40 g, 810% over three steps) as a pale yellow oil. $^1$H NMR (300 MHz, DMSO-d6) δ ppm 3.80-3.92 (m, 2H) 4.11-4.16 (m, 2H) 4.45-4.50 (m, 2H) 4.62-4.68 (m, 1H) 5.18-5.09 (m, 2H) 5.86-5.76 (m, 1H) 7.21-7.38 (m, 5H). Method 1; Rt: 1.49 min. m/z: 206 (M+H)$^+$.

Description 35: N-allyl-N-benzyl-2-oxoacetamide (D35)

A solution of dimethyl sulfoxide (0.31 mL, 4.39 mmol) in dry DCM (1 mL) was slowly added to a solution of oxalyl chloride (0.26 mL, 2.93 mmol) in dry DCM (7 ml) cooled to −78° C. The solution was stirred for 1 h at the same temperature then D34 (300.6 mg, 1.46 mmol) dissolved in dry DCM (4 mL) was added drop wised over 15 minutes. The mixture was stirred 1 h at the same temperature then triethylamine (1.02 mL, 7.32 mmol) was slowly added. The reaction mixture was allowed to warm to 0° C. over 1 hr and stirred at the same temperature for 3 hrs. The mixture was diluted with DCM and quench with sat NH$_4$Cl. The two phases were separated and the organic layer was washed with brine, dried over Na$_2$SO$_4$, filtered and concentrated under reduced pressure. Crude D35 (298 mg) was used without further purification. Method 1; Rt: 1.39 min. m/z: 222 (M+H$_2$O)$^+$.

Description 36: Cis 1,5-dibenzylhexahydro-6H-pyrrolo[3,4-c]isoxazol-6-one (D36)

Sodium bicarbonate (182.6 mg, 2.17 mmol) and N-Benzylhydroxylamine hydrochloride (284.7 mg, 1.78 mmol) were sequentially added to a solution of D35 (297.7 mg, 1.46 mmol) in ethanol (9 mL) and water (1 mL). The reaction mixture was stirred at 80° C. overnight then concentrated under reduce pressure. The residue was taken up in EtOAc and washed with sat NH$_4$Cl and brine. The organic layer was dried over Na$_2$SO$_4$, filtered and concentrated under reduced pressure. Purification by flash chromatography (reverse phase, eluent H$_2$O/MeCN+0.1% HCO$_2$H) afford D36 (272.2 mg, 60% over two steps) as an off white solid. $^1$H NMR (300 MHz, DMSO-d6) δ ppm 3.12-3.15 (m, 1H) 3.37-3.49 (m, 2H) 3.60-3.64 (m, 1H) 3.87-4.12 (m, 3H) 4.18-4.24 (m, 1H) 4.30-4.45 (m, 2H) 7.18-7.40 (m, 10H). Method 1; Rt: 1.76 min. m/z: 309 (M+H)$^+$.

Description 37: Cis 3-amino-1-benzyl-4-(hydroxymethyl)pyrrolidin-2-one (D37)

A solution of D36 (272 mg, 0.88 mmol) in EtOH (17 mL) and water (3 mL) was hydrogenated with a H-Cube continuous flow hydrogenator (flow 1 mL/min, pressure H$_2$=10 barr, T=80° C.). After complete conversion the solvent was removed under reduce pressure to afford D37 as a colourless oil (200 mg) that was used without further purification. Method 1; Rt: 0.83 min. m/z: 221 (M+H)$^+$.

Synthesis of Intermediates of General Formula (3) as Indicated in Scheme 1 or of General Formula (3a) as Indicated in Scheme 2

Description 38: Ethyl 3-fluoro-4-((2-(hydroxymethyl)piperidin-1-yl)sulfonyl)-1-methyl-1H-pyrrole-2-carboxylate (D38)

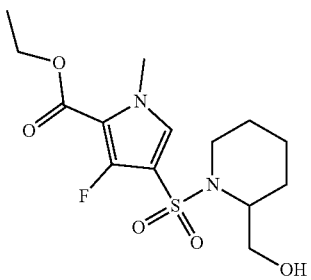 [SMILES: CCOC(=O)c1c(F)c(S(=O)(=O)N2CCCCC2CO)cn1C]

DIPEA (0.1 mL, 0.56 mmol) and piperidin-2-ylmethanol (32.03 mg, 0.28 mmol) were added to a stirred solution of ethyl 4-(chlorosulfonyl)-3-fluoro-1-methyl-1H-pyrrole-2-carboxylate (50 mg, 0.190 mmol) in MeCN (1.8 mL, 0.035 mol) and stirring was continued 1 h at room temperature. Volatiles were evaporated and the residue was partitioned between sat. NH$_4$Cl solution and EtOAc. The organic layer was separated, dried over Na$_2$SO$_4$, evaporated under reduced pressure and purified by flash chromatography on silica gel (Petroleum ether/EtOAc) to obtain the title compound D38 (41.62 mg). m/z=349 (M+H)$^+$.

Description 39: (1-((5-(ethoxycarbonyl)-4-fluoro-1-methyl-1H-pyrrol-3-yl)sulfonyl)piperidin-2-yl)methanaminium chloride (D39)

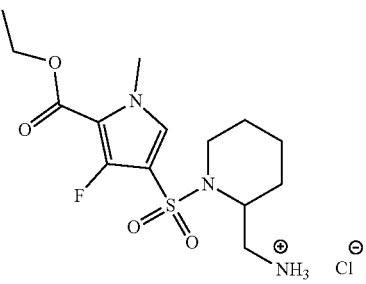 [SMILES: CCOC(=O)c1c(F)c(S(=O)(=O)N2CCCCC2C[NH3+])cn1C ; [Cl-]]

DIPEA (0.1 mL, 0.560 mmol) and tert-butyl (piperidin-2-ylmethyl)carbamate (59.6 mg, 0.28 mmol) were added to a stirred solution of ethyl 4-(chlorosulfonyl)-3-fluoro-1-methyl-1H-pyrrole-2-carboxylate (50 mg, 0.190 mmol) in MeCN (1.84 mL, 0.035 mol) and stirring was continued overnight at room temperature. Volatiles were evaporated and the residue was partitioned between sat. NH$_4$Cl solution and EtOAc. The organic layer was separated, dried over Na$_2$SO$_4$, evaporated under reduced pressure and purified by flash chromatography on silica gel (Petroleum ether/EtOAc) to give ethyl 4-((2-(((tert-butoxycarbonyl)amino)methyl)piperidin-1-yl)sulfonyl)-3-fluoro-1-methyl-1H-pyrrole-2-carboxylate (77.82 mg, y=93.8%). Method 1: Rt=2.15 min. m/z=348.18 (M−100)$^+$ Exact mass=447.18. The Boc protecting group was removed by dissolving the intermediate ethyl 4-((2-(((tert-butoxycarbonyl)amino)methyl)piperidin-1-yl)sulfonyl)-3-fluoro-1-methyl-1H-pyrrole-2-carboxylate in dioxane (1.7 mL) and treating with hydrogen chloride 4N in dioxane (2.81 mL, 11.25 mmol) at RT 1 h. Volatiles were evaporated under reduced pressure to afford D39 as HCl salt, in about quantitative yield (66.75 mg). Method 1: Rt=1.18 min. m/z=348.13 (M+H)$^+$ Exact mass=347.18.

Description 40: Ethyl 3-fluoro-4-((2-(hydroxymethyl)azetidin-1-yl)sulfonyl)-1-methyl-1H-pyrrole-2-carboxylate (D40)

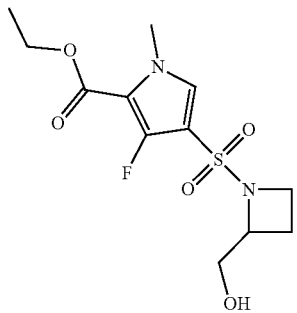 [SMILES: CCOC(=O)c1c(F)c(S(=O)(=O)N2CCC2CO)cn1C]

Methyl 2-azetidinecarboxylate hydrochloride (89.44 mg, 0.590 mmol) in THF (11.9 mL, 0.147 mol) was added to lithium aluminium hydride (1.48 mL, 1.48 mmol) 1M cooled to 0° C. The reaction mixture was stirred at 0° C. for 2 h. After quenching with water (5.0 equiv) the mixture was concentrated in vacuo to obtain azetidin-2-ylmethanol. DIPEA (0.16 mL, 0.930 mmol) and azetidin-2-ylmethanol (24.2 mg, 0.280 mmol) were added to a stirred solution of ethyl 4-(chlorosulfonyl)-3-fluoro-1-methyl-1H-pyrrole-2-carboxylate (50 mg, 0.190 mmol) in MeCN (1.8 mL, 0.035 mol) and stirring was continued for 2 h. Volatiles were evaporated and the residue was partitioned between saturated NH$_4$Cl solution and EtOAc. The organic layer was separated, dried over Na$_2$SO$_4$, evaporated under reduced pressure and purified by flash chromatography on silica gel (Petroleum ether/EtOAc) to obtain approximately 11 mg of the title compound D40. Method 1: Rt=1.44 min. m/z=320.97 (M+H)$^+$.

Description 41: Trans Ethyl 3-fluoro-4-(N-(4-hydroxytetrahydrofuran-3-yl)sulfamoyl)-1-methyl-1H-pyrrole-2-carboxylate (D41)

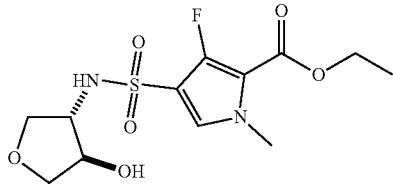

DIPEA (0.23 mL, 1.330 mmol) and trans-4-aminotetrahydrofuran-3-ol (68.8 mg, 0.670 mmol) were added to a stirred solution of ethyl 4-(chlorosulfonyl)-3-fluoro-1-methyl-1H-pyrrole-2-carboxylate (120 mg, 0.440 mmol) in MeCN (4.4 mL) and stirring was continued 1 h at room temperature. Volatiles were evaporated and the residue was partitioned between saturated NH$_4$Cl solution and EtOAc. The organic layer was separated, dried over Na$_2$SO$_4$, evaporated under reduced pressure and purified by flash chromatography on silica gel (Petroleum ether/EtOAc) to obtain the title compound D41 as a trans 3S,4R and 3R,4S racemate (133 mg, y=88.9%). Method 1: Rt=1.25 min. m/z=337 (M+H)$^+$.

Description 42: Cis-Ethyl 3-fluoro-4-(N-((3-(hydroxymethyl)cyclobutyl)sulfamoyl)-1-methyl-1H-pyrrole-2-carboxylate (D42)

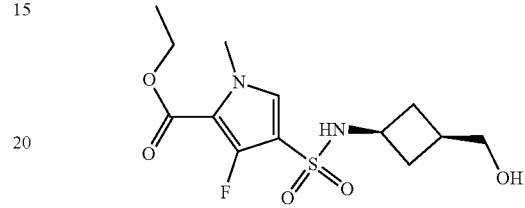

To a solution of tert-butyl (cis-3-(hydroxymethyl)cyclobutyl)carbamate (0.154 g, 0.765 mmol) in DCM (2 mL), HCl 4N in dioxane (0.4 mL, 1.6 mmol) was added at rt. After 5 h 30 min a further aliquot of HCl 4N in dioxane (0.8 mL, 3.2 mmol) was added and mixture was left at rt until complete conversion. Mixture was evaporated under reduced pressure to obtain cis-3-(hydroxymethyl)cyclobutan-1-aminium chloride as a white solid (128 mg). Method 1: Rt=0.83 min, m/z=102 (M+H)$^+$. The crude compound (38.5 mg, 0.280 mmol) was taken in dry acetonitrile (1.7 mL) and dry DIPEA (0.1 mL, 0.574 mmol) and ethyl 4-(chlorosulfonyl)-3-fluoro-1-methyl-1H-pyrrole-2-carboxylate (50 mg, 0.185 mmol) were added at room temperature. Reaction mixture was stirred overnight and then evaporated under reduced pressure to afford a light brown solid. Crude was purified with flash chromatography (Petroleum ether/AcOEt) to afford D42 as a white solid (45 mg). m/z=335 (M+H)$^+$.

Description 43: Cis-Ethyl 3-fluoro-4-(N-(2-(hydroxymethyl)cyclopentyl)sulfamoyl)-1-methyl-1H-pyrrole-2-carboxylate (D43)

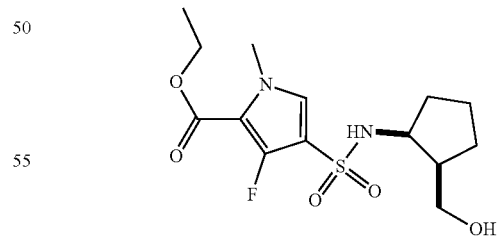

To a solution of D2 (176 mg, 0.371 theoretical mmol) and ethyl 4-(chlorosulfonyl)-3-fluoro-1-methyl-1H-pyrrole-2-carboxylate (50 mg, 0.185 mmol) in dry acetonitrile (1.7 mL), dry DIPEA (0.130 mL, 0.746 mmol) was added at room temperature. After 3 h a further aliquot of D2 (102 mg, 0.214 theoretical mmol) was added. Reaction was stopped after 6 h, crude was purified with preparative HPLC-MS (H$_2$O/CH$_3$CN+0.1% TFA) to give D43 as a white powder (18 mg, y=28%). The compound is the cis racemate at the cyclopentyl ring (SR and RS). Method 1: Rt=1.62 min, m/z=349 (M+H)+.

Description 44: Trans-Ethyl 3-fluoro-4-(N-(4-(hydroxymethyl)tetrahydrofuran-3-yl)sulfamoyl)-1-methyl-1H-pyrrole-2-carboxylate (D44)

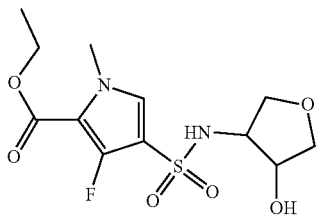 [SMILES: CCOC(=O)c1c(F)c(S(=O)(=O)NC2COCC2O)cn1C]

To a solution of 4-aminotetrahydrofuran-3-ol (74.5 mg, 0.722 mmol) and ethyl 4-(chlorosulfonyl)-3-fluoro-1-methyl-1H-pyrrole-2-carboxylate (150 mg, 0.556 mmol) in dry acetonitrile (4 mL), dry DIPEA (0.3 mL, 1.7223 mmol) was added at rt. After 1 h mixture was evaporated under reduced pressure to afford a yellow solid (325 mg). Crude was purified by flash chromatography (Petroleum ether/AcOEt) to afford D44 as a light yellow solid (178 mg, y=95%). Method 1: Rt=1.28 min, m/z=337 (M+H)+. The compound is the trans racemic mixture at the tetrahydrofuranyl ring.

Description 45: Ethyl 3-fluoro-4-(N-((1R,2R)-2-(hydroxymethyl)cyclopentyl)sulfamoyl)-1-methyl-1H-pyrrole-2-carboxylate (D45)

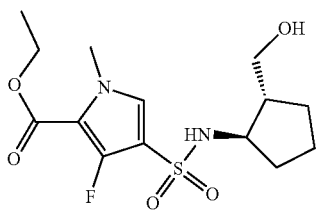 [SMILES: CCOC(=O)c1c(F)c(S(=O)(=O)N[C@@H]2CCC[C@H]2CO)cn1C]

To a solution of D4 (373 mg, 0.234 theoretical mmol) in dry acetonitrile (1.5 mL), ethyl 4-(chlorosulfonyl)-3-fluoro-1-methyl-1H-pyrrole-2-carboxylate (50 mg, 0.185 mmol) and dry DIPEA (0.1 mL, 0.574 mmol) were added at rt. After 1.5 h more D4 (124.3 mg, 0.191 mmol) in dry acetonitrile (0.5 mL) was added. Conversion was completed; mixture was diluted with DCM and washed with water (×2). Organic layer was dried over Na2SO4, filtered and then evaporated under reduced pressure. Crude was purified with flash chromatography (ETP/AcOEt to afford D45 as a yellow solid (59 mg). Method 1: Rt=1.60 min, m/z=349 (M+H)+.

Description 46: Ethyl 3-fluoro-4-(N-((1S,2S)-2-(hydroxymethyl)cyclopentyl)sulfamoyl)-1-methyl-1H-pyrrole-2-carboxylate (D46)

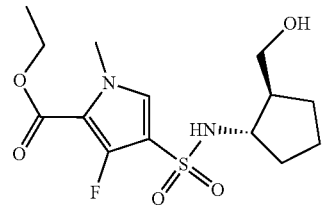 [SMILES: CCOC(=O)c1c(F)c(S(=O)(=O)N[C@H]2CCC[C@@H]2CO)cn1C]

The compound was prepared from D6, following the same procedure indicated for compound D45. Method 1: Rt=1.60 min, m/z=349 (M+H)+.

Description 47: Cis-Ethyl 4-(N-(1-(ethoxycarbonyl)-4-(hydroxymethyl)pyrrolidin-3-yl)sulfamoyl)-3-fluoro-1-methyl-1H-pyrrole-2-carboxylate (D47)

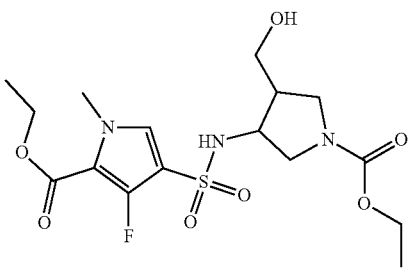 [SMILES: CCOC(=O)c1c(F)c(S(=O)(=O)NC2CN(C(=O)OCC)CC2CO)cn1C]

To a suspension of ethyl 4-(chlorosulfonyl)-3-fluoro-1-methyl-1H-pyrrole-2-carboxylate (70 mg, 0.260 mmol) and ethyl 3-amino-4-(hydroxymethyl)-1-pyrrolidinecarboxylate (56.2 mg, 0.299 mmol) in dry acetonitrile (2 mL), dry DIPEA (0.1 mL, 0.574 mmol) was added at room temperature. After 1.5 h mixture was diluted with DCM and washed with 5% citric acid solution. Organic layer was dried over Na2SO4, filtered and solvent removed under reduced pressure to afford D47 as a light yellow solid (162 mg). The compound is the cis racemate at the pyrrolidine ring (racemate of 3S,4S and 3R,4R). Crude was purified by flash chromatography (Petroleum ether/AcOEt) to afford a white solid (101 mg). Method 1: Rt=1.52 min, m/z=422 (M+H)+.

Description 48: Cis-Ethyl 4-(N-(1-(tert-butoxycarbonyl)-4-(hydroxymethyl)pyrrolidin-3-yl)sulfamoyl)-3-fluoro-1-methyl-1H-pyrrole-2-carboxylate (D48)

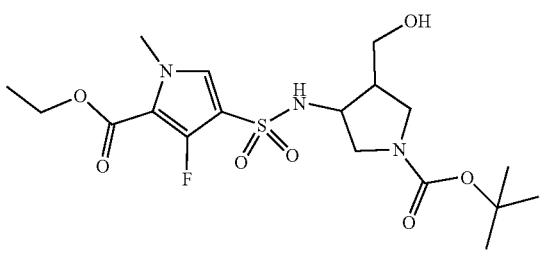 [SMILES: CCOC(=O)c1c(F)c(S(=O)(=O)NC2CN(C(=O)OC(C)(C)C)CC2CO)cn1C]

To a suspension of ethyl 4-(chlorosulfonyl)-3-fluoro-1-methyl-1H-pyrrole-2-carboxylate (449 mg, 1.66 mmol) and D10 (360 mg, 1.66 mmol) in dry MeCN (9 mL), DIPEA (0.72 mL, 4.16 mmol) was added dropwise at RT. Reaction mixture was stirred at RT for 2 h (a off-white solid precipitated). Solid was filtered and washed with a small amount of cold acetonitrile, to obtain D48 as off-white powder (570 mg). The compound is the cis racemate at the pyrrolidine ring (racemate of 3S,4S and 3R,4R). $^1$H NMR (300 MHz, DMSO-d$_6$+TFA) δ ppm 1.28 (t, J=6.97 Hz, 3H) 1.37 (d, J=8.99 Hz, 9H) 2.26-2.36 (m, 1H) 3.04-3.14 (m, 1H) 3.16-3.42 (m, 4H) 3.46-3.57 (m, 1H) 3.75-3.89 (m, 4H) 4.27 (q, J=6.79 Hz, 2H) 7.56 (d, J=4.77 Hz, 1H) 7.82-8.06 (m, 1H). Method 1: Rt=1.74 min. m/z=450.40 (M+H)$^+$.

Description 49: Ethyl 4-(N-((2S,3R)-1-(tert-butoxycarbonyl)-2-(hydroxymethyl)pyrrolidin-3-yl)sulfamoyl)-3-fluoro-1-methyl-1H-pyrrole-2-carboxylate (D49)

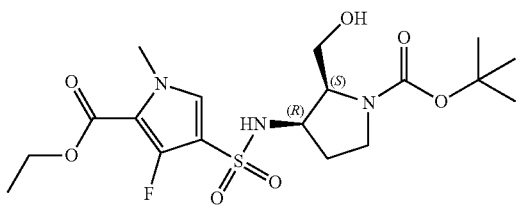

Crude D11, 100 mg, 0.462 mmol, 1 eq) and ethyl 4-(chlorosulfonyl)-3-fluoro-1-methyl-1H-pyrrole-2-carboxylate (125 mg, 0.464 mmol, 1 eq) were dissolved in dry acetonitrile (4 mL), N,N-diisopropylethylamine (165 uL, 0.925 mmol, 2 eq) was added dropwise and reaction mixture was stirred at rt. Complete conversion after 15 min. Reaction mixture was diluted with ethyl acetate, organic layer was washed once with saturated ammonium chloride aqueous solution and once with brine. Organic layer was dried over sodium sulfate, filtered and solvent was removed under reduced pressure affording an orange solid (256 mg). Crude product was purified by flash chromatography (DCM/EtOAc 70/30) to afford D49 as a white solid (181 mg). Method 1: Rt=1.85 min, MH+=450 m/z. Stereochemistry cis, single enantiomer.

Description 50: Ethyl 3-fluoro-4-(N-(2-(hydroxymethyl)-2-methylcyclopentyl)sulfamoyl)-1-methyl-1H-pyrrole-2-carboxylate (D50)

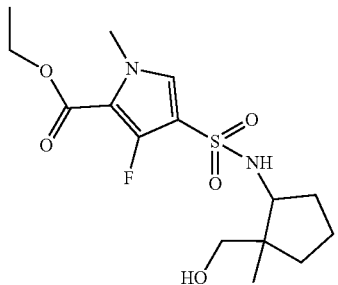 [SMILES: CCOC(=O)c1c(F)c(S(=O)(=O)NC2CCCC2(C)CO)cn1C]

(2-amino-1-methylcyclopentyl)methanol (58 mg, 0.449 mmol, 1.1 eq) was suspended in dry MeCN (2.5 mL) under a nitrogen atmosphere, ethyl 4-(chlorosulfonyl)-3-fluoro-1-methyl-1H-pyrrole-2-carboxylate (110 mg, 0.408 mmol) was added, followed by dry DIPEA (156 uL, 0.897 mmol, 2.2 eq) and the reaction was stirred at rt 1 h: complete conversion. The reaction was diluted with DCM and washed with 5% citric acid (2×); the organic phase was washed with brine, dried over Na$_2$SO$_4$ and evaporated, yielding 128 mg of D50 as a pale yellow powder, used without further purification. Method 1: Rt=1.70 min; m/z 363 (M+H)$^+$.

Description 51: cis-2-[(5-ethoxycarbonyl-4-fluoro-1-methyl-1H-pyrrole)-3-sulfonamido]-1-hydroxycyclopentane-1-carboxylic Acid (D51)

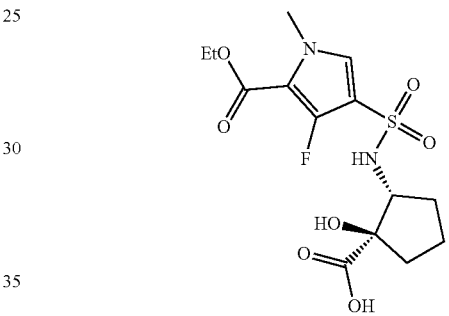

(1R2R and 1S2S) cis-methyl-2-amino-1-hydroxycyclopentane-1-carboxylate, oxalate salt (Sigma Aldrich EN300-1074287 or Ambinter Amb32646086) (72 mg, 0.29 mmol) was suspended in EtOH (2.8 mL); 2N NaOH (0.433 mL, 0.867 mmol, 3 eq) was added and the mixture was stirred at rt for 24 h. The mixture was brought to acidic pH with 2N HCl (0.5 mL) and the volatiles were evaporated, obtaining 128 mg of crude cis 2-amino-1-hydroxycyclopentane-1-carboxylic acid hydrochloride, used as such. Method 2: Rt=0.59 min, MH$^+$=146. The crude (racemate of 1R2R and 1S2S) cis-2-amino-1-hydroxycyclopentane-1-carboxylic acid hydrochloride (0.289 mmol, 1 eq) was suspended in dry MeCN (2.5 mL) under a nitrogen atmosphere; ethyl 4-(chlorosulfonyl)-3-fluoro-1-methyl-1H-pyrrole-2-carboxylate (85.7 mg, 0.318 mmol, 1.1 eq) was added, followed by dry DIPEA (262 uL, 1.5 mmol, 5.2 eq) and the reaction was stirred at rt for 2 h. The reaction was diluted with DCM and washed with 5% citric acid; the organic phase was dried over Na$_2$SO$_4$ and evaporated, yielding 95 mg of crude product. 35 mg of D51 were obtained after purification by preparative HPLC (H$_2$O, CH$_3$CN 0.1% HCOOH). Method 1: Rt=1.42 min; m/z 379 (M+H)$^+$.

Description 52: Ethyl 3-fluoro-4-(N-((1R,2R)-2-hydroxy-2-(hydroxymethyl)cyclopentyl)sulfamoyl)-1-methyl-1H-pyrrole-2-carboxylate (D52)

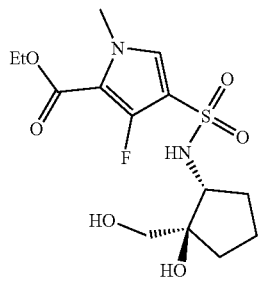 [SMILES: CCOC(=O)c1c(F)c(S(=O)(=O)N[C@@H]2CCC[C@]2(O)CO)cn1C]

D51 (35 mg, 0.093 mmol) was dissolved in dry THF (1.5 mL) under a nitrogen atmosphere. The solution was cooled in an ice bath and more aliquots of 2M $(CH_3)_2S.BH_3$ in THF (0.1 mL, 0.2 mmol, 2.16 eq) were added dropwise. The reaction was stirred at rt for 16 h and stopped when approximately 10% of the starting acid was still unreacted. The reaction was cooled in ice and MeOH (0.4 mL) was added up to end of foaming. The reaction was stored at –20° C. for 16 h, then it was diluted with DCM and washed with a saturated solution of $NaHCO_3$. The organic phase was dried over $Na_2SO_4$ and evaporated, yielding 21 mg of crude D52 as a colourless thick oil, used without further purification. Method 1: Rt=1.38 min; m/z 365 (M+H)$^+$.

Description 53: Ethyl 4-(N-((3R,5R)-1-(ethoxycarbonyl)-5-(hydroxymethyl)pyrrolidin-3-yl)sulfamoyl)-3-fluoro-1-methyl-1H-pyrrole-2-carboxylate (D53)

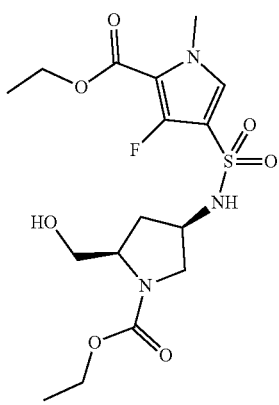 [SMILES: CCOC(=O)c1c(F)c(S(=O)(=O)N[C@@H]2C[C@H](CO)N(C(=O)OCC)C2)cn1C]

Ethyl 4-(chlorosulfonyl)-3-fluoro-1-methyl-1H-pyrrole-2-carboxylate (240 mg, 0.89 mmol) was added to a solution of D31 (200 mg, 0.89 mmol) and DIPEA (0.48 mL) in dry MeCN (9 mL). The solution was stirred at RT for 2 hrs then was concentrated under reduce pressure. The residue was taken up in EtOAc and washed whit 5% citric acid solution and brine. The organic layer was dried over $Na_2SO_4$ filtered and concentrated. Purification by FC (direct phase, eluent DCM/EtOAc) afford D53 (180 mg, 34% over four steps) as an off white foam. $^1$H NMR (300 MHz, DMSO-$d_6$) δ 1H NMR (300 MHz, DMSO-$d_6$) δ ppm 1.16 (t, J=7.06 Hz, 3H) 1.28 (t, J=7.06 Hz, 3H) 1.76-1.78 (m, 1H) 2.07-2.15 (m, 1H) 2.89-3.06 (m, 1H) 3.43-3.75 (m, 5H) 3.84 (s, 3H) 4.00 (quin, J=7.04 Hz, 2H) 4.28 (q, J=7.12 Hz, 2H) 4.91 (br s, 1H) 7.58 (d, J=4.77 Hz, 1H) 7.99 (d, J=6.14 Hz, 1H). Method 1; Rt: 1.61 min. m/z: 422 (M+H)+. Method 1; Rt: 1.61 min. m/z: 422.30 (M+H)$^+$.

Description 54: Ethyl 4-(N-(1-benzyl-4-(hydroxymethyl)-2-oxopyrrolidin-3-yl)sulfamoyl)-3-fluoro-1-methyl-1H-pyrrole-2-carboxylate (D54)

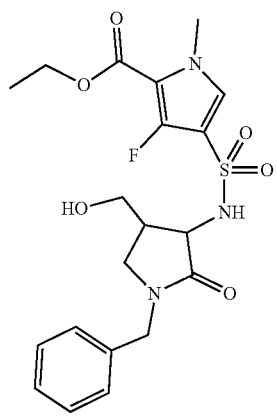 [SMILES: CCOC(=O)c1c(F)c(S(=O)(=O)NC2C(=O)N(Cc3ccccc3)CC2CO)cn1C]

Ethyl 4-chloranylsulfonyl-3-fluorenyl-1-methyl-pyrrole-2-carboxylate (238 mg, 0.88 mmol) was added to a solution of D37 (195 mg, 0.88 mmol) and DIPEA (0.35 mL) in dry MeCN (9 mL). The solution was stirred at RT for 2 hrs then was concentrated under reduce pressure. The residue was taken up in EtOAc and washed whit 5% citric acid solution and brine. The organic layer was dried over $Na_2SO_4$ filtered and concentrated. Purification by flash chromatography (direct phase, eluent DCM/EtOAc) afford D54 (235 mg, 59% over two steps) as an off white foam. 1H NMR (300 MHz, DMSO-d6) δ ppm 1.25-1.33 (m, 3H) 2.37-2.47 (m, 1H) 3.11-3.29 (m, 3H) 3.41-3.51 (m, 1H) 3.78-3.88 (m, 3H) 4.18-4.36 (m, 4H) 4.38-4.61 (m, 2H) 7.20-7.37 (m, 6H) 7.61 (d, J=4.68 Hz, 1H). Method 1; Rt: 1.71 min. m/z: 454 (M+H)$^+$.

Synthesis of Intermediates of General Formula (4) as Indicated in Scheme 1 or of General Formula (4a) as Indicated in Scheme 2

Description 55: N-(3,4-difluorophenyl)-3-fluoro-4-((2-(hydroxymethyl)piperidin-1-yl)sulfonyl)-1-methyl-1H-pyrrole-2-carboxamide (D55)

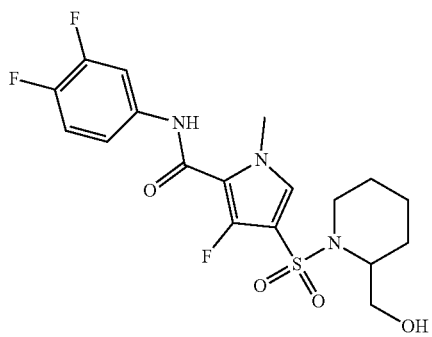 [SMILES: Cn1cc(S(=O)(=O)N2CCCCC2CO)c(F)c1C(=O)Nc1ccc(F)c(F)c1]

To a suspension of D38 (41.3 mg, 0.12 mmol) and 3,4-difluoroaniline (0.014 mL, 0.14 mmol) in dry THF (0.75 mL), lithium bis(trimethylsilyl)amide 1M in THF (0.66 mL, 0.66 mmol) was added dropwise. Reaction mixture was stirred at RT overnight, then was added $NH_4Cl$ and diluted with DCM. Organic layer was dried over $Na_2SO_4$, filtered and solvent removed under reduced pressure. The crude was purified by preparative HPLC ($H_2O/CH_3CN+0.1\%$ TFA) to afford the title compound D55 (45.8 mg). Method 1: Rt=1.93 min; m/z=432.4 $(M+H)^+$.

Description 56: 4-((2-(aminomethyl)piperidin-1-yl) sulfonyl)-N-(3,4-difluorophenyl)-3-fluoro-1-methyl-1H-pyrrole-2-carboxamide (D56)

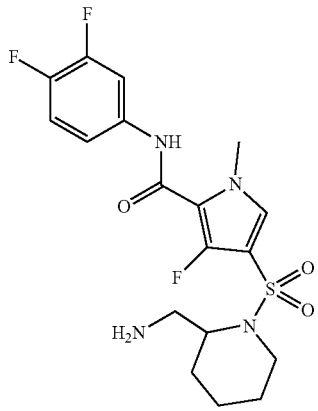 [SMILES: Cn1cc(S(=O)(=O)N2CCCCC2CN)c(F)c1C(=O)Nc1ccc(F)c(F)c1]

To a suspension of D39 (66.75 mg, 0.17 mmol) and 3,4-difluoroaniline (0.02 mL, 0.21 mmol) in dry THF (1.1 mL), lithium bis(trimethylsilyl)amide 1M in THF (1.22 mL, 1.22 mmol) was added dropwise. Reaction mixture was stirred at RT overnight, then was added saturated $NH_4Cl$ and diluted with DCM. Organic layer was dried over $Na_2SO_4$, filtered and solvent removed under reduced pressure to afford the title product D56 in approximately 78% yield. Method 1: Rt=1.43 min. m/z=431.15 $(M+H)^+$.

Description 57: Trans N-(3,4-difluorophenyl)-3-fluoro-4-(N-(4-hydroxytetrahydrofuran-3-yl)sulfamoyl)-1-methyl-1H-pyrrole-2-carboxamide (D57)

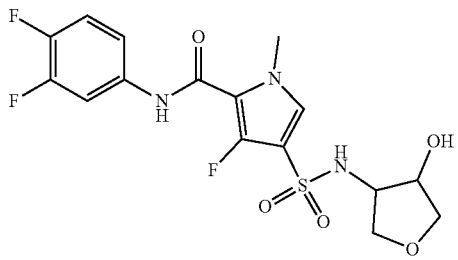 [SMILES: Cn1cc(S(=O)(=O)NC2COCC2O)c(F)c1C(=O)Nc1ccc(F)c(F)c1]

To a suspension of D41 (133 mg, 0.0395 mmol) and 3,4-difluoroaniline (0.05 mL, 0.04 mmol) in dry THF (0.7 mL), lithium bis(trimethylsilyl)amide 1M in THF (2.27 mL, 2.27 mmol) was added dropwise. Reaction mixture was stirred at RT overnight. Volatiles were evaporated and the residue was crystallized from hot petroleum ether and EtOAc affording the title compound D57, as a trans 3S4R and 3R4S racemate (139.5 mg, y=81%). Method 3: Rt=2.74 min. m/z=420.34 $(M+H)^+$.

Description 58: N-(3,4-difluorophenyl)-3-fluoro-4-((2-(hydroxymethyl)azetidin-1-yl)sulfonyl)-1-methyl-1H-pyrrole-2-carboxamide (D58)

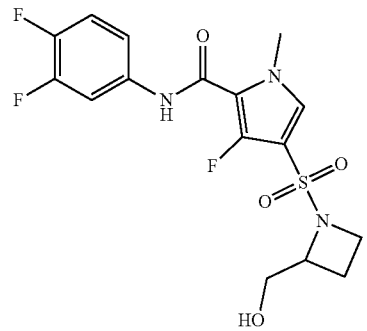 [SMILES: Cn1cc(S(=O)(=O)N2CCC2CO)c(F)c1C(=O)Nc1ccc(F)c(F)c1]

To a suspension of D40 (10.8 mg, 0.03 mmol) and 3,4-difluoroaniline (0.004 mL, 0.04 mmol) in dry THF (0.7 mL), lithium bis(trimethylsilyl)amide 1M in THF (0.19 mL, 0.19 mmol) was added dropwise. Reaction mixture was stirred at RT for 30 min, then was added saturated $NH_4Cl$ and diluted with DCM. Organic layer was dried over $Na_2SO_4$, filtered and solvent removed under reduced pressure to afford the title compound D58 in approximately quantitative yield (14 mg). Method 1: Rt=1.77 min. m/z=404.26 $(M+H)^+$.

Description 59: cis-N-(3,4-difluorophenyl)-3-fluoro-4-(N-(3-(hydroxymethyl)cyclobutyl)sulfamoyl)-1-methyl-1H-pyrrole-2-carboxamide (D59)

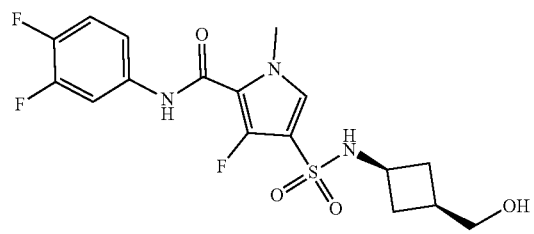 [SMILES: Cn1cc(S(=O)(=O)N[C@H]2C[C@@H](CO)C2)c(F)c1C(=O)Nc1ccc(F)c(F)c1]

To a solution of D42 (45 mg, 0.135 mmol) and 3,4-difluoroaniline (0.016 mL, 0.161 mmol) in dry THF (0.8 mL), lithium bis(trimethylsilyl)amide 1M in THF (0.750 mL, 0.750 mmol) was added at room temperature. After 1.5 h lithium bis(trimethylsilyl)amide 1M in THF (0.300 mL, 0.300 mmol) and 3,4-difluoroaniline (0.005 mL, 0.050 mmol) were added to have complete conversion. Mixture was diluted with DCM and washed with 5% citric acid solution (×2). Organic layer was dried over $Na_2SO_4$, filtered and solvent removed under reduced pressure to afford a brown solid (83 mg). Crude was purified with preparative HPLC-MS ($H_2O/CH_3CN+0.1\%$ TFA) to give D59 as pink powder (39.5 mg). $^1H$ NMR (300 MHz, DMSO-$d_6$) δ ppm 1.53-1.65 (m, 2H) 1.89-2.03 (m, 1H) 2.03-2.15 (m, 2H) 3.23-3.29 (m, 3H) 3.42-3.68 (m, 2H) 3.80 (s, 3H) 7.37-7.48 (m, 3H) 7.78-7.89 (m, 2H) 10.22 (s, 1H). Method 3: Rt=2.94 min, m/z=418 $(M+H)^+$.

Description 60: cis-N-(3,4-difluorophenyl)-3-fluoro-4-(N-(2-(hydroxymethyl)cyclopentyl)sulfamoyl)-1-methyl-1H-pyrrole-2-carboxamide (D60)

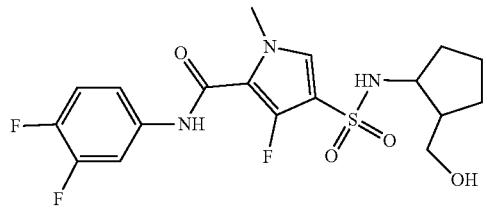 [SMILES: Cn1cc(S(=O)(=O)NC2CCCC2CO)c(F)c1C(=O)Nc1ccc(F)c(F)c1]

To a solution of D43 (18 mg, 0.052 mmol) and 3,4-difluoroaniline (0.006 mL, 0.062 mmol) in dry THF (1 mL), lithium bis(trimethylsilyl)amide 1M in THF (0.360 mL, 0.360 mmol) was added at rt. After 30 minutes mixture was diluted with DCM and washed with 5% citric acid solution. Organic layer was dried over $Na_2SO_4$, filtered and solvent removed under reduced pressure to afford a brown solid. Crude was purified with preparative HPLC-MS ($H_2O$/$CH_3CN$+0.10% TFA) to give D60 as a white powder (12.5 mg, y=56%). The compound is the cis racemic mixture of 1S,2R and 1R,2S at the cyclopentyl ring. Method 1: Rt=1.89 min, m/z=432 (M+H)$^+$.

Description 61: trans-3-fluoro-4-(N-(4-hydroxytetrahydrofuran-3-yl)sulfamoyl)-1-methyl-N-(3,4,5-trifluorophenyl)-1H-pyrrole-2-carboxamide (D61)

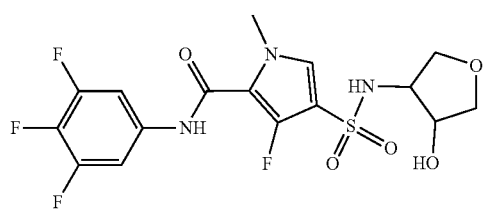 [SMILES: Cn1cc(S(=O)(=O)NC2COCC2O)c(F)c1C(=O)Nc1cc(F)c(F)c(F)c1]

To a solution of D44 (70 mg, 0.208 mmol) and 3,4,5-trifluoroaniline (0.025 mL, 0.221 mmol) in dry THF (1.5 mL), lithium bis(trimethylsilyl)amide 1M in THF (1.2 mL, 1.2 mmol) was added at room temperature. After 45 min, the mixture was evaporated under reduced pressure to afford a light violet solid (204 mg). Crude was purified with preparative HPLC-MS ($H_2O$/$CH_3CN$+0.1% TFA) to give D61 as a white powder (42.3 mg, y=46%). The compound is the trans racemic mixture of 3S,4R and 3R,4S at the tetrahydrofuranyl ring. $^1$H NMR (300 MHz, DMSO-$d_6$+TFA) δ ppm 3.43-3.60 (m, 1H) 3.45-3.49 (m, 1H) 3.52-3.58 (m, 1H) 3.77-3.86 (m, 5H) 4.07-4.12 (m, 1H) 7.49-7.66 (m, 3H) 7.95 (br d, J=4.77 Hz, 1H) 10.34 (s, 1H). Method 3: Rt=2.98 min, m/z=438 (M+H)$^+$.

Description 62: N-(3,4-difluorophenyl)-3-fluoro-4-(N-((1R,2R)-2-(hydroxymethyl)cyclopentyl)sulfamoyl)-1-methyl-1H-pyrrole-2-carboxamide (D62)

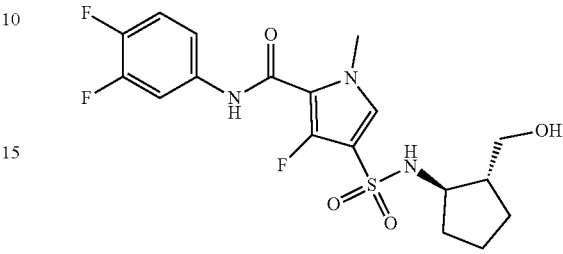

To a solution of D45 (59 mg, 0.169 mmol) and 3,4-difluoroaniline (0.020 mL, 0.203 mmol) in dry THF (1.5 mL), lithium bis(trimethylsilyl)amide 1M in THF (0.850 mL, 0.850 mmol) was added at room temperature. After 40 min UPLC-MS analysis showed conversion was not completed so (3,4-Difluoroaniline (0.010 mL, 0.101 mmol) and lithium bis(trimethylsilyl)amide 1M in THF (0.400 ml, 0.400 mmol) were added. 30 minutes after the addition mixture was diluted with DCM and washed with 5% citric acid solution. Organic layer was dried over $Na_2SO_4$, filtered, solvent removed under reduced pressure to afford a brown solid (118 mg). Crude was purified with preparative HPLC-MS ($H_2O$/$CH_3CN$+0.1% TFA) to give D62 as a white powder (44.7 mg). Method 1: Rt=1.90 min, m/z=432 (M+H)$^+$.

Description 63: N-(3,4-difluorophenyl)-3-fluoro-4-(N-((1S,2S)-2-(hydroxymethyl)cyclopentyl)sulfamoyl)-1-methyl-1H-pyrrole-2-carboxamide (D63)

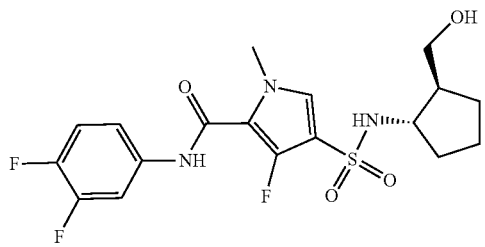 [SMILES: Cn1cc(S(=O)(=O)N[C@H]2CCC[C@@H]2CO)c(F)c1C(=O)Nc1ccc(F)c(F)c1]

Prepared similarly as described for compound D62 starting from D46. Method 1: Rt=1.90 min, m/z=432 (M+H)$^+$.

Description 64: Cis-Ethyl 3-((4-fluoro-1-methyl-5-((3,4,5-trifluorophenyl)carbamoyl)-1H-pyrrole)-3-sulfonamido)-4-(hydroxymethyl)pyrrolidine-1-carboxylate (D64)

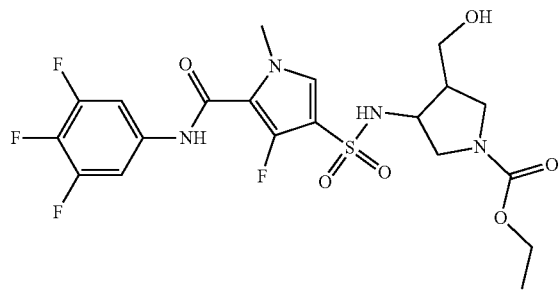 [SMILES: CCOC(=O)N1CC(CO)C(NS(=O)(=O)c2cn(C)c(C(=O)Nc3cc(F)c(F)c(F)c3)c2F)C1]

To a solution of D47 (101 mg, 0.240 mmol) and 3,4,5-trifluoroaniline (38.8 mg, 0.264 mmol) in dry THF (2 mL), lithium bis(trimethylsilyl)amide 1M in THF (1.2 mL, 1.2 mmol) was added at room temperature. After 1 h 3,4,5-trifluoroaniline (20 mg, 0.136 mmol) and lithium bis(trimethylsilyl)amide 1M in THF (0.5 mL, 0.5 mmol) were added. Reaction was stopped after 2.5 h, mixture diluted with DCM and washed with 5% citric acid solution and water. Organic layer was dried over Na$_2$SO4, filtered and solvent removed under reduced pressure. Crude was purified with flash chromatography (ETP/AcOEt) to afford D64 as a brown solid (106 mg). The compound is the cis racemate at the pyrrolidine ring (racemate of 3S,4S and 3R,4R). Method 1: Rt=1.94 min, m/z=523 (M+H)$^+$.

Description 65: Cis-Ethyl 3-((5-((3,4-difluorophenyl)carbamoyl)-4-fluoro-1-methyl-1H-pyrrole)-3-sulfonamido)-4-(hydroxymethyl)pyrrolidine-1-carboxylate (D65)

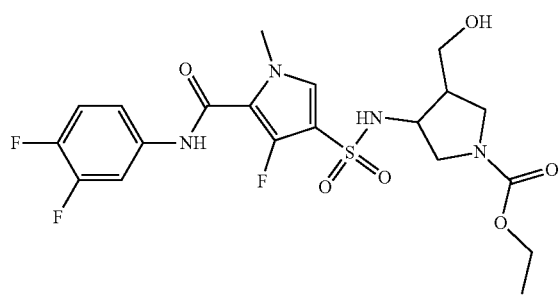 [SMILES: CCOC(=O)N1CC(CO)C(NS(=O)(=O)c2cn(C)c(C(=O)Nc3ccc(F)c(F)c3)c2F)C1]

Prepared similarly as described for compound D64 using 3,4-difluoroaniline instead of 3,4,5-trifluoroaniline to give D65. The compound is the cis racemate at the pyrrolidine ring (racemate of 3S,4S and 3R,4R). Method 1: Rt=1.82 min, m/z=505 (M+H)$^+$.

Description 66: Cis-Ethyl 3-((4-fluoro-5-((4-fluoro-3-methylphenyl)carbamoyl)-1-methyl-1H-pyrrole)-3-sulfonamido)-4-(hydroxymethyl)pyrrolidine-1-carboxylate (D66)

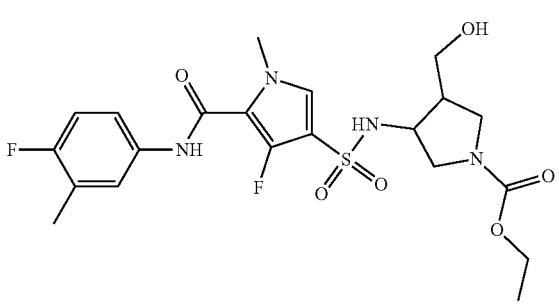 [SMILES: CCOC(=O)N1CC(CO)C(NS(=O)(=O)c2cn(C)c(C(=O)Nc3ccc(F)c(C)c3)c2F)C1]

Prepared similarly as described for compound D64 using 4-fluoro-3-methylaniline instead of 3,4,5-trifluoroaniline to give D66. The compound is the cis racemate at the pyrrolidine ring (racemate of 3S,4S and 3R,4R). Method 1: Rt=1.83 min, m/z=501 (M+H)$^+$.

Description 67: Cis-Ethyl 3-((5-((3-chloro-4-fluorophenyl)carbamoyl)-4-fluoro-1-methyl-1H-pyrrole)-3-sulfonamido)-4-(hydroxymethyl)pyrrolidine-1-carboxylate (D67)

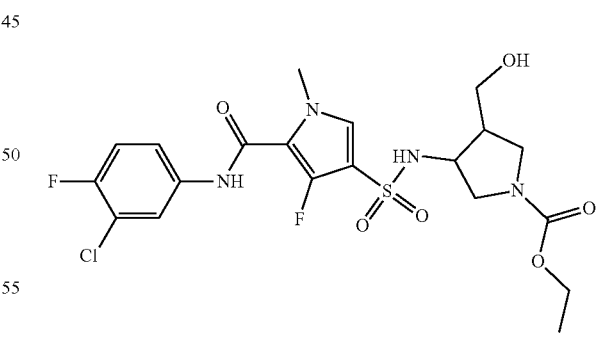

Prepared similarly as described for compound D64 using 3-chloro-4-fluoroaniline, instead of 3,4,5-trifluoroaniline to give D67. The compound is the cis racemate at the pyrrolidine ring (racemate of 3S,4S and 3R,4R). Method 1: Rt=1.91 min, m/z=521 (M+H)$^+$.

Description 68: Cis-Ethyl 3-((5-((3-(difluoromethyl)-4-fluorophenyl)carbamoyl)-4-fluoro-1-methyl-1H-pyrrole)-3-sulfonamido)-4-(hydroxymethyl)pyrrolidine-1-carboxylate (D68)

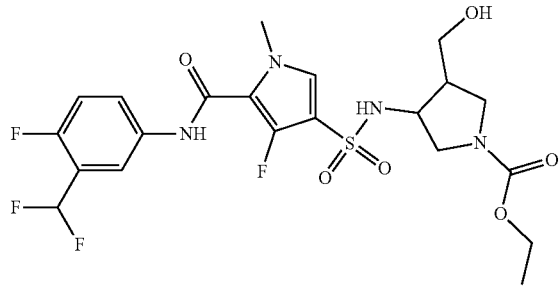 [SMILES: CCOC(=O)N1CC(CO)C(NS(=O)(=O)c2cn(C)c(C(=O)Nc3ccc(F)c(C(F)F)c3)c2F)C1]

Prepared similarly as described for compound D64 using 3-(difluoromethyl)-4-fluoroaniline, instead of 3,4,5-trifluoroaniline to give D68. The compound is the cis racemate at the pyrrolidine ring (racemate of 3S,4S and 3R,4R). Method 1: Rt=1.84 min, m/z=537 (M+H)⁺.

Description 69: Cis-Ethyl 3-((5-((3-cyano-4-fluorophenyl)carbamoyl)-4-fluoro-1-methyl-1H-pyrrole)-3-sulfonamido)-4-(hydroxymethyl)pyrrolidine-1-carboxylate (D69)

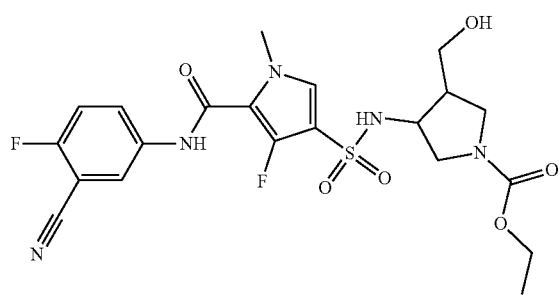 [SMILES: CCOC(=O)N1CC(CO)C(NS(=O)(=O)c2cn(C)c(C(=O)Nc3ccc(F)c(C#N)c3)c2F)C1]

Prepared similarly as described for compound D64 using 5-amino-2-fluorobenzonitrile instead of 3,4,5-trifluoroaniline to give D69. The compound is the cis racemate at the pyrrolidine ring (racemate of 3S,4S and 3R,4R). Method 1: Rt=1.75 min, m/z=512 (M+H)⁺.

Description 70: Cis-Tert-Butyl 3-((4-fluoro-1-methyl-5-((3,4,5-trifluorophenyl)carbamoyl)-1H-pyrrole)-3-sulfonamido)-4-(hydroxymethyl)pyrrolidine-1-carboxylate (D70)

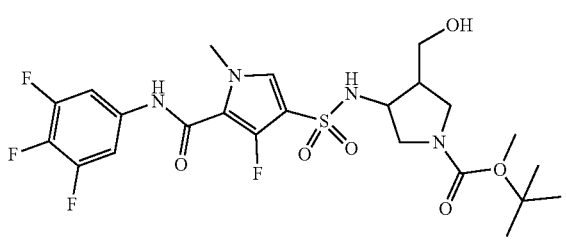

To a suspension of D48 (50 mg, 0.11 mmol) and 3,4,5-trifluoroaniline (32.7 mg, 0.22 mmol) in dry THF (1 mL), lithium bis(trimethylsilyl)amide 1M in THF (0.67 mL, 0.67 mmol) was added dropwise. Reaction mixture was stirred at RT for 1 h, then was diluted with DCM and washed with 5% citric acid solution and water. Organic layer was dried over Na₂SO₄, filtered and solvent removed under reduced pressure to afford crude D70 compound as orange oil (85 mg, y>100%), that was used without further purification. The compound is the cis racemate at the pyrrolidine ring.

Description 71: cis-3-fluoro-4-(N-(2-(hydroxymethyl)cyclopentyl)sulfamoyl)-1-methyl-N-(3,4,5-trifluorophenyl)-1H-pyrrole-2-carboxamide (D71)

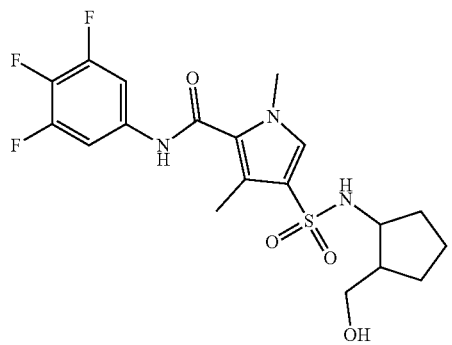 [SMILES: Cc1c(S(=O)(=O)NC2CCCC2CO)cn(C)c1C(=O)Nc1cc(F)c(F)c(F)c1]

Prepared similarly as described for compound D60 starting from D43 (52 mg, 0.149 mmol, 1 eq) and 3,4,5-trifluoroaniline (27 mg, 0.184 mmol, 1.23 eq) to give crude D71 (66.9 mg). Product was used without any purification. Method 1: Rt=2.06 min, m/z=450 (M+H)⁺. The compound is the cis racemate at the cyclopentyl ring.

Description 72: Tert-Butyl (2S,3R)-3-((5-((3,4-difluorophenyl)carbamoyl)-4-fluoro-1-methyl-1H-pyrrole)-3-sulfonamido)-2-(hydroxymethyl)pyrrolidine-1-carboxylate (D72)

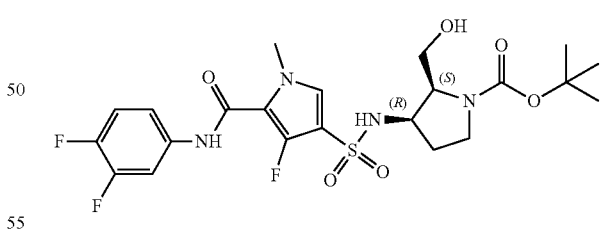

D49 (117.51 mg, 0.261 mmol, 1 eq) was dissolved in THF (1.5 mL, 0.174M), 3,4-difluoroaniline (34 uL, 0.343 mmol, 1.31 eq) was added and 1M solution of lithium bis(trimethylsilyl)amide in THF (1.5 mL, 1.5 mmol, 5.74 eq) was added dropwise. Reaction mixture was stirred at rt and complete conversion was observed after 35 min. Reaction mixture was diluted with DCM, organic layer was washed with 5% aqueous citric acid solution, dried over sodium sulfate, filtered and solvent was removed under reduced pressure to afford D72 as a crude product (141 mg). Method 1: Rt=2.09 min; m/z=523 (M+H)⁺.

Description 73: N-(3,4-difluorophenyl)-3-fluoro-4-(N-(2-(hydroxymethyl)-2-methylcyclopentyl)sulfamoyl)-1-methyl-1H-pyrrole-2-carboxamide (D73)

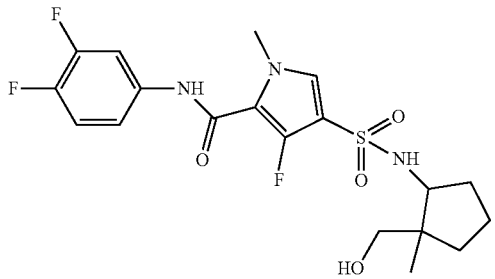 [SMILES: Cn1cc(S(=O)(=O)NC2CCCC2(C)CO)c(F)c1C(=O)Nc1ccc(F)c(F)c1]

D50 (70 mg, 0.193 mmol) was suspended in dry THF (2 mL) under a nitrogen atmosphere and 3,4-difluoroaniline (21 uL, 0.212 mmol, 1.1 eq) was added. LiHMDS 1M in THF (0.966 mL; 0.966 mmol, 5 eq) was added dropwise to the resulting pale yellow solution. The reaction turned dark red and was stirred at rt 1 h, until complete conversion. The reaction was diluted with DCM and washed with 5% citric acid (2×); the organic phase was dried over $Na_2SO_4$ and evaporated, yielding 114 mg of crude D73 as a brown gum, used without further purification. Method 1: Rt=1.70 min, m/z=363 $(M+H)^+$.

Description 74: N-(3,4-difluorophenyl)-3-fluoro-4-(N-((1R,2R and 1S,2S)-2-hydroxy-2-(hydroxymethyl)cyclopentyl)sulfamoyl)-1-methyl-1H-pyrrole-2-carboxamide (D74)

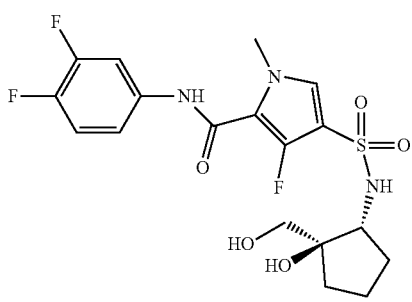 [SMILES: Cn1cc(S(=O)(=O)N[C@@H]2CCC[C@]2(O)CO)c(F)c1C(=O)Nc1ccc(F)c(F)c1]

Crude D52 (21 mg, 0.058 mmol) was suspended in dry THF (1 mL) under a nitrogen atmosphere; 3,4-difluoroaniline (7 uL, 0.066 mmol, 1.15 eq) was added and to the resulting solution LiHMDS 1M in THF (0.288 mL; 0.288 mmol, 5 eq) was added. The reaction turned dark red and was stirred at rt for 2 h: almost complete conversion. The reaction was diluted with DCM and washed with 5% citric acid; the organic phase was dried over $Na_2SO_4$ and evaporated, yielding 38 mg (greater than the theoretical amount) of crude D74 as a dark brown gum, used without further purification. Method 1: Rt=1.71 min, m/z=448 $(M+H)^+$.

Description 75: Cis-Ethyl 4-(N-(1-(ethoxycarbonyl)-4-(hydroxymethyl)-4-methylpyrrolidin-3-yl)sulfamoyl)-3-fluoro-1-methyl-1H-pyrrole-2-carboxylate (D75)

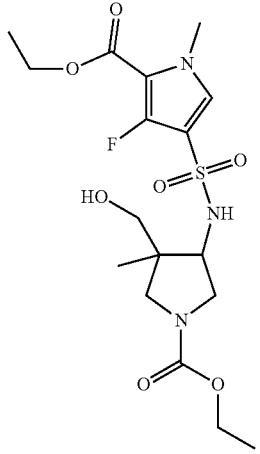 [SMILES: CCOC(=O)c1c(F)c(S(=O)(=O)NC2CN(C(=O)OCC)CC2(C)CO)cn1C]

D15 (110 mg, 0.54 mmol) was dissolved in MeCN (2 mL), cooled to 0° C., treated with ethyl 4-(chlorosulfonyl)-3-fluoro-1-methyl-1H-pyrrole-2-carboxylate (146.7 mg, 0.54 mmol) and then with DIPEA (0.21 mL, 1.2 mmol). The reaction was stirred at room temperature overnight. Solvent was removed in vacuo. The residue was partitioned between DCM and $NaHCO_3$ ss.; the organic layer was evaporated and the residue purified by flash chromatography (direct phase, eluent PE/EtOAc) giving D75 (100 mg, 0.23 mmol) as white solid. Method 1; Rt: 1.64. m/z: 436 $(M+H)^+$.

Description 76: Ethyl 4-((4-fluoro-5-((4-fluoro-3-methylphenyl)carbamoyl)-1-methyl-1H-pyrrole)-3-sulfonamido)-3-(hydroxymethyl)-3-methylpyrrolidine-1-carboxylate (D76)

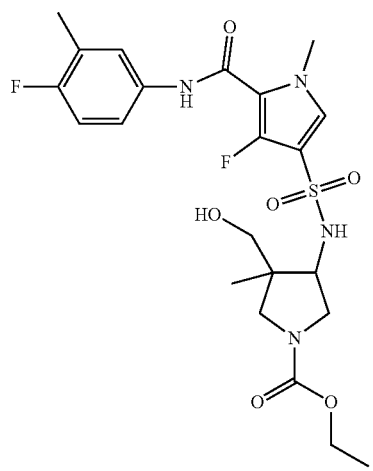 [SMILES: CCOC(=O)N1CC(NS(=O)(=O)c2cn(C)c(C(=O)Nc3ccc(F)c(C)c3)c2F)C(C)(CO)C1]

A solution of D75 (100 mg, 0.23 mmol) and 4-fluoro-3-methylaniline (30.2 mg, 0.24 mmol) in THF (1.45 mL) was treated with a single portion of 1M lithium bis(trimethylsilyl)amide in THF (1.16 mL, 1.16 mmol) at room temperature. The reaction mixture was stirred at room temperature for 1 h. The reaction was poured in water and extracted with EtOAc. The organic layer was washed with 5% citric acid and dried over Na$_2$SO$_4$ (anh), filtered and finally evaporated giving a residue. Purified by Fraction-Lynx (H2O/CH3CN+ 1‰ TFA) giving D76 (100 mg, 0.194 mmol, y:84.6%). $^1$H NMR (300 MHz, DMSO-d$_6$) δ ppm 0.83-0.91 (m, 3H) 1.05-1.12 (m, 3H) 2.16 (d, J=1.28 Hz, 3H) 2.49-2.70 (m, 1H) 2.82 (br t, J=10.22 Hz, 1H) 3.05 (br s, 1H) 3.27-3.54 (m, 4H) 3.67-3.80 (m, 3H) 3.84-4.05 (m, 2H) 4.55-4.78 (m, 1H) 7.05 (t, J=9.22 Hz, 1H) 7.42 (br d, J=4.40 Hz, 2H) 7.53 (br d, J=6.69 Hz, 1H) 7.77 (br d, J=8.62 Hz, 1H) 9.96 (s, 1H). Method 9; Rt: 1.93. m/z: 515.41 (M+H)$^+$.

Description 77: Cis-Ethyl 4-((4-fluoro-1-methyl-5-((3,4,5-trifluorophenyl)carbamoyl)-1H-pyrrole)-3-sulfonamido)-3-(hydroxymethyl)-3-methylpyrrolidine-1-carboxylate (D77)

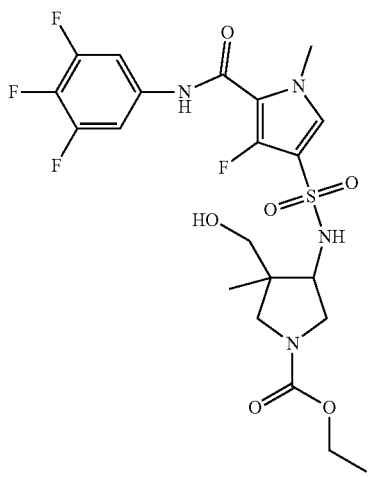 [SMILES: CCOC(=O)N1CC(NS(=O)(=O)c2cn(C)c(C(=O)Nc3cc(F)c(F)c(F)c3)c2F)C(C)(CO)C1]

A mixture of D75 (55 mg, 0.13 mmol), 3,4,5-trifluoroaniline (20.44 mg, 0.14 mmol) in THF (1 mL) was treated with a single portion of 1M lithium bis(trimethylsilyl)amide in THF (0.632 mL, 0.632 mmol) at room temperature. The resulting brown mixture was stirred at room temperature for 15 min. Solvent was removed in vacuo, the residue partitioned between water and EtOAc; the organic layer was dried over Na$_2$SO$_4$ (anh.), filtered and finally evaporated, giving D77 (30 mg, 0.056 mmol, yield: 44%) that was used in the next step without any further purification. Method 9; Rt: 2.04. m/z: 537 (M+H)$^+$.

Description D78: Ethyl (3R,4R)-3-((4-fluoro-5-((4-fluoro-3-methylphenyl)carbamoyl)-1-methyl-1H-pyrrole)-3-sulfonamido)-4-(hydroxymethyl)pyrrolidine-1-carboxylate (D78)

Compound D78 was prepared according to the Scheme 12 below:

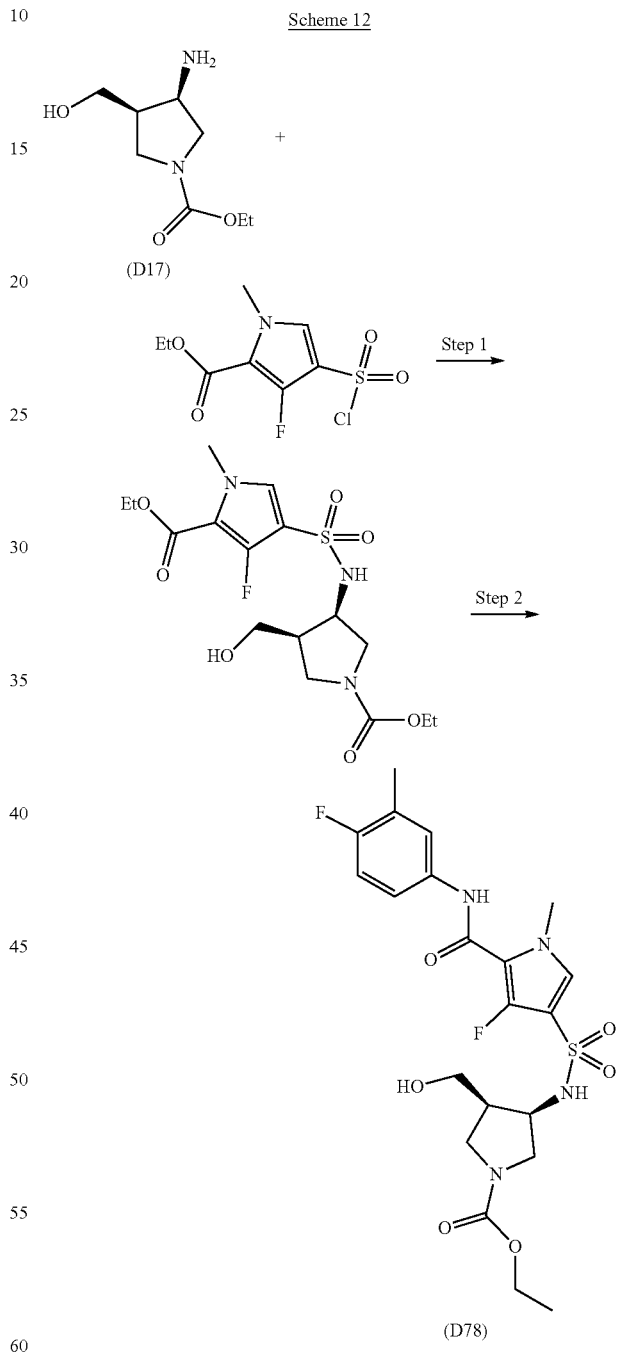

Step 1:
To a solution of D17 (1351.61 mg, 7.18 mmol) in dry MeCN (24 mL), DIPEA (2.5 mL, 14.36 mmol) was added; then a solution of ethyl 4-(chlorosulfonyl)-3-fluoro-1-methyl-1H-pyrrole-2-carboxylate (1936.57 mg, 7.18 mmol) in dry MeCN (12 mL) was added dropwise over 10 minutes.

The reaction was stirred at RT for 90 min then was concentrated under reduced pressure; diluted with EtOAc (130 mL) and washed with 5% citric acid solution (40 ml) and brine (20 ml), dried over Na$_2$SO$_4$ (anh.), filtered and solvent removed under reduced pressure. The crude was purified by direct flash chromatography (eluent DCM/AcOEt) to afford ethyl 4-(N-((3R,4R)-1-(ethoxycarbonyl)-4-(hydroxymethyl)pyrrolidin-3-yl)sulfamoyl)-3-fluoro-1-methyl-1H-pyrrole-2-carboxylate (2.9 g, yield=910%) as a white solid. Method 1: Rt=1.44 min; m/z=422.41 (M+H)$^+$.

Step 2:

To a solution of ethyl 4-(N-((3R,4R)-1-(ethoxycarbonyl)-4-(hydroxymethyl)pyrrolidin-3-yl)sulfamoyl)-3-fluoro-1-methyl-1H-pyrrole-2-carboxylate (2.7 g, 6.43 mmol) prepared in Step 1 and 4-fluoro-3-methylaniline (0.845 g, 6.75 mmol) in dry THF (50 mL), lithium bis(trimethylsilyl)amide (1M in THF) (3.33 mL, 20 mmol) was added dropwise at room temperature. After 60 min the reaction was quenched with water, diluted with DCM and washed with aq 5% citric acid and brine. The organic layer was dried over Na$_2$SO$_4$, filtered and concentrated under reduced pressure to afford D78 as a brown foam that was used without further purification. Method 1: Rt=1.81 min; m/z=501.16 (M+H)$^+$.

Synthesis of Ethyl (3R,4R)-3-((4-fluoro-5-((4-fluoro-3-methylphenyl)carbamoyl)-1-methyl-1H-pyrrole)-3-sulfonamido)-4-(mercaptomethyl)pyrrolidine-1-carboxylate (D81)

D81 was prepared according to the following Scheme 13. Synthetic steps are described below.

Scheme 13

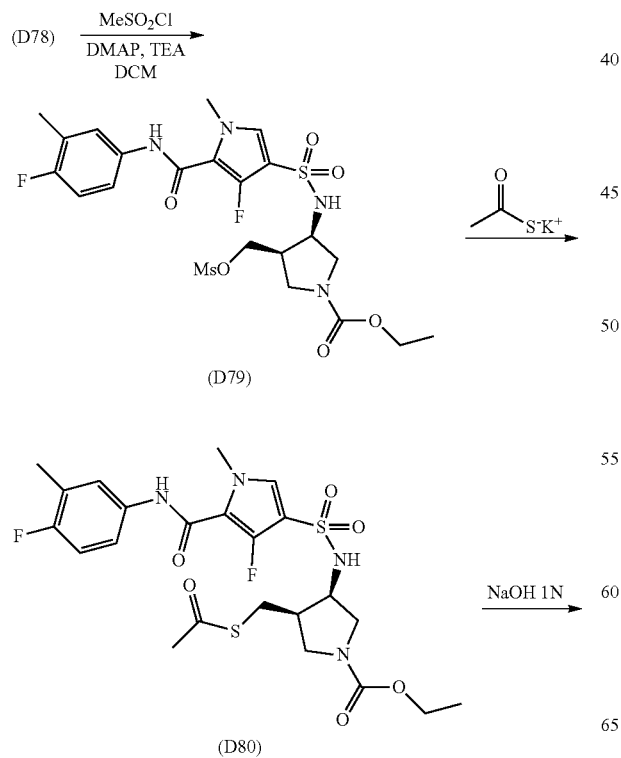

Description 79: Ethyl (3R,4R)-3-((4-fluoro-5-((4-fluoro-3-methylphenyl)carbamoyl)-1-methyl-1H-pyrrole)-3-sulfonamido)-4-(((methylsulfonyl)oxy)methyl)pyrrolidine-1-carboxylate (D79)

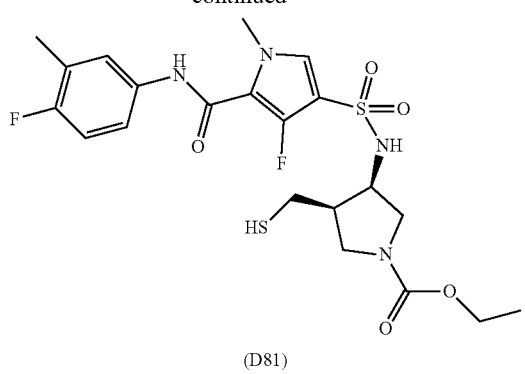

(D81)

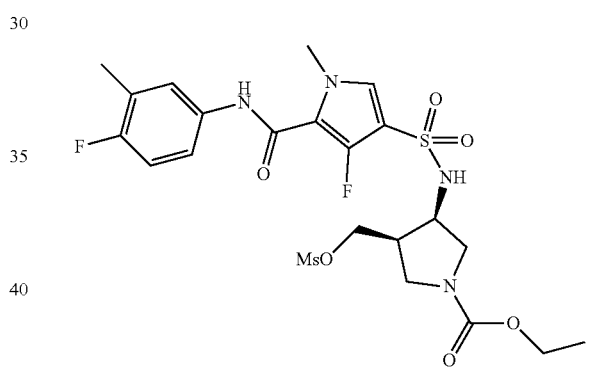

To a solution of D78 ethyl 3-((4-fluoro-5-((4-fluoro-3-methylphenyl)carbamoyl)-1-methyl-1H-pyrrole)-3-sulfonamido)-4-(hydroxymethyl)pyrrolidine-1-carboxylate (623 mg, 1.24 mmol) in dry DCM (27 mL), triethylamine (0.35 mL, 2.49 mmol) and DMAP (15.2 mg, 0.12 mmol) were sequentially added. The resulting solution was cooled to 0° C. and methanesulfonyl chloride (0.13 mL, 1.62 mmol) was added dropwise. The reaction mixture was stirred for 5 min at 0° C. then 1 h at RT. The mixture was diluted with DCM and washed twice with 5% citric acid solution and brine. Organic layer was dried over Na$_2$SO$_4$, filtered and concentrated under reduced pressure, to obtain a crude product D79 ethyl 3-((4-fluoro-5-((4-fluoro-3-methylphenyl)carbamoyl)-1-methyl-1H-pyrrole)-3-sulfonamido)-4-(((methylsulfonyl)oxy)methyl)pyrrolidine-1-carboxylate in almost quantitative yield (721 mg), that was used in the next step without further purification. Method 1; Rt=1.98 min; m/z=579 (M+H)$^+$.

Description 80: Ethyl (3R,4R)-3-((acetylthio)methyl)-4-((4-fluoro-5-((4-fluoro-3-methylphenyl)carbamoyl)-1-methyl-1H-pyrrole)-3-sulfonamido)pyrrolidine-1-carboxylate (D80)

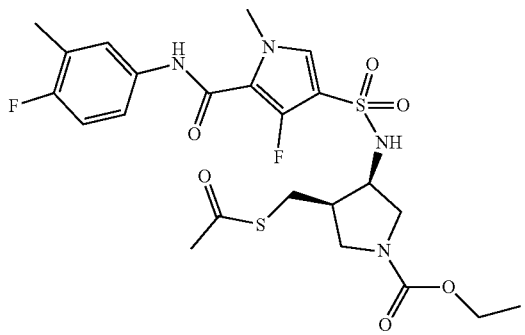 [SMILES: CCOC(=O)N1C[C@@H](CSC(C)=O)[C@@H](NS(=O)(=O)c2cn(C)c(C(=O)Nc3ccc(F)c(C)c3)c2F)C1]

To a solution of D79 (257 mg, 0.44 mmol) in dry DMF (7.6 ml) was added potassium thioacetate (634 mg, 5.55 mmol). The dark-red reaction mixture was stirred at room temperature overnight, then was diluted with EtOAc and washed with water. The organic layer was dried over $Na_2SO_4$ anhydrous, filtered and concentrated under reduced pressure. The resulting crude was purified by flash chromatography on silica (eluent petroleum ether/EtOAc) to obtain D80 (170 mg, y=68.5%) as off-white foam. Method 1; Rt=2.12 min; m/z=559 (M+H)$^+$.

Description 81: Ethyl (3R,4R)-3-((4-fluoro-5-((4-fluoro-3-methylphenyl)carbamoyl)-1-methyl-1H-pyrrole)-3-sulfonamido)-4-(mercaptomethyl)pyrrolidine-1-carboxylate (D81)

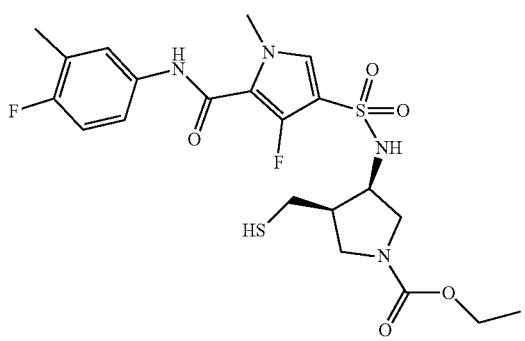 [SMILES: CCOC(=O)N1C[C@@H](CS)[C@@H](NS(=O)(=O)c2cn(C)c(C(=O)Nc3ccc(F)c(C)c3)c2F)C1]

To a solution of D80 (443 mg, 0.79 mmol) in methanol (3.7 mL) was added 1N NaOH solution (1.52 mL, 1.52 mmol), and the reaction mixture was stirred at room temperature for 40 min. The reaction was diluted with water, acidified with 1N HCl until pH=3 (a white solid precipitated), and extracted twice with EtOAc. Organic layer was dried over $Na_2SO_4$, filtered and concentrated under vacuo, to obtain 396 mg of a light-yellow foam (containing desired product and S—S dimer, ratio 1:1). The residue was dissolved in acetic acid (9 mL), zinc (1037 mg, 15.86 mmol) was added and the reaction mixture was stirred at 100° C. for 2 h. The reaction was filtered through a pad of celite, washed with DCM and concentrated under vacuo, to obtain crude D81 (431 mg) as white foam, that was used in the next step without further purification. Method 1; Rt=2.09 min; m/z=517 (M+H)$^+$.

Synthesis of Cis-Tert-Butyl 4-((4-fluoro-5-((4-fluoro-3-methylphenyl)carbamoyl)-1-methyl-1H-pyrrole)-3-sulfonamido)-3-(hydroxymethyl)piperidine-1-carboxylate (D83)

D83 was prepared according to the following Scheme 14:

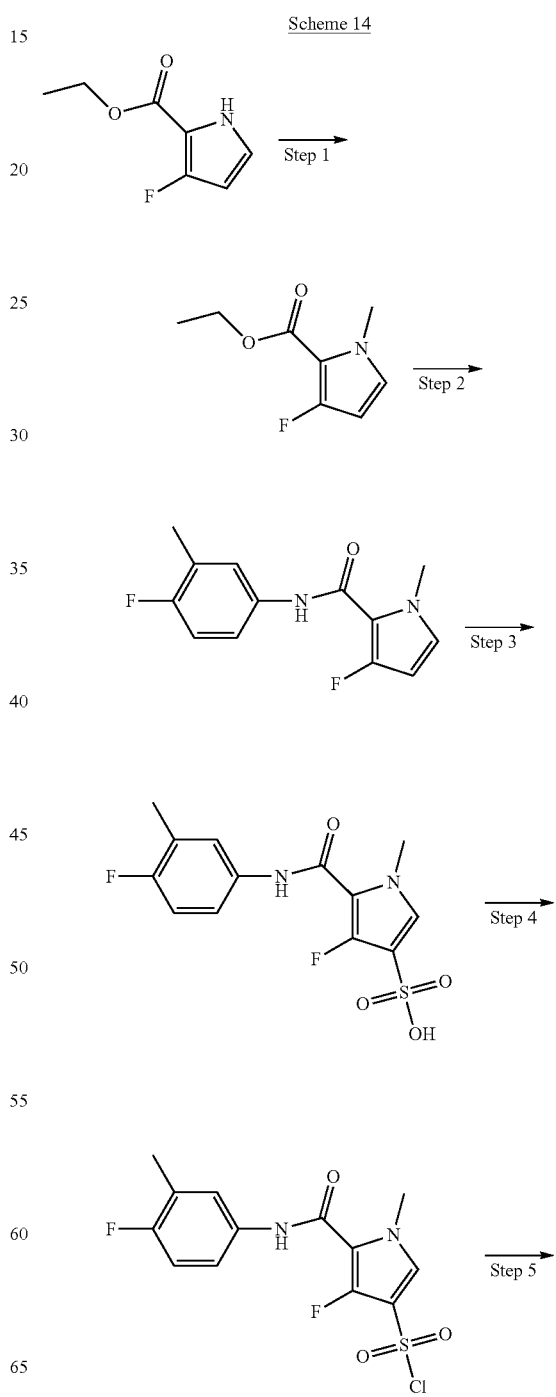

Scheme 14

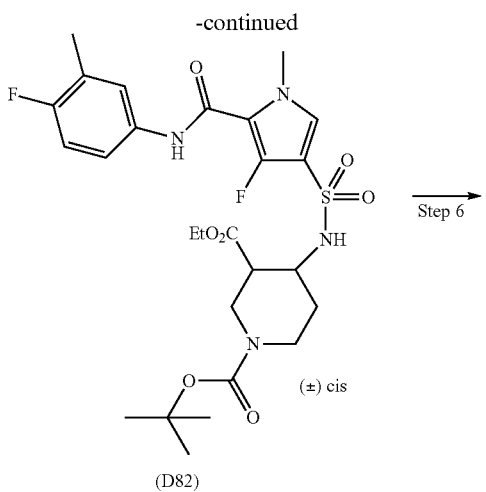

(D82)

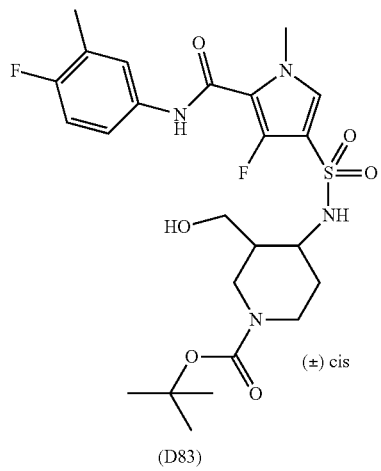

(D83)

Synthetic steps are described below.
Step 1
To a solution of ethyl 3-fluoro-1H-pyrrole-2-carboxylate (12.5 g, 79.6 mmol) in dry DMF (125 mL) cooled to 0° C. under nitrogen atmosphere, sodium hydride (60% weight in mineral oil, 3.7 g, 92.5 mmol) was added portion wise over 30 min. The reaction mixture was stirred for further 20 min then iodomethane (5.8 mL, 93.2 mmol) was added dropwise over 30 min. The mixture was stirred for further 30 min at the same temperature then quenched with 2N HCl (20 mL). The reaction mixture was dumped into water (120 mL) and toluene (650 mL) and the mixture was vigorously stirred for 10 min. The two phase were separated and the organic phase washed with water (250 mL) and brine (250 mL), dried over $Na_2SO_4$ (anh.) and filtered. Ethyl 3-fluoro-1-methyl-1H-pyrrole-2-carboxylate (13.6 g) was obtained as a pale yellow oil after solvent evaporation and used without further purification. $^1$H NMR (300 MHz, DMSO-d6) δ ppm 1.27 (t, J=7.11 Hz, 3H), 3.78 (s, 3H), 4.23 (q, J=7.06 Hz, 2H), 5.99 (d, J=3.03 Hz, 1H), 7.00 (dd, J=5.27, 3.07 Hz, 1H).
Step 2
Ethyl 3-fluoro-1-methyl-1H-pyrrole-2-carboxylate (13.6 g, 79.5 mmol), prepared in Step 1, and 4-Fluoro-3-methyl-aniline (10.3 g, 82.3 mmol) were dissolved in dry toluene (50 mL). Lithium bis(trimethylsilyl)amide (LHMDS, 140 mL, 1 M in toluene, 140 mmol) was added dropwise over 30 min and the reaction mixture was stirred at room temperature for further 30 min. The reaction mixture was cooled at 0° C. and slowly quenched with 2N HCl (200 mL), diluted with water (200 mL) and toluene (200 mL) and stirred at RT for 20 min. The two phases were separated and the organic phase washed with sat. $NaHCO_3$ (200 mL) and brine (200 mL), dried over $Na_2SO_4$ (anh.) and filtered. 3-fluoro-N-(4-fluoro-3-methylphenyl)-1-methyl-1H-pyrrole-2-carboxamide (19.8 g) was obtained as a light brown solid after solvent evaporation and used without further purification. $^1$H NMR (300 MHz, DMSO-d6) δ ppm 2.22 (s, 3H), 3.76 (s, 3H), 6.01 (d, J=3.03 Hz, 1H), 6.91 (dd, J=5.27, 3.07 Hz, 1H), 7.08 (t, J=9.22 Hz, 1H), 7.35-7.53 (m, 1H), 7.59 (dd, J=7.06, 2.20 Hz, 1H), 9.50 (br s, 1H).
Step 3
To a solution of 3-fluoro-N-(4-fluoro-3-methylphenyl)-1-methyl-1H-pyrrole-2-carboxamide (19.8 g, 79.5 mmol), prepared in Step 2, in dry DCM (90 mL) cooled to 0° C. under nitrogen atmosphere, chlorosulfonic acid (5.7 mL, 85.6 mmol) dissolved in dry DCM (120 mL) was added dropwise over 90 min. The reaction mixture was stirred at the same temperature for further 30 min; then the formed precipitate was filtered and washed several times with $Et_2O$. 4-fluoro-5-((4-fluoro-3-methylphenyl)carbamoyl)-1-methyl-1H-pyrrole-3-sulfonic acid (23.1 g, 88% yield over three steps) obtained as a light grey solid was dried under vacuum overnight and used without further purification. $^1$H NMR (300 MHz, DMSO-d6) δ ppm 2.22 (s, 3H), 3.70 (s, 3H), 6.93 (d, J=5.04 Hz, 1H), 7.07 (t, J=9.22 Hz, 1H), 7.44-7.52 (m, 1H), 7.60 (dd, J=7.06, 2.20 Hz, 1H), 9.64 (s, 1H).
Step 4
Dry DMF (0.35 mL, 4.51 mmol) was added to a suspension of 4-fluoro-5-((4-fluoro-3-methylphenyl)carbamoyl)-1-methyl-1H-pyrrole-3-sulfonic acid (14.9 g, 45.1 mmol), prepared in Step 3, in thionyl chloride (112 mL). The reaction mixture was heated to 75° C. and stirred at the same temperature for 45 min. The brown solution was cooled to RT, diluted with toluene (200 mL) and slowly poured into a mixture of toluene (200 mL) and ice (500 mL) under vigorous stirring. The biphasic system was stirred for 20 min, the two phases were separated and the organic phase washed with ice-water (200 mL) and brine (200 mL), dried over $Na_2SO_4$ (anh.), filtered and concentrated under reduced pressure. The residue was purified on silica (eluent ETP/AcOEt gradient) yielding 4-fluoro-5-((4-fluoro-3-methylphenyl)carbamoyl)-1-methyl-1H-pyrrole-3-sulfonyl chloride (13.9 g, 88% yield) as a beige powder. $^1$H NMR (300 MHz, CDCl3) δ ppm 2.31 (s, 3H), 4.06 (s, 3H), 7.03 (t, J=8.89 Hz, 1H), 7.26-7.36 (m, 2H), 7.39-7.46 (m, 1H), 7.72 (br d, J=8.16 Hz, 1H).
Step 5
4-fluoro-5-((4-fluoro-3-methylphenyl)carbamoyl)-1-methyl-1H-pyrrole-3-sulfonyl chloride, obtained from Step 4, (672 mg, 1.93 mmol) was added to a solution of D20 (525 mg, 1.93 mmol) and DIPEA (1.5 mL) in dry MeCN (12 mL). The dark orange solution was stirred at RT for 2 hrs then was concentrated under reduce pressure. The residue was taken up in EtOAc and washed with 5% citric acid solution and brine. The organic layer was dried over $Na_2SO_4$ filtered and concentrated. Purification by direct flash chromatography (eluent cyclohexane/EtOAc) afford cis-1-(tert-butyl) 3-ethyl 4-((4-fluoro-5-((4-fluoro-3-methylphenyl)carbamoyl)-1-methyl-1H-pyrrole)-3-sulfonamido)piperidine-1,3-dicarboxylate D82 (710 mg, 63%) as an off white foam. $^1$H NMR (300 MHz, DMSO-d₆) δ ppm 1.14-1.21 (m, 3H) 1.33-1.41 (m, 9H) 1.46-1.58 (m, 1H) 1.76-1.91 (m, 1H) 2.23 (s, 3H) 2.66-2.79 (m, 1H) 3.14-3.31 (m, 1H) 3.42-3.82 (m, 7H) 3.85-4.10 (m, 2H) 7.07-7.12 (m, 1H) 7.40-7.51 (m, 2H) 7.54-7.63 (m, 1H) 7.9 (d, J=8.16 Hz, 1H) 9.99 (s, 1H) Method 1; Rt: 2.31 min. m/z: 585 (M+H)⁺.

Step 6

LiAlH₄ (2M in THF, 0.9 mL) was added dropwise to a solution D82 (700 mg, 1.2 mmol) in dry THF (12 mL), cooled to −10° C. The resulting mixture was stirred at the same temperature 1 hr then diluted with AcOEt and treated with a sat. solution of Rochelle salt. The biphasic mixture was stirred at RT for 30 min then the two phases were separated and the organic layer was washed with brine, dried over Na₂SO₄, filtered and concentrated to obtain cis-tert-butyl 4-((4-fluoro-5-((4-fluoro-3-methylphenyl)carbamoyl)-1-methyl-1H-pyrrole)-3-sulfonamido)-3-(hydroxymethyl)piperidine-1-carboxylate D83 (430 mg) as a pale yellow foam used without further purification. Method 1; Rt: 2.05 min. m/z: 543 (M+H)⁺.

Description 84: trans-1-(tert-butyl) 3-ethyl 4-((4-fluoro-5-((4-fluoro-3-methylphenyl)carbamoyl)-1-methyl-1H-pyrrole)-3-sulfonamido)piperidine-1,3-dicarboxylate (D84)

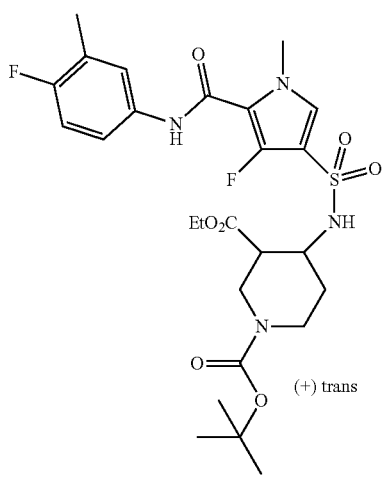 [SMILES: CCOC(=O)C1CN(C(=O)OC(C)(C)C)CCC1NS(=O)(=O)c1cn(C)c(C(=O)Nc2ccc(F)c(C)c2)c1F]

D84 (610 mg, 69%) was prepared similarly as described for compound D82 using D22 (406 mg, 1.49 mmol) in Step 5 of Scheme 14, instead of D20. ¹H NMR (300 MHz, DMSO-d6) δ ppm 1.15 (t, J=7.11 Hz, 3H) 1.33-1.43 (m, 10H) 1.71-1.85 (m, 1H) 2.23 (s, 3H) 2.32-2.42 (m, 1H) 2.84-3.14 (m, 2H) 3.43-3.58 (m, 1H) 3.70-3.84 (m, 4H) 3.84-4.06 (m, 3H) 7.11 (t, J=9.00 Hz, 1H) 7.39-7.51 (m, 2H) 7.59 (br d, J=6.97 Hz, 1H) 7.92 (br d, J=8.44 Hz, 1H) 9.97 (s, 1H). Method 1; Rt: 2.29 min. m/z: 585 (M+H)⁺.

Description 85: Trans-Tert-Butyl 4-((4-fluoro-5-((4-fluoro-3-methylphenyl)carbamoyl)-1-methyl-1H-pyrrole)-3-sulfonamido)-3-(hydroxymethyl)piperidine-1-carboxylate (D85)

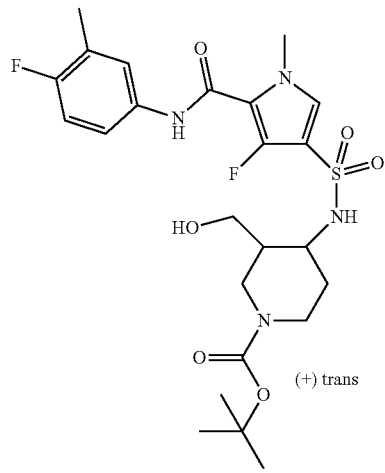 [SMILES: Cc1cc(NC(=O)c2c(F)c(S(=O)(=O)NC3CCN(C(=O)OC(C)(C)C)CC3CO)cn2C)ccc1F]

D85 (550 mg) was prepared similarly as described for compound D83 starting from D84 (600 mg, 0.79 mmol) instead of D82. ¹H NMR (300 MHz, DMSO-d6) δ ppm 1.31 (br s, 1H) 1.38 (s, 9H) 1.42-1.50 (m, 1H) 1.68 (br d, J=9.90 Hz, 1H) 2.23 (s, 3H) 2.52-2.64 (m, 1H) 2.72 (br t, J=11.69 Hz, 1H) 2.94-3.16 (m, 2H) 3.62 (br d, J=7.61 Hz, 1H) 3.73-3.86 (m, 4H) 4.07 (br d, J=11.74 Hz, 1H) 4.48 (br s, 1H) 7.11 (t, J=9.63 Hz, 1H) 7.40-7.52 (m, 2H) 7.56-7.64 (m, 1H) 7.72 (br d, J=6.24 Hz, 1H) 9.97 (s, 1H). Method 1; Rt: 2.04 min. m/z: 543.41 (M+H)⁺.

Description 86: Cis-1-(tert-butyl) 4-ethyl 3-((4-fluoro-5-((4-fluoro-3-methylphenyl)carbamoyl)-1-methyl-1H-pyrrole)-3-sulfonamido)piperidine-1,4-dicarboxylate (D86)

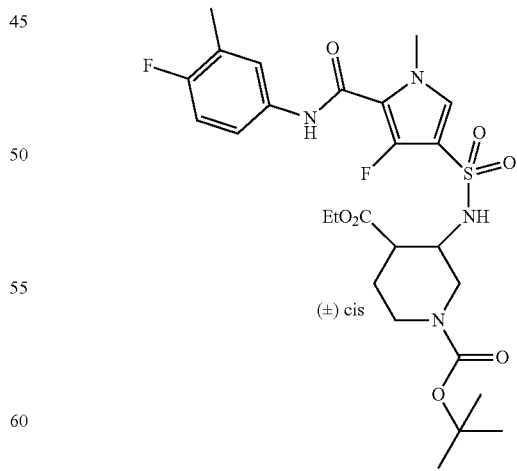

D86 (890 mg, 75%) was prepared similarly as described for compound D82 using D25 (556 mg, 2.04 mmol) in Step 5 of Scheme 14 instead of D20. ¹H NMR (300 MHz, DMSO-d₆) δ ppm 1.13 (t, J=7.20 Hz, 3H) 1.33 (s, 9H)

1.53-1.67 (m, 1H) 1.81-1.98 (m, 1H) 2.23 (s, 3H) 2.67-2.90 (m, 2H) 2.92-3.11 (m, 1H) 3.61-3.94 (m, 7H) 4.01-4.11 (m, 1H) 7.11 (t, J=9.17 Hz, 1H) 7.34-7.51 (m, 2H) 7.57 (br d, J=6.10 Hz, 1H) 7.87 (d, J=8.25 Hz, 1H) 9.90 (br s, 1H). Method 1; Rt: 2.28. m/z: 585.36 (M+H)+.

Description 87: Cis-Tert-Butyl 3-((4-fluoro-5-((4-fluoro-3-methylphenyl)carbamoyl)-1-methyl-1H-pyrrole)-3-sulfonamido)-4-(hydroxymethyl)piperidine-1-carboxylate (D87)

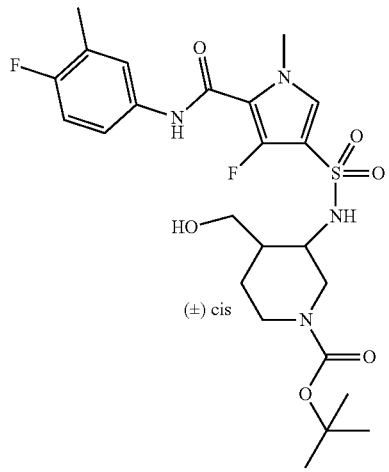 [SMILES: Cc1cc(NC(=O)c2c(F)c(S(=O)(=O)NC3CN(C(=O)OC(C)(C)C)CCC3CO)cn2C)ccc1F]

D87 (620 mg) was prepared similarly as described for compound D83 starting from D86 (890 mg, 1.52 mmol) instead of D82. $^1$H NMR (300 MHz, DMSO-$d_6$) δ ppm 1.36 (s, 9H) 1.42-1.61 (m, 2H) 1.63-1.75 (m, 1H) 2.23 (s, 3H) 2.58-2.77 (m, 1H) 2.85 (br d, J=13.30 Hz, 1H) 3.17-3.28 (m, 2H) 3.33-3.44 (m, 1H) 3.79 (s, 3H) 3.81-3.98 (m, 2H) 4.37 (brt, J=4.80 Hz, 1H) 7.11 (t, J=8.89 Hz, 1H) 7.38-7.52 (m, 2H) 7.52-7.66 (m, 2H) 9.90 (br s, 1H). Method 1; Rt: 2.03 min. m/z: 543.31 (M+H)+.

Description 88: Trans-1-(tert-butyl) 4-ethyl 3-((4-fluoro-5-((4-fluoro-3-methylphenyl)carbamoyl)-1-methyl-1H-pyrrole)-3-sulfonamido)piperidine-1,4-dicarboxylate (D88)

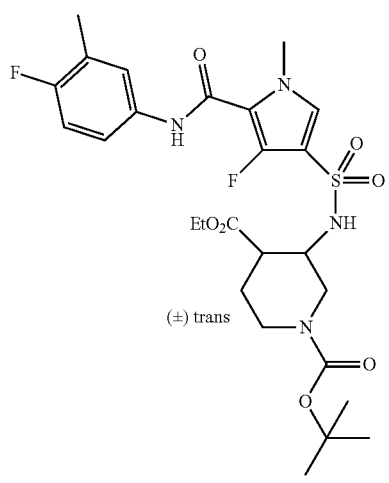 [SMILES: CCOC(=O)C1CCN(C(=O)OC(C)(C)C)CC1NS(=O)(=O)c1cn(C)c(C(=O)Nc2ccc(F)c(C)c2)c1F]

D88 (206 mg, 99%) was prepared similarly as described for compound D82 using D27 (96 mg, 0.35 mmol) in Step 5 of Scheme 14 instead of D20. Method 1; Rt: 2.28 min. m/z: 585 (M+H)+.

Description 89: Trans-Tert-Butyl 3-((4-fluoro-5-((4-fluoro-3-methylphenyl)carbamoyl)-1-methyl-1H-pyrrole)-3-sulfonamido)-4-(hydroxymethyl)piperidine-1-carboxylate (D89)

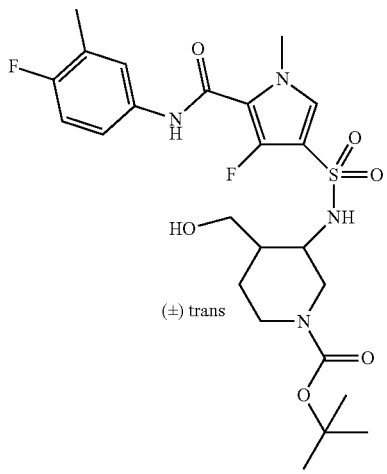 [SMILES: Cc1cc(NC(=O)c2c(F)c(S(=O)(=O)NC3CN(C(=O)OC(C)(C)C)CCC3CO)cn2C)ccc1F]

D89 (170 mg) was prepared similarly as described for compound D83 starting from D88 (206 mg, 0.35 mmol) instead of D82. Method 1; Rt: 2.04 min. m/z: 543 (M+H)+.

Synthesis of Trans-Tert-Butyl 3-((4-fluoro-5-((4-fluoro-3-methylphenyl)carbamoyl)-1-methyl-1H-pyrrole)-3-sulfonamido)-4-(hydroxymethyl)pyrrolidine-1-carboxylate (D91)

Scheme 15

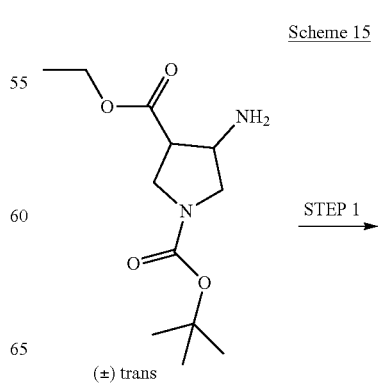

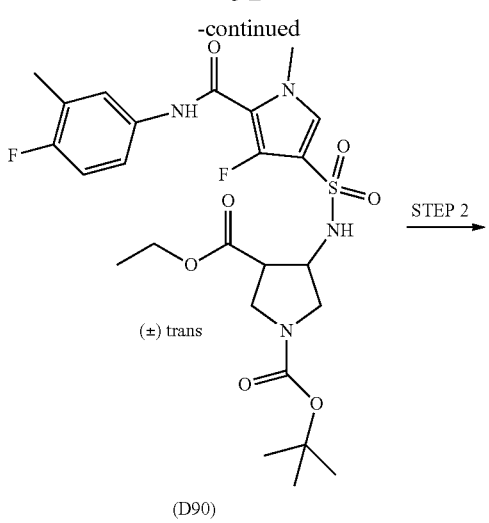

(D90)

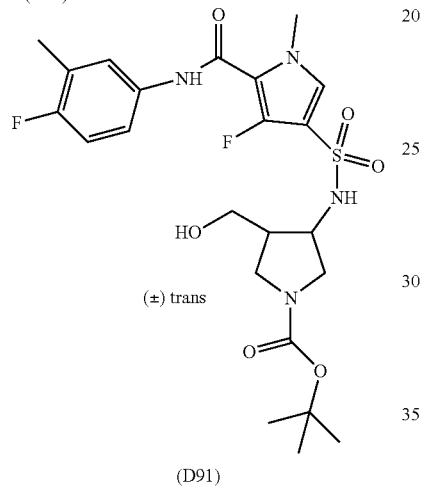

(D91)

Scheme 15 refers to the synthesis of D91. Synthetic steps are detailed below.

Step 1

To a solution of trans-1-tert-Butyl 3-ethyl 4-aminopyrrolidine-1,3-dicarboxylate (Fluorochem, cat no 317896) (200 mg, 0.77 mmol) in MeCN (1 mL) was added DIPEA (0.27 mL, 1.55 mmol) followed by 4-fluoro-5-((4-fluoro-3-methylphenyl)carbamoyl)-1-methyl-1H-pyrrole-3-sulfonyl chloride (prepared as in Step 4 of Scheme 14, 270 mg, 0.77 mmol). The reaction was stirred overnight at room temperature. Solvent was removed in vacuo and the residue was partitioned between EtOAc and 5% citric acid (acq, solution). The organic layer was dried over $Na_2SO_4$ (anh.), filtered and evaporated giving trans-1-(tert-butyl) 3-ethyl 4-((4-fluoro-5-((4-fluoro-3-methylphenyl)carbamoyl)-1-methyl-1H-pyrrole)-3-sulfonamido)pyrrolidine-1,3-dicarboxylate D90 trans-1-(tert-butyl) 3-ethyl 4-((4-fluoro-5-((4-fluoro-3-methylphenyl)carbamoyl)-1-methyl-1H-pyrrole)-3-sulfonamido)pyrrolidine-1,3-dicarboxylate (450 mg, 0.789 mmol) as white solid, used in the next step without any purification. $^1$H NMR (300 MHz, DMSO-$d_6$) δ ppm 1.05-1.23 (m, 3H) 1.38 (br s, 9H) 2.18-2.27 (m, 3H) 2.92-3.18 (m, 2H) 3.19-3.42 (m, 1H) 3.43-3.65 (m, 2H) 3.80 (s, 3H) 3.88-4.11 (m, 3H) 7.11 (t, J=9.17 Hz, 1H) 7.42-7.54 (m, 2H) 7.54-7.66 (m, 1H) 8.26 (br d, J=7.24 Hz, 1H) 10.02 (s, 1H). Method 1; Rt: 2.26 min. m/z: 571 (M+H)$^+$ Step 2

D90 trans-1-(tert-butyl) 3-ethyl 4-((4-fluoro-5-((4-fluoro-3-methylphenyl)carbamoyl)-1-methyl-1H-pyrrole)-3-sulfonamido)pyrrolidine-1,3-dicarboxylate (370 mg, 0.700 mmol) was dissolved in THF (5 mL) and treated with 1M $LiAlH_4$ in THF (946 uL, 0.946 mmol), added in portions (0.2 mL) over 5 min. After 15 min the reaction was stopped by slow addition of water (2 mL) and stirred 10 min. A saturated solution of Rochelle's salt was added (10 mL) followed by EtOAc (20 mL) and the reaction mixture was stirred further for 20 min. The resulting mixture was poured into a separating funnel and the aqueous layer extracted one time with EtOAc. The combined organic extracts were dried over $Na_2SO_4$ (anh.), filtered and finally evaporated in vacuo giving D91 trans-tert-butyl 3-((4-fluoro-5-((4-fluoro-3-methylphenyl)carbamoyl)-1-methyl-1H-pyrrole)-3-sulfonamido)-4 (hydroxymethyl)pyrrolidine-1-carboxylate (370 mg, 0.7 mmol) as white solid. Method 1; Rt: 1.98 min. m/z: 529 (M+H)$^+$.

Synthesis of Tert-Butyl (3R,4S)-3-((4-fluoro-5-((4-fluoro-3-methylphenyl)carbamoyl)-1-methyl-1H-pyrrole)-3-sulfonamido)-4-(hydroxymethyl)pyrrolidine-1-carboxylate (D93)

D93 was prepared according to the following Scheme16:

Scheme 16

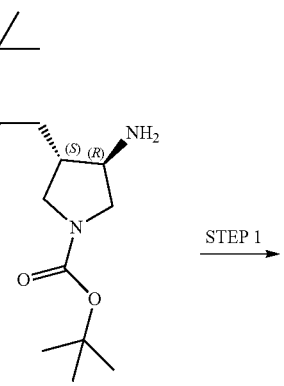

Org. Biomol. Chem. 2004, 2, 2763-2776

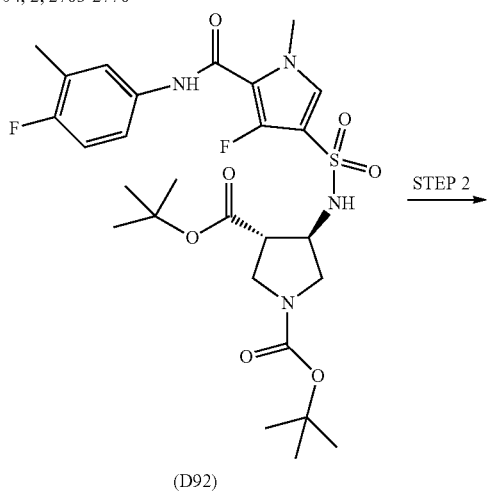

(D92)

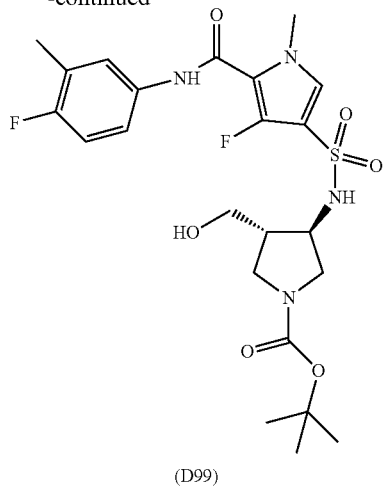

(D99)

Synthetic steps are described below.

Step 1

Prepared similarly as described for compound D90, using di-tert-butyl (3S,4R)-4-aminopyrrolidine-1,3-dicarboxylate (Org. Biomol. Chem., 2004, 2, 2763-2776) instead of trans-1-tert-Butyl 3-ethyl 4-aminopyrrolidine-1,3-dicarboxylate to obtain di-tert-butyl (3S,4R)-4-((4-fluoro-5-((4-fluoro-3-methylphenyl)carbamoyl)-1-methyl-1H-pyrrole)-3-sulfonamido)pyrrolidine-1,3-dicarboxylate D92 (38 mg, 0.063 mmol) as colourless oil. Method 1; Rt=2.40 min. m/z=599 (M+H)$^+$.

Step 2

Prepared similarly as described for compound D91, starting from D92 di-tert-butyl (3S,4R)-4-((4-fluoro-5-((4-fluoro-3-methylphenyl)carbamoyl)-1-methyl-1H-pyrrole)-3-sulfonamido)pyrrolidine-1,3-dicarboxylate to obtain tert-butyl (3R,4S)-3-((4-fluoro-5-((4-fluoro-3-methylphenyl)carbamoyl)-1-methyl-1H-pyrrole)-3-sulfonamido)-4-(hydroxymethyl)pyrrolidine-1-carboxylate D93 (21 mg) as colourless oil. Method 1; Rt=1.97 min. m/z=529 (M+H)$^+$.

Description 94: Ethyl (2R,4R)-4-((4-fluoro-1-methyl-5-((3,4,5-trifluorophenyl)carbamoyl)-1H-pyrrole)-3-sulfonamido)-2-(hydroxymethyl)pyrrolidine-1-carboxylate (D94)

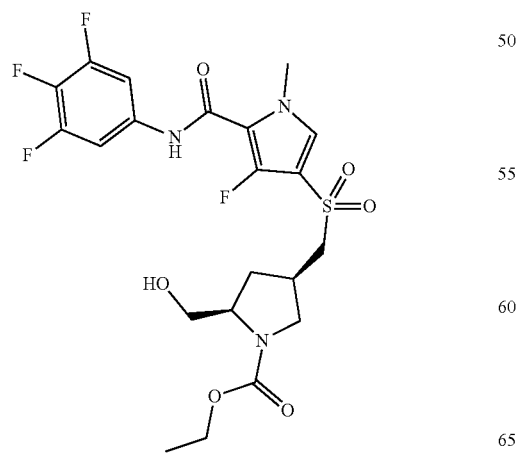

A 1M solution of LHMDS in THF (0.9 mL, 0.9 mmol) was added to a solution of 3,4,5-trifluoroaniline (25.7 mg, 0.17 mmol) and D53 (70 mg, 0.17 mmol) in dry THF (2 mL). The reaction was stirred at RT for 2 hrs then quenched with sat NH$_4$Cl solution and diluted with EtOAc The two phases were separated and the organic layer was washed with brine, dried over Na$_2$SO$_4$ filtered and concentrated to afford D94 (79 mg) as an orange solid used without further purification. Method 1; Rt: 1.99 min. m/z: 523 (M+H)$^+$.

Description 95: Cis 4-(N-(1-benzyl-4-(hydroxymethyl)-2-oxopyrrolidin-3-yl)sulfamoyl)-3-fluoro-N-(4-fluoro-3-methylphenyl)-1-methyl-1H-pyrrole-2-carboxamide (D95)

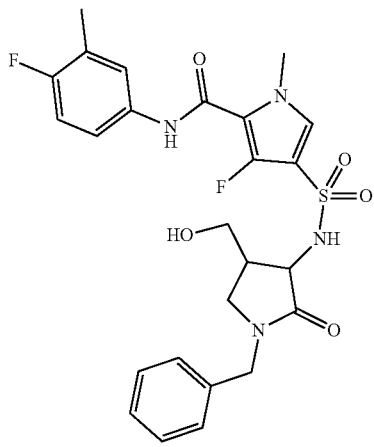 [SMILES: Cc1cc(NC(=O)c2c(F)c(S(=O)(=O)NC3C(=O)N(Cc4ccccc4)CC3CO)cn2C)ccc1F]

A 1M solution of LHMDS in THF (2.6 mL, 2.6 mmol) was added to a solution of 4-Fluoro-3-methylaniline (66 mg, 0.52 mmol) and D54 (232 mg, 0.51 mmol) in dry THF (5 mL). The reaction was stirred at RT for 2 hrs then quenched with sat NH$_4$Cl solution and diluted with EtOAc. The two phases were separated and the organic layer was washed with brine, dried over Na$_2$SO$_4$ filtered and concentrated to afford D95 (273 mg) as an orange solid used without further purification. Method 1; Rt: 1.97 min. m/z: 533 (M+H)$^+$.

Synthesis of Cis/Trans Ethyl 3-((4-fluoro-1-methyl-5-((3,4,5-trifluorophenyl)carbamoyl)-1H-pyrrole)-3-sulfonamido)-4-(2-hydroxyethyl)pyrrolidine-1-carboxylate (D99)

D99 was prepared according to the following Scheme 17.

Scheme 17

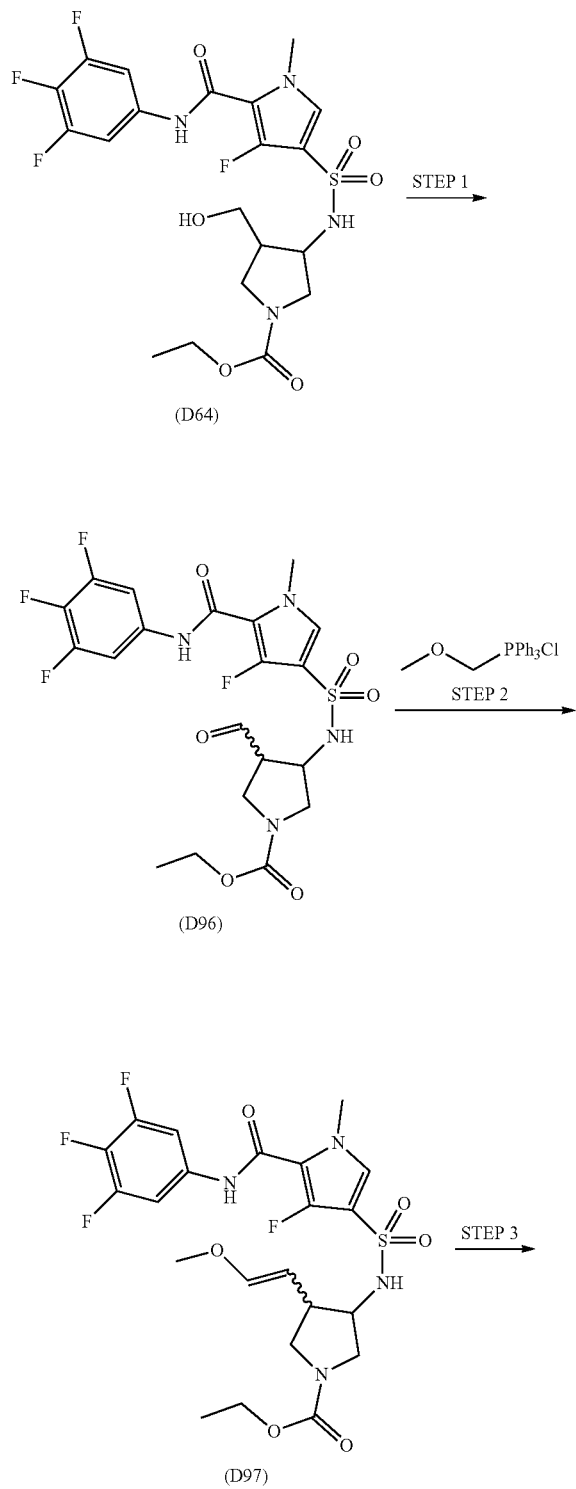

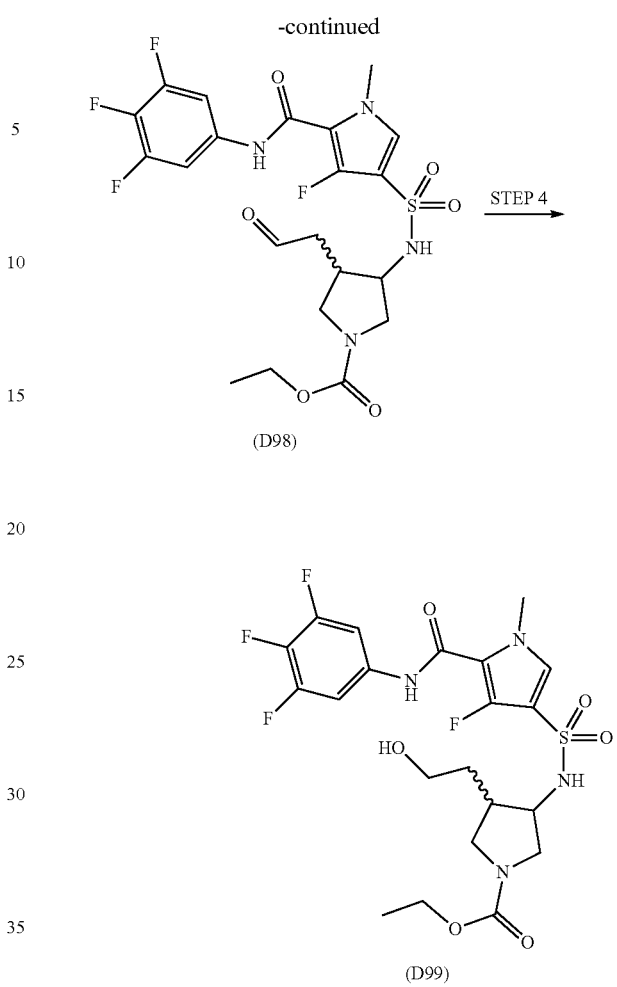

STEP 1) DMP, tBuOH, DCM. RT 16 hrs, 80%; STEP 2) BuLi, THF, -20° C. to RT, 4 hrs; STEP 3) HClaq, THF, 65° C. 2 hrs; STEP 4) NaBH₄, THF/MeOH, 0° C. to RT, 1 hr, 50% over three steps Synthetic steps are described below.

Step 1

$^t$BuOH (100 μL) followed by Dess Martin Periodinane (250 mg, 0.59 mmol) were added to a solution of D64 in DCM (6 mL) at 0° C., then the pale yellow suspension was stirred at RT for 4 hrs. The reaction was diluted with DCM and quenched by adding a 1:1 solution of 5% aqueous sodium thiosulfate and sat NaHCO₃. The biphasic mixture was stirred at RT for 30 min then the two phases were separated and the aqueous phase extract with DCM (×2). The combined organic layers were dried over Na₂SO₄, filtered and concentrated. Purification by flash chromatography (direct phase, eluent AcOEt/ETP) afford cis/trans ethyl 3-((4-fluoro-1-methyl-5-((3,4,5-trifluorophenyl)carbamoyl)-1H-pyrrole)-3-sulfonamido)-4-formylpyrrolidine-1-carboxylate D96 (121 mg, 81%) as a yellow solid. Method 1 Rt: 1.80 min. m/z: 521 (M+H)⁺.

Step 2

At −20° C., n-butyllithium (1.6M in hexane, 0.4 mL, 0.65 mmol) was added over 20 min to a suspension of (methoxymethyl)triphenylphosphonium chloride (239 mg, 0.70 mmol) in dry THF (4 mL). The red solution was stirred at the same temperature for 30 min then a solution of D96 (121 mg, 0.22 mmol) in dry THF (4 mL) was slowly added. The reaction was allow to warm to RT and stirred at the same temperature for 3 hrs then quenched with sat NH₄Cl solution and diluted with EtOAc. The two phases were separated and the organic layer was washed with brine, dried over Na$_2$SO$_4$ filtered and concentrated to afford cis/trans ethyl 3-((4-fluoro-1-methyl-5-((3,4,5-trifluorophenyl)carbamoyl)-1H-pyrrole)-3-sulfonamido)-4-(2-methoxyvinyl)pyrrolidine-1-carboxylate D97 as a yellow oil used without further purification. Method 14: Rt: 2.24, 2.30 min (cis/trans). m/z: 549 (M+H)$^+$.

Step 3

0.5M HCL$_{aq}$ (2 mL, 1 mmol) was added to a solution of crude D97 in THF (2 mL). The reaction was heated to 65° C. and stirred at the same temperature for 2 hrs. The reaction was cooled to RT then quenched with sat NaHCO$_3$ and extracted with EtOAc. The organic layer was washed with brine, dried over Na$_2$SO$_4$ filtered and concentrated to afford cis/trans ethyl 3-((4-fluoro-1-methyl-5-((3,4,5-trifluorophenyl)carbamoyl)-1H-pyrrole)-3-sulfonamido)-4-(2-oxoethyl)pyrrolidine-1-carboxylate D98 as a yellow oil used without further purification. Method 14: Rt: 1.98, 2.01 min(cis/trans) m/z: 535 (M+H)$^+$.

Step 4

NaBH$_4$ (18 mg, 0.5 mmol) was added to a solution of crude D98 in a 1:1 mixture of THF and MeOH (4 mL) at 0° C. The reaction was stirred at RT 1 hr then quenched with sat NaHCO$_3$ and extracted with EtOAc. The organic layer was washed with brine, dried over Na$_2$SO$_4$ filtered and concentrated. Purification by FC (reverse phase, eluent H$_2$O/MeCN+0.5% HCO$_2$H) and lyophilization afford cis/trans ethyl 3-((4-fluoro-1-methyl-5-((3,4,5-trifluorophenyl)carbamoyl)-1H-pyrrole)-3-sulfonamido)-4-(2-hydroxyethyl)pyrrolidine-1-carboxylate D99 (80 mg, 0.13 mmol, 50% over three steps) as an off white solid. Method 14: Rt: 1.74, 1.77 min(cis/trans) m/z: 537 (M+H)$^+$.

Synthesis of Cis Ethyl 3-(aminomethyl)-4-((4-fluoro-5-((4-fluoro-3-methylphenyl)carbamoyl)-1-methyl-1H-pyrrole)-3-sulfonamido)pyrrolidine-1-carboxylate Hydrochloride (D102)

D102 was prepared according to the following Scheme 18.

Scheme 18

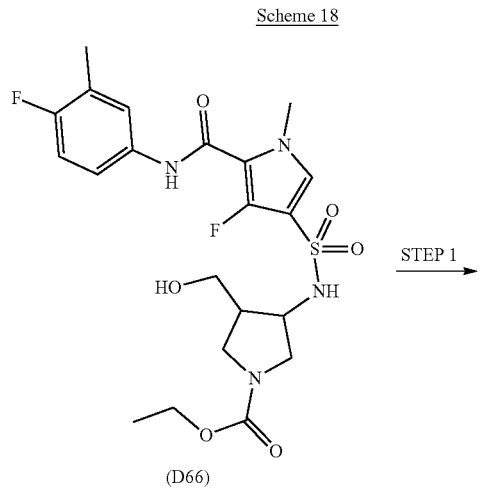

(D66)

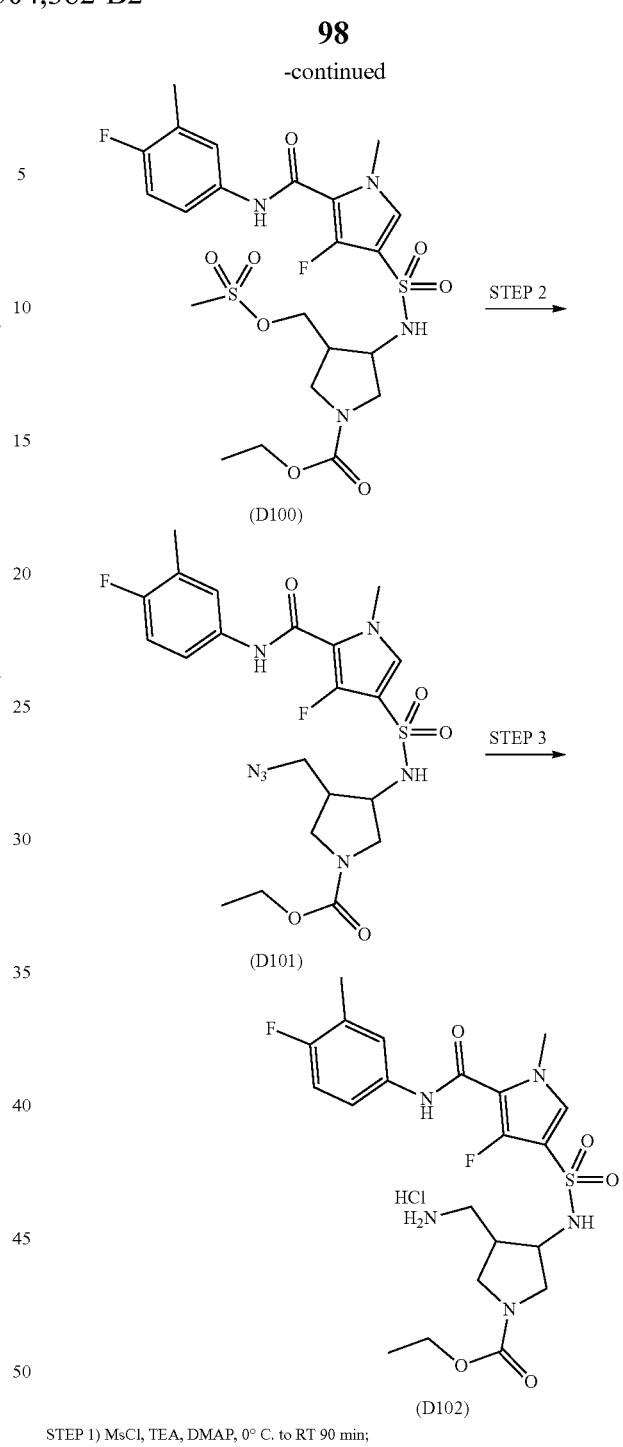

(D100)

(D101)

(D102)

STEP 1) MsCl, TEA, DMAP, 0° C. to RT 90 min;
STEP 2) NaN$_3$, DMF, 55° C., 16 hrs;
STEP 3) 1,4-cyclohexadiene, Pd/C (10% w), EtOH/THF, 50° C., 1 hrs Synthetic steps are described below.

Step 1

A solution of methanesulfonyl chloride (25 μL, 0.33 mmol) in dry DCM (1 mL) was added drop wise to a 0° C. cooled solution of D66 (110 mg, 0.22 mmol), triethylamine (60 μL, 0.61 mmol) and catalytic amount of DMAP (2 mg) in dry DCM (4 mL). The reaction was allowed to slowly warm up and stirred at RT for 2 hrs then was diluted with DCM and washed with 5% citric acid solution, water and brine. The organic layer was dried over Na$_2$SO$_4$ filtered and concentrated to afford cis ethyl 3-((4-fluoro-5-((4-fluoro-3- methylphenyl)carbamoyl)-1-methyl-1H-pyrrole)-3-sulfonamido)-4-(((methylsulfonyl)oxy)methyl)pyrrolidine-1-carboxylate D100 (126 mg) as a pale yellow oil that was used without further purification. Method 1; Rt: 2.00 min. m/z: 579 (M+H)$^+$.

Step 2

Sodium azide (150 mg, 2.31 mmol) was added to a solution of D100 (126 mg, 0.22 mmol) in dry DMF (4 mL). The reaction mixture was stirred at 55° C. for 16 hrs then cooled to RT, diluted with EtOAc and water, and stirred for 15 min. The two phases were separated and the organic phase washed with water and brine, dried over Na$_2$SO$_4$ filtered and concentrated to afford cis ethyl 3-(azidomethyl)-4-((4-fluoro-5-((4-fluoro-3-methylphenyl)carbamoyl)-1-methyl-1H-pyrrole)-3-sulfonamido)pyrrolidine-1-carboxylate D101 (115 mg) as a pale brown oil that was used without further purification. 1; Rt: 2.11 min. m/z: 526 (M+H)$^+$.

Step 2

In a closed vessels, Pd/C (10% weight, 20 mg) was added to solution of D101 (115 mg, 0.22 mmol) in degassed EtOH/THF 3:1 mixture (4 mL). 1,4-cyclohexadiene (0.21 mL, 2.2 mmol) was added and the reaction was stirred at 55° C. for 1 hr. Then the reaction was filtered and filter was washed with EtOH several times and the filtrate was concentrated under reduce pressure. Purification by FC (reverse phase, eluent H$_2$O/MeCN+0.3% HCO$_2$H) and lyophilization in the presence of diluted HCl afforded D102 (45 mg, 38% over three steps) as an off white foam. $^1$H NMR (300 MHz, DMSO-d6) δ ppm 1.09-1.24 (m, 3H) 2.23 (s, 3H) 2.52-2.63 (m, 1H) 2.71-2.86 (m, 1H) 2.91-3.05 (m, 1H) 3.12-3.28 (m, 2H) 3.40-3.58 (m, 2H) 3.81 (s, 3H) 3.89-4.10 (m, 3H) 7.11 (t, J=9.22 Hz, 1H) 7.46-7.54 (m, 2H) 7.57-7.65 (m, 1H) 7.98-8.16 (m, 3H) 8.25 (br d, J=7.61 Hz, 1H) 10.10 (br d, J=3.67 Hz, 1H). Rt: 1.46 min. m/z: 500 (M+H)$^+$.

Synthesis of Compounds of Formula 5 as Indicated in Scheme 1 or of Compounds of Formula 5a as Indicated in Scheme 2

Description 103: Cis-Ethyl 8-((4-fluoro-3-methylphenyl)carbamoyl)-7,10a-dimethyl-3a,4,10,10a-tetrahydro-1H,7H-dipyrrolo[3,4-b:3',4'-f][1,4,5]oxathiazocine-2(3H)-carboxylate 5,5-dioxide (D103)

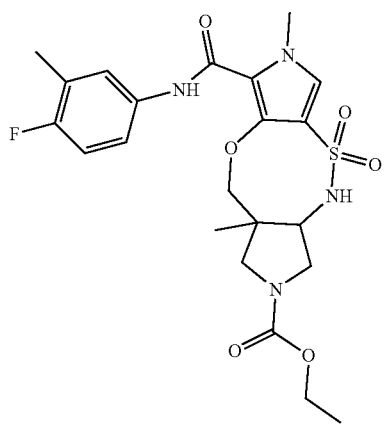 [SMILES: CCOC(=O)N1CC2NS(=O)(=O)c3cn(C)c(C(=O)Nc4ccc(F)c(C)c4)c3OCC2(C)C1]

Solution of D76 (100 mg, 0.19 mmol) in DMF (4 mL) was treated with a single portion of cesium carbonate (158.31 mg, 0.49 mmol) and heated at 130° C. for 9 hrs. Solvent was removed in vacuo and the residue partitioned between water and EtOAc. The org. were dried over Na$_2$SO$_4$ (anh.), filtered and finally evaporated giving a residue. Purification performed by FC (direct phase, DCM/EtOAc), gave D103 (78.41 mg, yield: 81.6%) $^1$H NMR (300 MHz, DMSO-d$_6$) δ ppm 1.15-1.25 (m, 3H) 1.27 (s, 3H) 2.24 (d, J=1.47 Hz, 3H) 3.07 (d, J=10.73 Hz, 1H) 3.16-3.28 (m, 1H) 3.36 (s, 1H) 3.72-3.84 (m, 3H) 3.84-4.16 (m, 5H) 4.31 (s, 1H) 7.12 (t, J=9.22 Hz, 1H) 7.36-7.52 (m, 2H) 7.52-7.67 (m, 1H) 8.31-8.57 (m, 1H) 9.24-9.45 (m, 1H). Method 3; Rt: 3.56 min. m/z: 495.35 (M+H)$^+$.

Description 104: cis-N-(4-fluoro-3-methylphenyl)-7,10a-dimethyl-2,3,3a,4,10,10a-hexahydro-1H,7H-dipyrrolo[3,4-b:3',4'-f][1,4,5]oxathiazocine-8-carboxamide 5,5-dioxide Hydroiodide (D104)

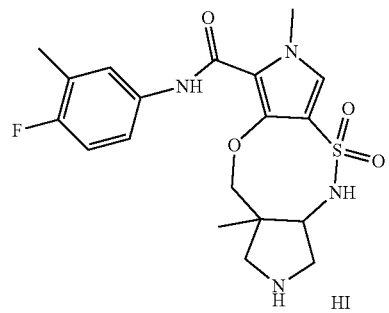

A solution of D103 (67 mg, 0.14 mmol) in DCM (1.5 mL) was treated with a single portion of trimethylsilyl iodide (0.14 mL, 0.95 mmol) and heated at 50° C. for 5 hrs. The reaction was diluted with MeOH and evaporated. The resulting solid was triturated two times in DEE, giving D104 (74 mg, 0.13 mmol) as brown solid. $^1$H NMR (300 MHz, DMSO-d$_6$+TFA) δ ppm 1.29 (s, 3H) 2.23 (s, 3H) 2.97-3.27 (m, 3H) 3.81 (s, 3H) 3.99 (s, 2H) 4.17-4.28 (m, 1H) 4.34 (d, J=11.65 Hz, 1H) 7.12 (t, J=9.22 Hz, 1H) 7.40-7.48 (m, 1H) 7.49 (s, 1H) 7.53-7.65 (m, 1H) 8.42 (d, J=9.72 Hz, 1H) 9.15 (br s, 2H) 9.37 (s, 1H). Method 1; Rt: 1.41 min. m/z: 422 (M+H)$^+$.

Description 105: Ethyl (3aR,10aR)-8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (D105)

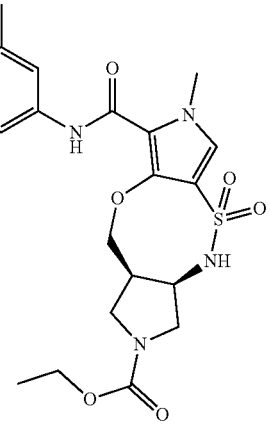

In a pressure vessel, D78 (3.13 g, 6.25 mmol) was dissolved in dry DMF (120 mL); cesium carbonate (5.3 g, 16.26 mmol) was added, the vial was sealed and mixture heated at 140° C. with oil bath for 4 h. The solvent was removed under reduced pressure, the residue was taken up with EtOAc and washed with water (×3). Organic layer was dried over Na₂SO₄ (anh.), filtered and solvent removed under reduced pressure. The resulting light-brown foam was then treated with Et₂O to remove residual solvent and obtain D105 (2.8 g, yield=93%) as light-brown solid, that was used in the next step without further purification. ¹H NMR (300 MHz, DMSO-d6) δ ppm 1.05-1.27 (m, 3H), 2.24 (d, J=1.47 Hz, 3H), 2.92-3.16 (m, 2H), 3.41 (br d, J=10.91 Hz, 2H), 3.64-4.10 (m, 7H), 4.32-4.69 (m, 2H), 7.11 (t, J=9.22 Hz, 1H), 7.39-7.67 (m, 3H), 7.96 (s, 1H), 9.34 (s, 1H). Method 1: Rt=2.00 min; m/z=481 (M+H)⁺. The compound corresponds to Example E39, which was obtained through chiral separation from E14 (vide infra).

Description 106: Ethyl (3aR,10aR)-7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide (D106)

The compound was prepared according to the following Scheme 19.

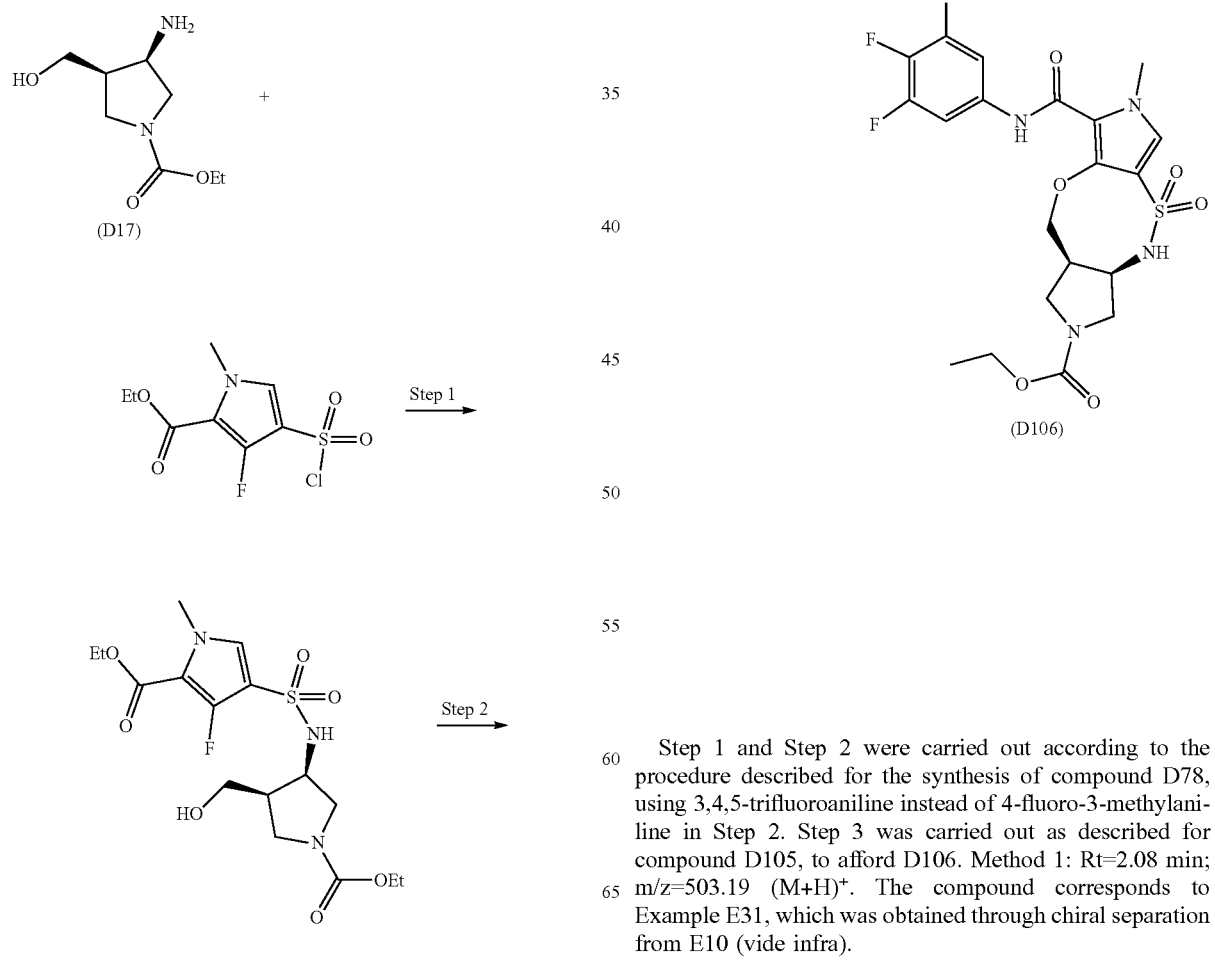

Step 1 and Step 2 were carried out according to the procedure described for the synthesis of compound D78, using 3,4,5-trifluoroaniline instead of 4-fluoro-3-methylaniline in Step 2. Step 3 was carried out as described for compound D105, to afford D106. Method 1: Rt=2.08 min; m/z=503.19 (M+H)⁺. The compound corresponds to Example E31, which was obtained through chiral separation from E10 (vide infra).

Description 107: Ethyl (3aR,10aR)-8-((3-chloro-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (D107)

The compound was prepared according to the following Scheme 20:

Scheme 20

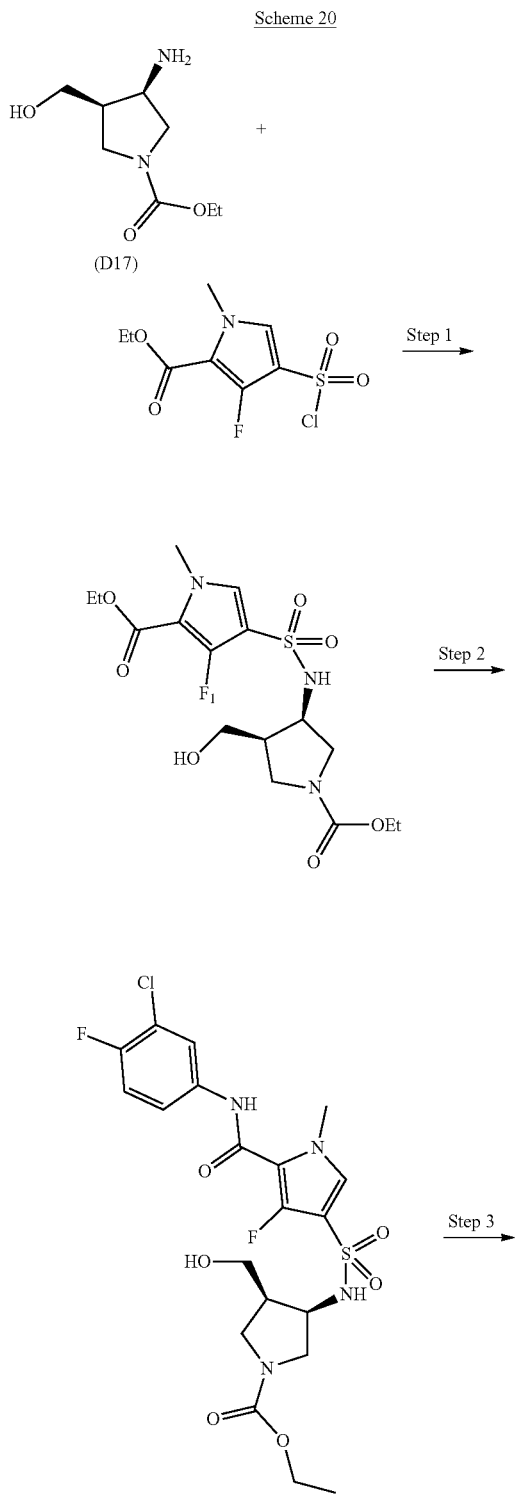

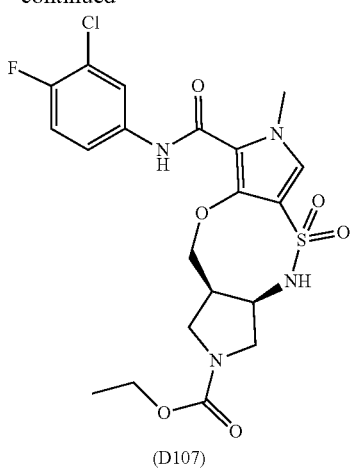

(D107)

Step 1 and Step 2 were carried out according to the procedure described for the synthesis of compound D78, using in Step 2 the 3-chloro-4-fluoroaniline instead of the 4-fluoro-3-methylaniline. Step 3 was carried out as described for compound D105 to afford D107. Method 1: Rt=2.09 min; m/z=501, 503 (M+H)⁺. The compound corresponds to Example E41, which was obtained through chiral separation from E15 (vide infra).

Description 108: (3aR,10aR)-8-((4-fluoro-3-methylphenyl)carbamoyl)-7-methyl-2,3,3a,4,10,10a-hexahydro-1H,7H-dipyrrolo[3,4-b:3',4'-f][1,4,5]oxathiazocin-2-ium 5,5-dioxide Iodide (D108)

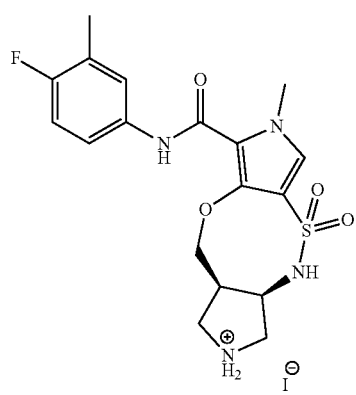 [SMILES: Cc1cc(NC(=O)c2c3c(cn2C)S(=O)(=O)N[C@H]2C[NH2+]C[C@H]2CO3)ccc1F ; [I-]]

In a sealed microwave vial, D105 was dissolved in dry DCM, treated with about 20 equivalents of trimethylsilyl iodide, and the mixture was heated at 50° C. After 4.5 h the crude was evaporated under reduced pressure to afford a brown solid. The solid residue was triturated with Et₂O and filtered, giving D108. Method 1: Rt=1.36 min; m/z=409 (M+H)⁺.

Description 109: (3aR,10aR)-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide Iodide (D109)

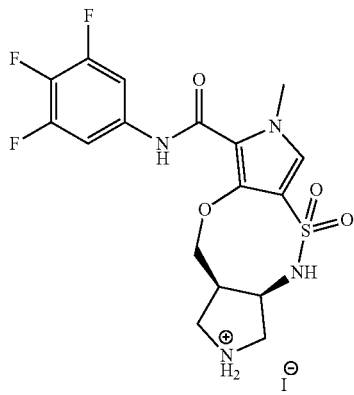 [SMILES: Cn1cc2c(c1C(=O)Nc1cc(F)c(F)c(F)c1)OC[C@@H]1C[NH2+]C[C@@H]1NS2(=O)=O ; [I-]]

Prepared similarly as described for compound D108 starting from D106 to afford D109. Method 1: Rt=1.46 min; m/z=431.39 (M+H)⁺. The compound corresponds to Example E36, which was obtained through Boc-deprotection from E33 (vide infra).

Description 110: (3aR,10aR)-8-((3-chloro-4-fluorophenyl)carbamoyl)-7-methyl-2,3,3a,4,10,10a-hexahydro-1H,7H-dipyrrolo[3,4-b:3',4'-f][1,4,5]oxathiazocin-2-ium 5,5-dioxide Iodide (D110)

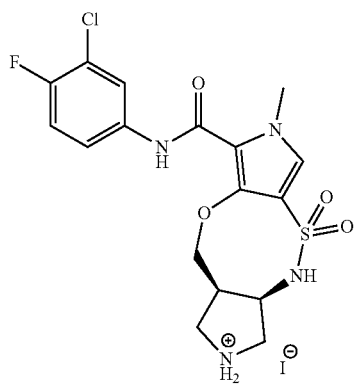 [SMILES: Cn1cc2c(c1C(=O)Nc1ccc(F)c(Cl)c1)OC[C@@H]1C[NH2+]C[C@@H]1NS2(=O)=O ; [I-]]

Prepared similarly as described for compound D108 starting from D107 to afford D110. Method 1: Rt=1.44 min; m/z=429.30, 431.39 (M+H)⁺.

Description 111: Cis-Tert-Butyl 1-((4-fluoro-3-methylphenyl)carbamoyl)-2-methyl-5,5a,6,7,9a,10-hexahydro-2H-pyrido[4,3-f]pyrrolo[3,4-b][1,4,5]oxathiazocine-8(9H)-carboxylate 4,4-dioxide (D111)

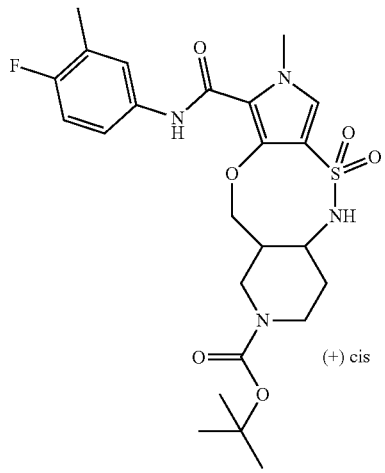 [SMILES: Cc1cc(NC(=O)c2c3c(cn2C)S(=O)(=O)NC2CCN(C(=O)OC(C)(C)C)CC2CO3)ccc1F]

Cesium carbonate (616 mg, 1.88 mmol) was added to a solution of D83 (430 mg, 0.79 mmol) in dry DMF (8 mL). The reaction mixture was stirred at 135° C. for 3 hrs then cooled to RT, diluted with toluene and water, and stirred for 15 min. The two phases were separated and the organic phase washed with water and brine, dried over Na₂SO₄ filtered and concentrated to afford D111 (280 mg) as a pale yellow foam that was used without further purification. ¹H NMR (300 MHz, DMSO-d₆) δ ppm 1.39 (s, 9H) 1.69-1.84 (m, 2H) 2.16-2.43 (m, 4H) 2.93-3.24 (m, 2H) 3.54-3.88 (m, 6H) 4.12-4.24 (m, 1H) 4.37-4.52 (m, 1H) 7.2 (t, J=9.20 Hz, 1H) 7.47-7.63 (m, 3H) 8.15-8.25 (m, 1H) 9.25-9.35 (m, 1H). Method 1; Rt: 2.23 min. m/z: 523 (M+H)⁺.

Description 112: Cis-N-(4-fluoro-3-methylphenyl)-2-methyl-5,5a,6,7,8,9,9a,10-octahydro-2H-pyrido[4,3-f]pyrrolo[3,4-b][1,4,5]oxathiazocine-1-carboxamide 4,4-dioxide Hydrochloride (D112)

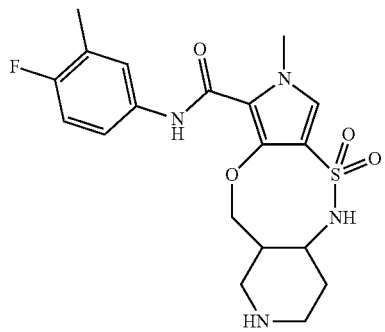

Hydrogen chloride (3N solution in MeOH, 1.5 mL, 4.5 mmol) was slowly added to a solution of D111 (250 mg, 0.48 mmol) in DCM (6 mL). The orange solution was stirred at RT for 6 hrs then concentrated under reduce pressure to afford D112 (220 mg) as a pale yellow solid. Method 1; Rt: 1.34 min. m/z: 423 (M+H)+.

Description 113: Trans-Tert-Butyl 1-((4-fluoro-3-methylphenyl)carbamoyl)-2-methyl-5,5a,6,7,9a,10-hexahydro-2H-pyrido[4,3-f]pyrrolo[3,4-b][1,4,5]oxathiazocine-8(9H)-carboxylate 4,4-dioxide (D113)

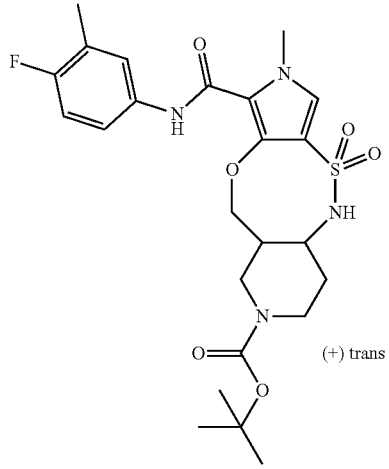 [SMILES: Cc1cc(NC(=O)c2c3c(cn2C)S(=O)(=O)NC2CCN(C(=O)OC(C)(C)C)CC2CO3)ccc1F]

(+) trans

D113 (460 mg) was prepared similarly as described for compound D111 starting from D85 (550 mg, 1.01 mmol) instead of D83. ¹H NMR (300 MHz, DMSO-d6) δ ppm 1.41 (s, 9H) 1.44-1.58 (m, 1H) 1.74-1.94 (m, 2H) 2.24 (s, 3H) 2.64-2.88 (m, 2H) 3.55-3.69 (m, 1H) 3.82 (s, 3H) 3.91-4.15 (m, 2H) 4.15-4.34 (m, 2H) 7.12 (t, J=9.54 Hz, 1H) 7.42-7.55 (m, 2H) 7.59 (br d, J=6.88 Hz, 1H) 7.96 (br d, J=8.80 Hz, 1H) 9.28 (s, 1H). Method 1; Rt: 2.24 min. m/z: 523.52 (M+H)+.

Description 114: Trans-N-(4-fluoro-3-methylphenyl)-2-methyl-5,5a,6,7,8,9,9a,10-octahydro-2H-pyrido[4,3-f]pyrrolo[3,4-b][1,4,5]oxathiazocine-1-carboxamide 4,4-dioxide Hydrochloride (D114)

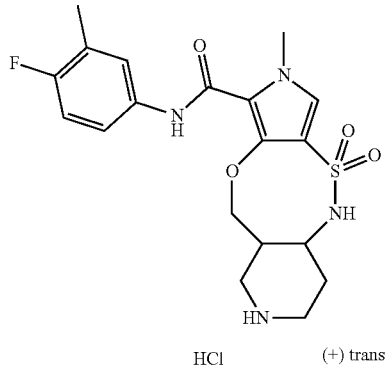 [SMILES: Cc1cc(NC(=O)c2c3c(cn2C)S(=O)(=O)NC2CCNCC2CO3)ccc1F ; Cl]

HCl (+) trans

D114 (390 mg) was prepared similarly as described for compound D112 starting from D113 (445 mg, 0.850 mmol) instead of D111. ¹H NMR (300 MHz, DMSO-d6) δ ppm 1.81-2.05 (m, 2H) 2.24 (s, 4H) 2.90-3.05 (m, 2H) 3.32 (br d, J=12.65 Hz, 1H) 3.39-3.47 (m, 2H) 3.71-3.84 (m, 4H) 4.18-4.37 (m, 2H) 7.12 (t, J=9.17 Hz, 1H) 7.44-7.52 (m, 2H) 7.57 (br d, J=6.97 Hz, 1H) 8.24 (d, J=8.71 Hz, 1H) 9.28 (s, 3H). Method 1; Rt: 1.30 min. m/z: 423.42 (M+H)+.

Description 115: Cis-Tert-Butyl 3-((4-fluoro-5-((4-fluoro-3-methylphenyl)carbamoyl)-1-methyl-1H-pyrrole)-3-sulfonamido)-4-(hydroxymethyl)piperidine-1-carboxylate (D115)

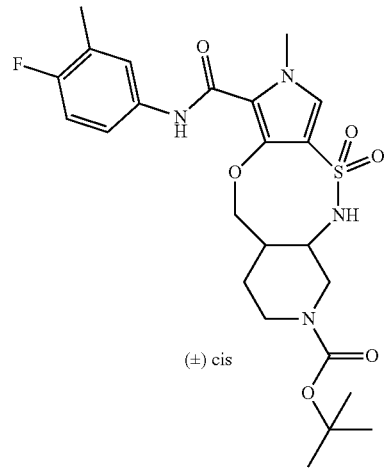 [SMILES: Cc1cc(NC(=O)c2c3c(cn2C)S(=O)(=O)NC2CN(C(=O)OC(C)(C)C)CCC2CO3)ccc1F]

(±) cis

D115 (594 mg) was prepared similarly as described for compound D111 starting from D87 (620 mg, 1.14 mmol) instead of D83. H NMR (300 MHz, DMSO-d$_6$) δ ppm 1.26-1.37 (m, 1H) 1.43 (s, 9H) 1.46-1.62 (m, 1H) 2.24 (s, 3H) 2.31-2.46 (m, 1H) 2.59-2.71 (m, 1H) 2.94-3.18 (m, 1H) 3.62 (t, J=11.19 Hz, 1H) 3.81 (s, 3H) 3.92-4.15 (m, 3H) 4.49 (dd, J=11.37, 5.32 Hz, 1H) 7.11 (t, J=9.26 Hz, 1H) 7.44 (s, 1H) 7.47-7.55 (m, 1H) 7.55-7.63 (m, 1H) 7.94 (s, 1H) 9.33 (s, 1H). Method 1; Rt: 2.22 min. m/z: 523 (M+H)+.

Description 116: cis-N-(4-fluoro-3-methylphenyl)-2-methyl-5,5a,6,7,8,9,9a,10-octahydro-2H-pyrido[3,4-f]pyrrolo[3,4-b][1,4,5]oxathiazocine-1-carboxamide 4,4-dioxide Hydrochloride (D116)

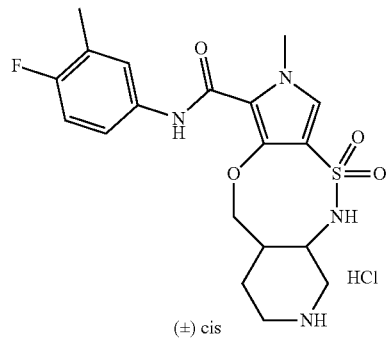 [SMILES: Cc1cc(NC(=O)c2c3c(cn2C)S(=O)(=O)NC2CNCCC2CO3)ccc1F ; Cl]

(±) cis

D116 (515 mg) was prepared similarly as described for compound D112 starting from D115 (592 mg, 1.13 mmol) instead of D111. ¹H NMR (300 MHz, DMSO-d$_6$) δ ppm 1.50-1.87 (m, 2H) 2.24 (s, 3H) 2.5 (m, 1H) 2.81-2.98 (m, 1H) 3.19-3.32 (m, 3H) 3.82 (s, 3H) 3.88 (t, J=11.10 Hz, 1H)

4.22-4.37 (m, 1H) 4.38-4.58 (m, 1H) 7.11 (t, J=9.17 Hz, 1H) 7.44-7.55 (m, 2H) 7.55-7.64 (m, 1H) 8.05 (d, J=9.45 Hz, 1H) 8.73 (br s, 1H) 9.20 (br s, 1H) 9.33 (s, 1H). Method 1; Rt: 1.39 min. m/z: 423.35 (M+H)+.

Description 117: Trans-Tert-Butyl 3-((4-fluoro-5-((4-fluoro-3-methylphenyl)carbamoyl)-1-methyl-1H-pyrrole)-3-sulfonamido)-4-(hydroxymethyl)piperidine-1-carboxylate (D117)

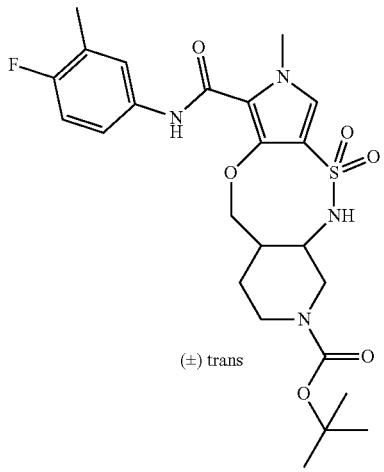 [SMILES: Cc1cc(NC(=O)c2c3c(cn2C)S(=O)(=O)NC2CN(C(=O)OC(C)(C)C)CCC2CO3)ccc1F]

D117 (150 mg) was prepared similarly as described for compound D111 starting from D89 (170 mg, 0.31 mmol) instead of D83. Method 1; Rt: 2.24 min. m/z: 523 (M+H)+.

Description 118: Trans-N-(4-fluoro-3-methylphenyl)-2-methyl-5,5a,6,7,8,9,9a,10-octahydro-2H-pyrido[3,4-f]pyrrolo[3,4-b][1,4,5]oxathiazocine-1-carboxamide 4,4-dioxide Hydrochloride (D118)

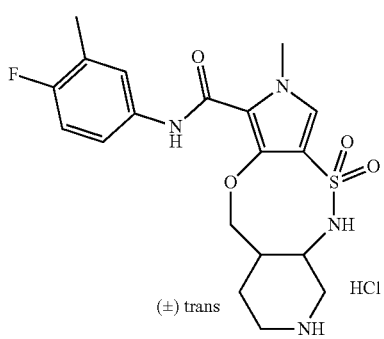 [SMILES: Cc1cc(NC(=O)c2c3c(cn2C)S(=O)(=O)NC2CNCCC2CO3)ccc1F ; Cl]

D118 (120 mg) was prepared similarly as described for compound D112 starting from D117 (150 mg, 0.29 mmol) instead of D111. Method 1; Rt: 1.33 min. m/z: 423 (M+H)+.

EXAMPLES

Example 1: N-(3,4-difluorophenyl)-2-methyl-6,7,8,9,9a,10-hexahydro-2H-pyrido[1,2-e]pyrrolo[3,4-b][1,4,5]oxathiazepine-1-carboxamide 4,4-dioxide (E1)

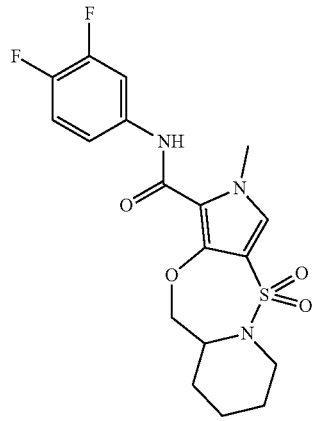 [SMILES: Cn1cc2c(c1C(=O)Nc1ccc(F)c(F)c1)OCC1CCCCN1S2(=O)=O]

D55 (35.77 mg, 0.080 mmol) and cesium carbonate (54.36 mg, 0.170 mmol) in DMF (0.543 mL, 0.007 mol) were heated at 130° C. for 45 min under microwave irradiation. A saturated aqueous ammonium chloride solution was added to the reaction mixture, and the mixture was extracted twice with ethyl acetate. The organic layer was washed with NH$_4$Cl, dried over Na$_2$SO$_4$, and concentrated in vacuo. The resulting crude was purified by preparative HPLC (H$_2$O/CH$_3$CN+0.1% TFA) to afford the title compound E1. $^1$H NMR (300 MHz, DMSO-d$_6$, 25° C.): δ=9.51 (s, 1H), 7.76-7.95 (m, 1H), 7.33-7.56 (m, 3H), 4.44-4.65 (m, 1H), 4.27-4.44 (m, 2H), 3.83 (s, 3H), 3.36-3.43 (m, 1H), 2.68-2.90 (m, 1H), 1.64-1.89 (m, 3H), 1.41-1.62 (m, 2H), 1.24 ppm (s, 1H). Method 3: Rt=3.80 min. m/z=412 (M+H)+.

Example 2: N-(3,4-difluorophenyl)-2-methyl-2,6,7,8,9,9a,10,11-octahydropyrido[1,2-b]pyrrolo[3,4-f][1,2,5]thiadiazepine-1-carboxamide 4,4-dioxide (E2)

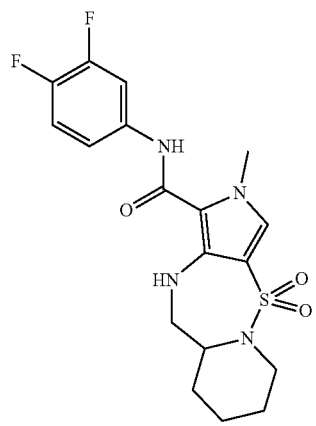 [SMILES: Cn1cc2c(c1C(=O)Nc1ccc(F)c(F)c1)NCC1CCCCN1S2(=O)=O]

D56 (47.96 mg, 0.090 mmol) and cesium carbonate (115.51 mg, 0.350 mmol) in DMSO (1.3 mL, 0.018 mol)

were heated at 160° C. for 7 h under microwave irradiation. The reaction mixture was filtered, and the filtrate was purified by preparative HPLC (H$_2$O/CH$_3$CN+0.1% TFA) to afford the title compound E2. $^1$H NMR (300 MHz, DMSO-d$_6$, 25° C.): δ=10.77-10.95 (m, 1H), 7.80 (ddd, J=13.0, 7.5, 2.2 Hz, 1H), 7.19-7.58 (m, 3H), 5.15 (br t, J=4.9 Hz, 1H), 4.08 (br d, J=9.1 Hz, 1H), 3.70-3.87 (m, 3H), 3.36-3.48 (m, 1H), 3.09 (br dd, J=14.8, 2.8 Hz, 1H), 2.67-2.80 (m, 1H), 1.61-1.80 (m, 3H), 1.27-1.59 ppm (m, 3H). Method 3: Rt=3.80 min. m/z=411.29 (M+H)$^+$.

Example 3: N-(3,4-difluorophenyl)-2-methyl-6,7,7a,8-tetrahydro-2H-azeto[1,2-e]pyrrolo[3,4-b][1,4,5]oxathiazepine-1-carboxamide 4,4-dioxide (E3)

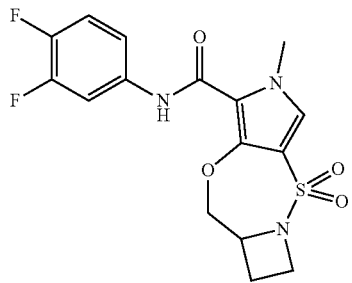 [SMILES: Cn1cc2c(c1C(=O)Nc1ccc(F)c(F)c1)OCC1CCN1S2(=O)=O]

D58 (13.71 mg, 0.030 mmol) and cesium carbonate (22.29 mg, 0.07 mmol) in DMF (0.7 mL, 0.009 mol) were heated at 130° C. 1 h under microwave irradiation. A saturated NH$_4$Cl solution was added to the reaction mixture, and the mixture was extracted twice with ethyl acetate. The organic layer was washed with saturated brine, dried over Na$_2$SO$_4$, and concentrated in vacuo. The resulting crude was purified by preparative HPLC (H$_2$O/CH$_3$CN+0.1% TFA) to afford the title compound E3. $^1$H NMR (300 MHz, DMSO-d$_6$, 25° C.): δ=9.37-9.53 (m, 1H), 7.88 (ddd, J=13.3, 7.5, 1.7 Hz, 1H), 7.54 (s, 1H), 7.37-7.51 (m, 2H), 4.87 (dd, J=14.0, 0.9 Hz, 1H), 4.55 (dd, J=14.1, 1.7 Hz, 1H), 4.48 (br dd, J=8.8, 4.4 Hz, 1H), 3.85 (s, 3H), 3.69-3.83 ppm (m, 2H). Method 3: Rt=3.46 min. m/z=383.93 (M+H)$^+$.

Example 4: trans-N-(3,4-difluorophenyl)-7-methyl-1,3a,4,9a-tetrahydro-3H,7H-furo[3,4-f]pyrrolo[3,4-b][1,4,5]oxathiazepine-8-carboxamide 5,5-dioxide (E4)

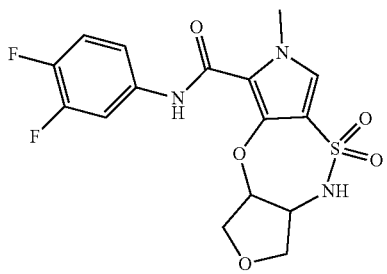 [SMILES: Cn1cc2c(c1C(=O)Nc1ccc(F)c(F)c1)OC1COCC1NS2(=O)=O]

Compound D57 (114.5 mg, 0.27 mmol) and cesium carbonate (179 mg, 0.55 mmol) in DMF (1.8 mL, 0.024 mol) were heated at 150° C. for 2 h under microwave irradiation. A saturated NH$_4$Cl solution was added to the reaction mixture, and the mixture was extracted twice with ethyl acetate. The organic layer was washed with saturated brine, dried over Na$_2$SO$_4$, and concentrated in vacuo. The resulting crude was purified by preparative HPLC (H$_2$O/CH$_3$CN+0.1% TFA) to afford the title compound E4. The compound is the trans racemate (3aS,9aR and 3aR,9aS). $^1$H NMR (300 MHz, DMSO-d$_6$, 25° C.): δ=9.51 (s, 1H), 7.95 (d, J=10.5 Hz, 1H), 7.84 (ddd, J=13.2, 7.5, 2.1 Hz, 1H), 7.58 (s, 1H), 7.29-7.49 (m, 2H), 4.56 (q, J=8.0 Hz, 1H), 4.06-4.36 (m, 3H), 3.89 (t, J=8.6 Hz, 1H), 3.79-3.85 (m, 3H), 3.58-3.62 ppm (m, 1H). Method 3: Rt=3.22 min. m/z=400.01 (M+H)$^+$.

Example 5: cis-N-(3,4-difluorophenyl)-9-methyl-3,4,5,6-tetrahydro-2H,9H-3,5-methanopyrrolo[3,4-b][1,4,5]oxathiazocine-8-carboxamide 1,1-dioxide (E5)

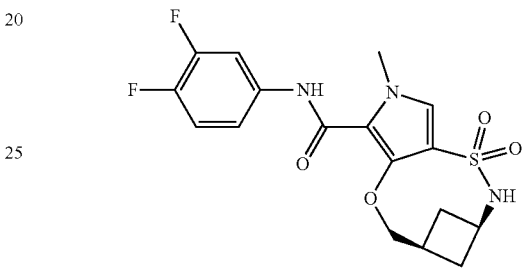

In a microwave vial D59 (30.5 mg, 0.073 mmol) was dissolved in dry DMF (1.5 mL); cesium carbonate (60 mg, 0.184 mmol) was added, the vial was sealed and mixture heated under microwave irradiations for 8 h at 150° C. Crude was purified with preparative HPLC-MS (H$_2$O/CH$_3$CN+0.1% TFA) to give E5 a pale pink powder (5.38 mg). $^1$H NMR (300 MHz, DMSO-d$_6$) δ ppm 2.31-2.45 (m, 3H) 2.55-2.68 (m, 2H) 3.80 (s, 5H) 3.99 (s, 2H) 7.34 (d, J=2.48 Hz, 1H) 7.37-7.46 (m, 2H) 7.46-7.53 (m, 1H) 7.86 (br dd, J=7.57, 2.52 Hz, 1H) 7.90 (br dd, J=7.57, 2.43 Hz, 1H) 9.99 (s, 1H). Method 3: Rt=3.22 min, m/z=398 (M+H)$^+$.

Example 6: cis-N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide (E6)

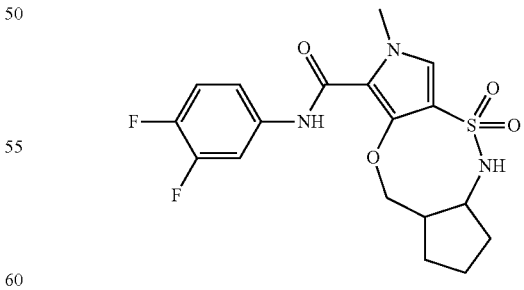

In a microwave vial D60 (10 mg, 0.023 mmol) was dissolved in dry DMF (1 mL); cesium carbonate (19.5 mg, 0.060 mmol) was added, the vial sealed and mixture heated at 130° for 40 min. Crude was purified with preparative HPLC-MS (H$_2$O/CH$_3$CN+0.1% TFA) to give E6 a white powder (5.37 mg). The compound is the cis racemate (5aS,8aR and 5aR,8aS). ¹H NMR (300 MHz, DMSO-d₆) δ ppm 1.11-1.30 (m, 1H) 1.39-1.78 (m, 4H) 2.01-2.17 (m, 1H) 3.76-3.95 (m, 4H) 4.20-4.34 (m, 1H) 4.49 (dd, J=11.28, 4.49 Hz, 1H) 7.32-7.53 (m, 3H) 7.81-7.95 (m, 2H) 9.55 (s, 1H). Method 3: Rt=3.68 min, m/z=412 (M+H)⁺.

Example 7: trans-7-methyl-N-(3,4,5-trifluorophenyl)-1,3a,4,9a-tetrahydro-3H,7H-furo[3,4-f]pyrrolo[3,4-b][1,4,5]oxathiazepine-8-carboxamide 5,5-dioxide (E7)

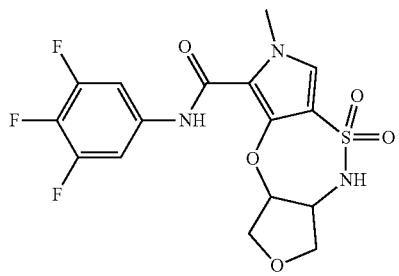 [SMILES: Cn1cc2c(c1C(=O)Nc1cc(F)c(F)c(F)c1)OC1COCC1NS2(=O)=O]

In a microwave vial D61 (40 mg, 0.091 mmol) was dissolved in dry DMF (2 mL); cesium carbonate (74.5 mg, 0.229 mmol) was added, the vial was sealed and mixture heated 3 h at 130° C. under microwave heating. Mixture was purified with preparative HPLC-MS (H₂O/CH₃CN+0.1% TFA) to give E7 a white powder (11.26 mg). The compound is the trans racemate (3aS,9aR and 3aR,9aS). ¹H NMR (300 MHz, DMSO-d₆) δ ppm 3.50-3.63 (m, 1H) 3.82 (s, 3H) 3.91 (t, J=8.67 Hz, 1H) 4.06-4.33 (m, 3H) 4.55 (q, J=7.89 Hz, 1H) 7.55-7.65 (m, 3H) 7.96 (d, J=10.36 Hz, 1H) 9.60 (s, 1H). Method 3: Rt=3.44 min, m/z=418 (M+H)⁺.

Example 8: (5aR,8aR)—N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide (E8)

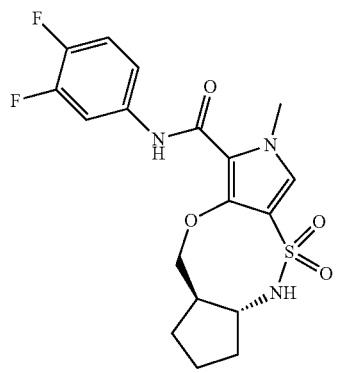 [SMILES: Cn1cc2c(c1C(=O)Nc1ccc(F)c(F)c1)OC[C@@H]1CCC[C@H]1NS2(=O)=O]

In a microwave vial D62 (40 mg, 0.093 mmol) was dissolved in dry DMF (2 mL); cesium carbonate (75.5 mg, 0.232 mmol) was added, the vial was sealed and mixture heated at 130° C. under MW for 40 min. Mixture was purified with preparative HPLC-MS (H₂O/CH₃CN+0.1% TFA) to afford E8 as a white powder (26.47 mg). ¹H NMR (300 MHz, DMSO-d₆) δ ppm 1.07 (br d, J=7.70 Hz, 1H) 1.37-1.69 (m, 4H) 2.00-2.23 (m, 2H) 3.77-3.98 (m, 6H) 7.27 (d, J=10.45 Hz, 1H) 7.36-7.50 (m, 3H) 7.87 (ddd, J=13.20, 7.47, 2.25 Hz, 1H) 9.83 (s, 1H). Method 3: Rt=3.55 min, m/z=412 (M+H)⁺.

Example 9: (5aS,8aS)—N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide (E9)

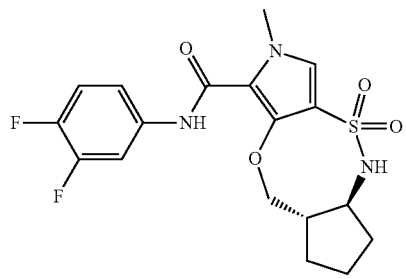 [SMILES: Cn1cc2c(c1C(=O)Nc1ccc(F)c(F)c1)OC[C@H]1CCC[C@@H]1NS2(=O)=O]

Prepared similarly as described for compound E8 starting from D63 to give E9. ¹H NMR (300 MHz, DMSO-d₆) δ ppm 1.02-1.16 (m, 1H) 1.32-1.72 (m, 1H) 2.00-2.27 (m, 2H) 3.76-4.00 (m, 6H) 7.27 (d, J=10.55 Hz, 1H) 7.35-7.51 (m, 3H) 7.87 (ddd, J=13.20, 7.47, 2.15 Hz, 1H) 9.83 (s, 1H). Method 3: Rt=3.55 min, m/z=412 (M+H)⁺.

Example 10: Cis-Ethyl 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide (E10)

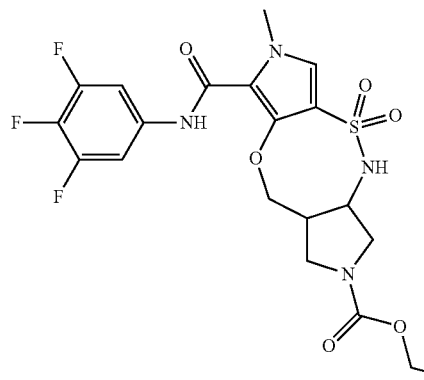

In a microwave vial D64 (106 mg, 0.203 mmol) was dissolved in dry DMF (5 mL); cesium carbonate (166 mg, 0.509 mmol) was added, the vial was sealed and mixture heated at 130° C. under MW for 70 min. Mixture was filtered and solvent removed under reduced pressure to afford a beige solid (152 mg). Crude was purified with preparative HPLC-MS (H₂O/CH₃CN+0.10% TFA) to afford E10 as a white powder (79.4 mg). The compound is the cis racemate at the pyrrolidine ring (racemate of 3aR,10aR and 3aS,10aS). ¹H NMR (300 MHz, DMSO-d₆+TFA) δ ppm 1.12-1.22 (m, 3H) 2.91-3.14 (m, 2H) 3.33-3.46 (m, 2H) 3.62-3.76 (m, 1H) 3.79 (s, 3H) 3.83-3.96 (m, 1H) 4.02 (q, J=7.06 Hz, 2H) 4.38-4.48 (m, 1H) 4.48-4.62 (m, 1H) 7.49 (s, 1H) 7.62-7.73 (m, 2H) 8.41 (br d, J=9.72 Hz, 1H) 9.64 (s, 1H). Method 3: Rt=3.57 min, m/z=503 (M+H)⁺.

Example 11: cis-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E11)

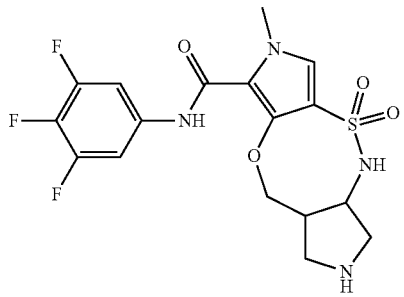 [SMILES: Cn1cc2c(c1C(=O)Nc1cc(F)c(F)c(F)c1)OCC1CNCC1NS2(=O)=O]

In a sealed microwave vial, E10 (185.5 mg, 0.369 mmol) was dissolved in dry DCM (2 mL). Trimethylsilyl iodide (1.1 mL, 7.6965 mmol) was added and mixture was heated at 50° C. After 4.5 h even if conversion was not completed, crude was evaporated under reduced pressure to afford a brown solid (350 mg). Then it was triturated with $Et_2O$ and filtered. Brown solid was dried at vacuum pump (232 mg) and it was used without any further purification (as iodidric acid salt, IUPAC name: cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide) for the synthesis of compounds E12; E18-E23; E56-E60; E64; E65; E73-E76; E78; E83; E84.

Part of crude was purified with preparative HPLC-MS ($H_2O/CH_3CN$+0.1% TFA) to afford E11 as white powder (15.65 mg). The compound is the cis racemate at the pyrrolidine ring (mixture of 3aR,10aR and 3aS,10aS). $^1$H NMR (300 MHz, DMSO-$d_6$) δ ppm 2.82-3.02 (m, 2H) 3.08-3.22 (m, 1H) 3.81 (s, 4H) 3.88-4.05 (m, 1H) 4.54-4.66 (m, 2H) 7.55 (s, 1H) 7.64-7.74 (m, 2H) 8.38 (d, J=9.90 Hz, 1H) 8.97 (br s, 2H) 9.68 (s, 1H). Method 3: Rt=2.50 min, m/z=431 (M+H)$^+$.

Example 12: cis-2,7-dimethyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E12)

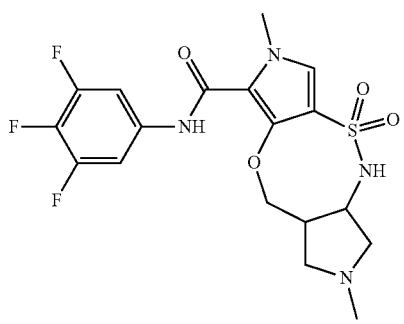 [SMILES: CN1CC2COc3c(cn(C)c3C(=O)Nc3cc(F)c(F)c(F)c3)S(=O)(=O)NC2C1]

cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) (7.2 mg, 0.017 mmol) was dissolved in 1 mL of a solution composed by MeOH (10 mL), formaldehyde 37% aq. (0.170 mL, 2.285 mmol) and acetic acid (0.030 mL, 0.506 mmol) at room temperature. After 10 minutes, sodium triacetyloxyborohydride (7.5 mg, 0.035 mmol) was added and the reaction mixture was stirred at room temperature. Further aliquots of formaldehyde and acetic acid were added until UPLC-MS analysis showed complete conversion. Crude was purified with preparative HPLC-MS (H2O/CH3CN+0.1% TFA) to afford E12 as a white powder (3.87 mg). The compound is the cis racemate at the pyrrolidine ring (mixture of 3aR,10aR and 3aS,10aS). $^1$H NMR (300 MHz, DMSO-$d_6$) δ ppm 2.79-3.07 (m, 5H) 3.15-3.39 (m, 1H) 3.49-3.74 (m, 1H) 3.80 (s, 3H) 3.93-4.11 (m, 1H) 4.15-4.31 (m, 1H) 4.51-4.76 (m, 2H) 7.50 (s, 1H) 7.67 (br dd, J=10.04, 6.56 Hz, 2H) 8.17-8.32 (m, 1H) 0.00 (d, J=9.20 Hz, 1H) 9.56-9.77 (m, 1H) 10.20 (br s, 1H).

Method 3: Rt=2.57 min, m/z=445 (M+H)+.

Example 13: Cis-Ethyl 8-((3,4-difluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (E13)

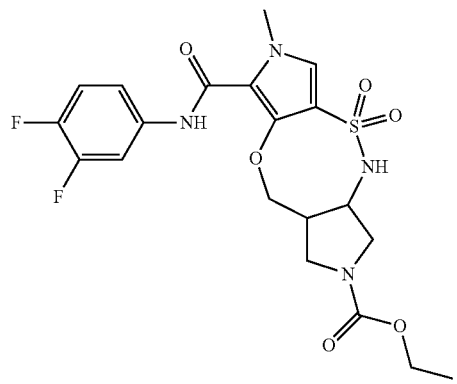 [SMILES: CCOC(=O)N1CC2COc3c(cn(C)c3C(=O)Nc3ccc(F)c(F)c3)S(=O)(=O)NC2C1]

Prepared similarly as described for compound E10 starting from D65 to give E13. The compound is the cis racemate at the pyrrolidine ring (racemate of 3aR,10aR and 3aS,10aS). $^1$H NMR (300 MHz, DMSO-$d_{6+}$TFA) δ ppm 1.12-1.22 (m, 3H) 2.91-3.15 (m, 2H) 3.31-3.49 (m, 2H) 3.66-3.86 (m, 4H) 3.91 (brt, J=11.05 Hz, 1H) 4.02 (q, J=6.97 Hz, 2H) 4.38-4.51 (m, 1H) 4.51-4.65 (m, 1H) 7.29-7.51 (m, 3H) 7.85 (ddd, J=13.14, 7.50, 2.29 Hz, 1H) 8.41 (br d, J=9.72 Hz, 1H) 9.55 (s, 1H). Method 3: Rt=3.38 min, m/z=485 (M+H)$^+$.

Example 14: Cis-Ethyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (E14)

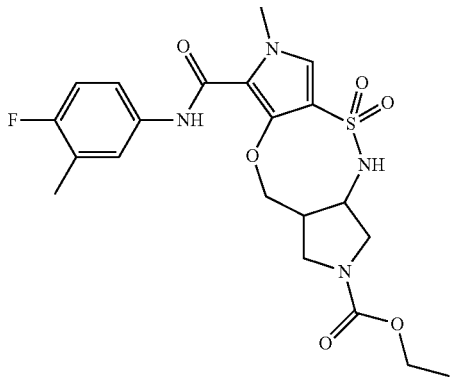 [SMILES: CCOC(=O)N1CC2COc3c(cn(C)c3C(=O)Nc3ccc(F)c(C)c3)S(=O)(=O)NC2C1]

Prepared similarly as described for compound E10 starting from D66 to give E14. The compound is the cis racemate at the pyrrolidine ring (racemate of 3aR,10aR and 3aS,10aS). $^1$H NMR (300 MHz, DMSO-d$_6$) δ ppm 1.14-1.24 (m, 3H) 2.24 (d, J=1.56 Hz, 3H) 2.91-3.14 (m, 2H) 3.33-3.42 (m, 2H) 3.67-3.85 (m, 4H) 3.91 (br t, J=10.87 Hz, 1H) 4.03 (q, J=7.12 Hz, 2H) 4.44 (br s, 1H) 4.57 (br s, 1H) 7.11 (t, J=9.22 Hz, 1H) 7.45-7.53 (m, 2H) 7.59 (dd, J=7.02, 2.43 Hz, 1H) 8.40 (br d, J=9.54 Hz, 1H) 9.34 (s, 1H). Method 3: Rt=3.40 min, m/z=481 (M+H)$^+$.

Example 15: Cis-Ethyl 8-((3-chloro-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (E15)

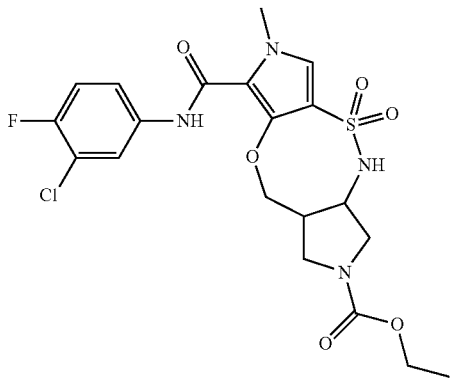 [SMILES: CCOC(=O)N1CC2COc3c(cn(C)c3C(=O)Nc3ccc(F)c(Cl)c3)S(=O)(=O)NC2C1]

Prepared similarly as described for compound E10 starting from D67 to give E15. The compound is the cis racemate at the pyrrolidine ring (mixture of 3aR,10aR and 3aS,10aS). $^1$H NMR (300 MHz, DMSO-d6) δ ppm 1.14-1.24 (m, 3H) 2.92-3.12 (m, 2H) 3.32-3.42 (m, 2H) 3.66-3.77 (m, 1H) 3.81 (s, 3H) 3.90 (br t, J=10.87 Hz, 1H) 4.03 (q, J=7.03 Hz, 2H) 4.39-4.49 (m, 1H) 4.51-4.64 (m, 1H) 7.41 (t, J=9.08 Hz, 1H) 7.48 (s, 1H) 7.61-7.67 (m, 1H) 7.99 (dd, J=6.88, 2.57 Hz, 1H) 8.41 (br d, J=9.81 Hz, 1H) 9.57 (s, 1H). Method 3: Rt=3.54 min, m/z=501 (M+H)$^+$.

Example 16: Cis-Ethyl 8-((3-(difluoromethyl)-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (E16)

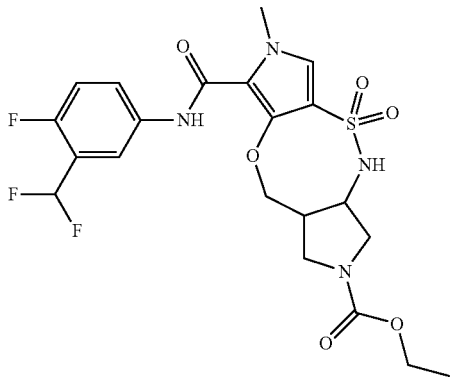 [SMILES: CCOC(=O)N1CC2COc3c(cn(C)c3C(=O)Nc3ccc(F)c(C(F)F)c3)S(=O)(=O)NC2C1]

Prepared similarly as described for compound E10 starting from D68 to give E16. The compound is the cis racemate at the pyrrolidine ring (racemate of 3aR,10aR and 3aS,10aS). $^1$H NMR (300 MHz, DMSO-d$_6$) δ ppm 1.13-1.23 (m, 3H) 2.91-3.14 (m, 2H) 3.32-3.43 (m, 2H) 3.71 (br dd, J=11.14, 5.82 Hz, 1H) 3.81 (s, 3H) 3.90 (br t, J=10.77 Hz, 1H) 4.03 (q, J=7.03 Hz, 2H) 4.39-4.49 (m, 1H) 4.51-4.64 (m, 1H) 7.03-7.43 (m, 2H) 7.48 (s, 1H) 7.76-7.83 (m, 1H) 8.06 (dd, J=6.24, 2.38 Hz, 1H) 8.41 (br d, J=10.00 Hz, 1H) 9.63 (s, 1H). Method 3: Rt=3.38 min, m/z=517 (M+H)$^+$.

Example 17: Cis-Ethyl 8-((3-cyano-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (E17)

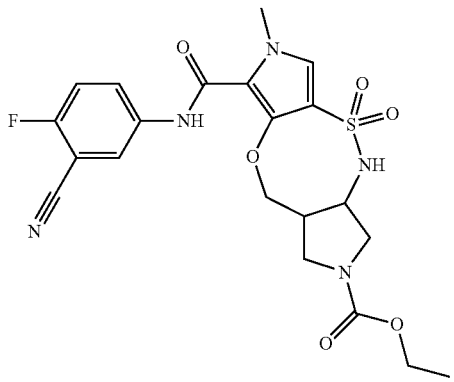 [SMILES: CCOC(=O)N1CC2COc3c(cn(C)c3C(=O)Nc3ccc(F)c(C#N)c3)S(=O)(=O)NC2C1]

Prepared similarly as described for compound E10 starting from D69 to give E17. The compound is the cis racemate at the pyrrolidine ring (mixture of 3aR,10aR and 3aS,10aS). $^1$H NMR (300 MHz, DMSO-d$_6$) δ ppm 1.14-1.24 (m, 3H) 2.92-3.14 (m, 2H) 3.31-3.43 (m, 2H) 3.72 (br dd, J=11.19, 5.87 Hz, 1H) 3.81 (s, 3H) 3.91 (br t, J=11.00 Hz, 1H) 4.04 (q, J=6.97 Hz, 2H) 4.38-4.50 (m, 1H) 4.52-4.67 (m, 1H) 7.49-7.57 (m, 2H) 8.01-8.08 (m, 1H) 8.19 (dd, J=5.73, 2.61 Hz, 1H) 8.43 (br d, J=9.90 Hz, 1H) 9.68 (s, 1H). Method 3: Rt=3.24 min, m/z=492 (M+H)$^+$.

Example 18: cis-2-(isopropylsulfonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E18)

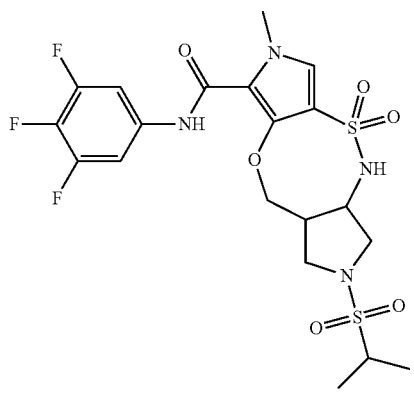 [SMILES: CC(C)S(=O)(=O)N1CC2COc3c(cn(C)c3C(=O)Nc3cc(F)c(F)c(F)c3)S(=O)(=O)NC2C1]

To a suspension of cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) (25 mg, 0.058 mmol) in dry DCM (0.5 mL) propane-2-sulfonyl chloride (0.007 mL, 0.062 mmol) and dry DIPEA (0.020 mL, 0.115 mmol) were added at room temperature. After 50 min, water (0.050 mL) was added and mixture evaporated under reduced pressure. Crude was purified with preparative HPLC-MS ($H_2O/CH_3CN+0.1\%$ TFA) to give E18 as a yellow powder (8.12 mg). The compound is the cis racemate at the pyrrolidine ring (racemate of 3aR,10aR and 3aS,10aS). $^1$H NMR (300 MHz, DMSO-$d_6$+TFA) δ ppm 1.25 (d, J=6.79 Hz, 6H) 2.98-3.13 (m, 2H) 3.25-3.52 (m, 3H) 3.76-3.99 (m, 5H) 4.48-4.63 (m, 2H) 7.51 (s, 1H) 7.60-7.74 (m, 2H) 8.48 (d, J=10.00 Hz, 1H) 9.65 (s, 1H). Method 3: Rt=3.60 min, m/z=537 (M+H)$^+$.

Example 19: cis-7-methyl-2-(methylsulfonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E19)

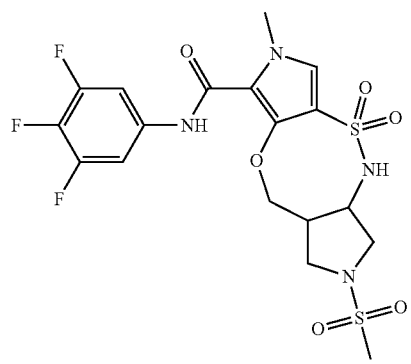 [SMILES: Cn1cc2c(c1C(=O)Nc1cc(F)c(F)c(F)c1)OCC1CN(S(C)(=O)=O)CC1NS2(=O)=O]

To a suspension of cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) (25 mg, 0.058 theoretical mmol) in dry acetonitrile (0.5 mL), methanesulfonyl chloride (5 ul, 0.065 mmol) and dry DIPEA (0.020 mL, 0.116 mmol) were added at room temperature. After 2 h methanesulfonyl chloride (5 ul, 0.065 mmol) and dry DIPEA (0.020 mL, 0.116 mmol) were added. After 1 h stirring, water (0.050 mL) was added and mixture evaporated under reduced pressure. Crude was purified by preparative HPLC-MS ($H_2O/CH_3CN+0.1\%$ TFA) to give E19 as a pale orange powder (9.17 mg). The compound is the cis racemate at the pyrrolidine ring (racemate of 3aR,10aR and 3aS,10aS). $^1$H NMR (300 MHz, DMSO-$d_6$) δ ppm 2.92 (s, 3H) 2.96-3.11 (m, 2H) 3.19-3.31 (m, 1H) 3.31-3.44 (m, 1H) 3.72-3.85 (m, 4H) 3.91 (t, J=11.00 Hz, 1H) 4.48-4.60 (m, 2H) 7.45 (s, 1H) 7.60-7.72 (m, 2H) 8.44 (d, J=9.90 Hz, 1H) 9.72 (s, 1H). Method 3: Rt=3.34 min, m/z=509 (M+H)$^+$.

Example 20: cis-2-(cyclopropylsulfonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E20)

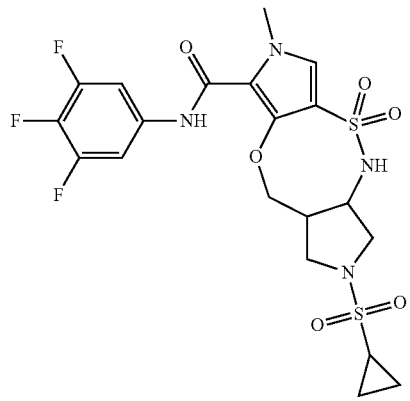 [SMILES: Cn1cc2c(c1C(=O)Nc1cc(F)c(F)c(F)c1)OCC1CN(S(=O)(=O)C3CC3)CC1NS2(=O)=O]

To a suspension of cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) (25 mg, 0.058 theoretical mmol) in dry acetonitrile (0.5 mL), cyclopropanesulfonyl chloride (7 ul, 0.069 mmol) and dry DIPEA (0.020 mL, 0.116 mmol) were added at room temperature and mixture stirred for 1.5 h. First purification with preparative HPLC-MS ($H_2O/CH_3CN+0.1\%$ TFA) was not enough to obtained a purity >95%, so a second purification was performed by flash chromatography (DCM/AcOEt) and a white powder was afford E20 (4.13 mg). The compound is the cis racemate at the pyrrolidine ring (racemate of 3aR,10aR and 3aS,10aS). $^1$H NMR (300 MHz, DMSO-$d_6$) δ ppm 0.91-1.04 (m, 4H) 2.63-2.75 (m, 1H) 2.98-3.13 (m, 2H) 3.28 (dd, J=10.68, 1.79 Hz, 1H) 3.39-3.52 (m, 1H) 3.78-3.89 (m, 4H) 3.94 (brt, J=10.96 Hz, 1H) 4.50-4.61 (m, 2H) 7.50 (s, 1H) 7.60-7.75 (m, 2H) 8.44 (d, J=10.00 Hz, 1H) 9.66 (s, 1H). Method 3: Rt=3.53 min, m/z=535 (M+H)$^+$.

Example 21: cis-2-(N-isopropylsulfamoyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E21)

Example 22: cis-(3R,3aS,6aR)-hexahydrofuro[2,3-b]furan-3-yl 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide (E22)

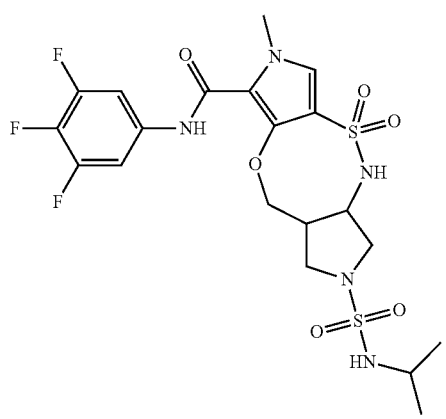 [SMILES: CC(C)NS(=O)(=O)N1CC2COc3c(cn(C)c3C(=O)Nc3cc(F)c(F)c(F)c3)S(=O)(=O)NC2C1]

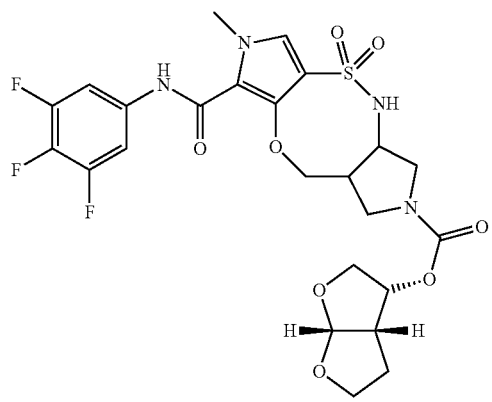

To a suspension of cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) (25 mg, 0.058 mmol) in dry acetonitrile (0.5 mL), isopropylsulfamoyl chloride (7.5 ul, 0.063 mmol) and dry DIPEA (0.025 mL, 0.144 mmol) were added at room temperature. After 1 h conversion was not completed so, dry DIPEA (0.025 mL, 0.144 mmol) and isopropylsulfamoyl chloride (7.5 ul, 0.063 mmol) were added. After a total of 4 h water (0.050 mL) was added and mixture evaporated under reduced pressure. Crude was purified with preparative HPLC-MS (H$_2$O/CH$_3$CN+0.1% TFA) to give E21 as a yellow powder (9.67 mg). The compound is the cis racemate at the pyrrolidine ring (mixture of 3aR,10aR and 3aS,10aS). $^1$H NMR (300 MHz, DMSO-d6) δ ppm 1.11 (dd, J=6.51, 2.11 Hz, 6H) 2.78-2.90 (m, 1H) 2.93-3.07 (m, 1H) 3.07-3.18 (m, 1H) 3.24-3.35 (m, 1H) 3.41 (dt, J=12.95, 6.41 Hz, 1H) 3.55-3.66 (m, 1H) 3.80 (s, 3H) 3.95 (t, J=11.28 Hz, 1H) 4.46-4.60 (m, 2H) 7.10 (br s, 1H) 7.49 (s, 1H) 7.62-7.72 (m, 2H) 8.35 (d, J=10.00 Hz, 1H) 9.63 (s, 1H). Method 3: Rt=3.62 min, m/z=552 (M+H)$^+$.

To a suspension of cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) (25 mg, 0.058 theoretical mmol) in dry DCM (0.5 mL), 2,5-dioxopyrrolidin-1-yl ((3R,3aS,6aR)-hexahydrofuro[2,3-b]furan-3-yl) carbonate (15.8 mg, 0.058 mmol) and dry DIPEA (0.020 mL, 0.115 mmol) were added at room temperature. After 1 h conversion was completed. Crude was diluted with DCM and washed with 5% citric acid solution. Organic layer was dried over Na$_2$SO$_4$, filtered and evaporated. Residue was purified with preparative HPLC-MS (H$_2$O/CH$_3$CN+0.1% TFA) to give E22 as a white powder (14.78 mg). The compound is the cis racemate at the pyrrolidine ring (racemate of 3aR,10aR and 3aS,10aS). $^1$H NMR (300 MHz, DMSO-d$_6$+TFA) δ ppm 1.73-1.89 (m, 1H) 1.89-2.06 (m, 1H) 2.94-3.15 (m, 3H) 3.37-3.49 (m, 2H) 3.58-3.97 (m, 9H) 4.40-4.51 (m, 1H) 4.51-4.63 (m, 1H) 5.00-5.08 (m, 1H) 5.60 (t, J=4.31 Hz, 1H) 7.50 (s, 1H) 7.62-7.73 (m, 2H) 8.41-8.49 (m, 1H) 9.64 (s, 1H). Method 3: Rt=3.37 min, m/z=587 (M+H)$^+$.

Example 23: (3aR,10aR) and (3aS,10aS)—N²,7-dimethyl-N⁸-(3,4,5-trifluorophenyl)-3a,4,10,10a-tetrahydro-1H,7H-dipyrrolo[3,4-b:3',4'-f][1,4,5]oxathiazocine-2,8(3H)-dicarboxamide 5,5-dioxide (E23)

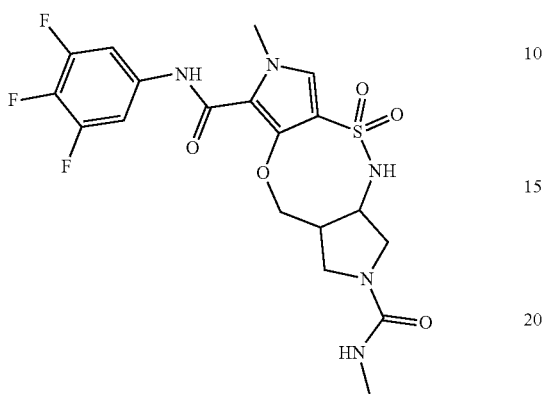

To a suspension of cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) (25 mg, 0.058 theoretical mmol), in dry acetonitrile (0.5 mL), N-methylcarbamoyl chloride (6.5 mg, 0.070 mmol) and dry DIPEA (0.025 mL, 0.058 mmol) were added at room temperature. Reaction was stopped after 2.5 h when conversion was completed. Water (0.050 mL) was added and mixture evaporated under reduced pressure. Crude was purified with preparative HPLC-MS (H₂O/CH₃CN+0.1% TFA) to give E23 as a pale yellow powder (13.26 mg). ¹H NMR (300 MHz, DMSO-d₆+TFA) δ ppm 2.58 (s, 3H) 2.90-3.07 (m, 2H) 3.28-3.46 (m, 2H) 3.59-3.70 (m, 1H) 3.80 (s, 3H) 3.91 (br t, J=10.73 Hz, 1H) 4.40-4.50 (m, 1H) 4.53-4.64 (m, 1H) 7.48 (s, 1H) 7.61-7.74 (m, 2H) 8.40 (d, J=10.00 Hz, 1H) 9.63 (s, 1H). Method 3: Rt=3.04 min, m/z=488 (M+H)⁺.

The compound is the cis racemate at the pyrrolidine ring.

Example 24: Tert-Butyl (3aS,10aS and 3aR,10aR) 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide (E24)

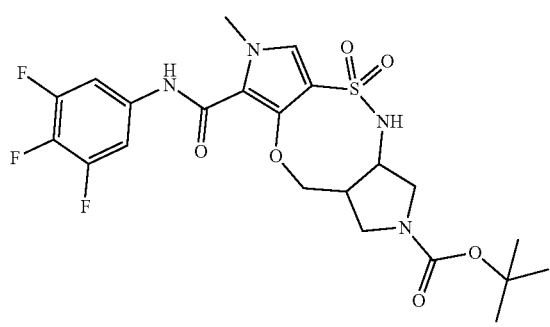 [SMILES: Cn1cc2c(c1C(=O)Nc1cc(F)c(F)c(F)c1)OCC1CN(C(=O)OC(C)(C)C)CC1NS2(=O)=O]

Crude D70 (61 mg, 0.11 mmol) was dissolved in DMF (2.8 ml), cesium carbonate (90.4 mg, 0.28 mmol) was added and the reaction mixture was heated at 130° C. under MW irradiation for 45 min. Reaction mixture was diluted with EtOAc and washed with 5% citric acid solution and water. Organic layer was dried over Na₂SO₄, filtered and concentrated under vacuo. The resulting crude was purified by flash chromatography on silica (DCM/EtOAc) to obtain the title compound E24 as a light brown powder (40 mg, y=67%). ¹H NMR (300 MHz, DMSO-d₆) δ ppm 1.41 (s, 9H) 2.82-3.11 (m, 2H) 3.33-3.44 (m, 2H) 3.62-3.76 (m, 1H) 3.80 (s, 3H) 3.84-3.97 (m, 1H) 4.31-4.48 (m, 1H) 4.49-4.71 (m, 1H) 7.50 (s, 1H) 7.61-7.81 (m, 2H) 8.46 (br s, 1H) 9.68 (s, 1H) Method 3: Rt=3.87 min. m/z=531.39 (M+H)⁺. The compound is the cis racemate at the pyrrolidine ring.

Example 25: (3aR,10aS)—N-(3,4-difluorophenyl)-7-methyl-2,3,3a,4,10,10a-hexahydro-1H,7H-dipyrrolo[3,4-b:3',2'-f][1,4,5]oxathiazocine-8-carboxamide 5,5-dioxide (E25)

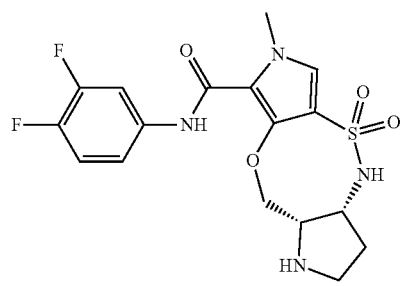 [SMILES: Cn1cc2c(c1C(=O)Nc1ccc(F)c(F)c1)OC[C@H]1NCC[C@H]1NS2(=O)=O]

In a 25 mL microwave vial, crude D72 (theoretical 0.261 mmol, 139 mg, 1 eq) was dissolved in dry DMF (8.6 mL, 0.030M), caesium carbonate (255 mg, 0.783 mmol, 3 eq) was added, the vial was sealed and reaction mixture was heated at microwave at 130° C. for a total of 4 h 10 min in 5 runs. Reaction mixture was quenched in 5% aqueous citric acid solution, product was extracted with ethyl acetate, organic layer was washed once with 5% aqueous citric acid solution and once with brine, dried over sodium sulfate, filtered and solvent was removed under reduced pressure affording 114 mg of brownish powder. Crude was purified with flash chromatography (DCM/AcOEt 7/3) to afford the Boc protected intermediate as a beige solid (71.2 mg, y=53%). Method 1: Rt=2.21 min, MH+=513 m/z. The compound from previous step (67 mg, 0.131 mmol, 1 eq) was dissolved in DCM (2 mL, 0.065M), triethylsilane (23 uL, 0.144 mol, 1.1 eq) was added and trifluoroacetic acid (200 uL, 2.612 mmol, 20 eq) was added and reaction mixture was stirred at rt. Complete conversion after 6 h. Reaction mixture was diluted with DCM, brine was added, organic layer was removed, NaOH 20% was added to brine until pH=10 and product was extracted twice with ethyl acetate. Organic layers were combined, dried over sodium sulfate, filtered and solvent was removed under reduced pressure affording 54 mg of crude product. 32 mg were used without any purification, 19 mg were purified with preparative HPLC-MS (H₂O, CH₃CN 0.1% TFA) to afford E25 as a white powder (9.56 mg). Method 3: Rt=2.21 min, MH+=413 m/z. Stereochemistry cis, single enantiomer. ¹H NMR (300 MHz, DMSO-d₆) δ ppm 1.97-2.10 (m, 1H) 2.32-2.45 (m, 1H) 3.27-3.46 (m, 2H) 3.81 (s, 3H) 3.92-4.05 (m, 1H) 4.40-4.53 (m, 1H) 4.53-4.68 (m, 2H) 7.32-7.56 (m, 3H) 7.83 (ddd, J=13.02, 7.34, 2.02 Hz, 1H) 8.22 (d, J=7.50 Hz, 1H) 8.61-8.83 (m, 1H) 9.17-9.37 (m, 1H) 9.58 (s, 1H).

Example 26: (3aR,10aS)—N8-(3,4-difluorophenyl)-N1,7-dimethyl-2,3,3a,4,10,10a-hexahydro-1H,7H-dipyrrolo[3,4-b:3',2'-f][1,4,5]oxathiazocine-1,8-dicarboxamide 5,5-dioxide (E26)

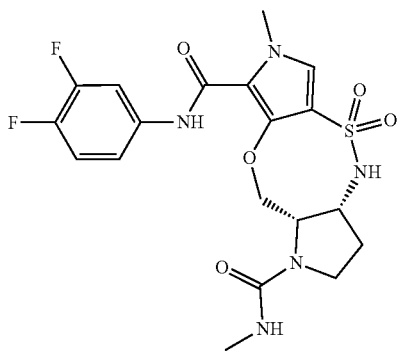 [SMILES: CNC(=O)N1CC[C@H]2NS(=O)(=O)c3cn(C)c(C(=O)Nc4ccc(F)c(F)c4)c3OC[C@H]21]

Crude E25 (16 mg, 0.039 mmol, 1 eq) was dissolved in dry MeCN (1.6 mL, 0.024M), N-methylcarbamoyl chloride (6.1 mg, 0.065 mmol, 1.68 eq) was added, N,N-diisopropylethylamine (40 uL, 0.230 mmol, 5.9 eq) was added and reaction mixture was stirred at rt. Complete conversion after 45 min. Reaction mixture was concentrated under reduced pressure and crude product was purified with preparative HPLC-MS (H$_2$O, CH$_3$CN 0.1% TFA) to afford E26 as a white yellow powder (6.98 mg). Method 3: Rt=2.85 min, MH+=470 m/z. Stereochemistry cis, single enantiomer. $^1$H NMR (300 MHz, DMSO-d$_6$) δ ppm 1.66-1.99 (m, 1H) 2.01-2.26 (m, 1H) 2.53-2.57 (m, 3H) 3.16-3.40 (m, 2H) 3.80 (s, 3H) 4.04-4.35 (m, 3H) 4.49 (br d, J=8.44 Hz, 1H) 7.33-7.52 (m, 3H) 7.87 (ddd, J=13.02, 7.52, 2.02 Hz, 1H) 8.18 (br d, J=8.44 Hz, 1H) 9.58 (s, 1H).

Example 27: Ethyl (3aR,10aS)-8-((3,4-difluorophenyl)carbamoyl)-7-methyl-2,3,3a,4,10,10a-hexahydro-1H,7H-dipyrrolo[3,4-b:3',2'-f][1,4,5]oxathiazocine-1-carboxylate 5,5-dioxide (E27)

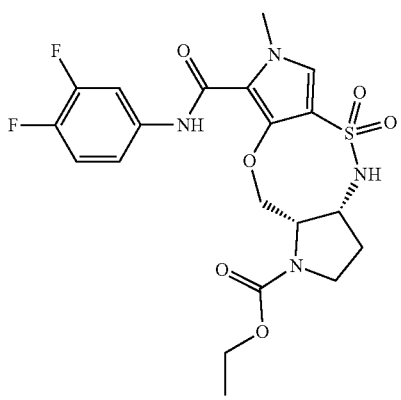 [SMILES: CCOC(=O)N1CC[C@H]2NS(=O)(=O)c3cn(C)c(C(=O)Nc4ccc(F)c(F)c4)c3OC[C@H]21]

Crude E25 (16 mg, 0.039 mmol, 1 eq) was dissolved in dry MeCN (1.6 mL, 0.024M), ethyl chloroformate (5 uL, 0.052 mmol, 1.35 eq) was added, N,N-diisopropylethylamine (40 uL, 0.230 mmol, 5.9 eq) was added and reaction mixture was stirred at rt. Complete conversion after 50 min. Reaction mixture was concentrated under reduced pressure and crude product was purified with preparative HPLC-MS (H$_2$O, CH$_3$CN 0.1% TFA) to afford E27 as a light yellow powder (9.38 mg). Method 3: Rt=3.42 min, MH+=485 m/z. $^1$H NMR (300 MHz, DMSO-d$_6$) δ ppm 1.13 (br s, 3H) 1.78-1.94 (m, 1H) 2.05-2.25 (m, 1H) 3.20-3.52 (m, 2H) 3.81 (s, 3H) 3.92-4.08 (m, 2H) 4.08-4.62 (m, 4H) 7.28-7.46 (m, 2H) 7.50 (br s, 1H) 7.71-7.97 (m, 1H) 8.08-8.38 (m, 1H) 9.62 (br s, 1H).

Example 28: cis (5aR,8aS and 5aS,8aR)-2-methyl-N-(3,4,5-trifluorophenyl)-5a,6,7,8,8a,9-hexahydro-2H,5H-cyclopenta[f]pyrrolo[3,4-b][1,4,5]oxathiazocine-1-carboxamide 4,4-dioxide (E28)

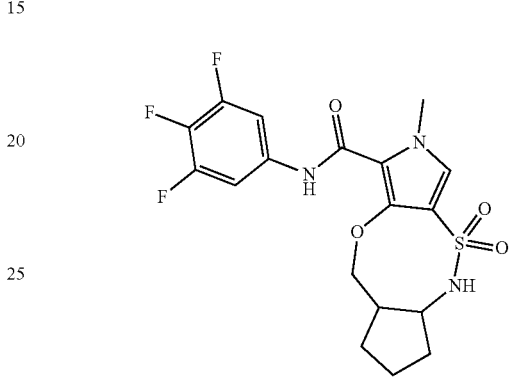

In a microwave D71 (66.9 mg, 0.149 mmol, 1 eq) was dissolved in dry DMF (6 mL), cesium carbonate (121.26 mg, 0.327 mmol, 2.5 eq) was added, the vial sealed and mixture heated at microwave at 130° C. for 30 min. The mixture was diluted with toluene, organic layer was washed with water, dried over Na$_2$SO$_4$, filtered and solvent was removed under reduced pressure. Crude product was purified on silica gel with flash chromatography affording 20 mg of pure E28. $^1$H NMR (300 MHz, DMSO-d$_6$) δ ppm 1.10-1.30 (m, 1H) 1.42-1.76 (m, 4H) 2.03-2.16 (m, 1H) 2.53-2.62 (m, 1H) 3.81 (s, 3H) 3.86 (t, J=11.60 Hz, 1H) 4.21-4.34 (m, 1H) 4.50 (br dd, J=11.10, 4.31 Hz, 1H) 7.47 (s, 1H) 7.70 (dd, J=10.27, 6.42 Hz, 2H) 7.89 (br d, J=9.90 Hz, 1H) 9.63 (s, 1H). Method 3: Rt=3.84 min, m/z=430 (M+H)$^+$.

Example 29: N-(3,4-difluorophenyl)-2,8a-dimethyl-5a,6,7,8,8a,9-hexahydro-2H,5H-cyclopenta[f]pyrrolo[3,4-b][1,4,5]oxathiazocine-1-carboxamide 4,4-dioxide (E29)

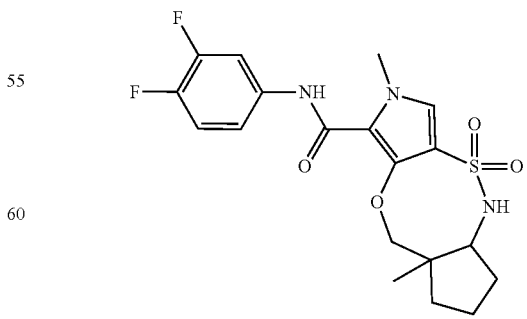

Crude D73 (114 mg, 0.193 theoretical mmol) was dissolved in dry DMF (4.8 mL); Cs$_2$CO$_3$ (158 mg, 0.482 mmol, 2.5 eq) was added and the mixture was heated to 130° C. under MW irradiation 1 h: complete conversion. The reaction was diluted with EtOAc and washed with water and 5% citric acid (2×); the organic phase was dried over Na₂SO₄ and evaporated, yielding 100 mg of crude as an orange solid which was purified by preparative HPLC (H₂O, CH₃CN 0.1% TFA). Fractions containing product were freeze-dried, yielding 30.44 mg (y=37%) of E29 as a white powder. Method 3: Rt=3.72 min, MH+=426 m/z. ¹H NMR (300 MHz, DMSO-d6) δ ppm 0.83 (s, 3H) 1.24-1.28 (m, 1H) 1.42-1.60 (m. 4H) 1.88-1.96 (m, 1H) 3.75-3.78 (m, 1H) 3.81 (s, 3H) 3.89-3.92 (d, J=11.76 Hz, 1H) 4.01-4.12 (d, J=11.76 Hz, 1H) 7.37-7.49 (m, 3H) 7.59-7.62 (d, J=9.81 Hz, 1H) 7.84-7.91 (m, 1H) 9.67 (s, 1H).

Example 30: cis-N-(3,4-difluorophenyl)-8a-hydroxy-2-methyl-5a,6,7,8,8a,9-hexahydro-2H,5H-cyclopenta[f]pyrrolo[3,4-b][1,4,5]oxathiazocine-1-carboxamide 4,4-dioxide (E30)

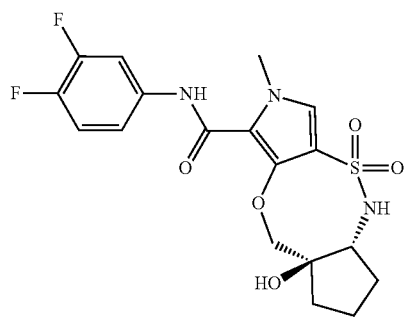 [SMILES: Cn1cc2c(c1C(=O)Nc1ccc(F)c(F)c1)OC[C@@]1(O)CCC[C@H]1NS2(=O)=O]

Crude D74 (38 mg, 0.058 mmol) was dissolved in dry DMF (1.5 mL); Cs₂CO₃ (47.2 mg, 0.145 mmol, 2.5 eq) was added and the mixture was heated to 130° C. under MW irradiation 1 h: complete conversion. The reaction was diluted with EtOAc and washed with water and 5% citric acid; the organic phase was dried over Na₂SO₄ and evaporated, yielding 47 mg of crude compound as a brown dense oil which was purified by preparative HPLC (H₂O, CH₃CN 0.1% HCOOH). Fractions containing product were freeze-dried, yielding 3.92 mg (y=15%) of E30 as a pale pink powder. Method 3: Rt=3.33 min, MH+=428 m/z. Stereochemistry cis, racemic. ¹H NMR (300 MHz, DMSO-d6) δ ppm 1.42-1.72 (m, 2H) 1.72-1.92 (m, 2H) 1.97-2.17 (m. 1H) 2.30-2.43 (m, 1H) 3.45 (br d, J=12.5 Hz, 1H) 3.71 (br d, J=12.0 Hz, 1H) 3.81 (s, 3H) 3.95-4.13 (m, 1H) 6.11 (br s, 1H) 7.14-7.33 (m, 1H) 7.34-7.58 (m, 2H) 7.79 (dddd, J=24.7, 13.1, 7.4, 2.5 Hz, 1H) 7.96-8.14 (m, 1H) 10.05-10.27 (m, 1H).

The synthesis of compounds E31-46 is reported in Table 1 below.

Example 47: cis-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide hydroiodide (E47)

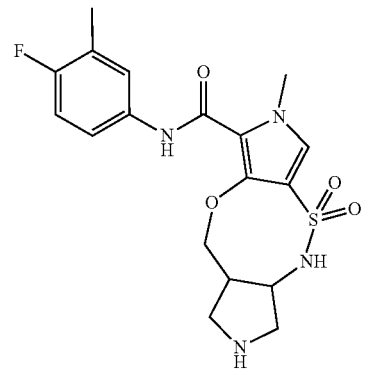

E47 was synthesized as described for the synthesis of E11 starting from E14. 1H NMR (300 MHz, DMSO-d6) δ ppm 2.21-2.28 (m, 3H) 2.91 (br d, J=8.44 Hz, 2H) 3.15 (dd, J=12.93, 3.58 Hz, 1H) 3.75-3.86 (m, 4H) 3.99 (s, 1H) 4.59 (br dd, J=11.51, 3.35 Hz, 2H) 7.12 (t, J=9.17 Hz, 1H) 7.47-7.54 (m, 2H) 7.60 (dd, J=6.97, 2.29 Hz, 1H) 8.34 (d, J=9.35 Hz, 1H) 8.91 (br s, 2H) 9.37 (s, 1H). Method 1: Rt=1.36 min; m/z=409.17 (M+H)⁺.

Example 48: cis-N-(4-fluoro-3-methylphenyl)-7-methyl-2-(pyridin-3-yl)-2,3,3a,4,10,10a-hexahydro-1H,7H-dipyrrolo[3,4-b:3',4'-f][1,4,5]oxathiazocine-8-carboxamide 5,5-dioxide (E48)

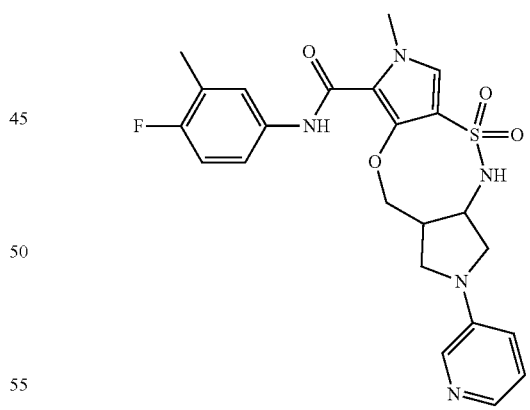

E47 (40 mg, 0.070 mmol) was suspended in water (3-4 mL), treated with 2M NaOH (1 mL) giving a clear solution. The pyrrolidine E47 as a free base was extracted with DCM and 2-Me-THF, concentrated under reduced pressure then was dissolved in toluene (1 mL) and THF (250 uL). A 5 mL vial was charged with 3-bromopyridine (12.96 mg, 0.080 mmol), 2,2'-bis(diphenylphosphinyl)-1,1'-binaphthalene (2.32 mg, 0.004 mmol), potassium tert-buthoxide (13.14 mg, 0.120 mmol) and a magnetic stirrer, the vial was sealed and evacuated, the previously prepared solution of E47 in toluene and THF, was added in a single portion and the reaction heated to 80-90° C. for 30 min. THF (dry) was added and the reaction mixture heated by microwave irradiation at 100° C. for 4 hrs.

The product was purified by preparative HPLC (H₂O, CH₃CN 0.1% TFA). Fractions containing the pure product were freeze-dried, to yield E48 (2.42 mg) as TFA salt. ¹H NMR (300 MHz, DMSO-d6) δ ppm 2.22-2.26 (m, 3H) 3.09-3.20 (m, 3H) 3.53 (s, 1H) 3.82 (s, 4H) 3.98-4.13 (m, 1H) 4.56-4.75 (m, 2H) 7.12 (t, J=9.30 Hz, 1H) 7.32-7.44 (m, 1H) 7.44-7.66 (m, 4H) 7.92-8.15 (m, 2H) 8.41 (d, J=9.90 Hz, 1H) 9.39 (s, 1H). Method 1: Rt=2.60 min. m/z=486.

Example 49: cis-N-(4-fluoro-3-methylphenyl)-7-methyl-2-(1,3,4-oxadiazol-2-yl)-2,3,3a,4,10,10a-hexahydro-1H,7H-dipyrrolo[3,4-b:3',4'-f][1,4,5]oxathiazocine-8-carboxamide 5,5-dioxide (E49)

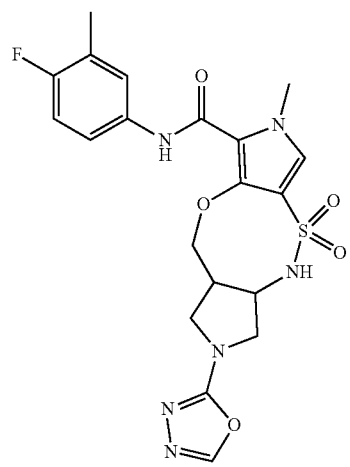 [SMILES: Cc1cc(NC(=O)c2c3c(cn2C)S(=O)(=O)NC2CN(c4nnco4)CC2CO3)ccc1F]

To a solution of 1,3,4-oxadiazol-2(3H)-one (Fluorochem, cat no 401697; 13.7 mg, 0.160 mmol) in DMF (2 mL) was added DIPEA (101 uL, 0.58 mmol) followed by E47 (78 mg, 0.150 mmol). To the stirring solution was added benzotriazol-1-yloxytris(dimethylamino)phosphonium hexafluorophosphate (70.75 mg, 0.160 mmol) (BOP) and the reaction mixture stirred at RT for 72 h. The reaction mixture was diluted with EtOAc (20 mL) and the solution washed with water (20 mL). The organic extracts additionally were washed with brine. The organic portion was dried (Na₂SO₄), filtered and concentrated under reduced pressure then the residue purified by Fraction-Lynx (H₂O/CH₃CN+1‰ HCOOH) to afford E49 (24.93 mg) as an off-white solid. ¹H NMR (300 MHz, DMSO-d6) δ ppm 2.21-2.28 (m, 3H) 3.05-3.20 (m, 1H) 3.20-3.29 (m, 1H) 3.55 (br d, J=2.11 Hz, 2H) 3.82 (s, 3H) 3.88-3.96 (m, 1H) 3.96-4.07 (m, 1H) 4.58 (br t, J=5.41 Hz, 1H) 4.64 (dd, J=11.69, 4.54 Hz, 1H) 7.11 (t, J=9.17 Hz, 1H) 7.30 (br s, 1H) 7.41-7.55 (m, 2H) 7.60 (dd, J=7.02, 2.34 Hz, 1H) 8.61 (s, 1H) 9.36 (s, 1H). Method 1: Rt=2.96 min. m/z=477 (M+H)⁺.

Example 50: cis-7-methyl-2-(oxazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E50)

Scheme 21 refers to the synthesis of E50, according to the steps described below.

Scheme 21

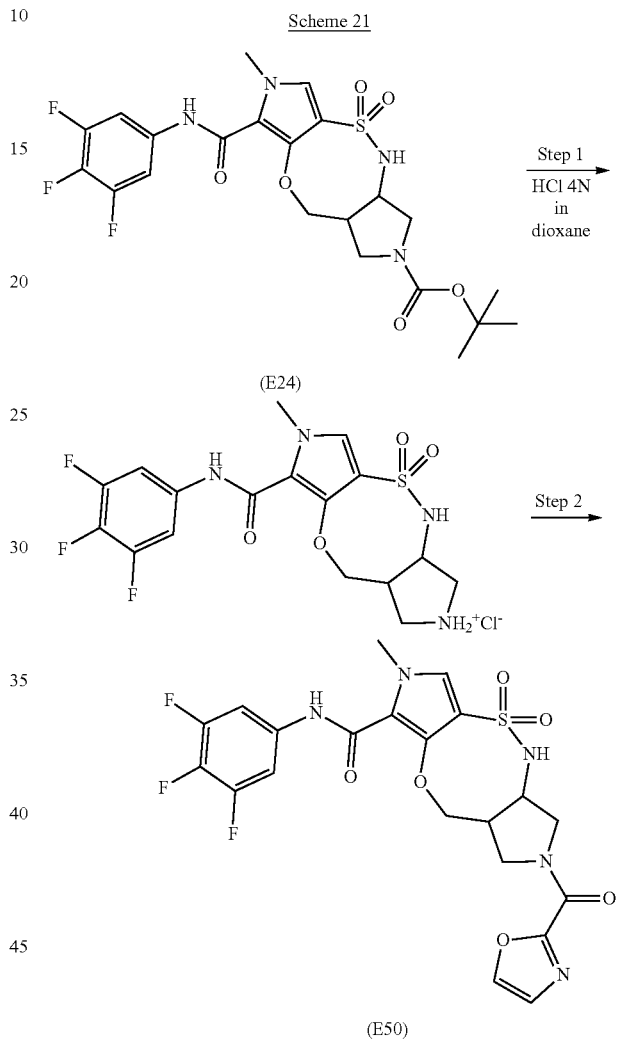

Step 1

E24 (20 mg, 0.040 mmol) was suspended in THF (0.3 mL). 4N HCl dioxane (0.38 mL, 1.51 mmol) was added, and the reaction mixture was stirred at RT overnight. The reaction was concentrated under vacuo, and the resulting solid was triturated with DCM, to obtain cis-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide hydrochloride (y=89%) as an off-white solid. Method 3; Rt=2.48 min. m/z=431.28 (M+H)⁺.

Step 2

A mixture of compound from Step 1 (30 mg, 0.060 mmol) and sodium 1,3-oxazole-2-carboxylate (Fluorochem, no 049914) (13 mg, 0.100 mmol), 2-(2,3-dihydro-1H-benzo[d][1,2,3]triazol-1-yl)-1,1,3,3-tetramethylisouronium hexafluorophosphate(V) (26.85 mg, 0.070 mmol) in DMF (0.8 mL) was treated with a single portion of triethylamine (0.027 mL, 0.190 mmol). The reaction mixture was stirred at room temperature 1 h, then solvent was concentrated under reduced pressure and the residue partitioned between water and EtOAc. The organic layer, was evaporated and the crude was purified by preparative HPLC (H₂O, CH₃CN 0.1% HCOOH) yielding E50 (8.44 mg). ¹H NMR (300 MHz, DMSO-d6) δ ppm 2.93-3.22 (m, 1H) 3.26-3.86 (m, 5H) 4.26 (s, 3H) 4.42-4.75 (m, 2H) 7.44 (d, J=11.00 Hz, 1H) 7.48 (s, 1H) 7.58-7.77 (m, 2H) 8.26 (d, J=4.86 Hz, 1H) 8.46 (dd, J=9.54, 4.68 Hz, 1H) 9.63 (s, 1H). Method 3: Rt=3.30 min, m/z=526 (M+H)⁺.

Example 51: cis-7-methyl-2-(5-methyl-1,3,4-oxadiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E51)

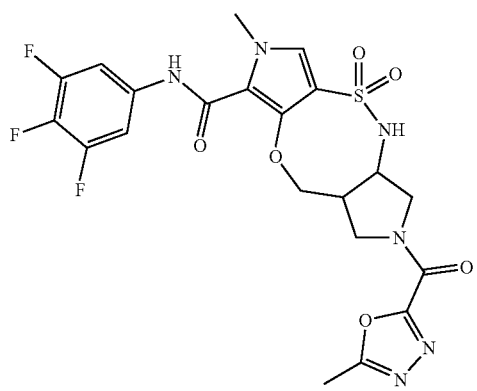 [SMILES: Cc1nnc(C(=O)N2CC3COc4c(cn(C)c4C(=O)Nc4cc(F)c(F)c(F)c4)S(=O)(=O)NC3C2)o1]

Prepared similarly as described for compound E50 using in Step 2 potassium 5-methyl-1,3,4-oxadiazole-2-carboxylate (Fluorochem, cat no 092836). The crude was purified by preparative HPLC (H₂O, CH₃CN 0.1% HCOOH) to afford E51 (7.23 mg). ¹H NMR (300 MHz, DMSO-d6) δ ppm 2.59 (d, J=3.12 Hz, 3H) 3.01-3.21 (m, 1H) 3.27-3.85 (m, 5H) 3.90-4.31 (m, 3H) 4.70 (s, 2H) 7.52 (d, J=1.19 Hz, 1H) 7.62-7.77 (m, 2H) 8.41-8.52 (m, 1H) 9.68 (s, 1H). Method 3: Rt=3.27 min, m/z=541 (M+H)⁺.

Example 52: cis-N-(4-fluoro-3-methylphenyl)-7-methyl-2-(5-methylisoxazole-3-carbonyl)-2,3,3a,4,10,10a-hexahydro-1H,7H-dipyrrolo[3,4-b:3',4'-f][1,4,5]oxathiazocine-8-carboxamide 5,5-dioxide (E52)

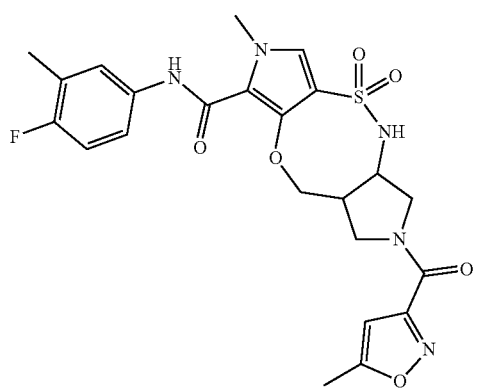 [SMILES: Cc1cc(C(=O)N2CC3COc4c(cn(C)c4C(=O)Nc4ccc(F)c(C)c4)S(=O)(=O)NC3C2)no1]

The compound was prepared by reacting E47, 5-methylisoxazole-3-carboxylic acid (Sigma Aldrich, cat no 644676) and 2-(2,3-dihydro-1H-benzo[d][1,2,3]triazol-1-yl)-1,1,3,3-tetramethylisouronium hexafluorophosphate(V) in DMF in the presence of triethylamine. The reaction mixture was stirred at room temperature for 1 h, then solvent was concentrated under reduced pressure and the residue partitioned between water and EtOAc. The organic layer, was evaporated and the crude was purified by preparative HPLC (H₂O, CH₃CN 0.1% HCOOH). The crude was purified by preparative HPLC (H₂O, CH₃CN 0.1% HCOOH) to afford E52 (32 mg) as white solid. ¹H NMR (300 MHz, DMSO-d6) δ ppm 2.16-2.26 (m, 3H) 2.45 (d, J=7.24 Hz, 3H) 2.95-3.21 (m, 1H) 3.23-3.54 (m, 1H) 3.59-3.77 (m, 3H) 3.81 (d, J=1.19 Hz, 3H) 3.86-4.16 (m, 3H) 4.34-4.75 (m, 2H) 6.49 (dd, J=4.03, 0.83 Hz, 1H) 7.10 (td, J=9.17, 3.03 Hz, 1H) 7.46 (m, J=1.90 Hz, 2H) 7.55-7.74 (m, 1H) 8.47 (dd, J=9.90, 3.94 Hz, 1H) 9.34 (d, J=5.23 Hz, 1H). Method 3; Rt=3.36 min. m/z=518 (M+H)⁺.

Example 53: cis-N-(4-fluoro-3-methylphenyl)-2-(6-hydroxynicotinoyl)-7-methyl-2,3,3a,4,10,10a-hexahydro-1H,7H-dipyrrolo[3,4-b:3',4'-f][1,4,5]oxathiazocine-8-carboxamide 5,5-dioxide (E53)

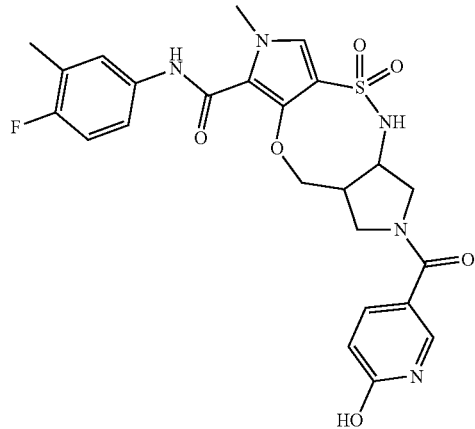 [SMILES: Cc1cc(NC(=O)c2c3c(cn2C)S(=O)(=O)NC2CN(C(=O)c4ccc(O)nc4)CC2CO3)ccc1F]

Prepared similarly as described for compound E52 starting from E47 and 6-Hydroxyniacin (Fluorochem, cat no 009265). The crude was purified by preparative HPLC (H₂O, CH₃CN 0.1% HCOOH) to afford E53 (10 mg) as white solid. ¹H NMR (300 MHz, DMSO-d6) δ ppm 2.24 (m, J=1.20 Hz, 3H) 2.92-3.11 (m, 1H) 3.35-3.43 (m, 1H) 3.48-3.67 (m, 2H) 3.81 (s, 3H) 3.87-4.12 (m, 2H) 4.38-4.51 (m, 1H) 4.52-4.69 (m, 1H) 6.35 (d, J=9.45 Hz, 1H) 7.11 (t, J=9.17 Hz, 1H) 7.47 (s, 2H) 7.54-7.69 (m, 3H) 8.42 (br s, 1H) 9.34 (s, 1H) 11.80 (br s, 1H). Method 3; Rt=2.71 min. m/z=530 (M+H)⁺.

Example 54: cis-N-(4-fluoro-3-methylphenyl)-7-methyl-2-nicotinoyl-2,3,3a,4,10,10a-hexahydro-1H,7H-dipyrrolo[3,4-b:3',4'-f][1,4,5]oxathiazocine-8-carboxamide 5,5-dioxide (E54)

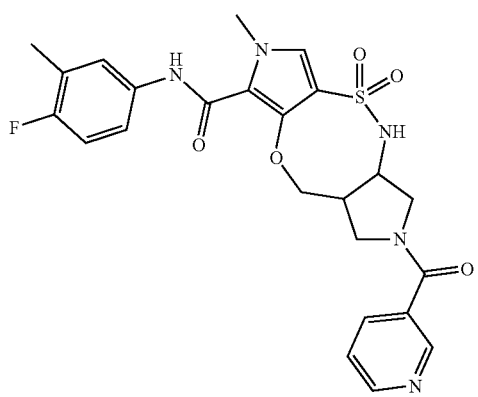 [SMILES: Cc1cc(NC(=O)c2c3c(cn2C)S(=O)(=O)NC2CN(C(=O)c4cccnc4)CC2CO3)ccc1F]

Prepared similarly as described for compound E52 starting from E47 and Niacin (Sigma Aldrich, cat no N-4126). The crude was purified by preparative HPLC (H₂O, CH₃CN 0.1% HCOOH) to afford E54 (27 mg) as white solid. ¹H NMR (300 MHz, DMSO-d6+TFA) δ ppm 2.23 (br d, J=11.00 Hz, 3H) 2.96-3.18 (m, 1H) 3.40 (s, 2H) 3.58-3.84 (m, 4H) 3.85-3.98 (m, 1H) 4.01-4.16 (m, 1H) 4.38-4.73 (m, 2H) 7.01-7.18 (m, 1H) 7.37-7.66 (m, 3H) 7.88-8.04 (m, 1H) 8.35-8.55 (m, 2H) 8.85-9.04 (m, 2H) 9.34 (d, J=6.51 Hz, 1H). Method 3; Rt=2.62 min. m/z=514 (M+H)⁺.

Example 55: cis-N-(4-fluoro-3-methylphenyl)-2-isonicotinoyl-7-methyl-2,3,3a,4,10,10a-hexahydro-1H,7H-dipyrrolo[3,4-b:3',4'-f][1,4,5]oxathiazocine-8-carboxamide 5,5-dioxide (E55)

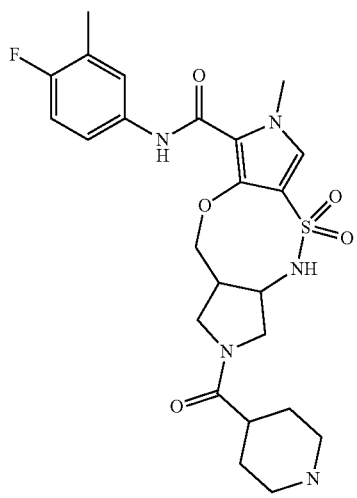 [SMILES: Cc1cc(NC(=O)c2c3c(cn2C)S(=O)(=O)NC2CN(C(=O)C4CCNCC4)CC2CO3)ccc1F]

E47 (30 mg, 0.060 mmol) and N-ethyl-N-isopropylpropan-2-amine (0.1 mL, 0.560 mmol) were added to isonicotinoyl chloride hydrochloride (Sigma Aldrich, cat no 228753) (79.66 mg, 0.450 mmol) in DCM (0.560 mL) and stirred for 2 h. Then the mixture was partitioned between water and DCM and concentrated in vacuo. The crude was directly purified by preparative HPLC (H₂O, CH₃CN 0.1% HCOOH). The pure fractions were combined and lyophilized to afford E55 (17.6 mg, 0.033 mmol). ¹H NMR (300 MHz, DMSO-d6+TFA) δ 2.16-2.26 (m, 3H), 2.96-3.12 (m, 1H), 3.14-3.49 (m, 2H), 3.58-4.12 (m, 6H), 4.37-4.72 (m, 2H), 6.94-7.18 (m, 1H), 7.38-7.67 (m, 3H), 7.94-8.12 (m, 2H), 8.37-8.54 (m, 1H), 8.94 (s, 2H), 9.26-9.41 (m, 1H). Method 3: Rt=2.55 min, m/z=514 (M+H)⁺.

Example 56: cis-7-methyl-2-(5-oxo-4,5-dihydropyrazine-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E56)

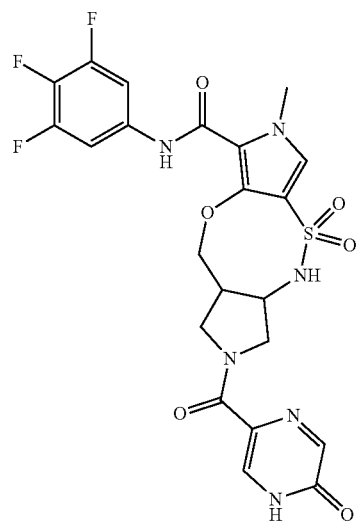 [SMILES: Cn1cc2c(c1C(=O)Nc1cc(F)c(F)c(F)c1)OCC1CN(C(=O)c3c[nH]c(=O)cn3)CC1NS2(=O)=O]

The compound was prepared by treating cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11), 5-hydroxy-2-pyrazine carboxylic acid (Sigma Aldrich, cat no N 56350) and 2-(2,3-dihydro-1H-benzo[d][1,2,3]triazol-1-yl)-1,1,3,3-tetramethylisouronium hexafluorophosphate(V) (26.85 mg, 0.070 mmol) in DMF (0.8 mL) with a single portion of trimethylamine, as described for the synthesis of E50, Step 2. The crude was purified by preparative HPLC (H₂O, CH₃CN 0.1% HCOOH) to afford E56 (9.7 mg) as white solid. Method 3; Rt=3.00 min. m/z=553 (M+H)⁺. ¹H NMR (300 MHz, DMSO-d₆+TFA) δ 2.92-3.13 (m, 1H), 3.23-3.75 (m, 2H), 3.80 (s, 3H), 3.86-4.30 (m, 3H), 4.39-4.74 (m, 2H), 7.49 (s, 1H), 7.57-7.79 (m, 2H), 7.86-8.06 (m, 2H), 8.32-8.54 (m, 1H), 9.65 (s, 1H).

Example 57: cis-7-methyl-2-(1-methyl-1H-pyrazole-4-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E57)

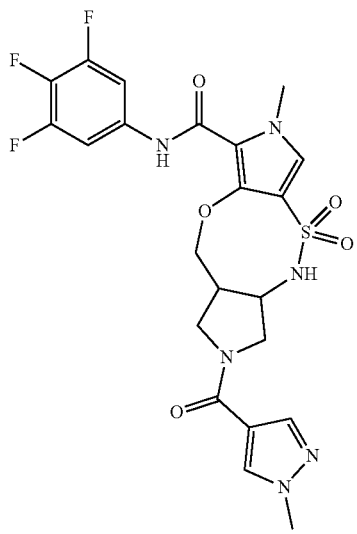 [SMILES: Cn1cc(C(=O)N2CC3COc4c(cn(C)c4C(=O)Nc4cc(F)c(F)c(F)c4)S(=O)(=O)NC3C2)cn1]

Prepared similarly as described for compound E56 starting from cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) and 1-methyl-1H-pyrazole-4-carboxylic acid (Sigma Aldrich, cat no N 682063). The crude was purified by preparative HPLC (H₂O, CH₃CN 0.1% HCOOH) to afford E57 (13.8 mg) as white solid. ¹H NMR (300 MHz, DMSO-d6+TFA) δ ppm 2.93-3.19 (m, 1H) 3.19-4.31 (m, 11H) 4.37-4.76 (m, 2H) 7.50 (d, J=2.80 Hz, 1H) 7.60-7.83 (m, 3H) 8.15 (d, J=27.05 Hz, 1H) 8.43-8.54 (m, 1H) 9.67 (d, J=6.70 Hz, 1H). Method 3; Rt=3.11 min. m/z=539 (M+H)⁺.

Example 58: cis-7-methyl-2-(thiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E58)

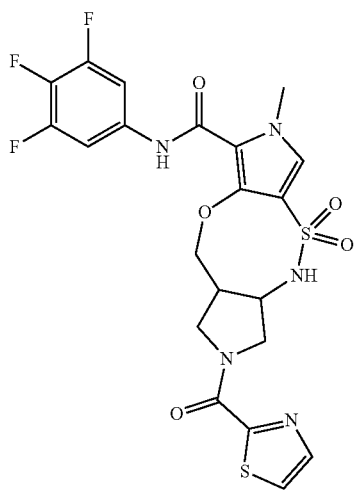 [SMILES: Cn1cc2c(c1C(=O)Nc1cc(F)c(F)c(F)c1)OCC1CN(C(=O)c3nccs3)CC1NS2(=O)=O]

Prepared similarly as described for compound E56 starting from cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) and 1,3-thiazole-2-carboxylic acid (Sigma Aldrich, cat no N 046193). The crude was purified by preparative HPLC (H₂O, CH₃CN 0.1% HCOOH) to afford E58 (5.85 mg) as white solid. Method 3; Rt=3.55 min. m/z=542 (M+H)⁺. ¹H NMR (300 MHz, DMSO-d6+TFA) δ 2.95-3.22 (m, 1H) 3.30-3.85 (m, 5H), 3.91-4.61 (m, 4H), 4.62-4.72 (m, 1H), 7.50 (s, 1H), 7.69 (dt, J=10.59, 5.94 Hz, 2H), 7.98-8.09 (m, 2H), 8.48 (dd, J=9.72, 3.03 Hz, 1H), 9.66 (s, 1H).

Example 59: cis-7-methyl-2-(6-oxo-1,6-dihydropyrimidin-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E59)

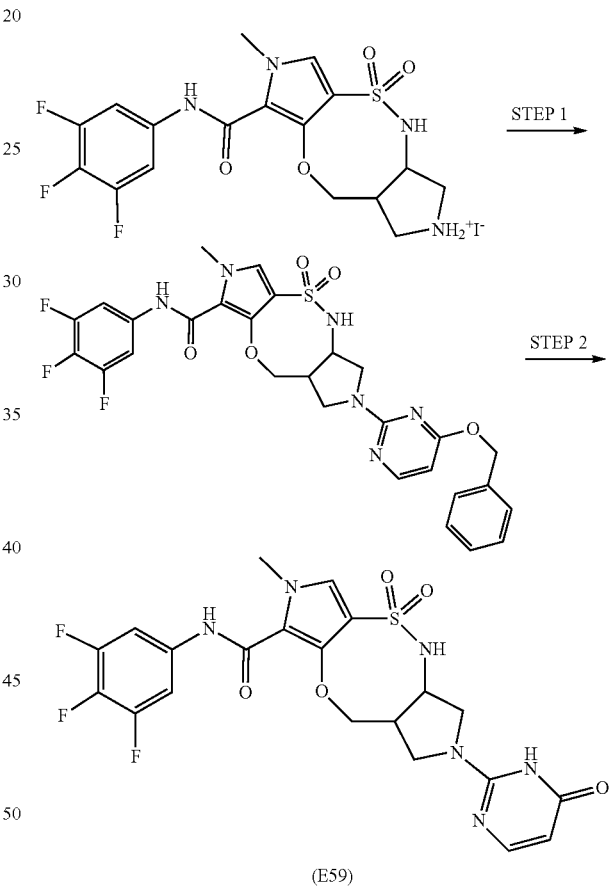

Step 1

In a microwave vial, cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) (30 mg, 0.054 mmol) and 4-(benzyloxy)-2-chloropyrimidine (24 mg, 0.109 mmol) were suspended in 1-Butanol (0.5 mL), dry DIPEA (0.030 mL, 0.172 mmol) was added and mixture was heated at 120° C. under MW heating 1 h. UPLC-MS showed complete conversion. The mixture was evaporated under reduced pressure to afford a brown solid. The residue was purified by preparative HPLC (H₂O, CH₃CN 0.1% TFA) to afford, after lyophilization, 2-(4-(benzyloxy)pyrimidin-2-yl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide as a beige powder (30 mg, yield=91%). 4-(benzyloxy)-2-chloropyrimidine was present as impurity. Product was used in next step without further purification.

Step 2

In a microwave vial the crude product from Step 1 (30 mg, 0.049 theoretical mmol) was dissolved in a mixture of DCM (0.3 mL) and methanol (0.5 mL). Pd/C 10% wt (5.2 mg, 0.005 mmol) was added and the vial was sealed. 1,4 cyclohexadiene (0.025 mL, 0.264 mmol) was added and mixture heated at 40° C. for 2 h 30 min. UPLC-MS showed complete conversion. Mixture was filtered on celite pad, solution was evaporated under reduced pressure to afford a beige solid (22 mg). The crude was purified by preparative HPLC ($H_2O$, $CH_3CN$ 0.1% TFA) to afford, after freeze-drying, E59 as a white powder (6.20 mg). $^1$H NMR (300 MHz, DMSO-d6+ TFA) δ ppm 3.15 (br s, 1H) 3.41 (m, J=10.10, 10.10 Hz, 1H) 3.59-3.93 (m, 5H) 3.93-4.22 (m, 2H) 4.53-4.74 (m, 2H) 6.09 (d, J=7.52 Hz, 1H) 7.51 (s, 1H) 7.67 (dd, J=10.27, 6.51 Hz, 2H) 7.77-7.95 (m, 1H) 8.30-8.50 (m, 1H) 9.69 (s, 1H). Method 3; Rt: 2.58 m/z: 525 $(M+H)^+$; 2.64 m/z: 525 $(M+H)^+$ (keto-enol tautomerism).

Example 60: cis-2-(4-amino-1,2,5-oxadiazole-3-carbonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E60)

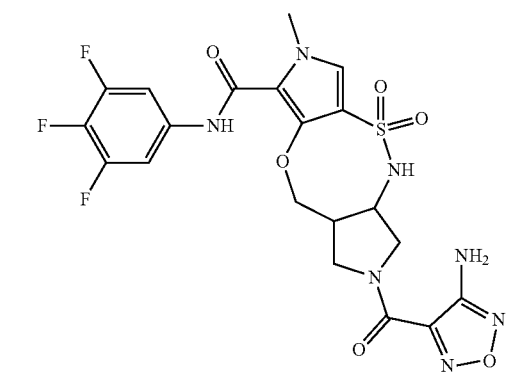 [SMILES: Cn1cc2c(c1C(=O)Nc1cc(F)c(F)c(F)c1)OCC1CN(C(=O)c3nonc3N)CC1NS2(=O)=O]

Prepared similarly as described for compound E56 starting from cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) and 4-amino-1,2,5-oxadiazole-3-carboxylic acid (Fluorochem, cat no 061142). The crude was purified by preparative HPLC ($H_2O$, $CH_3CN$ 0.1% HCOOH) to afford E60 (5.85 mg) as white solid. $^1$H NMR (300 MHz, DMSO-d6) δ ppm 2.96-3.23 (m, 1H) 3.47-3.61 (m, 1H) 3.64-4.07 (m, 6H) 4.14-4.27 (m, 1H) 4.45-4.73 (m, 2H) 6.42 (br d, J=3.76 Hz, 2H) 7.52 (s, 1H) 7.64-7.75 (m, 2H) 8.34-8.57 (m, 1H) 9.67 (d, J=3.12 Hz, 1H). Method 3; Rt=3.53 min. m/z=542 $(M+H)^+$.

Example 61: cis-2-(4-amino-1,2,5-oxadiazole-3-carbonyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide (E61)

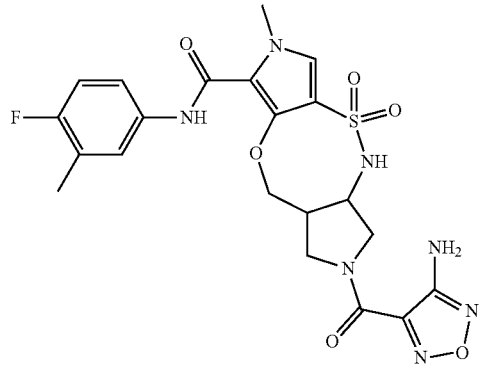 [SMILES: Cc1cc(NC(=O)c2c3c(cn2C)S(=O)(=O)NC2CN(C(=O)c4nonc4N)CC2CO3)ccc1F]

Prepared similarly as described for compound E52 starting from E47 and 4-amino-1,2,5-oxadiazole-3-carboxylic acid (Fluorochem, cat no 061142). The crude was purified by preparative HPLC ($H_2O$, $CH_3CN$ 0.1% HCOOH) to afford E61 (16 mg) as white solid. $^1$H NMR (300 MHz, DMSO-d6) δ ppm 2.15-2.26 (m, 2H) 2.27 (br s, 1H) 2.93-3.20 (m, 1H) 3.55 (br t, J=10.77 Hz, 1H) 3.63-4.09 (m, 6H) 4.12-4.28 (m, 1H) 4.42-4.74 (m, 2H) 6.43 (br s, 2H) 7.01-7.20 (m, 1H) 7.40-7.55 (m, 2H) 7.55-7.65 (m, 1H) 0.00 (d, J=8.80 Hz, 1H) 9.34 (d, J=5.70 Hz, 1H). Method 3; Rt=3.37 min. m/z=520 $(M+H)^+$.

Example 62: cis-N-(4-fluoro-3-methylphenyl)-7-methyl-2-(5-methyl-1,3,4-thiadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide (E62)

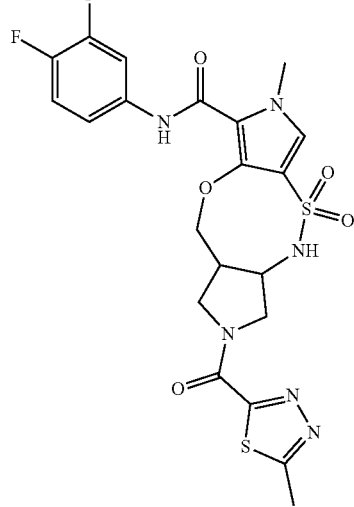

Prepared similarly as described for compound E52 starting from E47 and 5-methyl-1,3,4-thiadiazole-2-carboxylic acid. The crude was purified by preparative HPLC (H₂O, CH₃CN 0.1% HCOOH) to afford E62 (15 mg). ¹H NMR (300 MHz, DMSO-d6+TFA) δ ppm 2.24 (s, 3H) 2.77 (d, J=6.42 Hz, 3H) 2.93-3.24 (m, 1H) 3.28-3.79 (m, 2H) 3.81 (d, J=1.19 Hz, 3H) 3.91-4.23 (m, 2H) 4.24-4.36 (m, 1H) 4.46-4.60 (m, 1H) 4.61-4.71 (m, 1H) 7.10 (td, J=9.35, 1.83 Hz, 1H) 7.42-7.54 (m, 2H) 7.55-7.64 (m, 1H) 8.35-8.57 (m, 1H) 9.34 (d, J=3.58 Hz, 1H). Method 3; Rt=3.22 min. m/z=535 (M+H)⁺.

Example 63: cis-N-(4-fluoro-3-methylphenyl)-7-methyl-2-(1,2,4-oxadiazole-3-carbonyl)-2,3,3a,4,10,10a-hexahydro-1H,7H-dipyrrolo[3,4-b:3',4'-f][1,4,5]oxathiazocine-8-carboxamide 5,5-dioxide (E63)

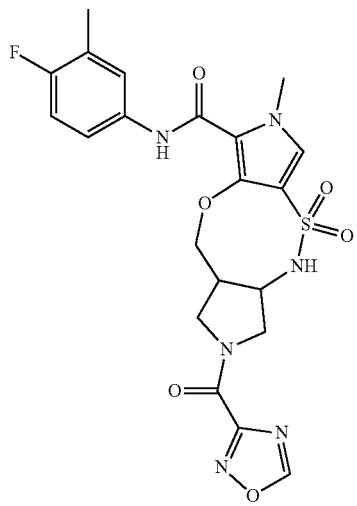 [SMILES: Cc1cc(NC(=O)c2c3c(cn2C)S(=O)(=O)NC2CN(C(=O)c4ncon4)CC2CO3)ccc1F]

To a solution of 1,2,4-oxadiazole-3-carboxylic acid (Fluorochem, cat No 66283) (21.2 mg, 0.190 mmol) in MeCN (0.5 mL) was added oxalyl dichloride (0.02 mL, 0.190 mmol) followed by some drops of DMF. The reaction mixture was stirred at RT 1 h, then was added to a solution of E47 (35 mg, 0.07 mmol) and DIPEA (0.056 mL, 0.33 mmol) in MeCN (0.5 mL), cooled to 0° C. The resulting solution was allowed to warm to RT and stirred over-weekend. The reaction was then diluted with EtOAc and washed with aq 5% citric acid solution (×2) and s.s. NaHCO₃. The organic layer was dried over Na₂SO₄, filtered and concentrated under vacuo. The resulting crude was purified by preparative HPLC (H₂O, CH₃CN 0.1% HCOOH) to afford E63 (18 mg) as white solid. ¹H NMR (300 MHz, DMSO-d6) δ ppm 2.17-2.27 (m, 3H) 3.00-3.20 (m, 1H) 3.35-3.50 (m, 1H) 3.60-3.85 (m, 5H) 3.87-4.17 (m, 2H) 4.43-4.75 (m, 2H) 6.98-7.21 (m, 1H) 7.39-7.54 (m, 2H) 7.55-7.66 (m, 1H) 8.36-8.62 (m, 1H) 9.35 (d, J=6.42 Hz, 1H) 9.82 (d, J=6.97 Hz, 1H). Method 3; Rt=3.11 min. m/z=505 (M+H)⁺.

Example 64: cis-7-methyl-2-(oxazole-5-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E64)

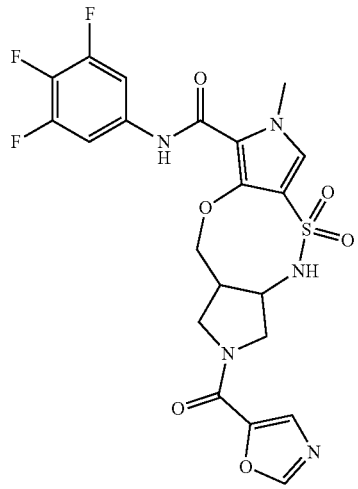 [SMILES: Cn1cc2c(c1C(=O)Nc1cc(F)c(F)c(F)c1)OCC1CN(C(=O)c3cnco3)CC1NS2(=O)=O]

Prepared similarly as described for compound E56 starting from cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) and 1,3-oxazole-5-carboxylic acid (Fluorochem, cat No 066222). The crude was purified by preparative HPLC (H₂O, CH₃CN 0.1% HCOOH) to afford E64 (14 mg). ¹H NMR (300 MHz, DMSO-d6+TFA) δ ppm 2.92-3.23 (m, 1H) 3.25-3.59 (m, 1H) 3.63-4.29 (m, 7H) 4.42-4.75 (m, 2H) 7.51 (d, J=2.75 Hz, 1H) 7.60-7.73 (m, 2H) 7.78 (d, J=22.01 Hz, 1H) 8.41-8.53 (m, 1H) 8.56 (s, 1H) 9.67 (d, J=5.50 Hz, 1H). Method 3; Rt=3.14 min. m/z=526 (M+H)⁺.

Example 65: cis-7-methyl-2-(oxazole-4-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E65)

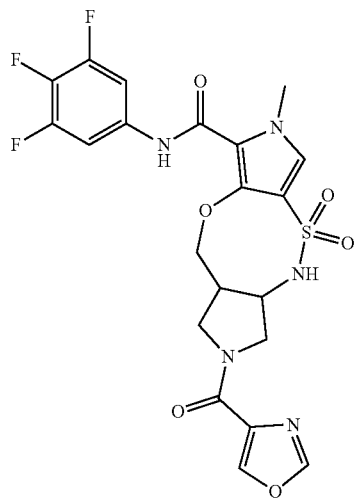 [SMILES: Cn1cc2c(c1C(=O)Nc1cc(F)c(F)c(F)c1)OCC1CN(C(=O)c3cocn3)CC1NS2(=O)=O]

Prepared similarly as described for compound E56 starting from cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) and 1,3-oxazole-5-carboxylic acid (Fluorochem, cat no 066222). The crude was purified by preparative HPLC (H₂O, CH₃CN 0.1% HCOOH) to afford E65 (17 mg). ¹H NMR (300 MHz, DMSO-d6+TFA) δ ppm 2.92-3.20 (m, 1H) 3.22-3.76 (m, 2H) 3.80 (s, 3H) 3.85-4.27 (m, 3H) 4.38-4.76 (m, 2H) 7.49 (s, 1H) 7.59-7.81 (m, 2H) 8.48 (d, J=11.10 Hz, 2H) 8.62 (d, J=7.98 Hz, 1H) 9.65 (s, 1H). Method 3; Rt=3.21 min. m/z=526 (M+H)⁺.

Example 66: cis-N-(4-fluoro-3-methylphenyl)-7-methyl-2-(3-methyloxetane-3-carbonyl)-2,3,3a,4,10,10a-hexahydro-1H,7H-dipyrrolo[3,4-b:3',4'-f][1,4,5]oxathiazocine-8-carboxamide 5,5-dioxide (E66)

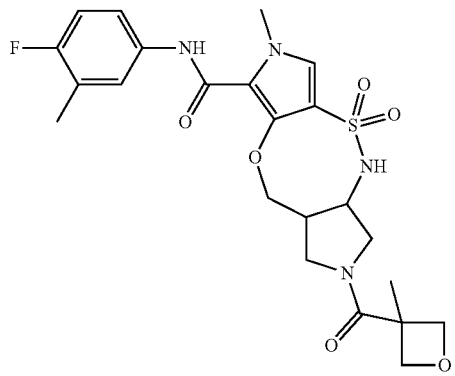 [SMILES: Cc1cc(NC(=O)c2c3c(cn2C)S(=O)(=O)NC2CN(C(=O)C4(C)COC4)CC2CO3)ccc1F]

Prepared similarly as described for compound E52 starting from E47 and 3-methyl-3-oxetanecarboxylic acid (Fluorochem, cat No 042959). The crude was purified by preparative HPLC (H₂O, CH₃CN 0.1% HCOOH) to afford E66 (17 mg).

¹H NMR (300 MHz, DMSO-d6) δ ppm 9.34 (br s, 1H) 8.39 (br s, 1H) 7.59 (dd, J=7.15, 2.20 Hz, 1H) 7.44-7.53 (m, 2H) 7.11 (t, J=9.22 Hz, 1H) 4.86 (t, J=5.80 Hz, 1H) 4.78 (d, J=5.80 Hz, 1H) 4.42-4.68 (m, 2H) 4.12-4.29 (m, 2H) 3.69-3.98 (m, 5H) 3.37-3.52 (m, 1H) 2.95-3.23 (m, 3H) 2.24 (s, 3H) 1.54 (d, J=7.80 Hz, 3H). Method 3; Rt=2.96 min. m/z=507 (M+H)⁺.

Example 67: cis-2-(L-alanyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E67)

E67 was prepared according to the following Scheme 22:

Scheme 22

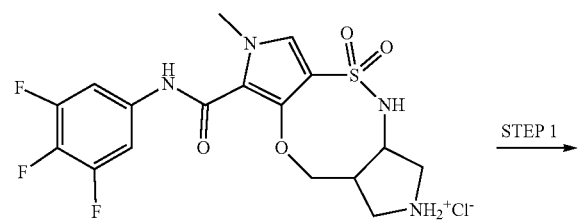

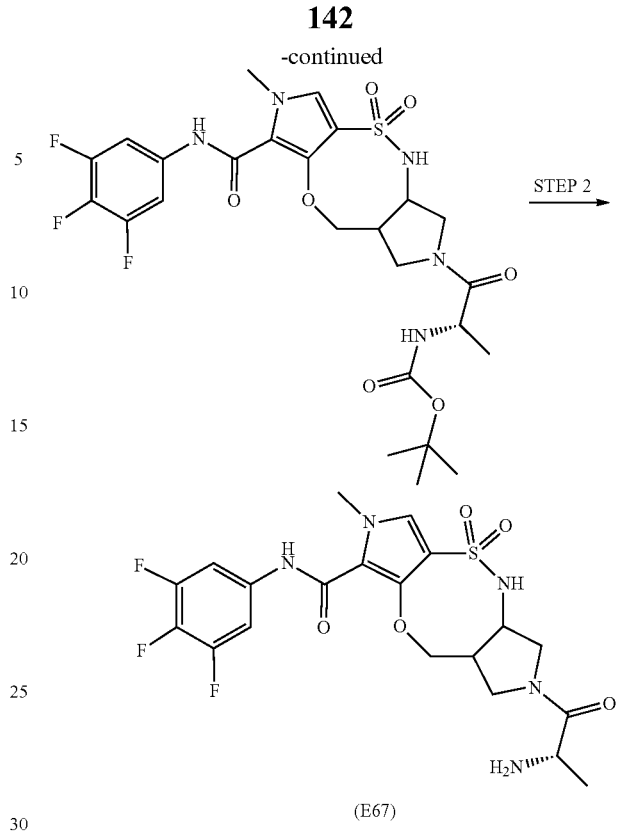

Synthetic steps are described below.

Step 1

Boc-Ala-OH (14.6 mg, 0.077 mmol, 1.2 eq) was dissolved in dry DCM (0.5 mL); EDC.HCl (14.8 mg, 0.077 mmol, 1.2 eq), HOBt (10.4 mg, 0.077 mmol, 1.2 eq), cis-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide hydrochloride (prepared as in Step 1 of Scheme 21, 30 mg, 0.064 mmol) and DIPEA (0.026 mL, 0.148 mmol, 2.3 eq) were added sequentially and the mixture was stirred at rt for 16 h. The reaction was diluted with DCM and washed with 5% citric acid and NaHCO₃ satd. sol. The organic phase was dried over Na₂SO₄ and evaporated, yielding 30 mg (y=78%) of product as a brown powder used in the next step without further purification (purity 90%, UV, 220 nm).

Step 2

The crude from previous step (30 mg, crude, 0.050 mmol) was dissolved in dry DCM (0.5 mL) and cooled in an ice bath. 4N HCl in dioxane (0.062 mL, 0.249 mmol, 5 eq) was added and the reaction was stirred at rt for 16 h: 6% starting material remaining. 0.2 mL of dry DCM were added, the mixture was cooled in an ice bath and more 4N HCl in dioxane (18.75 uL, 0.075 mmol, 1.5 eq) was added and stirring was continued for 3 h 30 min at rt: 3.2% starting material. After 3 h the reaction was diluted with DCM and basified with a saturated aqueous solution of NaHCO₃. ACN was added and the resulting mixture was evaporated under vacuum. The resulting crude was purified by preparative HPLC (H₂O, CH₃CN 0.1% HCOOH) to afford E67 (12.74 mg) product as a white powder. ¹H NMR (300 MHz, DMSO-d6+TFA): δ=9.38-9.87 (m, 1H), 8.21-8.46 (m, 1H), 8.07 (s, 1H), 8.00 (br s, 3H), 7.54-7.72 (m, 2H), 7.42-7.52 (m, 1H), 4.32-4.62 (m, 2H), 3.82-4.09 (m, 2H), 3.75 (s, 3H), 3.59-3.71 (m, 1H), 3.32-3.59 (m, 1H), 2.81-3.30 (m, 2H), 1.18-1.41 (m, 3H). Method 3; Rt=2.54 min. m/z=502 (M+H)⁺.

Example 68: cis-2-(L-seryl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E68)

E68 was prepared according to the following Scheme 23:

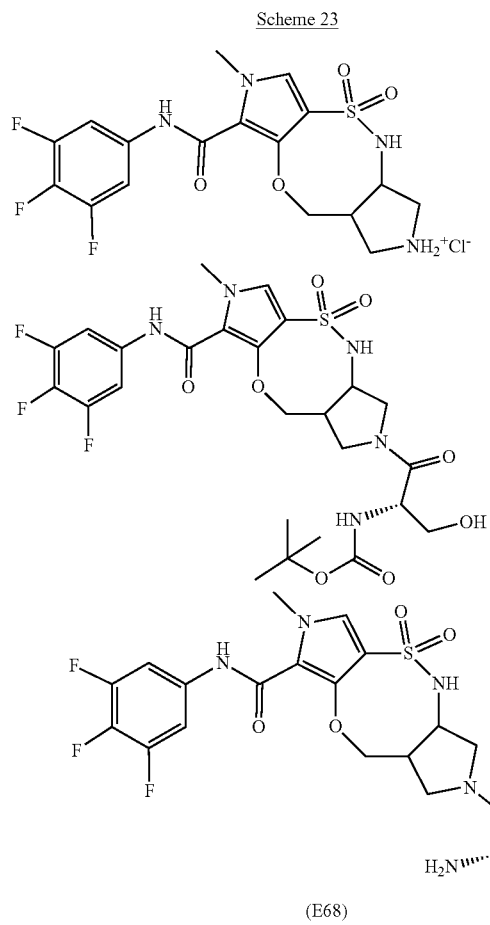

(E68)

Synthetic steps are described below.

Step 1

Boc-Ser-OH (15.8 mg, 0.077 mmol, 1.2 eq) was dissolved in dry DCM (0.5 mL); EDC.HCl (14.8 mg, 0.077 mmol, 1.2 eq), HOBt (10.4 mg, 0.077 mmol, 1.2 eq), cis-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide hydrochloride (prepared as in Step 1 of Scheme 21, 30 mg, 0.064 mmol) and DIPEA (26 uL, 0.148 mmol, 2.3 eq) were added sequentially and the mixture was stirred at rt for 16 h. The reaction was diluted with DCM and washed with 5% citric acid and NaHCO₃ sat. sol. The organic phase was dried over Na₂SO₃ and evaporated, yielding 36 mg (y=910%) of product as a brown powder, used in the next step without further purification (purity 64%, UV, 220 nm; analogue acylated at the hydroxyl group: 17%; other minor by-products).

Step 2

The intermediate from the previous step (36 mg, 0.058 mmol) was dissolved in dry DCM (0.7 mL) and cooled in an ice bath. 4N HCl in dioxane (102 uL, 0.408 mmol, 7 eq) was added and the reaction was stirred at rt for 3 h 30 min: 3.5% starting material. After 3 h the reaction was diluted with DCM and basified with NaHCO₃ sat., ACN was added to obtain a roughly homogeneous solution and the mixture was evaporated to dryness. The resulting crude was purified by preparative HPLC (H₂O, CH₃CN 0.1% HCOOH) to afford E68 (11.65 mg) product as a white powder. 1H NMR (300 MHz, DMSO-d₆+TFA): δ=9.58-9.77 (m, 1H), 8.25-8.49 (m, 1H), 8.13 (m, 4H), 7.68 (dd, J=10.3, 6.5 Hz, 2H), 7.46-7.56 (m, 1H), 4.37-4.67 (m, 2H), 3.88-4.14 (m, 2H), 3.81 (s, 3H), 3.42-3.77 (m, 4H), 3.17-3.39 (m, 1H), 2.87-3.16 ppm (m, 2H). Method 3; Rt=2.48 min. m/z=518 (M+H)⁺.

Example 69: cis-2-(L-threonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E69)

E69 was prepared according to the following Scheme 24:

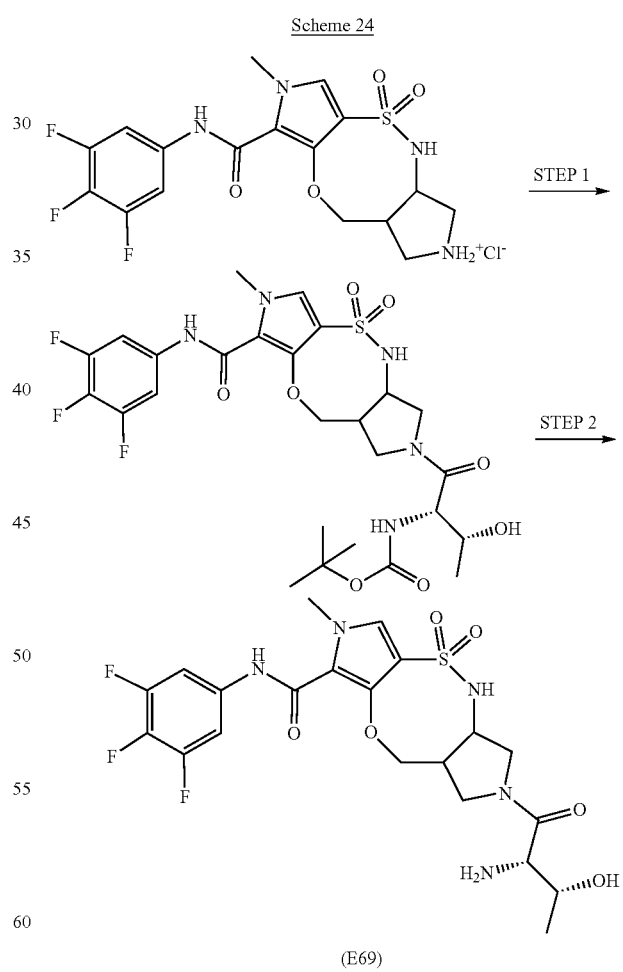

(E69)

Synthetic steps are described below.

Step 1

Boc-Thr-OH (16.9 mg, 0.077 mmol, 1.2 eq) was dissolved in dry DCM (0.5 mL); EDC.HCl (14.8 mg, 0.077 mmol, 1.2 eq), HOBt (10.4 mg, 0.077 mmol, 1.2 eq), cis-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide hydrochloride (prepared as in Step 1 of Scheme 21, 30 mg, 0.064 mmol) and DIPEA (26 uL, 0.148 mmol, 2.3 eq) were added sequentially and the mixture was stirred at rt for 16 h. The reaction was diluted with DCM and washed with 5% citric acid and NaHCO₃ satd. sol. The organic phase was dried over Na₂SO₄ and evaporated, yielding 32 mg (y=79%) of product as a brown powder used in the next step without further purification.

Step 2

The intermediate from Step 1 (32 mg, 0.051 theoretical mmol) was dissolved in dry DCM (0.7 mL) and cooled in an ice bath. 4N HCl in dioxane (0.089 mL, 0.355 mmol, 7 eq) was added and the reaction was stirred at rt for 4 h: the reaction was diluted with DCM and basified with NaHCO₃ sat. ACN was added and the resulting mixture was evaporated to dryness. The crude was purified by preparative HPLC (H₂O, CH₃CN 0.1% HCOOH) to afford E69 (9.61 mg) product as a white powder. 1H NMR (300 MHz, DMSO-d6): δ=9.60-9.77 (m, 1H), 8.20-8.52 (m, 1H), 8.13 (s, 1H), 8.05 (br d, J=5.0 Hz, 3H), 7.68 (br dd, J=10.2, 6.6 Hz, 2H), 7.43-7.59 (m, 1H), 4.34-4.71 (m, 2H), 3.72-4.13 (m, 8H), 2.80-3.72 (m, 3H), 1.08-1.33 (m, 3H). Method 3; Rt=2.51 min. m/z=532 (M+H)⁺.

Example 70: cis-2-(7-methyl-5,5-dioxido-8-((3,4,5-trifluorophenyl)carbamoyl)-3a,4,10,10a-tetrahydro-1H,7H-dipyrrolo[3,4-b:3',4'-f][1,4,5]oxathiazocin-2(3H)-yl)-2-oxoethyl acetate (E70)

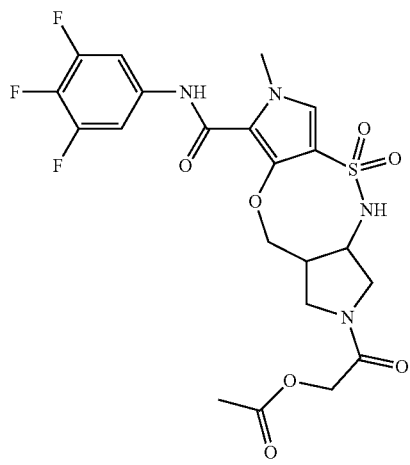 [SMILES: CC(=O)OCC(=O)N1CC2COc3c(cn(C)c3C(=O)Nc3cc(F)c(F)c(F)c3)S(=O)(=O)NC2C1]

cis-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide hydrochloride (prepared as in Step 1 of Scheme 21, 95 mg, 0.200 mmol) was suspended in MeCN (2 mL, 0.038 mol) and cooled to 0° C. N-ethyl-N-isopropylpropan-2-amine (0.14 mL, 0.810 mmol) and 2-chloro-2-oxoethyl acetate (0.02 mL, 0.220 mmol) were added, and the resulting brown solution was stirred at 0° C. for 30 min. The reaction was diluted with EtOAc and washed with 1N HCl solution (×2) and NaHCO₃ sat. solution. Organic layer was dried over Na₂SO₄, filtered and concentrated under vacuo. The resulting crude was purified by flash chromatography on silica (SNAP 10 g), eluent: DCM/MeOH (gradient 100% DCM to 96/4 DCM/MeOH) to obtain E70 (70 mg) as light-yellow solid. ¹H NMR (300 MHz, DMSO-d6) δ ppm 2.09 (s, 3H) 2.86-3.01 (m, 2H) 3.40-3.58 (m, 2H) 3.64-3.80 (m, 5H) 4.48-4.72 (m, 4H) 7.52 (d, J=5.6 Hz, 1H) 7.69 (dd, J=10.4, 6.6 Hz, 2H) 8.44 (t, J=9.3 Hz, 1H) 2H) 9.67 (s, 1H). Method 3; Rt=3.20 min. m/z=531 (M+H)⁺.

Example 71: cis-2-(2-hydroxyacetyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E71)

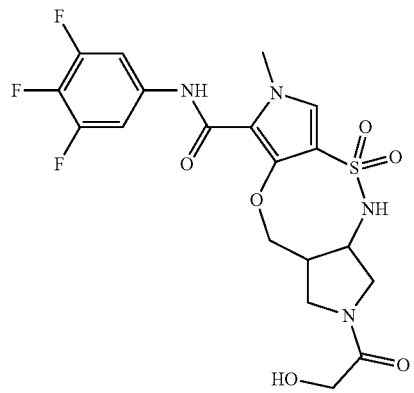 [SMILES: Cn1cc2c(c1C(=O)Nc1cc(F)c(F)c(F)c1)OCC1CN(C(=O)CO)CC1NS2(=O)=O]

E70 (67 mg, 0.130 mmol) was suspended in MeOH (1.8 mL) and MeONa 25% w/w solution in MeOH (0.058 mL, 0.253 mmol) was added. The reaction mixture was stirred at RT for 30 min (after 5 min the mixture became a yellow solution). The reaction was then cooled to 0° C., acidified with 1N HCl until pH=3, and concentrated under vacuo. The resulting solid was taken up in EtOAc and washed with water. Organic layer was dried over Na₂SO₄, filtered and concentrated, to obtain crude product (63 mg). 12 mg were purified by preparative HPLC (H₂O, CH₃CN 0.1% HCOOH) to afford E71 (7 mg) product as a white powder. ¹H NMR (300 MHz, DMSO-d6) δ ppm 2.83-3.18 (m, 2H) 3.40-3.74 (m, 3H) 3.78-4.11 (m, 6H) 4.35-4.72 (m, 3H) 7.51 (d, J=4.22 Hz, 1H) 7.60-7.78 (m, 2H) 8.40 (br s, 1H) 9.67 (s, 1H). Method 3; Rt=2.94 min. m/z=489 (M+H)⁺. Remaining crude (51 mg) was used in the next step without further purification.

Example 72: cis-2-(7-methyl-5,5-dioxido-8-((3,4,5-trifluorophenyl)carbamoyl)-3a,4,10,10a-tetrahydro-1H,7H-dipyrrolo[3,4-b:3',4'-f][1,4,5]oxathiazocin-2(3H)-yl)-2-oxoethyl Dihydrogen Phosphate (E72)

E72 was prepared according to the following Scheme 25:

Scheme 25

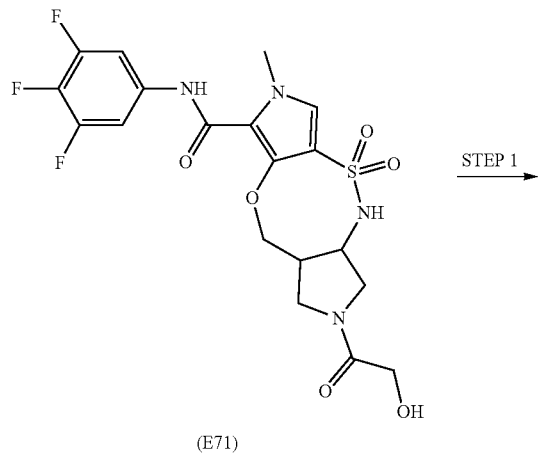

(E71)

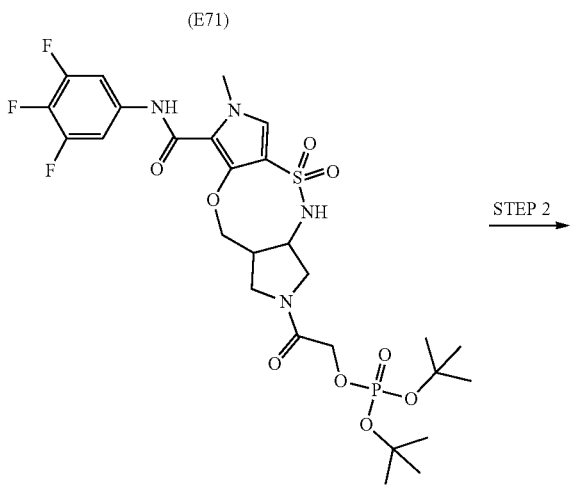

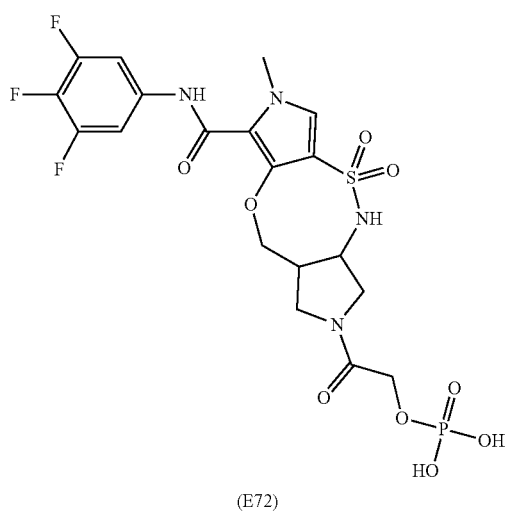

(E72)

Synthetic steps are described below.

Step 1

E71 (50 mg, 0.100 mmol) was dissolved in dry THF (0.8 mL), di-tert-butyl diisopropylphosphoramidite (0.05 mL, 0.160 mmol) and 0.45M tetrazole solution in ACN (0.02 mL, 0.220 mmol) were added at 0° C. After 2 min mixture was allowed to warm up at RT. After 2 h UPLC-MS analysis showed intermediate phosphite product (about 50% of conversion). More Di-tert-butyl diisopropylphosphoramidite (0.03 mL, 0.10 mmol) and tetrazole solution (0.3 mL, 0.132 mmol) were added, and the reaction mixture was stirred at RT for another 2 h. Mixture was then cooled to 0° C. and 30% aq. hydrogen peroxide (0.17 mL, 0.500 mmol) was added. After 1 h stirring at RT, ice water and sodium bisulfite (70 mg) were added. Mixture was diluted with DCM and washed with water (×2). Organic layer was dried over $Na_2SO_4$, filtered and solvent removed under reduced pressure. The resulting crude was purified by flash chromatography on silica gel (eluent gradient from DCM/EtOAc 70/30 to EtOAc 100%, to obtain crude cis-di-tert-butyl (2-(7-methyl-5,5-dioxido-8-((3,4,5-trifluorophenyl)carbamoyl)-3a,4,10,10a-tetrahydro-1H,7H-dipyrrolo[3,4-b:3',4'-f][1,4,5]oxathiazocin-2(3H)-yl)-2-oxoethyl) phosphate (50 mg, y=71.7%) as white solid.

Step 2

The crude intermediate from Step 1 (50 mg, 0.070 mmol) was dissolved in THF (0.7 mL) and HCl 4N dioxane (0.5 mL, 2 mmol) was added. The reaction was stirred at RT 1 h (UPLC-MS after 30 min showed reaction was complete). The reaction was concentrated under vacuo, and the resulting crude purified by preparative HPLC ($H_2O$, $CH_3CN$ 0.1% HCOOH) to afford E72 (32 mg) as white solid. $^1$H NMR (300 MHz, DMSO-d6+TFA) δ ppm 2.80-3.24 (m, 2H) 3.33-4.06 (m, 7H) 4.22-4.75 (m, 4H) 7.51 (d, J=3.39 Hz, 1H) 7.60-7.81 (m, 2H) 8.24-8.55 (m, 1H) 9.66 (s, 1H). Method 3; Rt=2.69 min m/z=569 (M+H)+.

Example 73: cis-7-methyl-2-(2,2,2-trifluoroethyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E73)

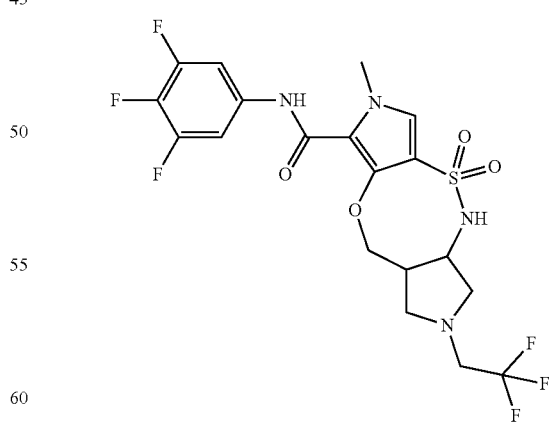

A solution of 2,2,2-trifluoroethanol (0.007 mL, 0.1 mmol) in DCM (0.07 mL) was treated with a solution of TEA (0.018 mL, 0.13 mmol) in DCM (0.17 mL). The resulting mixture was further diluted with DCM (1.7 mL) and cooled to 0° C. Trifluoromethanesulfonic anhydride (0.017 mL, 0.1 mmol) in DCM (0.17 mL) was added at 0° C. and the reaction solution was stirred at this temperature for 2 hrs.

In a separate flask, cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) (10 mg, 0.018 mmol) was suspended in water (3-4 mL), treated with 2M NaOH (1 mL) giving a clear solution then extracted with DCM and 2-Me-THF, thus giving the starting reagent as the corresponding free base (7.53 mg, 0.015 mmol). The compound was suspended in DCM (0.5 mL) and added to the solution stirred at 0° C.

The reaction suspension was stirred at room temperature overnight and heated at reflux for 1.5 hrs. DMF (0.5 mL) was added and the reaction heated by microwave irradiation at 60° C. for 3 hrs. The reaction was concentrated under vacuo, and the resulting crude purified by preparative HPLC (H$_2$O, CH$_3$CN 0.1% HCOOH) to afford E73 (7.5 mg) as white solid. $^1$H NMR (300 MHz, DMSO-d6+TFA) δ ppm 2.64-2.84 (m, 1H) 2.85-3.11 (m, 2H) 3.27 (br s, 1H) 3.81 (s, 6H) 4.04 (s, 1H) 4.53 (br dd, J=11.32, 3.62 Hz, 2H) 7.51 (s, 1H) 7.68 (dd, J=10.41, 6.46 Hz, 2H) 8.26 (d, J=9.72 Hz, 1H) 9.63 (s, 1H). Method 3; Rt=3.72 min m/z=513 (M+H)$^+$.

Example 74: cis-2-(cyanomethyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E74)

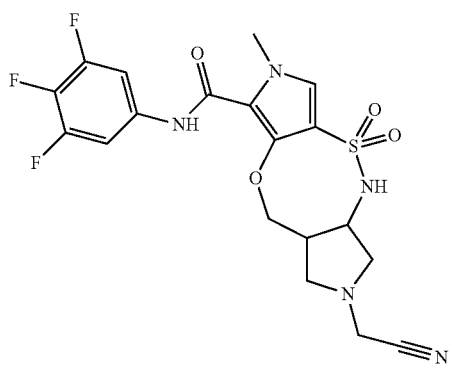 [SMILES: Cn1cc2c(c1C(=O)Nc1cc(F)c(F)c(F)c1)OCC1CN(CC#N)CC1NS2(=O)=O]

A solution of cis-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E11) (22 mg, 0.05 mmol), triethylamine (0.021 mL, 0.15 mmol) and bromoacetonitrile (0.004 mL, 0.06 mmol) in DMF (2 mL) was stirred overnight at room temperature. The reaction was concentrated under vacuo, and the resulting crude purified by preparative HPLC (H$_2$O, CH$_3$CN 0.1% TFA) to afford E74 (18 mg) as TFA salt. $^1$H NMR (300 MHz, DMSO-d6+TFA) δ ppm 2.58-2.70 (m, 1H) 2.79-3.24 (m, 3H) 3.51-3.67 (m, 1H) 3.72-3.89 (m, 3H) 3.96-4.10 (m, 1H) 4.13-4.24 (m, 2H) 4.39-4.69 (m, 2H) 7.41-7.57 (m, 1H) 7.59-7.81 (m, 2H) 8.30 (d, J=9.63 Hz, 1H) 9.65 (s, 1H). Method 3; Rt=3.39 min m/z=470 (M+H)$^+$.

Example 75: cis-2-(5-fluoropyrimidin-2-yl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E75)

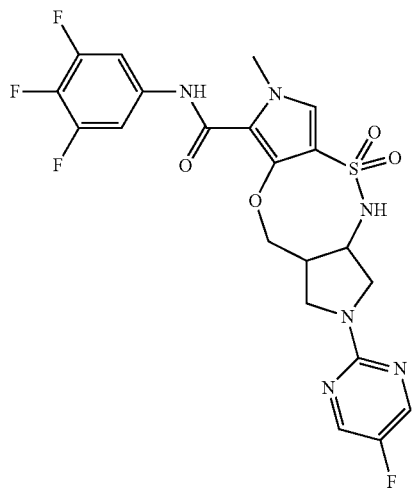 [SMILES: Cn1cc2c(c1C(=O)Nc1cc(F)c(F)c(F)c1)OCC1CN(c3ncc(F)cn3)CC1NS2(=O)=O]

Cis-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E11) (22 mg, 0.05 mmol), 2-chloro-5-fluoropyrimidine (035858, Fluorochem) (0.01 mL, 0.08 mmol), triethylamine (0.02 mL, 0.15 mmol) and DMSO (0.8 mL) were charged in a vial which was heated under microwave irradiation at 90° C. for 3 hrs. The reaction solution was diluted with water and purified by preparative HPLC (H$_2$O, CH$_3$CN 0.1% HCOOH) to afford E75 (12.33 mg). $^1$H NMR (300 MHz, DMSO-d6+TFA) δ ppm 2.98-3.35 (m, 2H) 3.54-3.73 (m, 2H) 3.76-3.83 (m, 3H) 3.83-4.10 (m, 2H) 4.35-4.89 (m, 2H) 7.42-7.57 (m, 1H) 7.58-7.85 (m, 2H) 8.30-8.59 (m, 3H) 9.56-9.80 (m, 1H). Method 3; Rt=3.70 min m/z=527 (M+H)$^+$.

Example 76: cis-2-(2-chloropyridin-4-yl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide (E76)

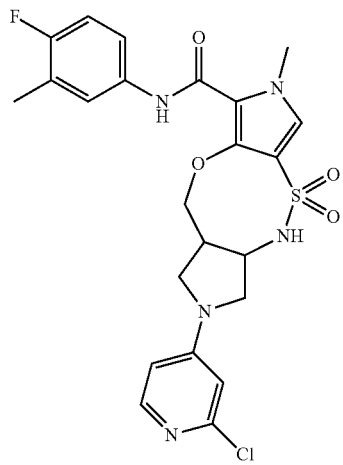 [SMILES: Cc1cc(NC(=O)c2c3c(cn2C)S(=O)(=O)NC2CN(c4ccnc(Cl)c4)CC2CO3)ccc1F]

cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) (30 mg, 0.060 mmol), 2-chloro-4-nitropyridine (13.3 mg, 0.080 mmol) were dissolved in DMF (0.5 mL) and potassium carbonate (23.53 mg, 0.170 mmol) was added. The reaction mixture was stirred at 55° C. for 24 h. The reaction was diluted with EtOAc and washed with $H_2O$. The reaction solution was diluted with water and purified by preparative HPLC ($H_2O$, $CH_3CN$ 0.1% HCOOH) to afford, after lyophilization, E76 (13 mg) as white solid. $^1$H NMR (300 MHz, DMSO-d6+TFA) δ ppm 2.09-2.25 (m, 3H) 3.05-3.26 (m, 1H) 3.28-3.43 (m, 1H) 3.55-3.73 (m, 1H) 3.74-3.89 (m, 4H) 3.90-4.17 (m, 2H) 4.53-4.76 (m, 2H) 6.86 (br s, 1H) 6.98-7.20 (m, 2H) 7.42-7.53 (m, 2H) 7.55-7.65 (m, 1H) 8.18 (d, J=6.24 Hz, 1H) 8.47 (d, J=9.81 Hz, 1H) 9.36 (s, 1H). Method 3; Rt=2.73 min. m/z=520 (M+H)$^+$.

Example 77: Ethyl (3R,6R)-10-methyl-9-((3,4,5-trifluorophenyl)carbamoyl)-3,4,6,7-tetrahydro-10H-3,6-methanopyrrolo[3,4-b][1,4,5,8]oxathiadiazecine-5(2H)-carboxylate 1,1-dioxide (E77)

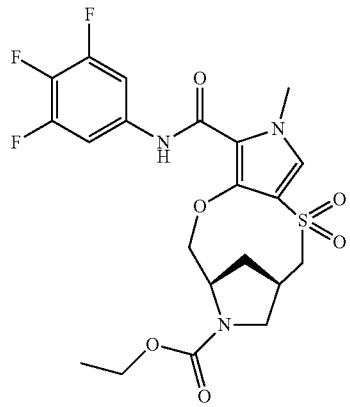 [SMILES: CCOC(=O)N1C[C@H]2C[C@@H]1COc1c(cn(C)c1C(=O)Nc1cc(F)c(F)c(F)c1)S(=O)(=O)C2]

Cesium carbonate (120 mg, 0.37 mmol) was added to a solution of D94 (77 mg, 0.15 mmol) in dry DMF (3 mL). The reaction mixture was stirred at 135° C. for 3 hrs then cooled to RT, diluted with EtOAc and water, and stirred for 15 min. The two phases were separated and the organic phase washed with water and brine, dried over $Na_2SO_4$ filtered and concentrated. Crude was purified by preparative HPLC to afford E77 (7 mg, 10% over two steps) as a white solid. $^1$H NMR (300 MHz, DMSO-d6) δ ppm 1.08-1.18 (m, 3H) 2.01-2.24 (m, 1H) 3.39-3.46 (m, 1H) 3.70-3.82 (m, 4H) 3.87-4.11 (m, 6H) 4.39-4.66 (m, 1H) 7.47-7.79 (m, 4H) 10.03 (s, 1H). Method 3; Rt: 3.45 min. m/z: 503.29 (M+H)$^+$.

Example 78: cis-7-methyl-2-(5-methyl-1,3,4-oxadiazol-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E78)

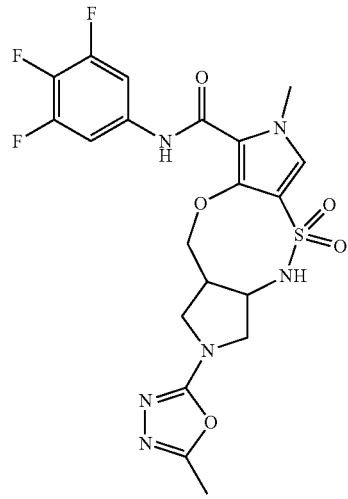 [SMILES: Cc1nnc(N2CC3COc4c(cn(C)c4C(=O)Nc4cc(F)c(F)c(F)c4)S(=O)(=O)NC3C2)o1]

cis-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E11) (37.25 mg, 0.08 mmol) in DMF (0.4 mL) was treated with N-ethyl-N-isopropylpropan-2-amine (0.014 mL, 0.08 mmol) and 5-methyl-1,3,4-oxadiazol-2(3H)-one (4 mg, 0.04 mmol). The resulting solution was treated with a single portion of BOP (19.44 mg, 0.044 mmol) and stirred overnight at room temperature. The reaction was poured into ice, extracted with EtOAc then the organic phase were dried and evaporated giving a residue. Purification by preparative HPLC ($H_2O$, $CH_3CN$ 0.1% HCOOH) give after lyophilisation E78 (10.4 mg, 0.020 mmol). $^1$H NMR (300 MHz, DMSO-d6+TFA) δ ppm 2.31-2.42 (m, 3H) 3.04-3.34 (m, 2H) 3.46-3.64 (m, 2H) 3.74-3.86 (m, 3H) 3.87-4.12 (m, 2H) 4.46-4.72 (m, 2H) 7.52 (s, 1H) 7.61-7.77 (m, 2H) 8.46 (d, J=9.72 Hz, 1H) 9.68 (s, 1H). Method 3; Rt: 3.15. m/z: 513 (M+H)$^+$.

Example 79: cis-2-(cyanomethyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide (E79)

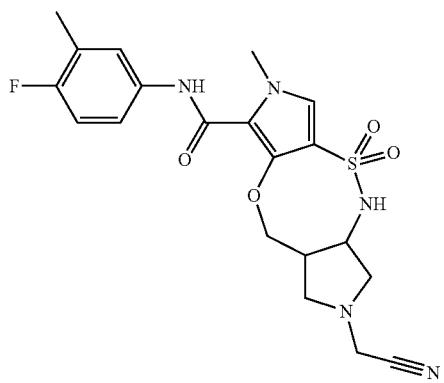

A mixture of E47 (25 mg, 0.050 mmol), bromoacetonitrile (0.004 mL, 0.060 mmol) and triethylamine (0.02 mL, 0.140 mmol) in DMF (1 mL) was heated by microwave irradiation at 80° C. 1 h. The reaction solution was diluted with water and purified by preparative HPLC (H$_2$O, CH$_3$CN 0.1% HCOOH) to afford, after lyophilization, E79 (10 mg, 0.022 mmol). $^1$H NMR (300 MHz, DMSO-d6+TFA) δ ppm 2.22 (s, 3H) 2.76-2.92 (m, 1H) 2.94-3.16 (m, 2H) 3.29 (br d, J=6.69 Hz, 1H) 3.65-3.91 (m, 4H) 4.06 (br t, J=11.05 Hz, 1H) 4.32 (br d, J=2.84 Hz, 2H) 4.55 (br dd, J=11.55, 3.76 Hz, 2H) 5.48-5.52 (m, 1H) 7.08 (t, J=9.17 Hz, 1H) 7.42-7.53 (m, 2H) 7.58 (dd, J=6.92, 2.25 Hz, 1H) 8.33 (br d, J=9.81 Hz, 1H) 9.31 (s, 1H). Method 3; Rt: 3.21. m/z: 448 (M+H)$^+$.

Example 80: cis-N-(4-fluoro-3-methylphenyl)-7-methyl-2-(2,2,2-trifluoroethyl)-2,3,3a,4,10,10a-hexahydro-1H,7H-dipyrrolo[3,4-b:3',4'-f][1,4,5]oxathiazocine-8-carboxamide 5,5-dioxide (E80)

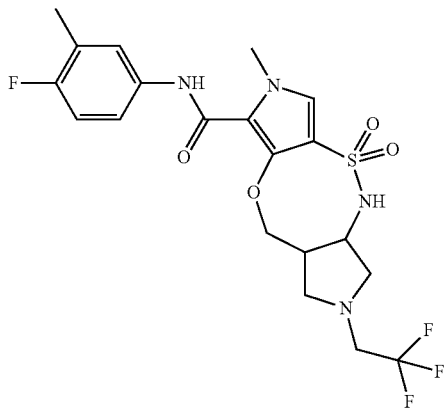 [SMILES: Cc1cc(NC(=O)c2c3c(cn2C)S(=O)(=O)NC2CN(CC(F)(F)F)CC2CO3)ccc1F]

A solution of E47 (25 mg, 0.047 mmol), 2,2,2-trifluoroethyl trifluoromethanesulfonate (8.8 uL, 0.060 mmol), DIPEA (0.02 mL, 0.120 mmol) in DMF (0.5 mL) and DCM (1.7 mL) was heated by microwave irradiation (80° C., 2 hrs, 2 runs). Solvent was removed, the residue was purified by preparative HPLC (H$_2$O, CH$_3$CN 0.1% HCOOH) to afford, after lyophilization, E80 (8.41 mg, 0.017 mmol). $^1$H NMR (300 MHz, DMSO-d6+TFA) δ ppm 2.22 (s, 3H) 2.79-2.91 (m, 1H) 2.92-3.15 (m, 2H) 3.26-3.49 (m, 1H) 3.81 (s, 3H) 3.84-4.01 (m, 3H) 4.01-4.15 (m, 1H) 4.44-4.70 (m, 2H) 7.07 (t, J=9.17 Hz, 1H) 7.38-7.53 (m, 2H) 7.53-7.65 (m, 1H) 8.26 (br d, J=9.81 Hz, 1H) 9.31 (s, 1H). Method 3; Rt: 3.56. m/z: 491 (M+H)$^+$.

Example 81: cis-7-methyl-2-(pyridin-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E81)

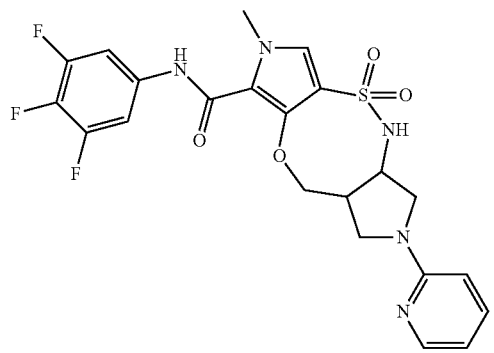 [SMILES: Cn1cc2c(c1C(=O)Nc1cc(F)c(F)c(F)c1)OCC1CN(c3ccccn3)CC1NS2(=O)=O]

A mixture of cis-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide hydrochloride (prepared as in Step 1 of Scheme 21, 25 mg, 0.050 mmol), N-ethyl-N-isopropylpropan-2-amine (0.046 mL, 0.270 mmol), 2-chloropyridine (0.015 mL, 0.160 mmol) in DMSO (0.5 mL) was heated at 100° C. for 3 hrs. The resulting brown solution was purified by preparative HPLC (H$_2$O, CH$_3$CN 0.1% HCOOH) to afford, after lyophilization, E81 (2.92 mg). $^1$H NMR (300 MHz, DMSO-d6+TFA) δ ppm 3.10-3.30 (m, 1H) 3.30-3.47 (m, 1H) 3.60-3.72 (m, 1H) 3.73-3.88 (m, 4H) 3.93-4.21 (m, 2H) 4.55-4.82 (m, 2H) 6.85-7.04 (m, 1H) 7.06-7.26 (m, 1H) 7.53 (s, 1H) 7.58-7.80 (m, 2H) 7.92-8.11 (m, 2H) 8.44 (d, J=9.81 Hz, 1H) 9.69 (s, 1H). Method 3; Rt: 2.74. m/z: 508 (M+H)$^+$.

Example 82: cis-7-methyl-2-(pyrazin-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E82)

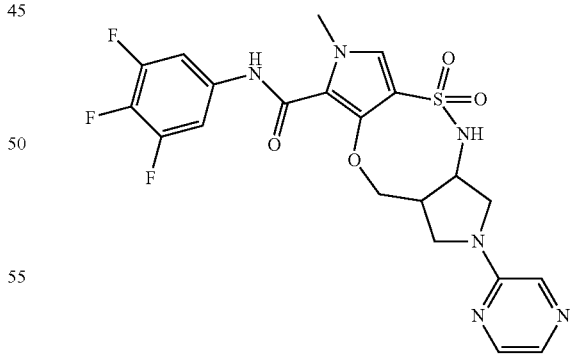

A mixture of cis-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide hydrochloride (prepared as in Step 1 of Scheme 21, 23 mg, 0.050 mmol), cesium carbonate (40.13 mg, 0.120 mmol) and 2-chloropyrazine (0.005 mL, 0.050 mmol) in DMSO (0.1 mL) was heated at 100° C. 1 h. The resulting brown solution was purified by preparative HPLC (H$_2$O, CH$_3$CN 0.1%

HCOOH) to afford, after lyophilization, E82 (3.62 mg). $^1$H NMR (300 MHz, DMSO-d6+TFA) δ ppm 3.07-3.34 (m, 2H) 3.56-3.69 (m, 1H) 3.69-3.86 (m, 4H) 3.86-3.97 (m, 1H) 3.98-4.12 (m, 1H) 4.54-4.78 (m, 2H) 7.46-7.55 (m, 1H) 7.61-7.78 (m, 2H) 7.82 (d, J=2.11 Hz, 1H) 8.10-8.24 (m, 2H) 8.43 (d, J=9.81 Hz, 1H) 9.68 (s, 1H). Method 3; Rt: 3.26. m/z: 509 (M+H)$^+$.

Example 83: cis-7-methyl-2-(3-methyl-1,2,4-oxadiazol-5-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E83)

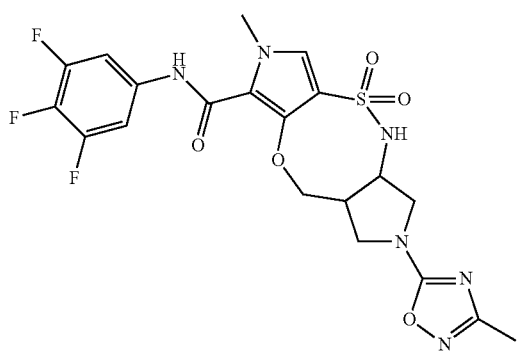 [SMILES: Cc1noc(N2CC3COc4c(cn(C)c4C(=O)Nc4cc(F)c(F)c(F)c4)S(=O)(=O)NC3C2)n1]

A 5 mL vial was charged with cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) (23 mg, 0.040 mmol) then a solution of 5-chloro-3-methyl-1,2,4-oxadiazole (10.25 mg, 0.090 mmol) in DMF (1 mL) was added in a single portion. The brown reaction solution was treated with N-ethyl-N-isopropylpropan-2-amine (0.1 mL, 0.570 mmol) and heated by microwave irradiation (130° C., 30 min). The resulting brown mixture was evaporated and the residue partitioned between water and EtOAc. The org. layer was evaporated and the residue was purified by preparative HPLC (H$_2$O, CH$_3$CN 0.1% HCOOH) to afford, after lyophilization, E83 (1.73 mg). $^1$H NMR (300 MHz, DMSO-d6+TFA) δ ppm 2.08 (s, 3H) 3.01-3.22 (m, 1H) 3.23-3.34 (m, 1H) 3.48-3.70 (m, 2H) 3.80 (s, 3H) 3.88-4.13 (m, 2H) 4.52-4.71 (m, 2H) 7.46 (s, 1H) 7.53-7.75 (m, 2H) 7.98-8.17 (m, 1H) 8.49 (br d, J=10.00 Hz, 1H) 9.60 (s, 1H). Method 3; Rt: 3.39 m/z: 513 (M+H)$^+$.

Example 84: cis-2-(5-hydroxypyrimidin-2-yl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E84)

E84 was prepared according to the following Scheme 26:

Scheme 26

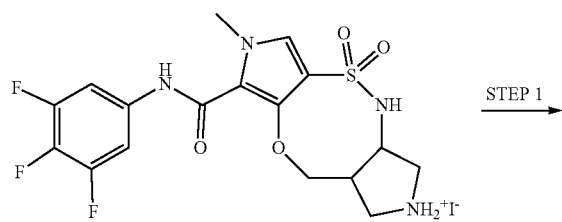

STEP 1

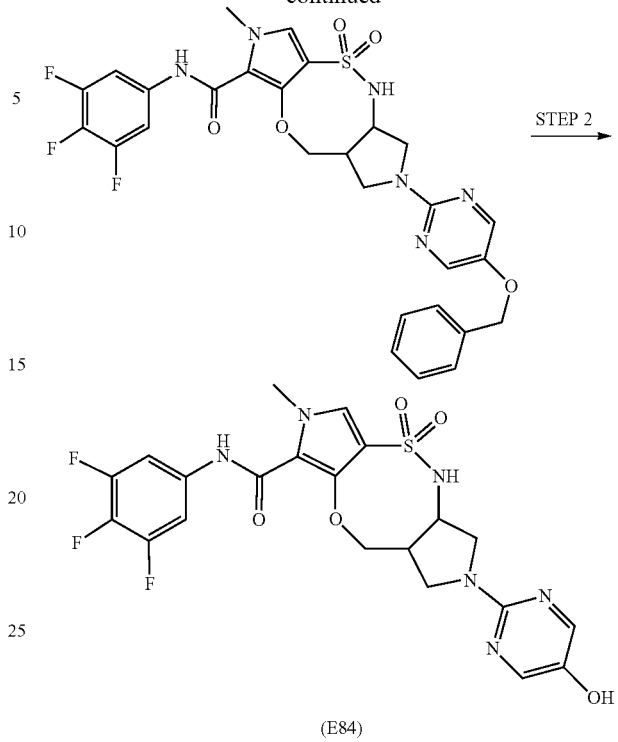

Synthetic steps are described below.

Step 1

In a microwave vial, cis-7-methyl-8-((3,4,5-trifluorophenyl)carbamoyl)-2,3,3a,4,10,10a-hexahydro-1H,7H-dipyrrolo[3,4-b:3',4'-f][1,4,5]oxathiazocin-2-ium 5,5-dioxide iodide (E11) (20 mg, 0.036 mmol) and 5-(benzyloxy)-2-chloropyrimidine (15.8 mg, 0.072 mmol) were suspended in 1-Butanol (0.3 mL), dry DIPEA (0.020 mL, 0.115 mmol) was added and mixture heated at 155° C. under MW for 2 h. The reaction mixture was evaporated under reduced pressure to afford a dark brown solid. The residue was purified by preparative HPLC (H$_2$O, CH$_3$CN 0.1% TFA) to afford, after lyophilization 2-(5-(benzyloxy)pyrimidin-2-yl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (10 mg, 0.016 mmol, yield=45%).

Step 2

In a microwave vial, the intermediate product from Step 1 (10 mg, 0.016 mmol) was suspended in a mixture of DCM (0.4 mL) and MeOH (0.4 mL). Pd/C 10% wt (1.75 mg, 0.002 mmol) was added. The vial was sealed and 1,4 cyclohexadiene (0.010 mL, 0.106 mmol) was added and mixture was heated at 40° C. for a total of 7 h. UPLC-MS analysis showed incomplete conversion but reaction was stopped. The reaction mixture was filtered on a celite pad: the celite was washed with DCM and MeOH. The light yellow solution was evaporated under reduced pressure to afford a beige solid. The residue was purified by preparative HPLC (H$_2$O, CH$_3$CN 0.1% HCOOH) to afford, after lyophilization, E84 as a pale yellow powder (3.26 mg). $^1$H NMR (300 MHz, DMSO-d$_6$+TFA) δ ppm 3.16 (br s, 1H) 3.25-3.38 (m, 1H) 3.55-3.71 (m, 1H) 3.71-3.86 (m, 4H) 3.88-4.00 (m, 1H) 4.07 (br t, J=11.14 Hz, 1H) 4.54-4.73 (m, 2H) 7.50 (s, 1H) 7.61-7.75 (m, 2H) 8.27 (s, 2H) 8.40 (d, J=9.81 Hz, 1H) 9.66 (s, 1H). Method 3; Rt: 3.02. m/z: 525 (M+H)$^+$.

Example 85: cis-ethyl 7,10a-dimethyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide (E85)

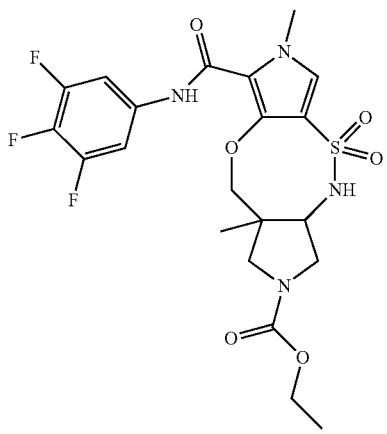 [SMILES: CCOC(=O)N1CC2NS(=O)(=O)c3cn(C)c(C(=O)Nc4cc(F)c(F)c(F)c4)c3OCC2(C)C1]

A mixture of D77 (30 mg, 0.06 mmol) and cesium carbonate (45.55 mg, 0.14 mmol) in DMF (1.4 mL) was heated by microwave irradiation at 130° C. for 5 hrs. The reaction was cooled to room temperature and evaporated. The residue was dissolved in water and EtOAc and the resulting mixture was poured into a separating funnel. The organic layer was dried over $Na_2SO_4$ (anh.), filtered and finally evaporated giving a brown residue (30 mg). Purified by Fraction-Lynx (H2O/CH3CN+1‰ TFA) giving E85 (10 mg, 0.019 mmol, yield 32%). $^1$H NMR (300 MHz, DMSO-d$_6$+TFA) δ ppm 1.12-1.23 (m, 3H) 1.27 (s, 3H) 3.06 (d, J=10.55 Hz, 1H) 3.16-3.28 (m, 1H) 3.28-3.44 (m, 1H) 3.72-3.84 (m, 3H) 3.84-4.14 (m, 5H) 4.30 (brt, J=10.82 Hz, 1H) 7.49 (s, 1H) 7.54-7.71 (m, 2H) 8.38-8.54 (m, 1H) 9.67 (br s, 1H). Method 3; Rt: 3.71 min. m/z: 517 (M+H)$^+$.

Example 86: cis-N-(4-fluoro-3-methylphenyl)-7,10a-dimethyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide (E86)

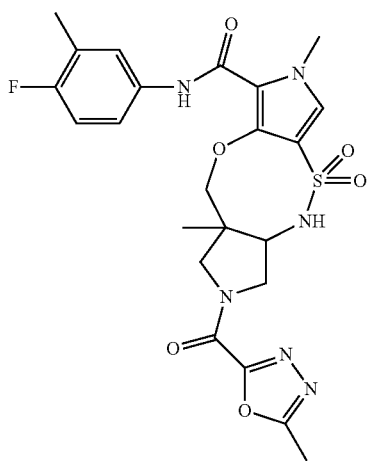 [SMILES: Cc1nnc(C(=O)N2CC3NS(=O)(=O)c4cn(C)c(C(=O)Nc5ccc(F)c(C)c5)c4OCC3(C)C2)o1]

A solution of D104 (55 mg, 0.1 mmol) in MeCN (2 mL) was treated with triethylamine (0.04 mL, 0.29 mmol) and the resulting solution treated at 0° C. with a solution of 1.2M solution of 5-methyl-1,3,4-oxadiazole-2-carbonyl chloride (17.6 mg, 0.12 mmol) in MeCN. After 20 min, the reaction was stopped by addition of MeOH and solvent was removed. The residue was purified by preparative HPLC (H$_2$O/CH$_3$CN+0.1% HCOOH) to afford E86 (23.7 mg, 0.044 mmol, yield=44%) as white solid. $^1$H NMR (300 MHz, DMSO-d6) δ ppm 1.32 (d, J=2.66 Hz, 3H) 2.22-2.26 (m, 3H) 2.59 (d, J=4.40 Hz, 3H) 3.36-3.56 (m, 1H) 3.59-3.90 (m, 5H) 3.92-4.58 (m, 4H) 7.13 (td, J=9.17, 1.74 Hz, 1H) 7.38-7.51 (m, 2H) 7.59 (td, J=6.69, 2.48 Hz, 1H) 8.38-8.61 (m, 1H) 9.35 (d, J=5.59 Hz, 1H). Method 3; Rt: 3.24 min. m/z: 533 (M+H)$^+$.

Example 87: cis-N-(4-fluoro-3-methylphenyl)-7,10a-dimethyl-2-(5-methyloxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide (E87)

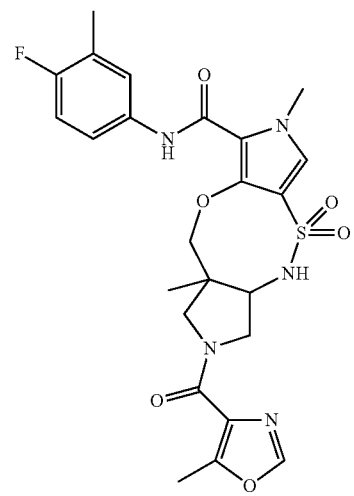 [SMILES: Cc1cc(NC(=O)c2c3c(cn2C)S(=O)(=O)NC2CN(C(=O)c4ncoc4C)CC2(C)CO3)ccc1F]

A solution of D104 (29.7 mg, 0.05 mmol) in DMF (0.650 mL) was treated with DIPEA (0.04 mL, 0.23 mmol) and 5-Methyl-1,3-oxazole-4-carboxylic acid (Fluorochem, cat no 0372559) (9.77 mg, 0.08 mmol). After 10 min at room temperature, benzotriazol-1-yloxytris(dimethylamino)phosphonium hexafluorophosphate (34 mg, 0.08 mmol) (BOP) was added in a single portion. The reaction was stirred for 40 min at room temperature. Water (1 mL) was added and solvent was removed in vacuo. The residue was purified by preparative HPLC (H$_2$O/CH$_3$CN+0.1% HCOOH) to afford E87 cis-N-(4-fluoro-3-methylphenyl)-7,10a-dimethyl-2-(5-methyloxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide (13.86 mg, 0.026 mmol) as white solid. $^1$H NMR (300 MHz, DMSO-d$_6$+TFA) δ ppm 1.22-1.38 (m, 3H) 2.24 (s, 3H) 2.54 (s, 3H) 3.23-3.49 (m, 1H) 3.51-3.89 (m, 5H) 3.94-4.22 (m, 3H) 4.30-4.45 (m, 1H) 7.11 (td, J=9.17, 3.03 Hz, 1H) 7.38-7.51 (m, 2H) 7.58 (td, J=6.56, 2.38 Hz, 1H) 8.31 (d, J=14.12 Hz, 1H) 8.41-8.59 (m, 1H) 9.33 (d, J=4.58 Hz, 1H). Method 3; Rt: 4.27. m/z: 532.43 (M+H)+ Exact mass: 531.16

Example 88: cis-N-(4-fluoro-3-methylphenyl)-7,10a-dimethyl-2-(2-methyltetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide (E88)

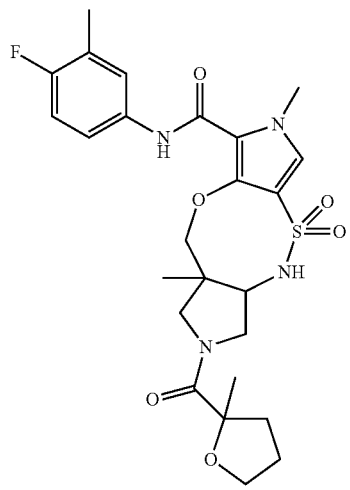 [SMILES: Cc1cc(NC(=O)c2c3c(cn2C)S(=O)(=O)NC2CN(C(=O)C4(C)CCCO4)CC2(C)CO3)ccc1F]

Prepared similarly as described for compound E87 using 2-methyloxolane-2-carboxylic acid (Enamine, cat no EN300-100748) instead of 5-methyl-1,3-oxazole-4-carboxylic acid to obtain E88 (17 mg, 0.032 mmol) as white powder. $^1$H NMR (300 MHz, DMSO-d6+TFA) δ ppm 1.10-1.41 (m, 6H) 1.44-1.95 (m, 3H) 2.19-2.26 (m, 3H) 2.42-2.47 (m, 1H) 3.07-3.51 (m, 2H) 3.57-4.06 (m, 8H) 4.07-4.28 (m, 1H) 4.28-4.46 (m, 1H) 7.11 (t, J=9.22 Hz, 1H) 7.38-7.50 (m, 2H) 7.52-7.64 (m, 1H) 8.29-8.56 (m, 1H) 9.20-9.42 (m, 1H). Method 3; Rt: 4.43 min. m/z: 535 (M+H)$^+$.

Example 89: cis-N-(4-fluoro-3-methylphenyl)-7,10a-dimethyl-2-(3-methyloxetane-3-carbonyl)-2,3,3a,4,10,10a-hexahydro-1H,7H-dipyrrolo[3,4-b:3',4'-f][1,4,5]oxathiazocine-8-carboxamide 5,5-dioxide (E89)

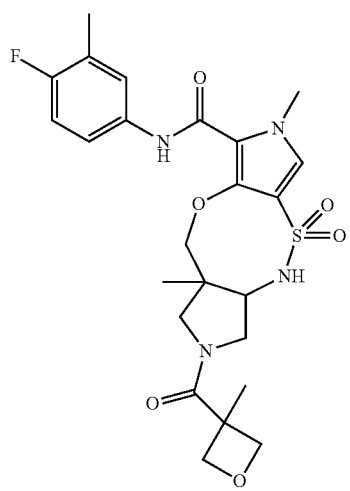 [SMILES: Cc1cc(NC(=O)c2c3c(cn2C)S(=O)(=O)NC2CN(C(=O)C4(C)COC4)CC2(C)CO3)ccc1F]

Prepared similarly as described for compound E87 using 3-methyl-3-oxetanecarboxylic acid (Fluorochem, cat no 042959) instead of 5-methyl-1,3-oxazole-4-carboxylic acid to obtain E89 (10.75 mg, 0.021 mmol). $^1$H NMR (300 MHz, DMSO-d$_6$) δ ppm 1.17-1.35 (m, 3H) 1.44-1.67 (m, 3H) 2.24 (s, 3H) 2.76-3.10 (m, 1H) 3.11-3.28 (m, 2H) 3.81 (s, 3H) 3.87-4.13 (m, 3H) 4.13-4.41 (m, 3H) 4.77 (dd, J=16.18, 5.73 Hz, 1H) 4.87 (dd, J=10.73, 5.96 Hz, 1H) 7.13 (t, J=9.22 Hz, 1H) 7.46 (d, J=2.20 Hz, 2H) 7.51-7.65 (m, 1H) 8.47 (br s, 1H) 9.35 (d, J=9.63 Hz, 1H). Method 3; Rt: 4.05. m/z: 521 (M+H)$^+$.

Example 90: cis-2-(2-oxabicyclo[2.1.1]hexane-1-carbonyl)-N-(4-fluoro-3-methylphenyl)-7,10a-dimethyl-2,3,3a,4,10,10a-hexahydro-1H,7H-dipyrrolo[3,4-b:3',4'-f][1,4,5]oxathiazocine-8-carboxamide 5,5-dioxide (E90)

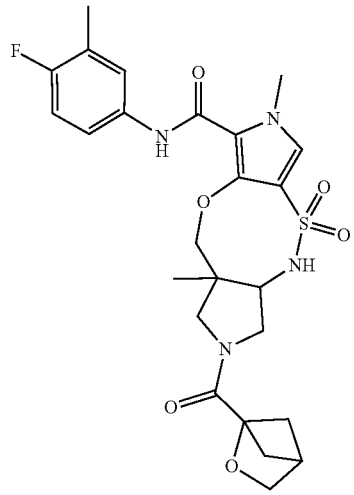 [SMILES: Cc1cc(NC(=O)c2c3c(cn2C)S(=O)(=O)NC2CN(C(=O)C45CC(CO4)C5)CC2(C)CO3)ccc1F]

Prepared similarly as described for compound E87 using 2-oxabicyclo[2.1.1]hexane-1-carboxylic acid (Enamine, cat no EN300-2007648) instead of 5-methyl-1,3-oxazole-4-carboxylic acid to obtain E90 (17 mg, 0.032 mmol). $^1$H NMR (300 MHz, DMSO-d6+TFA) 1.18-1.34 (m, 3H), 1.49-1.74 (m, 2H), 1.86-2.09 (m, 2H), 2.23 (s, 3H), 2.79-2.95 (m, 1H), 3.13-3.31 (m, 1H), 3.33-3.88 (m, 7H), 3.91-4.22 (m, 3H), 4.36 (br d, J=11.28 Hz, 1H), 7.11 (t, J=9.17 Hz, 1H), 7.35-7.51 (m, 2H), 7.51-7.65 (m, 1H) 8.48 (br dd, J=9.31, 3.71 Hz, 1H), 9.32 (s, 1H). Method 3; Rt: 4.45 min. m/z: 533.38 (M+H)$^+$.

The synthesis of compounds E91-96 is reported in Table 1 below.

Example 97: (3aR,10aR)-7-methyl-2-(5-methyl-1,3,4-oxadiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E97)

Example 98: (3aR,10aR)—N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide (E98)

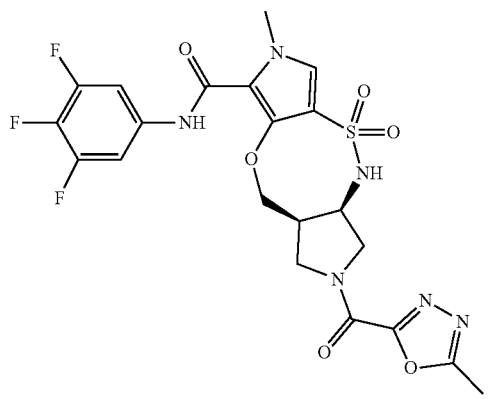 [SMILES: Cc1nnc(C(=O)N2C[C@H]3COc4c(cn(C)c4C(=O)Nc4cc(F)c(F)c(F)c4)S(=O)(=O)N[C@H]3C2)o1]

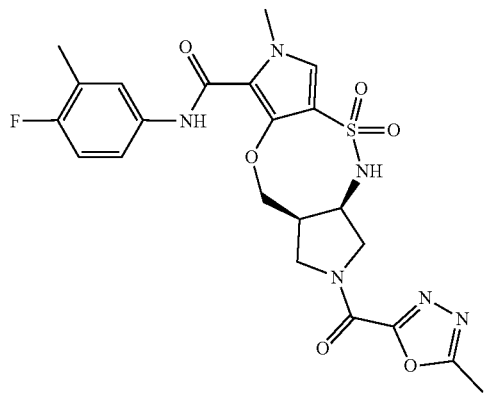 [SMILES: Cc1nnc(C(=O)N2C[C@H]3COc4c(cn(C)c4C(=O)Nc4ccc(F)c(Cl)c4)S(=O)(=O)N[C@H]3C2)o1]

D109 (99.94 mg, 0.180 mmol) was suspended in MeCN (1 mL) and treated with a single portion of N-methylmorpholine (98.4 uL, 0.90 mmol), giving a white suspension. To this mixture, 5-methyl-1,3,4-oxadiazole-2-carbonyl chloride (1.17M in MeCN, 50 uL) (Org. Proc. Res. Develop. 2011, 15, 73-83) was added in a single portion. The reaction was stirred at room temperature. After 2 hrs at room temperature more 5-methyl-1,3,4-oxadiazole-2-carbonyl chloride (1.17M in MeCN, 300 uL) was added and the reaction stirred at room temperature 1 h (complete reaction). The reaction was quenched by MeOH, the solvent was removed, the residue dissolved in DCM, then was washed with brine and aq 5% citric acid. The organic phase was dried over Na$_2$SO$_4$, filtered and concentrated under reduced pressure to give a crude product, that was purified by preparative HPLC (H$_2$O, CH$_3$CN 0.1% HCOOH) to yield E97 (50 mg, 0.093 mmol). $^1$H NMR (300 MHz, DMSO-d6+TFA) δ ppm 2.54-2.63 (m, 3H) 2.97-3.23 (m, 1H) 3.27-3.85 (m, 5H) 3.86-4.32 (m, 3H) 4.42-4.75 (m, 2H) 7.50 (s, 1H) 7.58-7.82 (m, 2H) 8.47 (dd, J=9.54, 7.61 Hz, 1H) 9.49-9.82 (m, 1H). Method 3; Rt=3.24 min. m/z=541 (M+H)$^+$.

D108 (380 mg, 0.710 mmol 9 was suspended in MeCN (20 mL, dry), cooled to −10° C., basified with TEA (300 uL), added over 5 min in 3 equal portions. The resulting solution was treated at −10° C. with 5-methyl-1,3,4-oxadiazole-2-carbonyl chloride (0.827 mL, 0.990 mmol) (1.29M in MeCN/DMF) (Org. Proc. Res. Develop. 2011, 15, 73-83) added in small amounts. The reaction was monitored by UPLC_MS. The reaction was stopped by addition of MeOH (about 3 mL) at −10° C. Solvent was removed in vacuo. The residue was partitioned between EtOAc and water. The organic layer was washed with brine and 5% NaHCO$_3$ (acq. sol). The organic layer was evaporated giving a residue (oil, 400 mg). Purification performed by flash chromatography (eluent DCM/EtOAc). The fractions were monitored by TLC (eluent EtOAc/DCM 1/1, 2 runs) and the fractions containing the title product were combined and evaporated. The residue was dissolved in MeCN/H2O and purified by reverse flash chromatography (H$_2$O, CH$_3$CN 0.1% TFA), giving E98 (237.34 mg, 0.456 mmol). $^1$H NMR (300 MHz, DMSO-d6) δ ppm 2.23 (s, 3H) 2.58 (d, J=3.39 Hz, 3H) 2.94-3.23 (m, 1H) 3.29-3.78 (m, 2H) 3.81 (d, J=1.10 Hz, 3H) 3.87-4.32 (m, 3H) 4.64 (br d, J=11.55 Hz, 2H) 7.08 (t, J=9.17 Hz, 1H) 7.38-7.65 (m, 3H) 8.44 (dd, J=9.72, 7.15 Hz, 1H) 9.33 (d, J=3.03 Hz, 1H). Method 3; Rt=3.06 min. m/z=519 (M+H)$^+$.

Example 99: (3aR,10aR)—N-(3-chloro-4-fluorophenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide (E99)

Example 100: (3aR,10aR)—N-(4-fluoro-3-methylphenyl)-7-methyl-2-((R)-tetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide (E100)

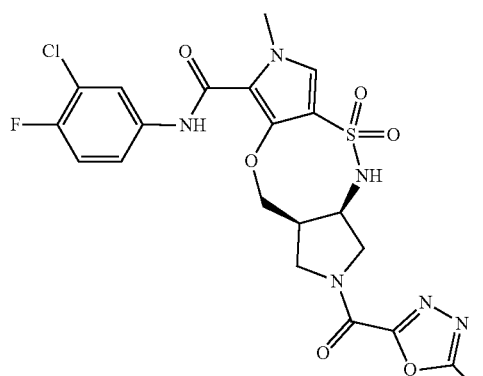

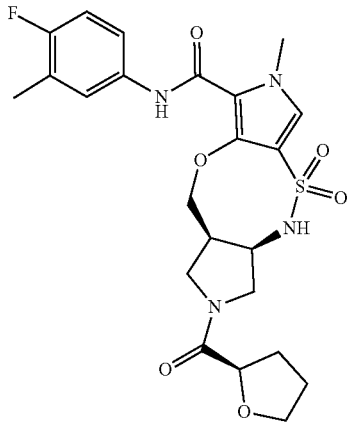 [SMILES: Cc1cc(NC(=O)c2c3c(cn2C)S(=O)(=O)N[C@H]2CN(C(=O)[C@H]4CCCO4)C[C@H]2CO3)ccc1F]

D110 (3aR,10aR)—N-(3-chloro-4-fluorophenyl)-7-methyl-2,3,3a,4,10,10a-hexahydro-1H,7H-dipyrrolo[3,4-b:3',4'-f][1,4,5]oxathiazocine-8-carboxamide 5,5-dioxide hydroiodide (83 mg, 0.150 mmol) was dissolved in MeCN (2 mL) and triethylamine (0.06 mL, 0.430 mmol) cooled to 0° C. with ice bath and treated with 5-methyl-1,3,4-oxadiazole-2-carbonyl chloride (1.17M in MeCN, 0.28 mL, 0.330 mmol) (Org. Proc. Res. Develop. 2011, 15, 73-83). The reaction was stirred at 0° C. for 15 min then left to room temperature. Reaction was stopped by MeOH addition, solvent was removed, the residue dissolved in DCM and washed with brine and 5% citric acid. The organic phase were dried over $Na_2SO_4$, filtered and concentrated under reduced pressure to give a residue (100 mg). The crude was purified by preparative HPLC ($H_2O$, $CH_3CN$ 0.1% HCOOH) to yield E99 (34.13 mg, 0.063 mmol). $^1$H NMR (300 MHz, DMSO-d6+TFA) δ ppm 2.55-2.64 (m, 3H) 2.95-3.24 (m, 1H) 3.28-3.86 (m, 5H) 3.87-4.31 (m, 3H) 4.40-4.76 (m, 2H) 7.31-7.43 (m, 1H) 7.44-7.54 (m, 1H) 7.56-7.73 (m, 1H) 7.90-8.05 (m, 1H) 8.32-8.59 (m, 1H) 9.41-9.70 (m, 1H). Method 3; Rt=3.21 min. m/z=539; 541 $(M+H)^+$.

To a solution of D108 (20 mg, 0.040 mmol) in dry DMF (0.5 mL) was added D-tetrahydro-furan-2-carboxylic acid (Fluorochem, cat no 040030) (0.005 mL, 0.050 mmol) followed by DIPEA (0.026 mL, 0.150 mmol) under nitrogen atmosphere. To the stirring solution was added Benzotriazol-1-yloxytris(dimethylamino)phosphonium hexafluorophosphate 23.09 mg, 0.050 mmol (BOP) and the reaction mixture stirred at 2 h at RT (UPLC-MS showed reaction was complete). The reaction mixture was diluted with EtOAc then washed with water (×3). The organic portion was dried ($Na_2SO_4$), filtered and concentrated under reduced pressure. The crude was purified by preparative HPLC ($H_2O$, $CH_3CN$ 0.1% HCOOH) to afford E100 (13 mg, y=68%, purity=99.76%) as white solid. $^1$H NMR (300 MHz, DMSO-d$_6$) δ ppm 1.70-2.15 (m, 4H) 2.24 (s, 3H) 2.82-3.28 (m, 2H) 3.40-4.07 (m, 9H) 4.34-4.73 (m, 3H) 7.11 (t, J=9.63 Hz, 1H) 7.41-7.55 (m, 2H) 7.59 (d, J=6.42 Hz, 1H) 8.39 (br s, 1H) 9.22-9.49 (m, 1H). Method 3; Rt=3.01 min. m/z=507 $(M+H)^+$.

Example 101: (3aR,10aR)—N-(4-fluoro-3-methylphenyl)-7-methyl-2-((S)-tetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide (E101)

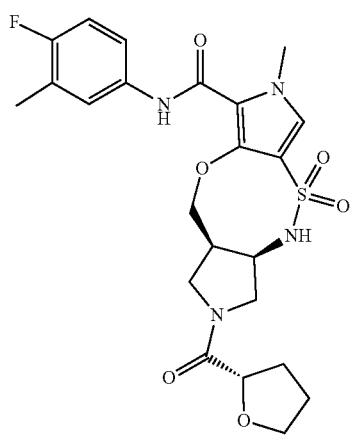 [SMILES: Cc1cc(NC(=O)c2c3c(cn2C)S(=O)(=O)N[C@H]2CN(C(=O)[C@@H]4CCCO4)C[C@H]2CO3)ccc1F]

To a solution of D108 (20 mg, 0.040 mmol) in dry DMF (0.5 mL) was added (S)-(−)-2-Carboxytetrahydrofuroic acid (Fluorochem, cat no 093764) (0.005 mL, 0.05 mmol) followed by DIPEA (0.026 mL, 0.150 mmol) under nitrogen atmosphere. To the stirring solution was added Benzotriazol-1-yloxytris(dimethylamino)phosphonium hexafluorophosphate (23.1 mg, 0.050 mmol) (BOP) and the reaction mixture stirred at 2 h at RT (UPLC-MS showed reaction was complete). The reaction mixture was diluted with EtOAc then washed with water (×3). The organic portion was dried (Na$_2$SO4), filtered and concentrated under reduced pressure, then the crude was purified by preparative HPLC (H$_2$O, CH$_3$CN 0.1% HCOOH) to afford E101 (14 mg, y=73.8%, purity=99.51%) as white solid. $^1$H NMR (300 MHz, DMSO-d$_6$) δ ppm 1.70-2.14 (m, 4H) 2.24 (br d, J=1.30 Hz, 3H) 2.85-3.29 (m, 2H) 3.40-4.03 (m, 9H) 4.33-4.71 (m, 3H) 7.11 (t, J=9.22 Hz, 1H) 7.37-7.55 (m, 2H) 7.59 (dd, J=6.88, 2.38 Hz, 1H) 8.27-8.49 (m, 1H) 9.35 (s, 1H). Method 3; Rt=3.01 min. m/z=507 (M+H)$^+$.

Example 102: (3aR,10aR)-2-(5-amino-1,3,4-oxadiazole-2-carbonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E102)

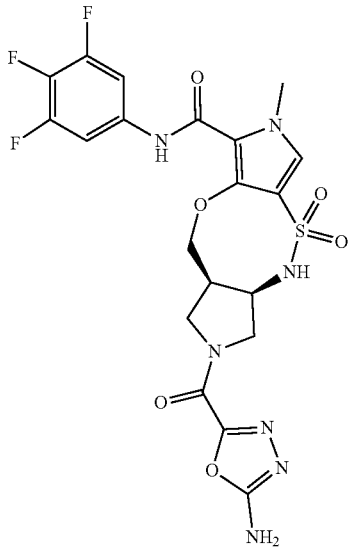 [SMILES: Cn1cc2c(c1C(=O)Nc1cc(F)c(F)c(F)c1)OC[C@@H]1CN(C(=O)c3nnc(N)o3)C[C@@H]1NS2(=O)=O]

Sodium 5-amino-1,3,4-oxadiazole-2-carboxylate was obtained by treating a solution of 5-amino-1,3,4-oxadiazole-2-carboxylic acid ethyl ester (Fluorochem, cat no 009872) with a single portion of sodium hydroxide (41 mg, 1.02 mmol) dissolved in water (0.500 mL), giving a white suspension. The reaction was stirred for 1 h. The reaction was diluted with water, solvent was removed in vacuo. The residue was treated with THF and the resulting suspension filtered, giving sodium 5-amino-1,3,4-oxadiazole-2-carboxylate as a light brown solid (126 mg, 0.834 mmol, yield=82%). Method 1; Rt=0.33 min; m/z=130 (M+H)$^+$.

To a suspension of D109 (3aR,10aR)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide hydroiodide (30 mg, 0.054 mmol) and sodium 5-amino-1,3,4-oxadiazole-2-carboxylate (12.17 mg, 0.081 mmol) in DMF (0.6 mL) was added DIPEA (37.4 uL, 0.215 mmol) in a single portion. Then BOP (35.6 mg, 0.081 mmol) was added in a single portion. The suspension was stirred at room temperature for 2 hrs then DMF (0.4 mL), DIPEA (0.037 mL), sodium 5-amino-1,3,4-oxadiazole-2-carboxylate (12.2 mg, 0.081 mmol) and BOP (35.6 mg, 0.081) were added in this order. The reaction was heated at 50° C. for 40 min, then at room temperature for 2 days. The reaction mixture was diluted with EtOAc then washed with water (×2) and brine. The organic portion was dried (Na$_2$SO4), filtered and concentrated under reduced pressure, then the crude was purified by preparative HPLC (H$_2$O, CH$_3$CN 0.1% HCOOH) to afford E102 (3.99 mg, 0.006 mmol). $^1$H NMR (300 MHz, DMSO-d$_6$) δ ppm 2.87-3.23 (m, 1H) 3.51-4.13 (m, 7H) 4.14-4.28 (m, 1H) 4.62 (br d, J=2.38 Hz, 2H) 7.41-7.63 (m, 3H) 7.70 (ddd, J=10.32, 6.28, 4.31 Hz, 2H) 8.35-8.52 (m, 1H) 9.68 (s, 1H). Method 3; Rt=3.02 min. m/z=542 (M+H)$^+$.

Example 103: (3aR,10aR)—N-(4-fluoro-3-methylphenyl)-7-methyl-2-(3-methyl-1,2,4-oxadiazole-5-carbonyl)-2,3,3a,4,10,10a-hexahydro-1H,7H-dipyrrolo[3,4-b:3',4'-f][1,4,5]oxathiazocine-8-carboxamide 5,5-dioxide (E103)

Example 104: (3aR,10aR)—N-(4-fluoro-3-methylphenyl)-7-methyl-2-(oxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide (E104)

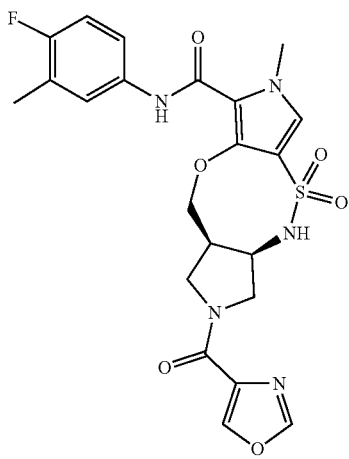

Prepared similarly as described for compound E100 using 4-oxazolecarboxylic acid (Fluorochem, cat no 040016) instead of D-Tetrahydro-furan-2-carboxylic acid to obtain E104. $^1$H NMR (300 MHz, DMSO-d6) δ ppm 2.22-2.26 (m, 3H) 3.06 (dt, J=10.29, 5.17 Hz, 1H) 3.52-3.75 (m, 2H) 3.81 (s, 3H) 3.85-4.26 (m, 3H) 4.45-4.69 (m, 2H) 7.11 (t, J=9.08 Hz, 1H) 7.44-7.54 (m, 2H) 7.59 (br s, 1H) 8.41-8.54 (m, 2H) 8.64 (d, J=7.79 Hz, 1H) 9.35 (s, 1H). Method 3; Rt=3.01 min. m/z=504 (M+H)$^+$.

Example 105: (3aR,10aR)—N-(4-fluoro-3-methylphenyl)-7-methyl-2-(1,2,5-oxadiazole-3-carbonyl)-2,3,3a,4,10,10a-hexahydro-1H,7H-dipyrrolo[3,4-b:3',4'-f][1,4,5]oxathiazocine-8-carboxamide 5,5-dioxide (E105)

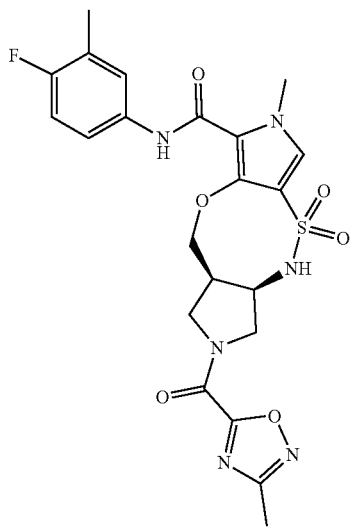 [SMILES: Cc1noc(C(=O)N2C[C@H]3COc4c(cn(C)c4C(=O)Nc4ccc(F)c(C)c4)S(=O)(=O)N[C@H]3C2)n1]

Sodium 3-methyl-1,2,4-oxadiazole-5-carboxylate was obtained by treating 3-methyl-[1,2,4]oxadiazole-5-carboxylic acid ethylester (Fluorochem, cat no 047495) (160 mg, 1.02 mmol) in THF (1 mL) with a single portion of NaOH (41 mg, 1.02 mmol) previously dissolved in water (0.460 mL). The resulting solution was stirred for 2 hrs at room temperature. Solvent was removed in vacuo, the residue treated with THF, filtered and evaporated giving sodium 3-methyl-1,2,4-oxadiazole-5-carboxylate (125 mg, 0.833 mmol, yield=81%) as off white solid. Method 1; Rt=0.59 min; m/z=129 (M+H)$^+$.

Compound E103 was prepared similarly as described for compound E100 using sodium 3-methyl-1,2,4-oxadiazole-5-carboxylate instead of D-tetrahydro-furan-2-carboxylic acid. $^1$H NMR (300 MHz, DMSO-d6) δ ppm 2.24 (s, 3H) 2.45 (d, J=12.01 Hz, 3H) 2.96-3.21 (m, 1H) 3.35-3.78 (m, 2H) 3.81 (d, J=2.20 Hz, 3H) 3.87-4.29 (m, 3H) 4.41-4.76 (m, 2H) 7.11 (td, J=9.17, 2.29 Hz, 1H) 7.43-7.55 (m, 2H) 7.59 (td, J=7.29, 2.48 Hz, 1H) 8.44 (dd, J=9.58, 6.01 Hz, 1H) 9.35 (d, J=3.48 Hz, 1H). Method 3; Rt=3.30 min. m/z=519 (M+H)$^+$.

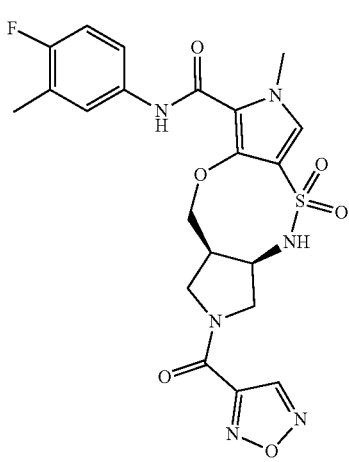 [SMILES: Cc1cc(NC(=O)c2c3c(cn2C)S(=O)(=O)N[C@H]2CN(C(=O)c4cnon4)C[C@H]2CO3)ccc1F]

Prepared similarly as described for compound E100 using 1,2,5-oxadiazole-3-carboxylic acid (Fluorochem, cat no 066290) instead of D-Tetrahydro-furan-2-carboxylic acid to obtain E105. $^1$H NMR (300 MHz, DMSO-d$_6$) δ ppm 2.24 (s, 3H) 2.87-3.16 (m, 1H) 3.33-3.48 (m, 1H) 3.49-3.95 (m, 6H) 3.95-4.13 (m, 1H) 4.36-4.52 (m, 1H) 4.53-4.71 (m, 1H) 7.11 (t, J=8.80 Hz, 1H) 7.41-7.54 (m, 2H) 7.55-7.65 (m, 1H) 8.40 (t, J=9.26 Hz, 1H) 9.20-9.48 (m, 1H) 14.47 (br s, 1H). Method 3; Rt=3.21 min. m/z=505 (M+H)+.

Example 106: (3aR,10aR)-7-methyl-2-(oxazole-4-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E106)

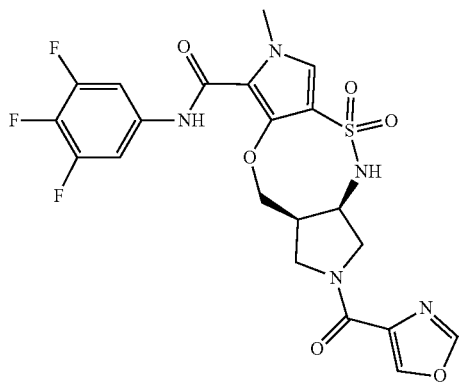 [SMILES: Cn1cc2c(c1C(=O)Nc1cc(F)c(F)c(F)c1)OC[C@@H]1CN(C(=O)c3cocn3)C[C@@H]1NS2(=O)=O]

To a solution of D109 (268 mg, 0.480 mmol) in dry DMF (4.7 mL), at room temperature and under nitrogen atmosphere, 4-Oxazolecarboxylic acid (Fluorochem, cat no 040016) (70.6 mg, 0.624 mmol) was added followed by dry DIPEA (0.350 mL, 2.0 mmol) and Benzotriazol-1-yloxytris(dimethylamino)phosphonium hexafluorophosphate (BOP) (276 mg, 0.624 mmol). The mixture reaction was stirred at the same conditions for 15 h, then was diluted with EtOAc, washed with water (×2) and brine. Organic layer was dried over Na$_2$SO$_4$, filtered and concentrated under reduced pressure to afford a brown solid. The crude was purified by reversed phase (H$_2$O, CH$_3$CN 0.1% HCOOH) to afford after freeze-drying E106 as a white powder (215.78 mg). $^1$H NMR (300 MHz, DMSO-d$_6$) δ ppm 2.95-3.15 (m, 1H) 3.25-3.33 (m, 1H) 3.52-3.76 (m, 1H) 3.81 (s, 3H) 3.86-4.24 (m, 3H) 4.45-4.70 (m, 2H) 7.51 (d, J=2.02 Hz, 1H) 7.64-7.75 (m, 2H) 8.43-8.55 (m, 2H) 8.65 (d, J=7.79 Hz, 1H) 9.68 (s, 1H).

Method 3; Rt=3.21 min. m/z=526 (M+H)+.

Example 107: (3aR,10aR)—N-(4-fluoro-3-methylphenyl)-7-methyl-2-(5-methyl-1,3,4-thiadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide (E107)

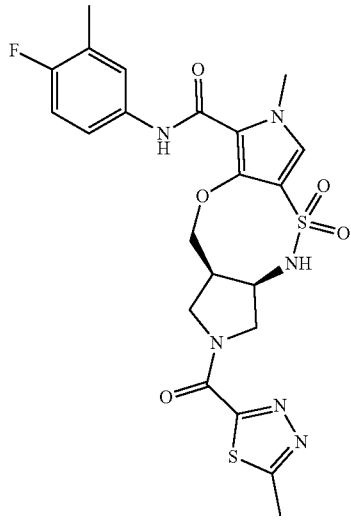 [SMILES: Cc1nnc(C(=O)N2C[C@H]3COc4c(cn(C)c4C(=O)Nc4ccc(F)c(C)c4)S(=O)(=O)N[C@H]3C2)s1]

Prepared similarly as described for compound E100 using 5-methyl-1,3,4-thiadiazole-2-carboxylic acid (CAS no 501698-31-3) instead of D-Tetrahydro-furan-2-carboxylic acid to obtain E107. $^1$H NMR (300 MHz, DMSO-d6) δ 2.24 (s, 3H), 2.78 (d, J=6.42 Hz, 3H), 2.98-3.23 (m, 1H), 3.34-4.23 (m, 7H), 4.25-4.32 (m, 1H), 4.46-4.61 (m, 1H), 4.65 (br dd, J=11.74, 2.57 Hz, 1H), 7.12 (td, J=9.19, 1.88 Hz, 1H), 7.45-7.55 (m, 2H), 7.55-7.63 (m, 1H), 8.45 (br s, 1H), 9.36 (d, J=3.76 Hz, 1H). Method 3; Rt=3.22 min. m/z=535 (M+H)+.

Example 108: (3aR,10aR)—N-(4-fluoro-3-methylphenyl)-7-methyl-2-(oxetane-3-carbonyl)-2,3,3a,4, 10,10a-hexahydro-1H,7H-dipyrrolo[3,4-b:3',4'-f][1, 4,5]oxathiazocine-8-carboxamide 5,5-dioxide (E108)

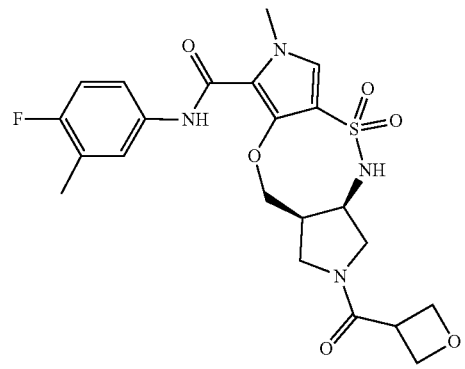 [SMILES: Cc1cc(NC(=O)c2c3c(cn2C)S(=O)(=O)N[C@H]2CN(C(=O)C4COC4)C[C@H]2CO3)ccc1F]

Prepared similarly as described for compound E100 using 3-Oxetanecarboxylic acid (Fluorochem, cat no 050554) instead of D-tetrahydro-furan-2-carboxylic acid to obtain E108. $^1$H NMR (300 MHz, DMSO-d6+TFA) δ ppm 2.16-

2.27 (m, 3H) 2.85-3.19 (m, 2H) 3.23-3.39 (m, 1H) 3.42-4.09 (m, 7H) 4.37-4.77 (m, 6H) 7.09 (t, J=9.12 Hz, 1H) 7.37-7.53 (m, 2H) 7.57 (br d, J=6.51 Hz, 1H) 8.31-8.43 (m, 1H) 9.32 (s, 1H). Method 3; Rt=2.87 min. m/z=493 (M+H)+.

Example 109: (3aR,10aR)-2-(2-oxabicyclo[2.1.1]hexane-1-carbonyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide (E109)

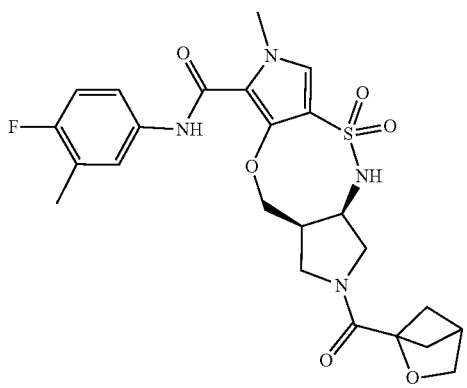 [SMILES: Cc1cc(NC(=O)c2c3c(cn2C)S(=O)(=O)N[C@H]2CN(C(=O)C45CC(CO4)C5)C[C@H]2CO3)ccc1F]

Prepared similarly as described for compound E100 using 2-oxabicyclo[2.1.1]hexane-1-carboxylic acid (Enamine, cat no EN300-2007648) instead of D-Tetrahydro-furan-2-carboxylic acid to obtain E109. ¹H NMR (300 MHz, DMSO-d6+TFA) δ ppm 1.57-1.68 (m, 2H) 1.97 (br d, J=4.58 Hz, 2H) 2.23 (s, 3H) 2.82-2.90 (m, 1H) 2.91-3.07 (m, 1H) 3.07-3.36 (m, 1H) 3.41-3.57 (m, 1H) 3.73 (s, 1H) 3.74-3.96 (m, 7H) 4.41-4.56 (m, 1H) 4.56-4.66 (m, 1H) 7.08 (t, J=9.17 Hz, 1H) 7.43-7.54 (m, 2H) 7.58 (br d, J=6.97 Hz, 1H) 8.43 (d, J=10.00 Hz, 1H) 9.32 (s, 1H). Method 3; Rt=3.16 min. m/z=519 (M+H)+.

Example 110: (3aR,10aR)—N-(4-fluoro-3-methylphenyl)-7-methyl-2-(oxetane-2-carbonyl)-2,3,3a,4,10,10a-hexahydro-1H,7H-dipyrrolo[3,4-b:3',4'-f][1,4,5]oxathiazocine-8-carboxamide 5,5-dioxide (E110)

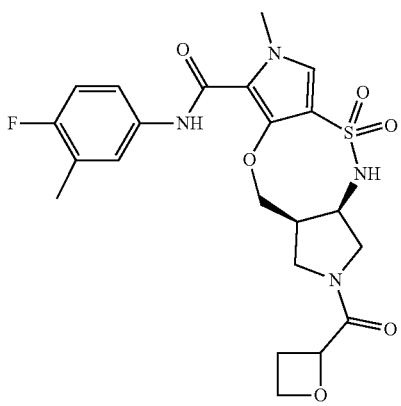 [SMILES: Cc1cc(NC(=O)c2c3c(cn2C)S(=O)(=O)N[C@H]2CN(C(=O)C4CCO4)C[C@H]2CO3)ccc1F]

Prepared similarly as described for compound E100 using oxetane-2-carboxylic acid (Fluorochem, cat no 225298) instead of D-Tetrahydro-furan-2-carboxylic acid to obtain E110. ¹H NMR (300 MHz, DMSO-d6) δ ppm 2.24 (s, 3H) 2.64-2.86 (m, 2H) 2.88-3.25 (m, 2H) 3.73 (s, 7H) 4.32-4.72 (m, 4H) 5.14-5.33 (m, 1H) 7.11 (t, J=9.22 Hz, 1H) 7.43-7.55 (m, 2H) 7.59 (br d, J=6.97 Hz, 1H) 8.23-8.55 (m, 1H) 9.34 (s, 1H). Method 3; Rt=2.86 min. m/z=493 (M+H)+.

Example 111: (3aR,10aR)—N-(4-fluoro-3-methylphenyl)-7-methyl-2-(2-methyltetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide (E111)

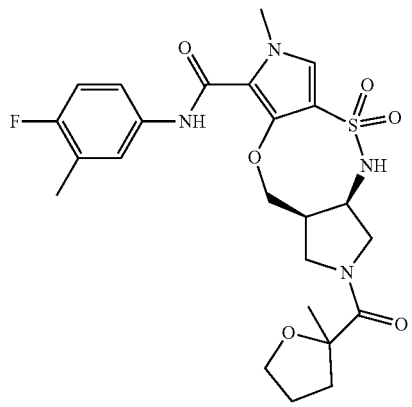 [SMILES: Cc1cc(NC(=O)c2c3c(cn2C)S(=O)(=O)N[C@H]2CN(C(=O)C4(C)CCCO4)C[C@H]2CO3)ccc1F]

Prepared similarly as described for compound E100 using 2-methyloxolane-2-carboxylic acid (Enamine, cat no EN300-100748) instead of D-Tetrahydro-furan-2-carboxylic acid to obtain E111. ¹H NMR (300 MHz, DMSO-d6) δ ppm 1.26-1.41 (m, 3H) 1.48-1.65 (m, 1H) 1.65-1.97 (m, 2H) 2.24 (d, J=1.01 Hz, 3H) 2.39-2.60 (m, 1H) 2.79-3.81 (m, 11H) 4.30-4.53 (m, 1H) 4.60 (br s, 1H) 7.10 (t, J=9.17 Hz, 1H) 7.38-7.66 (m, 3H) 8.40 (br d, J=10.00 Hz, 1H) 9.17-9.49 (m, 1H). Method 3; Rt=3.29 min. m/z=521 (M+H)+. Method 3; Rt=3.29 min. m/z=521 (M+H)+.

Example 112: (3aR,10aR)—N-(4-fluoro-3-meth-
ylphenyl)-7-methyl-2-(2-methyloxazole-4-carbonyl)-
2,3,3a,4,10,10a-hexahydro-1H,7H-dipyrrolo[3,4-b:
3',4'-f][1,4,5]oxathiazocine-8-carboxamide 5,5-
dioxide (E112)

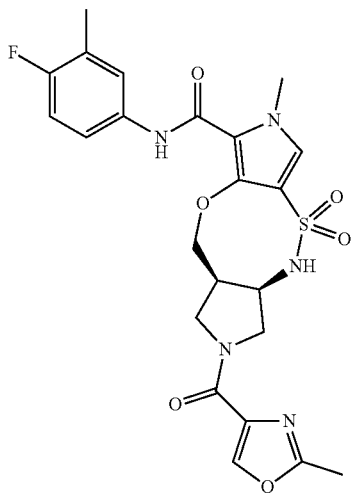 [SMILES: Cc1nc(C(=O)N2C[C@H]3COc4c(cn(C)c4C(=O)Nc4ccc(F)c(C)c4)S(=O)(=O)N[C@H]3C2)co1]

Prepared similarly as described for compound E100 using
2-Methyl-1,3-oxazole-4-carboxylic acid (Fluorochem, cat
no 044793) instead of D-Tetrahydro-furan-2-carboxylic acid
to obtain E112. $^1$H NMR (300 MHz, DMSO-d6+TFA) δ
ppm 2.24 (s, 3H) 2.45 (d, J=12.56 Hz, 3H) 2.89-3.18 (m,
1H) 3.20-3.74 (m, 2H) 3.81 (s, 3H) 3.85-4.12 (m, 2H)
4.13-4.25 (m, 1H) 4.41-4.58 (m, 1H) 4.59-4.73 (m, 1H) 7.10
(t, J=9.22 Hz, 1H) 7.40-7.54 (m, 2H) 7.55-7.67 (m, 1H)
8.38-8.54 (m, 2H) 9.33 (s, 1H). Method 3; Rt=3.10 min.
m/z=518 (M+H)$^+$.

Example 113: (3aR,10aR)—N-(4-fluoro-3-meth-
ylphenyl)-7-methyl-2-(5-methyloxazole-4-carbonyl)-
2,3,3a,4,10,10a-hexahydro-1H,7H-dipyrrolo[3,4-b:
3',4'-f][1,4,5]oxathiazocine-8-carboxamide 5,5-
dioxide (E113)

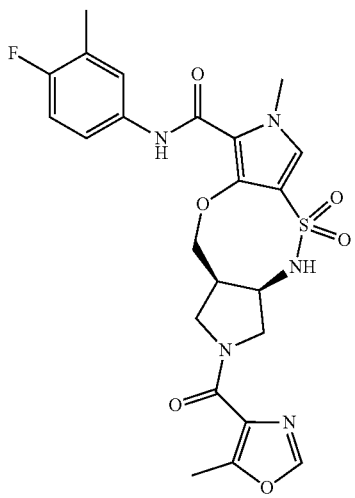 [SMILES: Cc1cc(NC(=O)c2c3c(cn2C)S(=O)(=O)N[C@H]2CN(C(=O)c4ncoc4C)C[C@H]2CO3)ccc1F]

Prepared similarly as described for compound E100 using
5-Methyl-1,3-oxazole-4-carboxylic acid (Fluorochem, cat
no 037255) instead of D-tetrahydro-furan-2-carboxylic acid
to obtain E113. $^1$H NMR (300 MHz, DMSO-d6+TFA) δ
ppm 2.23 (s, 3H) 2.5 (s, 3H) 2.92-3.15 (m, 1H) 3.20-3.73 (m,
2H) 3.81 (s, 3H) 3.86-4.26 (m, 3H) 4.38-4.57 (m, 1H)
4.57-4.74 (m, 1H) 7.09 (td, J=9.17, 2.29 Hz, 1H) 7.40-7.55
(m, 2H) 7.55-7.67 (m, 1H) 8.30 (d, J=13.30 Hz, 1H)
8.37-8.52 (m, 1H) 9.34 (br d, J=2.60 Hz, 1H).

Example 114: (3aR,10aR)-2-(2,5-dimethyloxazole-
4-carbonyl)-N-(4-fluoro-3-methylphenyl)-7-methyl-
2,3,3a,4,10,10a-hexahydro-1H,7H-dipyrrolo[3,4-b:
3',4'-f][1,4,5]oxathiazocine-8-carboxamide 5,5-
dioxide (E114)

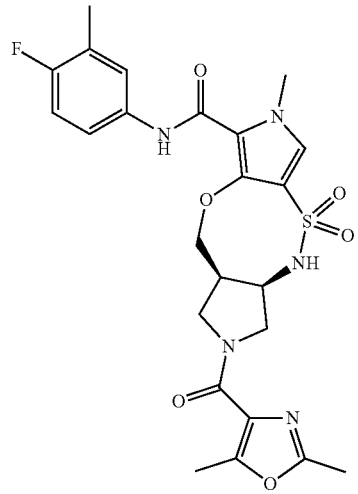 [SMILES: Cc1nc(C(=O)N2C[C@H]3COc4c(cn(C)c4C(=O)Nc4ccc(F)c(C)c4)S(=O)(=O)N[C@H]3C2)c(C)o1]

Prepared similarly as described for compound E100 using
2,5-dimethyl-1,3-oxazole-4-carboxylic acid (Fluorochem,
cat no 066205) instead of D-tetrahydro-furan-2-carboxylic
acid to obtain E114. $^1$H NMR (300 MHz, DMSO-d6) δ ppm
2.24 (s, 3H) 2.35-2.44 (m, 3H) 2.47-2.50 (m, 3H) 3.02 (br
dd, J=9.72, 4.86 Hz, 1H) 3.19-3.68 (m, 2H) 3.81 (s, 3H)
3.86-4.11 (m, 2H) 4.15 (br s, 1H) 4.43-4.56 (m, 1H) 4.56-
4.70 (m, 1H) 7.11 (t, J=9.17 Hz, 1H) 7.42-7.47 (m, 1H)
7.47-7.55 (m, 1H) 7.55-7.64 (m, 1H) 8.43 (dd, J=9.90, 4.49
Hz, 1H) 9.34 (d, J=5.04 Hz, 1H).

Method 3; Rt: 3.29. m/z: 532.30 (M+H)$^+$.

Example 115: (3aR,10aR)—N-(4-fluoro-3-methylphenyl)-7-methyl-2-(3-methyl-1,2,4-oxadiazol-5-yl)-2,3,3a,4,10,10a-hexahydro-1H,7H-dipyrrolo[3,4-b:3',4'-f][1,4,5]oxathiazocine-8-carboxamide 5,5-dioxide (E115)

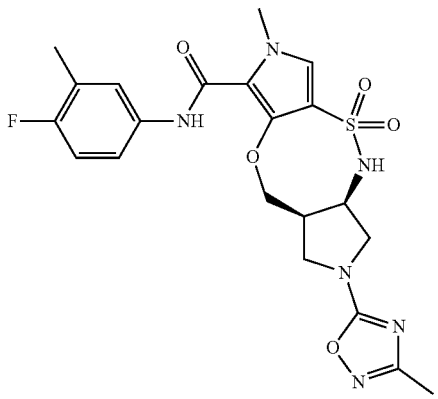 [SMILES: Cc1noc(N2C[C@H]3COc4c(cn(C)c4C(=O)Nc4ccc(F)c(C)c4)S(=O)(=O)N[C@H]3C2)n1]

To a solution of 3-methyl-1,2,4-oxadiazol-5-ol (Enamine, cat no EN300-72037) (29.85 mg, 0.300 mmol) and Bromotripyrrolidinophosphonium hexafluorophosphate (Py-Brop) (139.07 mg, 0.300 mmol) in 1,4-Dioxane (4.5 mL), dry DIPEA (0.150 mL, 0.860 mmol) was added. The solution was stirred at 50° C. for 90 min. Then D108 (80 mg, 0.150 mmol) was added and the mixture was additionally stirred at the same temperature for 6 hrs and then at RT overnight. The crude was diluted with AcOEt (15 mL), then was washed with water and brine. The organic layer was dried over $Na_2SO_4$, filtered and concentrated. The crude was purified by preparative HPLC-MS ($H_2O$/$CH_3CN$+0.1% HCOOH) to obtain, after freeze-drying, E115 as a cream colour solid (22.4 mg). $^1$H NMR (300 MHz, DMSO-$d_6$) δ ppm 2.12 (s, 3H) 2.24 (s, 3H) 3.09-3.22 (m, 1H) 3.28-3.59 (m, 3H) 3.81 (m, 3H) 3.89-4.06 (m, 2H) 4.48-4.80 (m, 2H) 7.11 (m, 1H) 7.47 (m, 3H) 8.40-8.58 (bs, 1H) 9.36 (s, 1H). Method 3; Rt=3.22 min. m/z=491 (M+H)$^+$.

Example 116: (3aR,10aR)—N-(3-chloro-4-fluorophenyl)-7-methyl-2-(3-methyl-1,2,4-oxadiazol-5-yl)-2,3,3a,4,10,10a-hexahydro-1H,7H-dipyrrolo[3,4-b:3',4'-f][1,4,5]oxathiazocine-8-carboxamide 5,5-dioxide (E116)

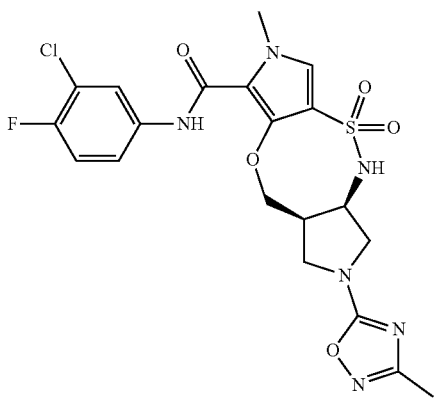 [SMILES: Cc1noc(N2C[C@H]3COc4c(cn(C)c4C(=O)Nc4ccc(F)c(Cl)c4)S(=O)(=O)N[C@H]3C2)n1]

Prepared similarly as described for compound E115 using D110 instead of D108 to obtain E116. $^1$H NMR (300 MHz, DMSO-$d_6$) δ ppm 2.12 (s, 3H) 3.09-3.22 (m, 1H) 3.30 (m, 1H) 3.58-3.70 (m, 2H) 3.81 (s, 3H) 3.89-4.03 (m, 2H) 4.51-4.69 (m, 2H) 7.41 (t, J=9.40 Hz, 1H) 7.50 (s, 1H) 7.61-7.70 (m, 1H) 7.99 (dd, J=6.79, 2.48 Hz, 1H) 8.50 (br d, J=5.96 Hz, 1H) 9.59 (s, 1H).
Method 3; Rt=3.36 min. m/z=511, 513 (M+H)$^+$.

Example 117: (3aR,10aR)-7-methyl-2-(3-methyl-1,2,4-oxadiazol-5-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E117)

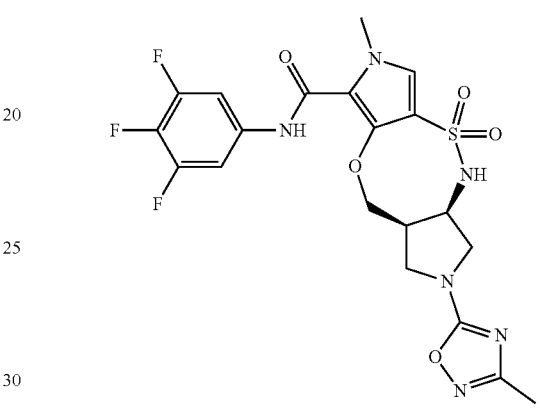

Prepared similarly as described for compound E115 using D109 instead of D108 to obtain E117. $^1$H NMR (300 MHz, DMSO-d6) δ ppm 2.01-2.19 (m, 3H) 3.05-3.22 (m, 1H) 3.22-3.36 (m, 1H) 3.50-3.68 (m, 2H) 3.81 (s, 3H) 3.89-4.11 (m, 2H) 4.38-4.78 (m, 2H) 7.50 (s, 1H) 7.68 (dd, J=10.36, 6.51 Hz, 2H) 8.51 (d, J=9.81 Hz, 1H) 9.66 (s, 1H). Method 3; Rt=3.39 min. m/z=513 (M+H)$^+$.

Example 118: (3aR,10aR)—N-(4-fluoro-3-methylphenyl)-7-methyl-2-(5-methyl-1,3,4-oxadiazol-2-yl)-2,3,3a,4,10,10a-hexahydro-1H,7H-dipyrrolo[3,4-b:3',4'-f][1,4,5]oxathiazocine-8-carboxamide 5,5-dioxide (E118)

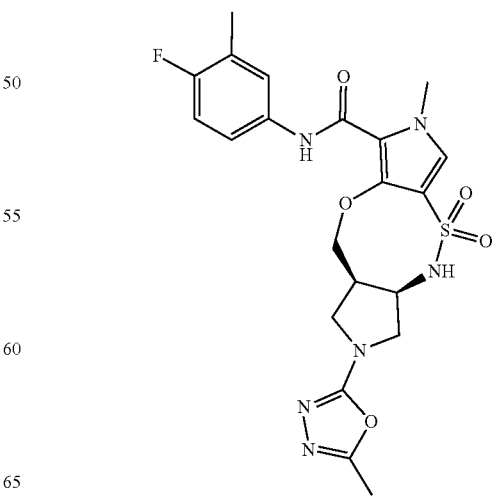

To a solution of 5-methyl-1,3,4-oxadiazol-2(3H)-one (Fluorochem, cat no 079200) (16 mg, 0.160 mmol) in DMF (2 mL) was added dry DIPEA (0.101 mL, 0.580 mmol) followed by D108 (78 mg, 0.150 mmol). To the stirring solution was added Benzotriazol-1-yloxytris(dimethylamino)phosphonium hexafluorophosphate (BOP) (70.75 mg, 0.160 mmol) and the reaction mixture stirred at RT for 72 h. The reaction mixture was diluted with EtOAc. The organic layer was washed with water and brine, then was dried (Na$_2$SO$_4$), filtered and concentrated under reduced pressure. The crude was purified by preparative HPLC-MS (H$_2$O/CH$_3$CN+0.1% HCOOH) to obtain, after freeze-drying, E118 (24.93 mg) as an off white solid. $^1$H NMR (300 MHz, DMSO-d$_6$) δ ppm 2.24 (s, 3H) 2.33 (s, 3H) 3.10-3.23 (m, 2H) 3.46-3.57 (m, 2H) 3.81 (s, 3H) 3.86-4.08 (m, 2H) 4.49-4.72 (m, 2H) 7.11 (t, J=9.17 Hz, 1H) 7.45-7.62 (m, 3H) 8.45 (br d, J=9.17 Hz, 1H) 9.36 (s, 1H). Method 3; Rt=2.97 min. m/z=491 (M+H)$^+$.

Example 119: (3aR,10aR)—N-(3-chloro-4-fluorophenyl)-7-methyl-2-(5-methyl-1,3,4-oxadiazol-2-yl)-2,3,3a,4,10,10a-hexahydro-1H,7H-dipyrrolo[3,4-b:3',4'-f][1,4,5]oxathiazocine-8-carboxamide 5,5-dioxide (E119)

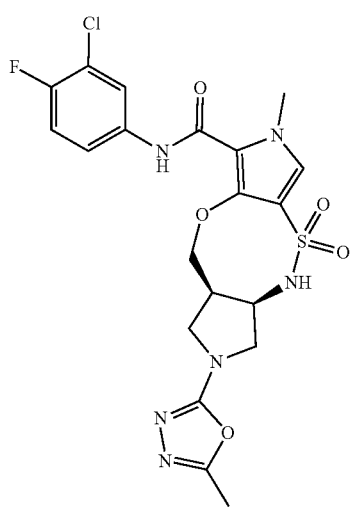 [SMILES: Cc1nnc(N2C[C@H]3COc4c(cn(C)c4C(=O)Nc4ccc(F)c(Cl)c4)S(=O)(=O)N[C@H]3C2)o1]

Prepared similarly as described for compound E118 using D110 instead of D108 to obtain E119. $^1$H NMR (300 MHz, DMSO-d6) δ ppm 2.33 (s, 3H) 3.08-3.24 (m, 2H) 3.47-3.53 (m, 2H) 3.81 (s, 3H) 3.86-4.03 (m, 2H) 4.50-4.70 (m, 2H) 7.41 (t, J=9.12 Hz, 1H) 7.50 (s, 1H) 7.60-7.70 (m, 1H) 8.00 (dd, J=6.88, 2.57 Hz, 1H) 8.46 (br d, J=8.16 Hz, 1H) 9.59 (s, 1H). Method 3; Rt=3.11 min. m/z=511, 513 (M+H)$^+$.

Example 120: (3aR,10aR)-7-methyl-2-(5-methyl-1,3,4-oxadiazol-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (E120)

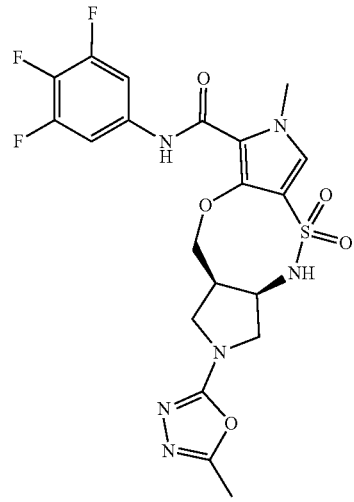 [SMILES: Cc1nnc(N2C[C@H]3COc4c(cn(C)c4C(=O)Nc4cc(F)c(F)c(F)c4)S(=O)(=O)N[C@H]3C2)o1]

Prepared similarly as described for compound E118 using D109 instead of D108 to obtain E120 (43.4 mg). $^1$H NMR (300 MHz, DMSO-d6) δ ppm 2.30-2.38 (m, 3H) 3.07-3.25 (m, 2H) 3.42-3.60 (m, 2H) 3.81 (s, 3H) 3.86-4.06 (m, 2H) 4.35-4.82 (m, 2H) 7.52 (s, 1H) 7.59-7.82 (m, 2H) 8.31-8.61 (m, 1H) 9.61-9.77 (m, 1H). Method 3; Rt=3.14 min. m/z=513 (M+H)$^+$.

Example 121: Ethyl (3aR,10aR)-8-((4-fluoro-3-methylphenyl)carbamoyl)-7-methyl-3a,4,10,10a-tetrahydro-1H,7H-dipyrrolo[3,4-c:3',4'-g][1,6,2]dithiazocine-2(3H)-carboxylate 5,5-dioxide (E121)

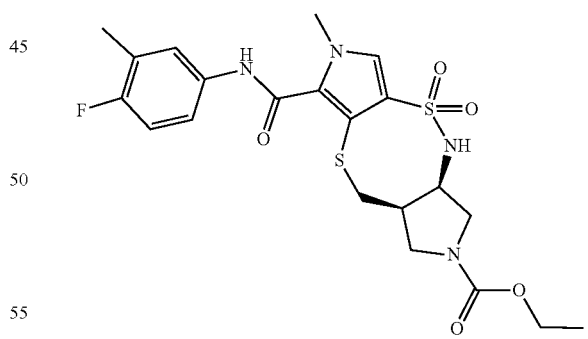

To a solution of crude D81 (0.793 mmol) in DMF (14.5 mL) was added cesium carbonate (646 mg, 1.98 mmol), and the reaction mixture was stirred at 135° C. with oil bath 1 h. Reaction was diluted with EtOAc and washed with water (×3). Organic layer was dried over Na$_2$SO$_4$ (anh.), filtered and concentrated under vacuo. The resulting crude was purified by flash chromatography on silica (eluent DCM/MeOH), then by preparative HPLC-MS (H$_2$O/CH$_3$CN+ 0.1% HCOOH) to obtain, after freeze-drying, E121 (280 mg, yield=71%) as white solid. $^1$H NMR (300 MHz, DMSO-$d_6$) δ ppm 1.17 (q, J=6.82 Hz, 3H), 2.23 (s, 3H), 2.31-2.44 (m, 1H), 2.56-2.71 (m, 1H), 2.87-3.09 (m, 1H), 3.16-3.44 (m, 3H), 3.54-3.83 (m, 4H), 3.88-4.13 (m, 2H), 4.59-4.85 (m, 1H), 7.10 (t, J=9.35 Hz, 1H), 7.42-7.60 (m, 2H), 7.61-7.74 (m, 1H), 8.01-8.25 (m, 1H), 10.32 (s, 1H). Method 3; Rt=3.47 min; m/z=497 (M+H)$^+$.

Example 122: Ethyl (3aR,10aR)-8-((4-fluoro-3-methylphenyl)carbamoyl)-7-methyl-3a,4,10,10a-tetrahydro-1H,7H-dipyrrolo[3,4-c:3',4'-g][1,6,2]dithiazocine-2(3H)-carboxylate 5,5,9-trioxide (E122)

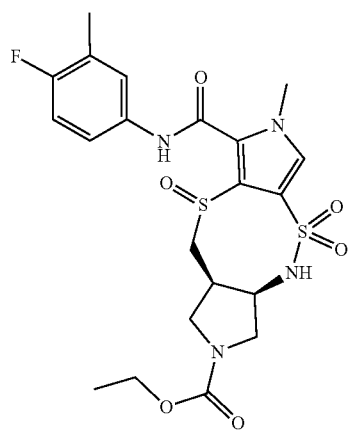

To a solution of E121 (40 mg, 0.080 mmol) in DCM (0.800 mL) was added 3-chlorobenzoperoxoic acid (20 mg, 0.080 mmol). The reaction mixture was stirred at 0° C. for 10 min then 1 h at RT. Reaction was diluted with DCM and washed with sat. NaHCO$_3$ solution. Organic layer was dried over Na$_2$SO$_4$, filtered and concentrated under vacuo. The resulting crude by preparative HPLC-MS (H$_2$O/CH$_3$CN+ 0.1% HCOOH) to obtain, after freeze-drying, E122 (26 mg) as white solid. $^1$H NMR (300 MHz, DMSO-d6) δ ppm 1.18 (q, J=6.80 Hz, 3H) 2.24 (s, 3H) 2.54-2.66 (m, 1H) 3.11-3.31 (m, 4H) 3.46-3.60 (m, 1H) 3.64-3.89 (m, 4H) 3.96-4.10 (m, 2H) 4.11-4.32 (m, 1H) 7.15 (t, J=9.35 Hz, 1H) 7.41-7.52 (m, 1H) 7.54-7.65 (m, 1H) 7.87 (s, 1H) 8.08-8.31 (m, 1H) 10.79 (s, 1H). Method 3; Rt=3.04 min. m/z=513 (M+H)$^+$.

Example 123: Ethyl (3aR,10aR)-8-((4-fluoro-3-methylphenyl)carbamoyl)-7-methyl-3a,4,10,10a-tetrahydro-1H,7H-dipyrrolo[3,4-c:3',4'-g][1,6,2]dithiazocine-2(3H)-carboxylate 5,5,9,9-tetraoxide (E123)

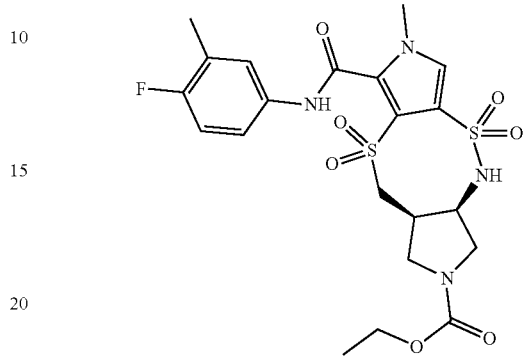

To a solution of E121 (40 mg, 0.080 mmol) in DCM (0.800 mL, 0.012 mol) was added 3-chlorobenzoperoxoic acid (40 mg, 0.160 mmol), and the reaction mixture was stirred at 0° C. for 10 min then at RT overnight. The reaction was dilute with DCM and washed sat. NaHCO$_3$ solution (×2). Organic layer was dried over Na$_2$SO$_4$, filtered and concentrated under vacuo. The resulting crude by preparative HPLC-MS (H$_2$O/CH$_3$CN+0.1% HCOOH) to obtain, after freeze-drying, E123 (27 mg) as white solid. $^1$H NMR (300 MHz, DMSO-d6+TFA) δ ppm 1.18 (t, J=6.79 Hz, 3H) 2.23 (s, 3H) 2.79-3.00 (m, 1H) 3.01-3.14 (m, 1H) 3.35 (d, J=11.65 Hz, 1H) 3.57-3.83 (m, 6H) 3.44-3.56 (m, 1H) 3.95-4.12 (m, 2H) 4.66-4.85 (m, 1H) 7.12 (t, J=9.17 Hz, 1H) 7.39-7.49 (m, 1H) 7.52-7.62 (m, 1H) 7.67 (s, 1H) 8.45-8.69 (m, 1H) 10.80 (s, 1H). Method 3; Rt=2.96 min m/z=529 (M+H)$^+$.

Example 124: (3aR,10aR)—N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-c:3',4'-g][1,6,2]dithiazocine-8-carboxamide 5,5-dioxide (E124)

E124 was prepared according to the procedure indicated in the Scheme 27.

Scheme 27

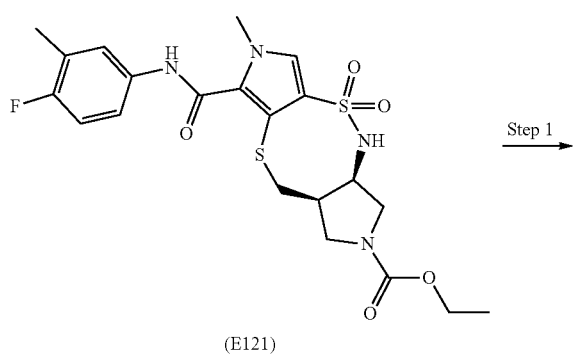

Step 1

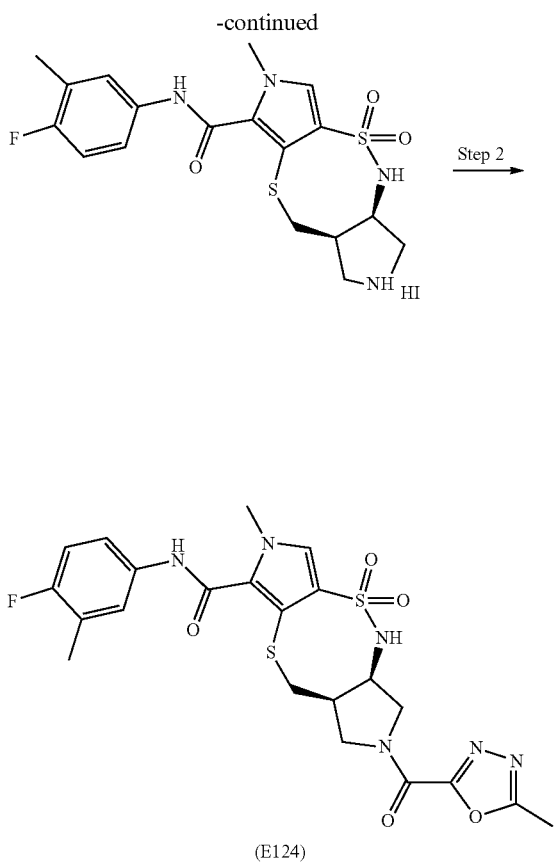

(E124)

Synthetic steps are described below.

Step 1

In a sealed vial E121 (54 mg, 0.11 mmol) was dissolved in dry DCM (1 mL). Trimethylsilyl iodide (0.08 mL, 0.55 mmol) was added and reaction mixture was heated at reflux (50° C.) for 3 h. Mixture was quenched by addition of methanol at 0° C., then evaporated under reduced pressure. The residue was triturated with Et$_2$O to obtain crude (3aR, 10aR)—N-(4-fluoro-3-methylphenyl)-7-methyl-2,3,3a,4,10,10a-hexahydro-1H,7H-dipyrrolo[3,4-c:3',4'-g][1,6,2]dithiazocine-8-carboxamide 5,5-dioxide hydroiodide (62 mg) as orange solid, that was used in the next step without further purification. Method 1; Rt=1.37 min; m/z=425 (M+H)$^+$.

Step 2

Step 2 was carried out similarly as described for compound the synthesis of compound E98, using (3aR,10aR)—N-(4-fluoro-3-methylphenyl)-7-methyl-2,3,3a,4,10,10a-hexahydro-1H,7H-dipyrrolo[3,4-c:3',4'-g][1,6,2]dithiazocine-8-carboxamide 5,5-dioxide hydroiodide instead of D108. E124 (29 mg) was obtained as a light yellow solid. $^1$H NMR (300 MHz, DMSO-d6+TFA) δ ppm 2.23 (s, 3H) 2.32-2.46 (m, 1H) 2.58 (d, J=3.67 Hz, 3H) 2.68-2.89 (m, 1H) 3.18-3.79 (m, 6H) 3.84-4.26 (m, 2H) 4.76-4.94 (m, 1H) 7.11 (t, J=9.17 Hz, 1H) 7.46-7.61 (m, 2H) 7.66 (br d, J=6.69 Hz, 1H) 8.15-8.29 (m, 1H) 10.33 (d, J=3.30 Hz, 1H). Method 3; Rt=3.12 min m/z=535 (M+H)$^+$.

Example 125: Cis-N-(4-fluoro-3-methylphenyl)-2-methyl-8-(5-methyl-1,3,4-oxadiazole-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide (E125)

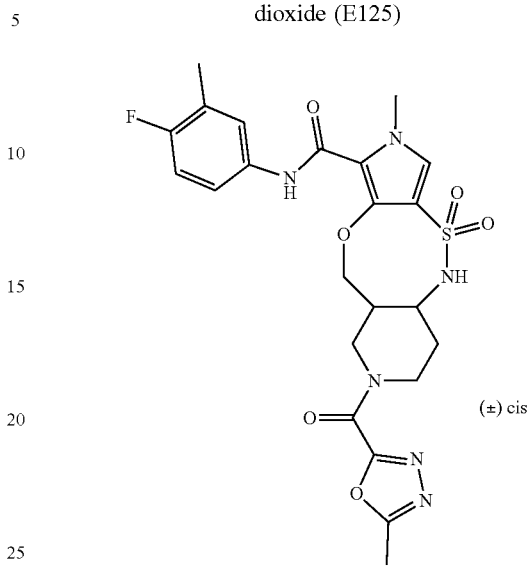

A solution of 5-methyl-1,3,4-oxadiazol-2-carbonyl chloride (1.2M in MeCN, 0.066 mL, 0.08 mmol) (Org. Proc. Res. Develop. 2011, 15, 73-83) was added dropwise to a cooled suspension of D112 (30 mg, 0.07 mmol) and Triethylamine (0.027 mL, 0.2 mmol) in dry MeCN (1 mL). The dark solution was stirred at 0° C. for 10 min then quenched with MeOH (1 mL) and stirred at RT for further 1 hr. Solvent was removed under reduce pressure and crude was purified by preparative HPLC (eluent: H$_2$O/CH$_3$CN+1‰ HCOOH) to afford E125 as a white foam (13.37 mg, 37%). $^1$H NMR (300 MHz, DMSO-d6) δ ppm 1.77-2.07 (m, 2H) 2.24 (br d, J=3.94 Hz, 3H) 2.55-2.61 (m, 3H) 2.99-3.21 (m, 1H) 3.41-3.55 (m, 1H) 3.68-3.94 (m, 4H) 4.16-4.59 (m, 4H) 7.06-7.17 (m, 1H) 7.42-7.66 (m, 3H) 8.34-8.47 (m, 1H) 9.27-9.38 (m, 1H). Method 3; Rt: 3.13 m/z: 533 (M+H)$^+$.

Example 126: Cis-N-(4-fluoro-3-methylphenyl)-2-methyl-8-(3-methyloxetane-3-carbonyl)-5,5a,6,7,8,9,9a,10-octahydro-2H-pyrido[4,3-f]pyrrolo[3,4-b][1,4,5]oxathiazocine-1-carboxamide 4,4-dioxide (E126)

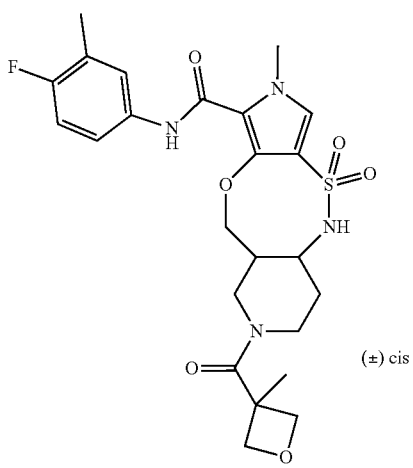 [SMILES: Cc1cc(NC(=O)c2c3c(cn2C)S(=O)(=O)NC2CCN(C(=O)C4(C)COC4)CC2CO3)ccc1F]

BOP reagent (40 mg, 0.09 mmol) was added to a solution of D112 (30 mg, 0.07 mmol), 3-methyloxetane-3-carboxylic acid (10 mg, 0.09 mmol) and DIPEA (34 uL, 0.197) in dry DMF (0.5 mL). The orange solution was stirred at RT for 90 min then quenched with formic acid (50 uL), diluted with water (400 uL) and purified by preparative HPLC (eluent: H2O/CH3CN+1‰ HCOOH) to afford E126 as a white foam (18.38 mg, 53%). $^1$H NMR (300 MHz, DMSO-$d_6$) δ ppm 1.48-1.58 (m, 3H) 1.69-1.96 (m, 2H) 2.23-2.28 (m, 3H) 2.39 (br d, J=5.59 Hz, 1H) 2.71-3.19 (m, 3H) 3.56-3.88 (m, 4H) 4.00-4.33 (m, 4H) 4.43-4.55 (m, 1H) 4.69-4.80 (m, 2H) 7.11 (t, J=9.17 Hz, 1H) 7.42-7.65 (m, 3H) 8.20-8.37 (m, 1H) 9.22-9.43 (m, 1H). Method 3; Rt: 3.02 m/z: 521 (M+H)$^+$.

Example 127: Cis-N-(4-fluoro-3-methylphenyl)-2-methyl-8-(2-methyltetrahydrofuran-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide (E127)

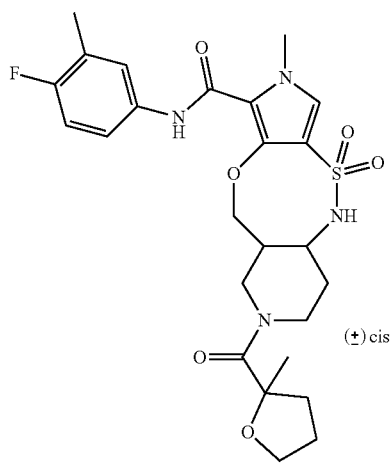 [SMILES: Cc1cc(NC(=O)c2c3c(cn2C)S(=O)(=O)NC2CCN(C(=O)C4(C)CCCO4)CC2CO3)ccc1F]

E127 (17.9 mg, 51%) was prepared similarly as described for compound E126 using 2-methyltetrahydrofuran-2-carboxylic acid (12 mg, 0.09 mmol) instead of 3-methyloxetane-3-carboxylic acid. $^1$H NMR (300 MHz, DMSO-d6) δ ppm 1.37 (br d, J=4.49 Hz, 3H) 1.55 (m, 1H) 1.65-1.96 (m, 5H) 2.23-2.45 (m, 4H) 2.57-2.71 (m, 1H) 3.65-4.56 (m, 11H) 7.11 (t, J=9.17 Hz, 1H) 7.45-7.63 (m, 3H) 8.20-8.33 (m, 1H) 9.28 (s, 1H). Method 3; Rt: 3.46 m/z: 535 (M+H)$^+$.

Example 128: Cis-8-(2-oxabicyclo[2.1.1]hexane-1-carbonyl)-N-(4-fluoro-3-methylphenyl)-2-methyl-5,5a,6,7,8,9,9a,10-octahydro-2H-pyrido[4,3-f]pyrrolo[3,4-b][1,4,5]oxathiazocine-1-carboxamide 4,4-dioxide (E128)

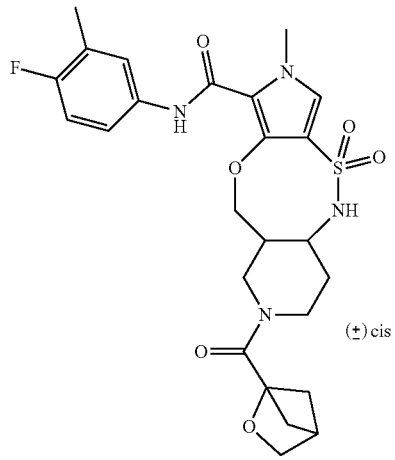 [SMILES: Cc1cc(NC(=O)c2c3c(cn2C)S(=O)(=O)NC2CCN(C(=O)C45CC(CO4)C5)CC2CO3)ccc1F]

E128 (5.52 mg, 15%) was prepared similarly as described for compound E126 using 2-oxabicyclo[2.1.1]hexane-1-carboxylic acid (12 mg, 0.09 mmol) instead of 3-methyloxetane-3-carboxylic acid. $^1$H NMR (300 MHz, DMSO-$d_6$) δ ppm 1.61-2.06 (m, 6H) 2.23-2.42 (m, 4H) 2.74-2.90 (m, 2H) 3.74 (s, 7H) 3.97-4.11 (m, 2H) 4.18-4.27 (m, 1H) 4.40-4.51 (m, 1H) 7.04-7.18 (m, 1H) 7.45-7.62 (m, 3H) 8.50-8.59 (m, 1H) 9.24-9.42 (m, 1H). Method 3; Rt: 3.24 m/z: 533 (M+H)$^+$.

Example 129: Cis-N-(4-fluoro-3-methylphenyl)-2-methyl-8-(5-methyloxazole-4-carbonyl)-5,5a,6,7,8,9,9a,10-octahydro-2H-pyrido[4,3-f]pyrrolo[3,4-b][1,4,5]oxathiazocine-1-carboxamide 4,4-dioxide (E129)

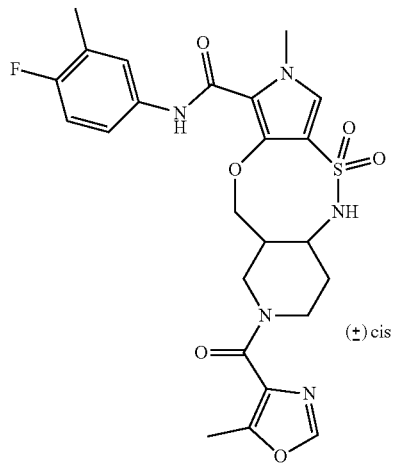 [SMILES: Cc1cc(NC(=O)c2c3c(cn2C)S(=O)(=O)NC2CCN(C(=O)c4ncoc4C)CC2CO3)ccc1F]

E129 (16.15 mg, 46%) was prepared similarly as described for compound E126 using 5-methyloxazole-4-carboxylic acid (12 mg, 0.09 mmol) instead of 3-methyloxetane-3-carboxylic acid. $^1$H NMR (300 MHz, DMSO-d6)

δ ppm 1.71-2.01 (m, 2H) 2.24 (s, 3H) 2.45 (s, 3H) 2.86-3.12 (m, 1H) 3.65-3.93 (m, 5H) 4.01-4.65 (m, 5H) 7.11 (t, J=9.10 Hz, 1H) 7.44-7.63 (m, 3H) 8.32 (br s, 2H) 9.30 (br s, 1H). Method 3; Rt: 3.20 m/z: 532 (M+H)⁺.

Example 130: Trans-N-(4-fluoro-3-methylphenyl)-2-methyl-8-(5-methyl-1,3,4-oxadiazole-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide (E130)

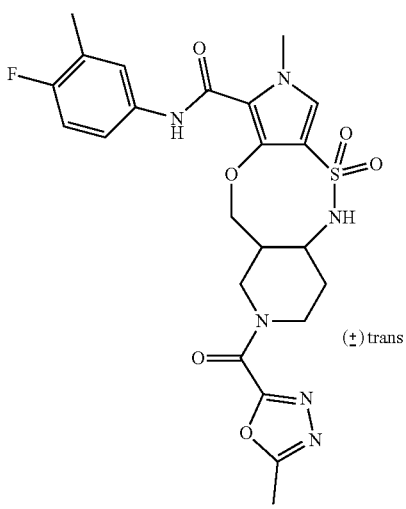 [SMILES: Cc1nnc(C(=O)N2CCC3NS(=O)(=O)c4cn(C)c(C(=O)Nc5ccc(F)c(C)c5)c4OCC3C2)o1]

E130 (6.2 mg, 19%) was prepared similarly as described for compound E125 starting from D114 (28 mg, 0.06 mmol) instead of D112. ¹H NMR (300 MHz, DMSO-d6) δ ppm 1.51-1.72 (m, 1H) 1.86-2.08 (m, 2H) 2.24 (br d, J=5.23 Hz, 3H) 2.58 (d, J=6.60 Hz, 3H) 2.84-3.06 (m, 1H) 3.20-3.29 (m, 1H) 3.69-3.94 (m, 4H) 4.18-4.25 (m, 1H) 4.26-4.41 (m, 1H) 4.42-4.67 (m, 2H) 6.94-7.26 (m, 1H) 7.30-7.75 (m, 3H) 8.07 (br s, 1H) 9.30 (d, J=15.22 Hz, 1H). Method 3; Rt: 4.22 min. m/z: 533 (M+H)⁺.

Example 131: Trans-N-(4-fluoro-3-methylphenyl)-2-methyl-8-(3-methyloxetane-3-carbonyl)-5,5a,6,7,8,9,9a,10-octahydro-2H-pyrido[4,3-f]pyrrolo[3,4-b][1,4,5]oxathiazocine-1-carboxamide 4,4-dioxide (E131)

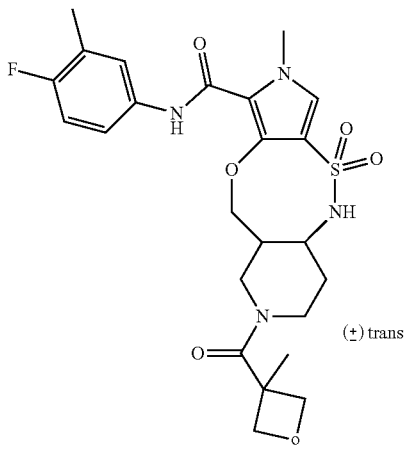

BOP reagent (41 mg, 0.09 mmol) was added to a solution of D114 (33 mg, 0.07 mmol), 3-methyloxetane-3-carboxylic acid (11 mg, 0.09 mmol) and DIPEA (0.037 mL, 0.2) in dry DMF (0.5 mL). The orange solution was stirred at RT for 90 min then quenched with formic acid (0.05 mL), diluted with water (0.4 mL) and purified by preparative HPLC (eluent: H₂O/CH₃CN+1‰ HCOOH) to afford E131 as a white foam (29 mg, 78%). ¹H NMR (300 MHz, DMSO-d₆) δ ppm 1.44-1.60 (m, 4H) 1.70-1.96 (m, 2H) 2.25 (s, 3H) 2.55-2.75 (m, 1H) 2.95-3.18 (m, 2H) 3.61-3.76 (m, 1H) 3.77-3.88 (m, 3H) 4.16-4.57 (m, 5H) 4.67-4.85 (m, 2H) 7.12 (br t, J=9.12 Hz, 1H) 7.48 (m, 2H) 7.53-7.62 (m, 1H) 8.01 (br d, J=8.71 Hz, 1H) 9.14-9.47 (m, 1H). Method 3; Rt: 3.01 min. m/z: 521 (M+H)⁺.

Example 132: Trans-N-(4-fluoro-3-methylphenyl)-2-methyl-8-(2-methyltetrahydrofuran-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide (E132)

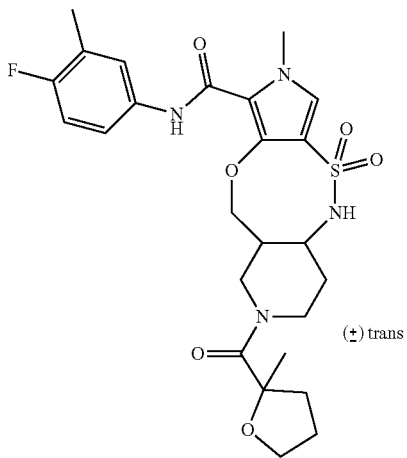 [SMILES: Cc1cc(NC(=O)c2c3c(cn2C)S(=O)(=O)NC2CCN(C(=O)C4(C)CCCO4)CC2CO3)ccc1F]

E132 (25 mg, 71%) was prepared similarly as described for compound E131 using 2-methyltetrahydrofuran-2-carboxylic acid (11 mg, 0.09 mmol) instead of 3-methyloxetane-3-carboxylic acid. $^1$H NMR (300 MHz, DMSO-$d_6$) δ ppm 1.38 (s, 3H) 1.41-1.64 (m, 2H) 1.67-1.95 (m, 4H) 2.24 (s, 3H) 2.62 (br s, 2H) 2.86-3.20 (m, 1H) 3.58-3.76 (m, 2H) 3.76-3.91 (m, 4H) 4.23 (br s, 2H) 4.37-4.82 (m, 2H) 7.12 (t, J=9.17 Hz, 1H) 7.43-7.52 (m, 2H) 7.53-7.61 (m, 1H) 7.94 (br s, 1H) 9.28 (br s, 1H). Method 3; Rt: 3.43 min. m/z: 535 (M+H)$^+$.

Example 133: Trans-8-(2-oxabicyclo[2.1.1]hexane-1-carbonyl)-N-(4-fluoro-3-methylphenyl)-2-methyl-5,5a,6,7,8,9,9a,10-octahydro-2H-pyrido[4,3-f]pyrrolo[3,4-b][1,4,5]oxathiazocine-1-carboxamide 4,4-dioxide (E133)

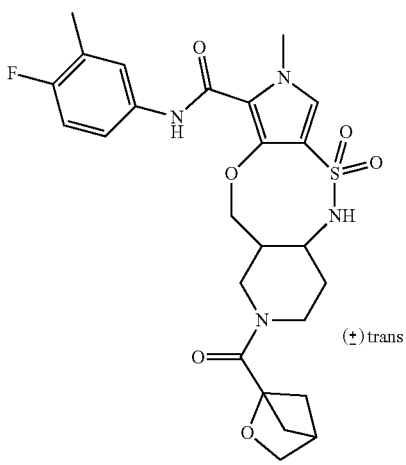 [SMILES: Cc1cc(NC(=O)c2c3c(cn2C)S(=O)(=O)NC2CCN(C(=O)C45CC(CO4)C5)CC2CO3)ccc1F]

E133 (26 mg, 76%) was prepared similarly as described for compound E131 using 2-oxabicyclo[2.1.1]hexane-1-carboxylic acid (11 mg, 0.09 mmol) instead of 3-methyloxetane-3-carboxylic acid. $^1$H NMR (300 MHz, DMSO-$d_6$) δ ppm 1.31-1.54 (m, 1H) 1.56-1.73 (m, 2H) 1.78-1.95 (m, 2H) 1.96-2.08 (m, 2H) 2.24 (s, 3H) 2.55-2.71 (m, 1H) 2.71-2.93 (m, 1H) 2.95-3.19 (m, 1H) 3.64-3.74 (m, 1H) 3.75-3.89 (m, 5H) 4.13-4.48 (m, 4H) 7.08-7.16 (m, 1H) 7.45-7.52 (m, 2H) 7.54-7.61 (m, 1H) 7.92-8.03 (m, 1H) 9.11-9.48 (m, 1H). Method 3; Rt: 3.23 min. m/z: 533 (M+H)$^+$.

Example 134: Trans-N-(4-fluoro-3-methylphenyl)-2-methyl-8-(5-methyloxazole-4-carbonyl)-5,5a,6,7,8,9,9a,10-octahydro-2H-pyrido[4,3-f]pyrrolo[3,4-b][1,4,5]oxathiazocine-1-carboxamide 4,4-dioxide (E134)

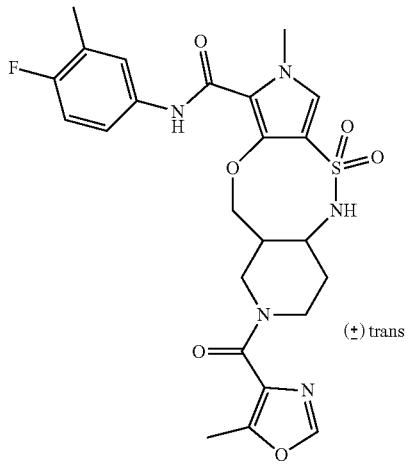 [SMILES: Cc1cc(NC(=O)c2c3c(cn2C)S(=O)(=O)NC2CCN(C(=O)c4ncoc4C)CC2CO3)ccc1F]

E134 (25 mg, 72%) was prepared similarly as described for compound E131 using 5-methyloxazole-4-carboxylic acid (11 mg, 0.09 mmol) instead of 3-methyloxetane-3-carboxylic acid. $^1$H NMR (300 MHz, DMSO-$d_6$) δ ppm 1.44-1.68 (m, 1H) 1.92 (br s, 2H) 2.25 (s, 3H) 2.45 (s, 3H) 2.66-2.87 (m, 1H) 2.98-3.21 (m, 1H) 3.65-3.77 (m, 1H) 3.83 (s, 3H) 4.09-4.40 (m, 2H) 4.50 (br d, J=12.93 Hz, 2H) 7.12 (t, J=9.17 Hz, 1H) 7.42-7.54 (m, 2H) 7.59 (br s, 1H) 8.02 (br d, J=7.34 Hz, 1H) 8.32 (br s, 1H) 9.29 (br s, 1H). Method 3; Rt: 3.18 min. m/z: 532 (M+H)$^+$.

Example 135: Cis-N-(4-fluoro-3-methylphenyl)-2-methyl-7-(5-methyl-1,3,4-oxadiazole-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide (E135)

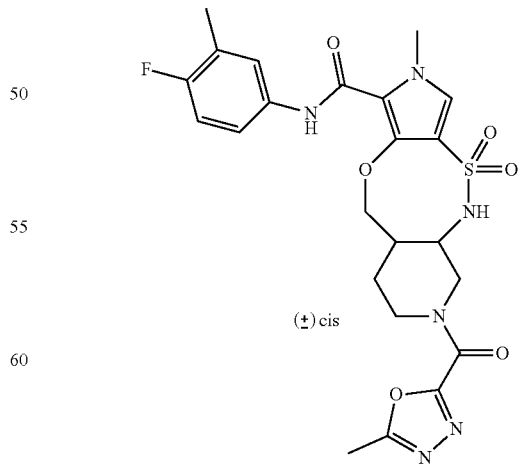

E135 (25 mg, 54%) was prepared similarly as described for compound E125 starting from D116 (40 mg, 0.09 mmol)

instead of D112. $^1$H NMR (300 MHz, DMSO-$d_6$) δ ppm 1.41-1.55 (m, 1H) 1.55-1.77 (m, 1H) 2.24 (s, 3H) 2.54-2.68 (m, 4H) 2.80-3.29 (m, 2H) 3.59-3.72 (m, 1H) 3.80 (d, J=3.85 Hz, 3H) 4.04-4.33 (m, 1H) 4.40-4.77 (m, 3H) 7.11 (t, J=9.35 Hz, 1H) 7.44 (d, J=6.51 Hz, 1H) 7.47-7.55 (m, 1H) 7.55-7.62 (m, 1H) 8.08-8.41 (m, 1H) 9.34 (s, 1H). Method 3; Rt: 3.17 min. m/z: 533 (M+H)$^+$.

Example 136: Cis-N-(4-fluoro-3-methylphenyl)-2-methyl-7-(3-methyloxetane-3-carbonyl)-5,5a,6,7,8,9,9a,10-octahydro-2H-pyrido[3,4-f]pyrrolo[3,4-b][1,4,5]oxathiazocine-1-carboxamide 4,4-dioxide (E136)

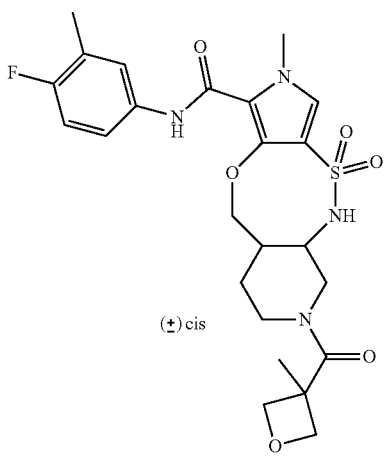 [SMILES: Cc1cc(NC(=O)c2c3c(cn2C)S(=O)(=O)NC2CN(C(=O)C4(C)COC4)CCC2CO3)ccc1F]

BOP reagent (40 mg, 0.09 mmol) was added to a solution of D116 (30 mg, 0.07 mmol), 3-methyloxetane-3-carboxylic acid (10 mg, 0.09 mmol) and DIPEA (34 uL, 0.197 mmol) in dry DMF (0.5 mL). The orange solution was stirred at RT for 90 min then quenched with formic acid (0.05 mL), diluted with water (0.4 mL) and purified by preparative HPLC (eluent: H$_2$O/CH$_3$CN+1% HCOOH) to afford E136 as a white foam (26 mg, 76%). $^1$H NMR (300 MHz, DMSO-$d_6$) δ ppm 1.30-1.72 (m, 5H) 2.24 (s, 3H) 2.39-2.49 (m, 1H) 2.80-3.07 (m, 2H) 3.34-3.47 (m, 1H) 3.49-3.69 (m, 1H) 3.81 (s, 3H) 4.04-4.18 (m, 1H) 4.19-4.35 (m, 2H) 4.37-4.64 (m, 2H) 4.76-4.90 (m, 1H) 4.91-5.17 (m, 1H) 7.11 (t, J=9.35 Hz, 1H) 7.42-7.55 (m, 2H) 7.55-7.65 (m, 1H) 8.10-8.33 (m, 1H) 9.34 (s, 1H). Method 3; Rt: 3.09 min. m/z: 521 (M+H)$^+$.

Example 137: Cis-N-(4-fluoro-3-methylphenyl)-2-methyl-8-(2-methyltetrahydrofuran-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide (E137)

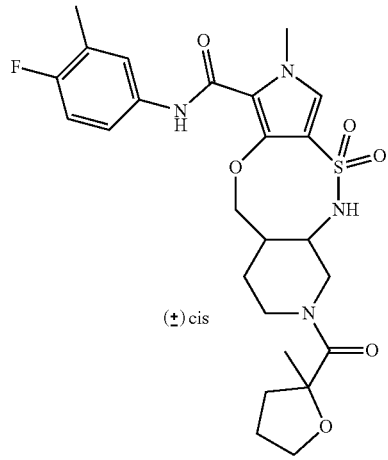 [SMILES: Cc1cc(NC(=O)c2c3c(cn2C)S(=O)(=O)NC2CN(C(=O)C4(C)CCCO4)CCC2CO3)ccc1F]

E137 (24 mg, 68%) was prepared similarly as described for compound E136 using 2-methyltetrahydrofuran-2-carboxylic acid (12 mg, 0.09 mmol) instead of 3-methyloxetane-3-carboxylic acid. $^1$H NMR (300 MHz, DMSO-$d_6$) δ ppm 1.39 (s, 3H) 1.44-1.66 (m, 3H) 1.66-1.95 (m, 2H) 2.24 (s, 3H) 2.42-2.47 (m, 1H) 2.57-2.76 (m, 2H) 2.78-3.09 (m, 1H) 3.52-3.98 (m, 6H) 4.03-4.24 (m, 1H) 4.28-4.86 (m, 3H) 7.11 (t, J=9.26 Hz, 1H) 7.45 (d, J=4.86 Hz, 1H) 7.48-7.55 (m, 1H) 7.56-7.64 (m, 1H) 7.94 (br s, 1H) 9.34 (s, 1H). Method 3; Rt: 3.47 min. m/z: 535 (M+H)$^+$. Method 3; Rt: 3.47 min. m/z: 535 (M+H)$^+$.

Example 138: Cis-7-(2-oxabicyclo[2.1.1]hexane-1-carbonyl)-N-(4-fluoro-3-methylphenyl)-2-methyl-5,5a,6,7,8,9,9a,10-octahydro-2H-pyrido[3,4-f]pyrrolo[3,4-b][1,4,5]oxathiazocine-1-carboxamide 4,4-dioxide (E138)

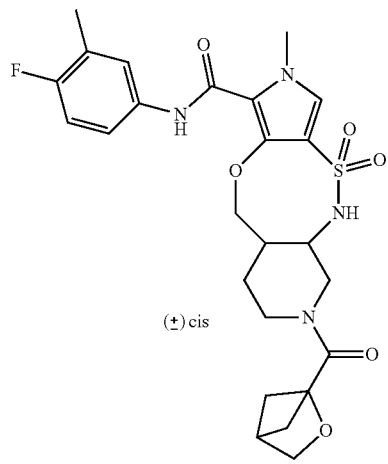 [SMILES: Cc1cc(NC(=O)c2c3c(cn2C)S(=O)(=O)NC2CN(C(=O)C45CC(CO4)C5)CCC2CO3)ccc1F]

E138 (28 mg, 80%) was prepared similarly as described for compound E136 using 2-oxabicyclo[2.1.1]hexane-1-carboxylic acid (12 mg, 0.09 mmol) instead of 3-methyloxetane-3-carboxylic acid. $^1$H NMR (300 MHz, DMSO-d$_6$+TFA) δ ppm 1.28-1.42 (m, 1H) 1.44-1.66 (m, 2H) 1.69-2.03 (m, 2H) 2.04-2.25 (m, 4H) 2.53-2.64 (m, 1H) 2.78-3.05 (m, 2H) 3.26-3.69 (m, 2H) 3.71-3.91 (m, 5H) 4.01-4.18 (m, 1H) 4.18-4.30 (m, 1H) 4.31-4.59 (m, 2H) 7.09 (t, J=9.08 Hz, 1H) 7.43 (s, 1H) 7.46-7.54 (m, 1H) 7.57 (br d, J=6.79 Hz, 1H) 7.90-8.21 (m, 1H) 9.33 (s, 1H). Method 3; Rt: 3.29 min. m/z: 533 (M+H)$^+$.

Example 139: Cis-N-(4-fluoro-3-methylphenyl)-2-methyl-7-(5-methyloxazole-4-carbonyl)-5,5a,6,7,8,9,9a,10-octahydro-2H-pyrido[3,4-f]pyrrolo[3,4-b][1,4,5]oxathiazocine-1-carboxamide 4,4-dioxide (E139)

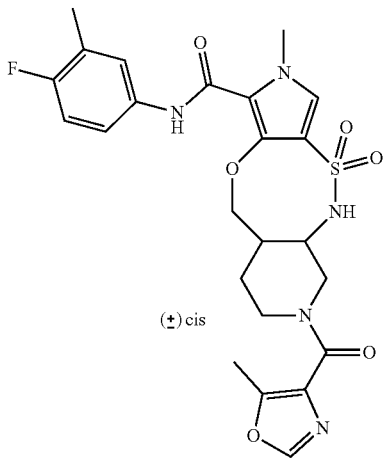 [SMILES: Cc1cc(NC(=O)c2c3c(cn2C)S(=O)(=O)NC2CN(C(=O)c4ncoc4C)CCC2CO3)ccc1F]

E139 (25 mg, 71%) was prepared similarly as described for compound E136 using 5-methyloxazole-4-carboxylic acid (11 mg, 0.09 mmol) instead of 3-methyloxetane-3-carboxylic acid. $^1$H NMR (300 MHz, DMSO-d$_6$+TFA) δ ppm 1.29-1.49 (m, 1H) 1.49-1.77 (m, 1H) 2.23 (s, 3H) 2.48 (s, 3H) 2.62-2.85 (m, 1H) 2.87-3.20 (m, 1H) 3.30-3.57 (m, 1H) 3.65 (t, J=11.65 Hz, 1H) 3.80 (s, 3H) 3.97-4.33 (m, 1H) 4.36-4.79 (m, 3H) 7.08 (t, J=9.26 Hz, 1H) 7.41 (s, 1H) 7.46-7.54 (m, 1H) 7.54-7.62 (m, 1H) 7.85-8.26 (m, 1H) 8.31 (s, 1H) 9.31 (br s, 1H). Method 3; Rt: 3.24 min. m/z: 532 (M+H)$^+$.

Example 140: Trans-N-(4-fluoro-3-methylphenyl)-2-methyl-7-(5-methyl-1,3,4-oxadiazole-2-carbonyl)-5,5a,6,7,8,9,9a,10-octahydro-2H-pyrido[3,4-f]pyrrolo[3,4-b][1,4,5]oxathiazocine-1-carboxamide 4,4-dioxide (E140)

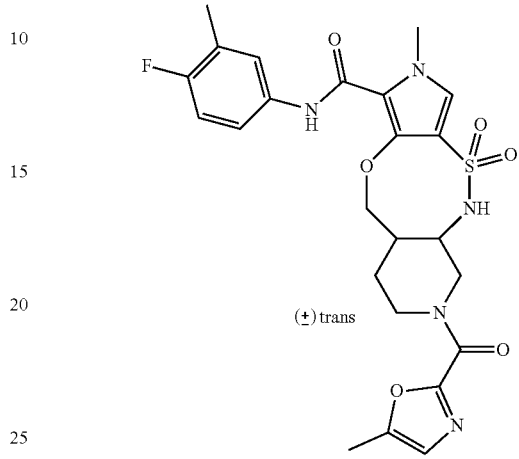

E140 (8.5 mg, 37%) was prepared similarly as described for compound E125 starting from D118 (20 mg, 0.04 mmol) instead of D112. $^1$H NMR (300 MHz, DMSO-d$_6$+TFA) δ ppm 1.33-1.64 (m, 1H) 1.74-1.90 (m, 1H) 2.04-2.25 (m, 4H) 2.55 (d, J=4.22 Hz, 3H) 2.79-2.96 (m, 1H) 3.13-3.33 (m, 1H) 3.43-3.68 (m, 1H) 3.82 (s, 3H) 4.11 (br dd, J=11.00, 4.31 Hz, 1H) 4.26-4.71 (m, 3H) 0.00 (br t, J=9.00 Hz, 1H) 7.42-7.51 (m, 2H) 7.55 (br d, J=6.33 Hz, 1H) 8.11-8.26 (m, 1H) 9.28 (s, 1H) Method 3; Rt: 3.11 min. m/z: 533 (M+H)$^+$.

Example 141: Trans-N-(4-fluoro-3-methylphenyl)-2-methyl-7-(3-methyloxetane-3-carbonyl)-5,5a,6,7,8,9,9a,10-octahydro-2H-pyrido[3,4-f]pyrrolo[3,4-b][1,4,5]oxathiazocine-1-carboxamide 4,4-dioxide (E141)

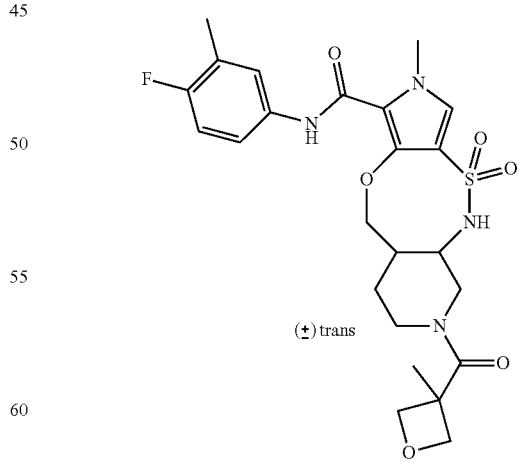

BOP reagent (26 mg, 0.06 mmol) was added to a solution of D118 (21 mg, 0.05 mmol), 3-methyloxetane-3-carboxylic acid (7 mg, 0.06 mmol) and DIPEA (24 uL, 0.14 mmol) in dry DMF (0.5 mL). The orange solution was stirred at RT for 90 min then quenched with formic acid (50 uL), diluted with water (400 uL) and purified by preparative HPLC (eluent: H2O/CH3CN+1% HCOOH) to afford E141 as a white foam (10 mg, 42%). $^1$H NMR (300 MHz, DMSO-d$_6$+TFA) δ ppm 1.31-1.48 (m, 1H) 1.55 (br d, J=11.00 Hz, 3H) 1.73 (br d, J=11.10 Hz, 1H) 1.95-2.06 (m, 1H) 2.21-2.25 (m, 3H) 2.44-2.61 (m, 1H) 2.89-3.07 (m, 2H) 3.31-3.52 (m, 1H) 3.82 (s, 3H) 4.08 (dd, J=11.97, 4.91 Hz, 1H) 4.22-4.52 (m, 4H) 4.75-4.84 (m, 2H) 7.09 (t, J=9.17 Hz, 1H) 7.43-7.51 (m, 2H) 7.58 (br d, J=6.69 Hz, 1H) 8.08-8.23 (m, 1H) 9.30 (br d, J=7.98 Hz, 1H). Method 3; Rt: 3.03 min. m/z: 521 (M+H)$^+$.

Example 142: Trans-N-(4-fluoro-3-methylphenyl)-2-methyl-8-(2-methyltetrahydrofuran-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide (E142)

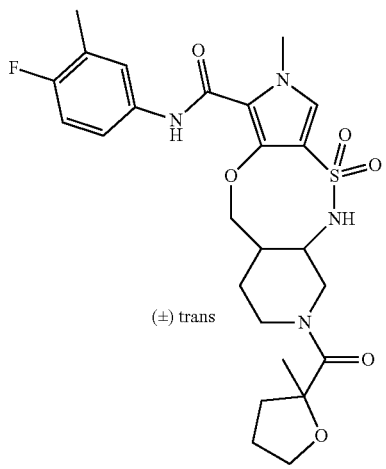 [SMILES: Cc1cc(NC(=O)c2c3c(cn2C)S(=O)(=O)NC2CN(C(=O)C4(C)CCCO4)CCC2CO3)ccc1F]
(±) trans

E142 (10 mg, 40%) was prepared similarly as described for compound E141 using 2-methyltetrahydrofuran-2-carboxylic acid (8 mg, 0.06 mmol) instead of 3-methyloxetane-3-carboxylic acid. H NMR (300 MHz, DMSO-d$_6$+TFA) δ ppm 1.18-1.45 (m, 4H) 1.46-1.61 (m, 1H) 1.64-1.90 (m, 3H) 1.94-2.11 (m, 1H) 2.13-2.26 (m, 3H) 2.41 (m, 1H) 2.55-2.71 (m, 1H) 3.07 (s, 1H) 3.20 (s, 1H) 3.61-3.92 (m, 5H) 4.00-4.16 (m, 1H) 4.20-4.91 (m, 3H) 7.08 (t, J=9.17 Hz, 1H) 7.37-7.52 (m, 2H) 7.52-7.66 (m, 1H) 7.98-8.25 (m, 1H) 9.20 (s, 1H). Method 3; Rt: 3.43 min. m/z: 535 (M+H)$^+$.

Example 143: Trans-7-(2-oxabicyclo[2.1.1]hexane-1-carbonyl)-N-(4-fluoro-3-methylphenyl)-2-methyl-5,5a,6,7,8,9,9a,10-octahydro-2H-pyrido[3,4-f]pyrrolo[3,4-b][1,4,5]oxathiazocine-1-carboxamide 4,4-dioxide (E143)

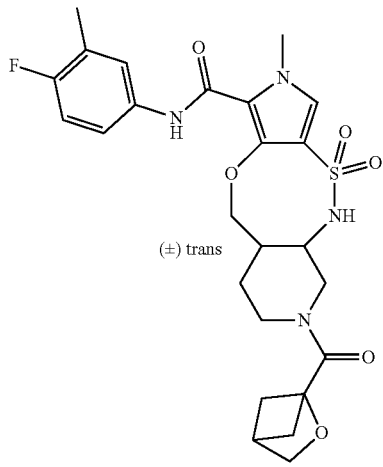 [SMILES: Cc1cc(NC(=O)c2c3c(cn2C)S(=O)(=O)NC2CN(C(=O)C45CC(CO4)C5)CCC2CO3)ccc1F]
(±) trans

E143 (11 mg, 44%) was prepared similarly as described for compound E141 using 2-oxabicyclo[2.1.1]hexane-1-carboxylic acid (8 mg, 0.06 mmol) instead of 3-methyloxetane-3-carboxylic acid. $^1$H NMR (300 MHz, DMSO-d$_6$+TFA) δ ppm 1.19-1.46 (m, 1H) 1.49-1.82 (m, 3H) 1.95-2.10 (m, 3H) 2.22 (s, 3H) 2.45-2.62 (m, 1H) 2.79-3.03 (m, 2H) 3.26-3.46 (m, 1H) 3.71-3.89 (m, 5H) 4.07 (td, J=11.90, 5.09 Hz, 1H) 4.16-4.54 (m, 3H) 7.08 (t, J=9.17 Hz, 1H) 7.41-7.51 (m, 2H) 7.57 (br d, J=6.88 Hz, 1H) 8.07-8.15 (m, 1H) 9.28 (s, 1H). Method 3; Rt: 3.24 min. m/z: 533 (M+H)$^+$.

Example 144: Trans-N-(4-fluoro-3-methylphenyl)-2-methyl-7-(5-methyloxazole-4-carbonyl)-5,5a,6,7,8,9,9a,10-octahydro-2H-pyrido[3,4-f]pyrrolo[3,4-b][1,4,5]oxathiazocine-1-carboxamide 4,4-dioxide (E144)

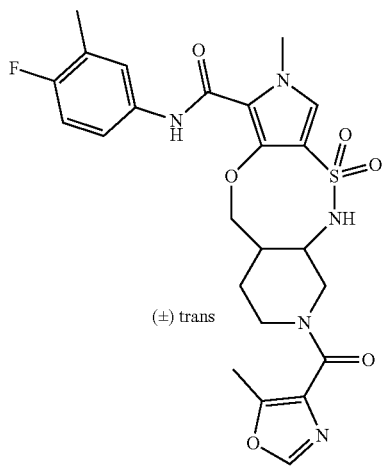 [SMILES: Cc1cc(NC(=O)c2c3c(cn2C)S(=O)(=O)NC2CN(C(=O)c4ncoc4C)CCC2CO3)ccc1F]
(±) trans

E144 (13 mg, 52%) was prepared similarly as described for compound E141 using 5-methyloxazole-4-carboxylic acid (8 mg, 0.06 mmol) instead of 3-methyloxetane-3-carboxylic acid. $^1$H NMR (300 MHz, DMSO-d$_6$+TFA) δ ppm 1.43 (br s, 1H) 1.69-1.87 (m, 1H) 1.99-2.15 (m, 1H) 2.22 (s, 3H) 2.44 (s, 3H) 2.57-2.81 (m, 1H) 2.92-3.17 (m, 1H) 3.45 (br dd, J=8.85, 3.62 Hz, 1H) 3.79-3.85 (m, 3H) 4.10 (dd, J=12.01, 5.32 Hz, 1H) 4.27-4.42 (m, 1H) 4.42-4.64 (m, 2H) 7.07 (t, J=9.17 Hz, 1H) 7.42-7.52 (m, 2H) 7.52-7.59 (m, 1H) 8.04-8.23 (m, 1H) 8.29 (br s, 1H) 9.28 (s, 1H). Method 3; Rt: 3.19 min. m/z: 532 (M+H)$^+$.

Example 145: Trans-Tert-Butyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (E145)

D91 (0.13 g, 0.25 mmol) was dissolved in DMF (2.46 mL), treated with a single portion of cesium carbonate (0.24 g, 0.74 mmol) and heated by microwave irradiation at 130° C. for 2 hrs. The reaction was diluted with water and extracted with EtOAc. The organic layer was dried over Na$_2$SO$_4$ (anh.), filtered and finally evaporated. The residue was purified by flash chromatography (eluent DCM/EtOAc), and triturated in DEE/DCM, giving E145 (55 mg, 0.106 mmol) as white solid. $^1$H NMR (300 MHz, DMSO-d$_6$) δ ppm 1.38 (s, 9H) 2.23 (s, 3H) 2.55-2.66 (m, 1H) 2.81-2.93 (m, 1H) 2.94-3.10 (m, 1H) 3.35-3.48 (m, 1H) 3.73-3.90 (m, 4H) 3.93-4.14 (m, 2H) 4.22 (br dd, J=11.14, 4.45 Hz, 1H) 7.11 (t, J=9.26 Hz, 1H) 7.42-7.55 (m, 2H) 7.56-7.70 (m, 2H) 9.51 (br s, 1H). Method 3; Rt=3.74 min. m/z=509.28 (M+H)$^+$.

Example 146: Trans-N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide (E146)

E146 was prepared according to the procedure reported in Scheme 28.

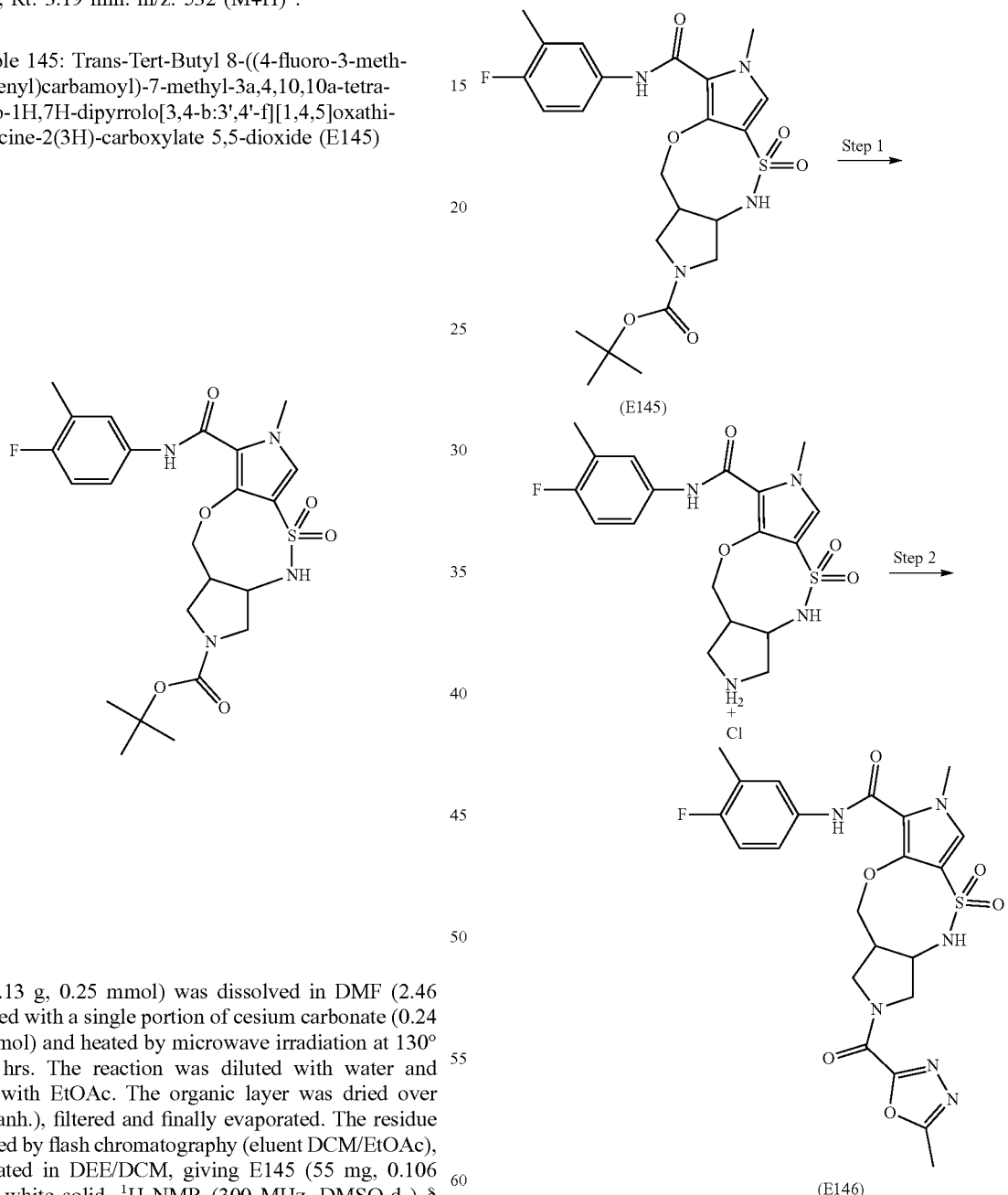

Step 1

A solution of E145 (44 mg, 0.08 mmol) in DCM (1 mL) was treated with a single portion of 3M HCl in MeOH (0.45 mL, 1.35 mmol) and the resulting yellow solution stirred at room temperature for 2 hrs. Then solvent was removed, giving trans-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide hydrochloride (37 mg, 0.083 mmol) in quantitative yield. $^1$H NMR (300 MHz, DMSO-$d_6$+TFA) δ ppm 2.18-2.26 (m, 3H) 2.56-2.71 (m, 1H) 2.80-3.03 (m, 2H) 3.18-3.32 (m, 1H) 3.55-3.88 (m, 5H) 4.07 (br d, J=9.17 Hz, 2H) 4.17-4.32 (m, 1H) 7.11 (t, J=9.22 Hz, 1H) 7.42-7.57 (m, 3H) 7.57-7.67 (m, 1H) 8.97 (br s, 2H) 9.68 (s, 1H). Method 1; Rt: 1.32 min. m/z: 409 (M+H)$^+$. Method 1; Rt: 1.32 min. m/z: 409 (M+H)$^+$.

Step 2

A suspension of trans-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide hydrochloride (37 mg, 0.08 mmol) in MeCN (1 mL) was cooled to 0° C. with an ice bath and treated with a single portion of TEA (0.035 mL, 0.25 mmol). A 1.28M solution of 5-methyl-1,3,4-oxadiazole-2-carbonyl chloride (0.068 mL, 0.09 mmol) (Org. Proc. Res. Develop. 2011, 15, 73-83) in MeCN was added in a single portion and the reaction mixture was stirred at 0° C. for 20 min then at room temperature for 10 min. The reaction was stopped by addition of MeOH (2 mL), stirred at room temperature then solvent was removed in vacuo. The residue was dissolved in DCM (10 mL) and washed with 5% citric acid (aq. solution) (10 mL) and brine (5 mL×3) then dried over Na$_2$SO$_4$ (anh.), filtered and evaporated giving a residue (70 mg) that was purified by FC (direct phase, eluent DCM/EtOAc) giving E146 (23 mg, 0.044 mmol) as white solid. $^1$H NMR (300 MHz, DMSO-d6) δ ppm 2.24 (br s, 3H) 2.58 (d, J=7.43 Hz, 3H) 3.16-3.31 (m, 1H) 3.45-3.80 (m, 2H) 3.83 (s, 3H) 3.97-4.67 (m, 5H) 7.11 (td, J=9.22, 4.77 Hz, 1H) 7.43-7.56 (m, 2H) 7.57-7.65 (m, 1H) 7.70-7.84 (m, 1H) 9.52 (d, J=8.80 Hz, 1H).

Example 147: Trans-N-(4-fluoro-3-methylphenyl)-7-methyl-2-(5-methyloxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide (E147)

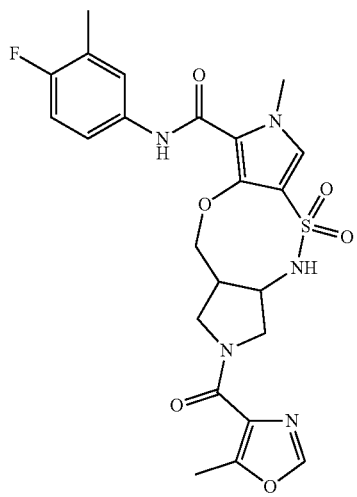 [SMILES: Cc1cc(NC(=O)c2c3c(cn2C)S(=O)(=O)NC2CN(C(=O)c4ncoc4C)CC2CO3)ccc1F]

To a suspension of trans-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide hydrochloride (prepared as in Step 1 of Scheme 28, 30 mg, 0.07 mmol) in dry DMF (0.7 mL) 5-Methyl-1,3-oxazole-4-carboxylic acid (12 mg, 0.09 mmol) was added, followed by DIPEA (0.047 mL, 0.27 mmol). To the stirring solution Benzotriazol-1-yloxytris(dimethylamino)phosphonium hexafluorophosphate (BOP) (41.8 mg, 0.09 mmol) was added and the reaction mixture stirred 1 h at RT. The reaction was diluted with EtOAc and water, then organic layer was washed with 5% citric acid solution and water. The organic portion was dried over Na$_2$SO4, filtered and concentrated under reduced pressure, then the residue was purified by preparative HPLC (H$_2$O/CH$_3$CN+0.1% HCOOH) to afford E147 (28 mg) as white solid. $^1$H NMR (300 MHz, DMSO-$d_6$+TFA) δ ppm 2.23 (s, 3H) 2.49 (s, 3H) 2.55-2.71 (m, 1H) 3.07-3.39 (m, 1H) 3.47-3.66 (m, 1H) 3.83 (s, 3H) 3.95-4.22 (m, 3H) 4.22-4.68 (m, 2H) 7.08 (t, J=9.17 Hz, 1H) 7.41-7.56 (m, 2H) 7.60 (br d, J=6.90 Hz, 1H) 7.65-7.85 (m, 1H) 8.26 (d, J=18.52 Hz, 1H) 9.32-9.59 (m, 1H). Method 3; Rt=3.94 min. m/z=518 (M+H)$^+$.

Example 148: Trans-N-(4-fluoro-3-methylphenyl)-7-methyl-2-(2-methyltetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide (E148)

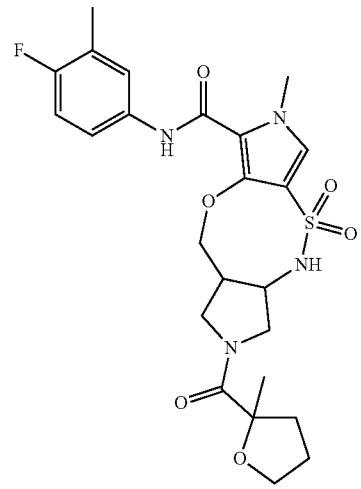 [SMILES: Cc1cc(NC(=O)c2c3c(cn2C)S(=O)(=O)NC2CN(C(=O)C4(C)CCCO4)CC2CO3)ccc1F]

E148 was prepared similarly as described for compound E147 using 2-methyloxolane-2-carboxylic acid instead of 5-Methyl-1,3-oxazole-4-carboxylic acid. $^1$H NMR (300 MHz, DMSO-$d_6$+TFA) δ ppm 1.30 (br s, 3H) 1.44-1.62 (m, 1H) 1.63-1.94 (m, 2H) 2.23 (s, 3H) 2.54-2.70 (m, 1H) 2.92-3.41 (m, 2H) 3.41-3.73 (m, 2H) 3.75-3.90 (m, 4H) 3.91-4.16 (m, 3H) 4.17-4.58 (m, 2H) 7.09 (t, J=9.35 Hz, 1H) 7.42-7.55 (m, 2H) 7.56-7.64 (m, 1H) 7.64-7.78 (m, 1H) 9.48 (d, J=6.88 Hz, 1H). Method 3; Rt=4.11 min. m/z=521.42 (M+H)$^+$.

Example 149: Trans-N-(4-fluoro-3-methylphenyl)-7-methyl-2-(3-methyloxetane-3-carbonyl)-2,3,3a,4,10,10a-hexahydro-1H,7H-dipyrrolo[3,4-b:3',4'-f][1,4,5]oxathiazocine-8-carboxamide 5,5-dioxide (E149)

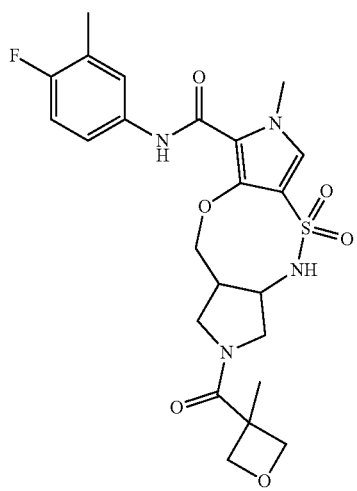 [SMILES: Cc1cc(NC(=O)c2c3c(cn2C)S(=O)(=O)NC2CN(C(=O)C4(C)COC4)CC2CO3)ccc1F]

E149 was prepared similarly as described for compound E147 using 3-Methyl-3-oxetanecarboxylic acid instead of 5-Methyl-1,3-oxazole-4-carboxylic acid. $^1$H NMR (300 MHz, DMSO-d$_6$) δ ppm 1.50 (d, J=16.40 Hz, 3H) 2.23 (s, 3H) 2.58-2.88 (m, 1H) 2.97-3.15 (m, 1H) 3.16-3.29 (m, 1H) 3.41-3.67 (m, 1H) 3.82 (s, 3H) 3.85-4.36 (m, 6H) 4.67-4.88 (m, 2H) 7.11 (t, J=9.17 Hz, 1H) 7.41-7.56 (m, 2H) 7.56-7.76 (m, 2H) 9.55 (d, J=14.21 Hz, 1H). Method 3; Rt=3.75 min. m/z=507 (M+H)$^+$.

Example 150: Trans-2-(2-oxabicyclo[2.1.1]hexane-1-carbonyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide (E150)

E150 was prepared similarly as described for compound E147 using 2-oxabicyclo[2.1.1]hexane-1-carboxylic acid instead of 5-Methyl-1,3-oxazole-4-carboxylic acid. $^1$H NMR (300 MHz, DMSO-d$_6$+TFA) δ ppm 1.50-1.71 (m, 2H) 1.82-2.05 (m, 2H) 2.23 (s, 3H) 2.54-2.71 (m, 1H) 2.78-2.93 (m, 1H) 2.97-3.56 (m, 3H) 3.74 (d, J=25.77 Hz, 2H) 3.82 (s, 3H) 3.91-4.36 (m, 4H) 7.09 (t, J=9.17 Hz, 1H) 7.41-7.55 (m, 2H) 7.56-7.79 (m, 2H) 9.51 (d, J=4.77 Hz, 1H). Method 3; Rt=4.01 min. m/z=519 (M+H)$^+$ The synthesis of compound E151 is reported in Table 1 below.

Example 152: Tert-Butyl (3aR,10aS)-8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (E152)

Prepared similarly as described for compound E145, starting from D93 to obtain E152 (10 mg). Method 3; Rt=3.74 min. m/z=509.33 (M+H)$^+$.

E152 was also obtained from chiral separation of E145, as the second eluted isomer (Chiral HPLC Separation in reverse phase by Daicel Chiralpack Semipreparative IG Column, 1 cm I.D.×25 cm L, followed by analysis of both isolated enantiomers through Daicel Chiralpack Analytical IG Column, 0.46 cm I.D.×25 cm L), as indicated in Table 1. The first eluted isomer corresponds to compound E151.

The synthesis of compound E153 is reported in Table 1 below.

Example 154: (3aR,10aS)—N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide (E154)

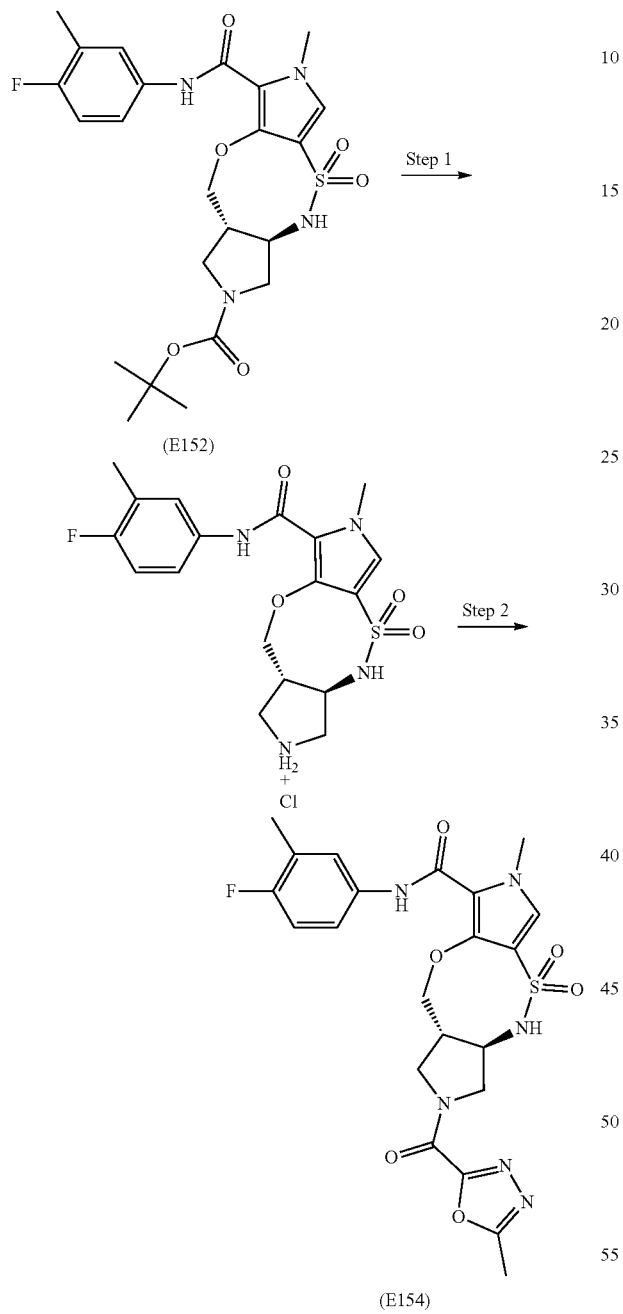

Step 1

E152 in DCM (1 mL) was treated with a single portion of 3M HCl in MeOH (approx. 10 equivalents) and the resulting yellow solution was stirred at room temperature for 2 hrs. Then solvent was removed, giving (3aR,10aS)—N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide hydrochloride (8 mg) as white powder. Method 1; Rt=1.20 min. m/z=409 (M+H)+.

Step 2

A solution of (3aR,10aS)—N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide hydrochloride (1 mg, 0002 mmol) in MeCN (0.5 mL) was treated with a single portion of TEA (0.009 mL, 0.007 mmol) and then with a solution of 5-methyl-1,3,4-oxadiazole-2-carbonyl chloride (1.2M in MeCN, 0.002 mL, 0.002 mmol) (Org. Proc. Res. Develop. 2011, 15, 73-83). The reaction was stirred at room temperature 1 h, treated with MeOH and stirred additionally at room temperature for 3 hrs. Solvent was removed in vacuo, the residue was dissolved in MeOH (500 uL) and passed through a C18 solid phase extraction cartridge (SPE) (GracePure C18-Fast). The cartridge was washed with 95/5 H2O/MeCN (3 mL), then product was collected by washing with MeCN (1 mL). Solvent was removed by evaporation giving E154 3aR,10aS)—N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide (0.6 mg). Method 1; Rt=1.61 min. m/z=519.40 (M+H)+.

E154 was also obtained from chiral separation of E146, as the second eluted isomer (Chiral HPLC Separation in reverse phase by Daicel Chiralpack Semipreparative IG Column, 1 cm I.D.×25 cm L, followed by analysis of both isolated enantiomers through Daicel Chiralpack Analytical IG Column, 0.46 cm I.D.×25 cm L), as indicated in Table 1. The first eluted isomer corresponds to compound E153.

Example 155: Cis 2-benzyl-N-(4-fluoro-3-methylphenyl)-7-methyl-3-oxo-2,3,3a,4,10,10a-hexahydro-1H,7H-dipyrrolo[3,4-b:3',4'-f][1,4,5]oxathiazocine-8-carboxamide 5,5-dioxide (E155)

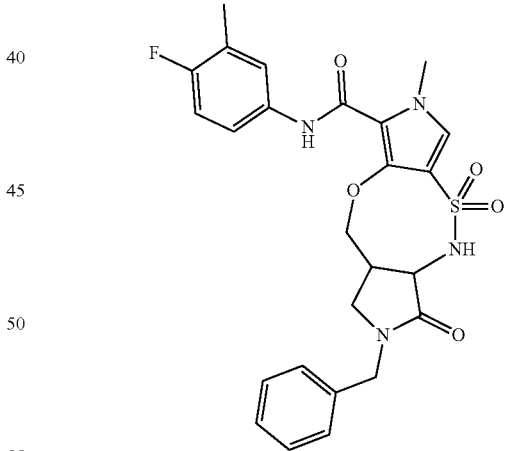

Cesium carbonate (334 mg, 1.03 mmol) was added to a solution of D95 (273 mg, 0.52 mmol) in dry DMF (10 mL). The reaction mixture was stirred at 135° C. for 3 hrs then cooled to RT, diluted with EtOAc and water, and stirred for 15 min. The two phases were separated and the organic phase washed with water and brine, dried over Na2SO4 filtered and concentrated. Purification by FC (direct phase, eluent DCM/EtOAc) afforded E155 (130 mg, 50% over two steps) as an off white foam. A small amount of this compound (20 mg) was further purified by preparative HPLC for full characterization. 1H NMR (300 MHz, DMSO-d6) δ ppm 2.22 (s, 3H) 2.80-2.89 (m, 1H) 3.07-3.18 (m, 1H) 3.20-3.27 (m, 1H) 3.81 (s, 3H) 4.00 (s, 1H) 4.36-4.52 (m, 4H) 7.09 (t, J=9.26 Hz, 1H) 7.23-7.39 (m, 5H) 7.45-7.53 (m, 2H) 7.54-7.60 (m, 1H) 8.51 (br s, 1H) 9.36 (s, 1H). Method 1; Rt: 3.54 min. m/z: 513.12 (M+H)$^+$.

Example 156: Cis/Trans Ethyl 7-methyl-8-((3,4,5-trifluorophenyl)carbamoyl)-1,3a,4,10,11,11a-hexahydro-7H-dipyrrolo[3,4-b:3',4'-f][1,4,5]oxathiazocine-2(3H)-carboxylate 5,5-dioxide (E156)

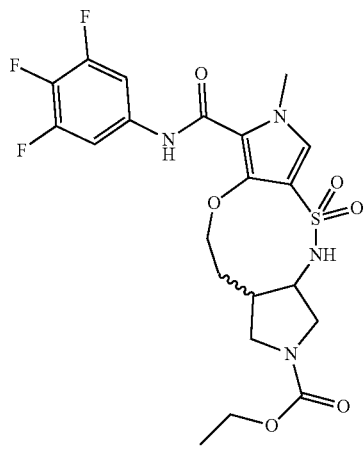 [SMILES: CCOC(=O)N1CC2CCOc3c(cn(C)c3C(=O)Nc3cc(F)c(F)c(F)c3)S(=O)(=O)NC2C1]

Cesium carbonate (122 mg, 0.38 mmol) was added to a solution of D99 (80 mg, 0.015 mmol) in dry DMF (4 mL). The reaction mixture was stirred at 150° C. under microwave irradiation for 16 hrs then cooled to RT, diluted with EtOAc and water, and stirred for 15 min. The two phases were separated and the organic phase washed with water and brine, dried over Na$_2$SO$_4$ filtered and concentrated. Crude was purified by preparative HPLC to afford E156 (7 mg, 9%) as a white solid. $^1$H NMR (300 MHz, DMSO-d$_6$) δ ppm 1.12-1.27 (m, 3H) 1.44-1.70 (m, 1H) 1.73-1.96 (m, 1H) 2.19-2.38 (m, 1H) 2.84-3.17 (m, 2H) 3.42-3.74 (m, 2H) 3.74-3.83 (m, 3H) 3.90-4.25 (m, 3H) 4.25-4.25 (m, 1H) 4.29-4.51 (m, 1H) 7.40-7.58 (m, 1H) 8.08 (m, 3H) 9.79-10.35 (m, 1H). Method 3; Rt: 3.54 min. m/z: 517.24 (M+H)+.

Example 157: Cis Ethyl 8-((4-fluoro-3-methylphenyl)carbamoyl)-7-methyl-3a,4,7,9,10,10a-hexahydro-1H-dipyrrolo[3,4-c:3',4'-g][1,2,6]thiadiazocine-2(3H)-carboxylate 5,5-dioxide (E157)

Cesium carbonate (86 mg, 0.27 mmol) and DBU (50 µL, 0.34 mmol) were added to a solution of D102 (40 mg, 0.08 mmol) in dry DMF (3 mL). The reaction mixture was stirred at 180° C. under microwave irradiation for 6 hrs then cooled to RT, diluted with EtOAc and water, and stirred for 15 min. The two phases were separated and the organic phase washed with water and brine, dried over Na$_2$SO$_4$ filtered and concentrated. Crude was purified by preparative HPLC to afford E157 (3 mg, 8%) as a white solid. $^1$H NMR (300 MHz, DMSO-d$_6$) δ ppm 1.15-1.25 (m, 3H) 2.22-2.25 (m, 3H) 3.08-3.19 (m, 1H) 3.45-3.61 (m, 5H) 3.83-3.88 (m, 3H) 3.88-3.95 (m, 1H) 3.95-4.08 (m, 2H) 4.12-4.22 (m, 1H) 6.26-6.37 (m, 1H) 6.98-7.16 (m, 2H) 7.44-7.70 (m, 2H) 8.14-8.25 (m, 1H) 9.37-9.46 (m, 1H). Method 3; Rt: 3.35 min. m/z: 480 (M+H)$^+$.

The compounds shown in Table 1 were obtained from Examples of the invention through the indicated preparative methods.

Method 15: Chiral HPLC Separation in reverse phase by Daicel Chiralpack Semipreparative IG Column, 1 cm I.D.× 25 cm L followed by analysis of both isolated enantiomers through Daicel Chiralpack Analytical IG Column, 0.46 cm I.D.×25 cm L.

Method 16: Chiral HPLC Separation in reverse phase by Daicel Chiralpack Semipreparative IB-N5 Column, 1 cm I.D.×25 cm L followed by analysis of both isolated enantiomers through Daicel Chiralpack Analytical IB-N5 Column, 0.46 cm I.D.×25 cm L.

Compound E36 was obtained through deprotection by standard chemistry of compound E33.

TABLE 1

Examples obained through chiral resolution of racemic compounds

| Example | Compound Name | Preparative Method | | 
|---|---|---|---|
| | | RP-HPLC method | Starting Material |
| E31 | ethyl 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide (3aR,10aR) | Chiral Separation First eluted isomer | Method 15 E10 |

TABLE 1-continued

Examples obtained through chiral resolution of racemic compounds

| Example | Compound Name | Preparative Method RP-HPLC method | Starting Material |
|---|---|---|---|
| E32 | ethyl 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide (3aS,10aS) | Chiral Separation Second eluted isomer | Method 15 E10 |
| E33 | tert-butyl 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide (3aR,10aR) | Chiral Separation First eluted isomer | Method 15 E24 |
| E34 | N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide (Chiral 5aS,8aR or 5aR,8aS - Stereochemistry unknown) | Chiral Separation First eluted isomer | Method 15 E6 |
| E35 | N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide (Chiral 5aS,8aR or 5aR,8aS - Stereochemistry unknown) | Chiral Separation Second eluted isomer | Method 15 E6 |
| E36 | 7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (3aR,10aR) | Removal of the Boc protecting group | E33 |
| E37 | Ethyl 8-((3,4-difluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | Chiral Separation First eluted isomer | Method 15 E13 |
| E38 | Ethyl 8-((3,4-difluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | Chiral Separation Second eluted isomer | Method 15 E13 |
| E39 | Ethyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (3aR,10aR) | Chiral Separation First eluted isomer | Method 15 E14 |
| E40 | Ethyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (3aS,10aS) | Chiral Separation Second eluted isomer | Method 15 E14 |
| E41 | Ethyl 8-((3-chloro-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (3aR,10aR) | Chiral Separation First eluted isomer | Method 15 E15 |
| E42 | Ethyl 8-((3-chloro-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (3aS,10aS) | Chiral Separation Second eluted isomer | Method 15 E15 |
| E43 | Ethyl 8-((3-(difluoromethyl)-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | Chiral Separation First eluted isomer | Method 15 E16 |
| E44 | Ethyl 8-((3-(difluoromethyl)-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | Chiral Separation Second eluted isomer | Method 15 E16 |

TABLE 1-continued

Examples obained through chiral resolution of racemic compounds

| Example | Compound Name | Preparative Method | RP-HPLC method | Starting Material |
|---|---|---|---|---|
| E45 | Ethyl 8-((3-cyano-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | Chiral Separation First eluted isomer | Method 15 | E17 |
| E46 | Ethyl 8-((3-cyano-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | Chiral Separation Second eluted isomer | Method 15 | E17 |
| E91 | Ethyl 7,10a-dimethyl-8-((3,4,5-trifluorophenyl)carbamoyl)-3a,4,10,10a-tetrahydro-1H,7H-dipyrrolo[3,4-b:3',d'-f][1,4,5]oxathiazocine-2(3H)-carboxylate 5,5-dioxide (Chiral 3aS,10aS or 3aR,10aR - Stereochemistry unknown) | Chiral Separation First eluted isomer | Method 16 | E85 |
| E92 | Ethyl 7,10a-dimethyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | Chiral Separation Second eluted isomer | Method 16 | E85 |
| E93 | Ethyl 8-((4-fluoro-3-methylphenyl)carbamoyl)-7,10a-dimethyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | Chiral Separation First eluted isomer | Method 16 | D103 |
| E94 | Ethyl 8-((4-fluoro-3-methylphenyl)carbamoyl)-7,10a-dimethyl-3a,4,10,10a-tetrahydro-1H,7H-dipyrrolo[3,4-b:3',4'-f][1,4,5]oxathiazocine-2(3H)-carboxylate 5,5-dioxide(Chiral 3aS,10aS or 3aR,10aR - Stereochemistry unknown) | Chiral Separation Second eluted isomer | Method 16 | D103 |
| E95 | N-(4-fluoro-3-methylphenyl)-7,10a-dimethyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide (Chiral 3aS,10aS or 3aR,10aR - Stereochemistry unknown) | Chiral Separation First eluted isomer | Method 16 | E86 |
| E96 | N-(4-fluoro-3-methylphenyl)-7,10a-dimethyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide (Chiral 3aS,10aS or 3aR,10aR - Stereochemistry unknown) | Chiral Separation Second eluted isomer | Method 16 | E86 |
| E151 | tert-butyl (3aS,10aR)-8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide | Chiral Separation First eluted isomer | Method 15 | E145 |
| E152 | tert-butyl (3aR,10aS)-8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide | Chiral Separation Second eluted isomer | Method 15 | E145 |
| E153 | (3aS,10aR)-N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide | Chiral Separation First eluted isomer | Method 15 | E146 |
| E154 | (3aR,10aS)-N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide | Chiral Separation Second eluted isomer | Method 15 | E146 |

Biology

Assay

Cells and Culture Conditions

HepAD38 cell line (Ladner et al., Antimicrob Agents Chemother, 1997, 41, 1715-20) was used for HBV inhibition assays. HepAD38 is a subclone, derived from hepatoblastoma cell line HepG2 (ATCC® Number: HB-8065™), that expresses HBV genome under the transcriptional control of a tetracycline-responsive promoter in a TET-OFF system: addition of tetracycline (TET) or doxycycline suppresses HBV replication, while its removal switches on the process allowing HBV viral particles release in the cell supernatant. HepAD38 cell line is maintained in DMEM/F12, supplemented with 10% of fetal bovine serum, 1% of glutamine, 1% of penicillin/streptomycin, 0.4 mg/ml G418 and 0.3 ug/ml tetracycline. For the HBV inhibition assay, doxycycline-free medium is used in order to allow virion production.

Anti-HBV Activity In Vitro

HBV inhibition activity in vitro was performed in 96 multiwell plates. During the initial (primary) screening compounds were first tested in triplicates at concentrations of 0.1 µM, 0.5 µM and 1 µM. For selected compounds, an 8-point dose-response curve was obtained using 1:2 serial dilutions (starting from 2.5 µM, 1.25 µM or 0.4 µM, depending on the degree of inhibition observed during the primary screening). From the dose-response curves, half maximal effective concentration ($EC_{50}$) could be calculated (see also below).

In more detail, compounds—typically dissolved in DMSO stock solutions—were diluted to 2× the final desired concentration in 100 µl of the above medium (without doxycycline) and plated in three replicates in the 96-well plates.

Simultaneously, HepAD38 cells—extensively pre-washed in tetracycline-free medium in order to induce HBV production—were suspended at $2*10^4$ cells in 100 µl of tetracycline-free medium and added to each well of the plate, to yield a final assay volume of 200 µl.

DMSO, used for stock solutions and compounds dilutions, was always present in the assays at a final concentration of 0.5%.

Plates were then incubated 96 hours at 37° C. and then subjected to cell viability assays and extracellular HBV quantification, in order to evaluate both the cytotoxic potential and the antiviral activity of compounds.

Cytotoxicity was assessed by a commercial fluorescence assay that measures the metabolic activity of cells, directly related to cell viability (Cell Titer Blue, Promega). For each compound, cytotoxicity was evaluated at the same concentration employed to evaluate its anti-HBV activity. Anti-HBV activity was evaluated by quantification of extracellular HBV DNA with direct qPCR. In particular, supernatant was collected and centrifuged for cell debris clarification, viral DNA was extracted from virions by addition of lysis buffer (1 mM 1,4-dithiothreitol, 0.2% sodium dodecyl sulphate) and incubated at 95° C. for 10 min. Samples were then diluted 1:40 and real time PCR amplification was performed with SYBR green assay (Power SYBR™ Green PCR Master Mix-Thermo Fisher Scientific) and specific HBV primer (HBV-DF:5'-AT-TGTTCAGTGGTTCGTAGGG-3' (SEQ ID No. 1), HBV-DR:5'-CGGTAAAAAGGGACTCAAGATG-3' (SEQ ID No. 2)).

All HBV inhibition or antiviral activity data are typically reported in percent (%) relative to a non-treated reference sample. Excel and Graphpad Prism programs are typically used for data elaboration and $EC_{50}$ calculation.

Results

The exemplified compounds described herein were tested in the assays described above. All the compounds displayed no measurable cytotoxicity at the tested compound concentration.

Results for HBV inhibition are reported in the following Table 2.

Legend: A indicates HBV inhibition greater than 50% at the concentration indicated in the table or $EC_{50}$ less than 1 µM; B indicates HBV inhibition less than 50% at the concentration indicated in the table or $EC_{50}$ greater than 1 µM.

TABLE 2

Antiviral activity of the compounds of the invention

| Example | Compound Name | Anti HBV Activity (conc µM) | HBV inh $EC_{50}$ (µM) |
|---|---|---|---|
| E1 | N-(3,4-difluorophenyl)-2-methyl-6,7,8,9,9a,10-hexahydro-2H-pyrido[1,2-e]pyrrolo[3,4-b][1,4,5]oxathiazepine-1-carboxamide 4,4-dioxide | B (1) | B |
| E2 | N-(3,4-difluorophenyl)-2-methyl-2,6,7,8,9,9a,10,11-octahydropyrido[1,2-b]pyrrolo[3,4-f][1,2,5]thiadiazepine-1-carboxamide 4,4-dioxide | B (1) | — |
| E3 | N-(3,4-difluorophenyl)-2-methyl-6,7,7a,8-tetrahydro-2H-azeto[1,2-e]pyrrolo[3,4-b][1,4,5]oxathiazepine-1-carboxamide 4,4-dioxide | A(1) | A |
| E4 | trans-N-(3,4-difluorophenyl)-7-methyl-1,3a,4,9a-tetrahydro-3H,7H-furo[3,4-f]pyrrolo[3,4-b][1,4,5]oxathiazepine-8-carboxamide 5,5-dioxide | A (1) | A |
| E5 | cis-N-(3,4-difluorophenyl)-9-methyl-3,4,5,6-tetrahydro-2H,9H-3,5-methanopyrrolo[3,4-b][1,4,5]oxathiazonine-8-carboxamide 1,1-dioxide | B (1) | — |
| E6 | cis-N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide | A (0.5) | A |
| E7 | trans-7-methyl-N-(3,4,5-trifluorophenyl)-1,3a,4,9a-tetrahydro-3H,7H-furo[3,4-f]pyrrolo[3,4-b][1,4,5]oxathiazepine-8-carboxamide 5,5-dioxide | — | A |

TABLE 2-continued

Antiviral activity of the compounds of the invention

| Example | Compound Name | Anti HBV Activity (conc μM) | HBV inh EC$_{50}$ (μM) |
|---|---|---|---|
| E8 | (5aR,8aR)-N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide | — | A |
| E9 | (5aS,8aS)-N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide | — | A |
| E10 | cis-Ethyl 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide | A (0.5) | A |
| E11 | cis-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A (0.1) | A |
| E12 | cis-2,7-dimethyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A (0.1) | A |
| E13 | cis-Ethyl 8-((3,4-difluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide | A (0.1) | A |
| E14 | cis-Ethyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide | A (0.1) | A |
| E15 | cis-Ethyl 8-((3-chloro-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide | A (0.1) | A |
| E16 | cis-Ethyl 8-((3-(difluoromethyl)-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide | A (0.1) | A |
| E17 | cis-Ethyl 8-((3-cyano-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide | A (0.1) | A |
| E18 | cis-2-(isopropylsulfonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A (0.1) | A |
| E19 | cis-7-methyl-2-(methylsulfonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A(0.1) | A |
| E20 | cis-2-(cyclopropylsulfonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A (0.1) | A |
| E21 | cis-2-(N-isopropylsulfamoyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A (0.1) | A |
| E22 | cis-(3R,3aS,6aR)-hexahydrofuro[2,3-b]furan-3-yl 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide | A (0.1) | A |
| E23 | N$^2$,7-dimethyl-N$^8$-(3,4,5-trifluorophenyl)-3a,4,10,10a-tetrahydro-1H,7H-dipyrrolo[3,4-b:3',4'-f][1,4,5]oxathiazocine-2,8(3H)-dicarboxamide 5,5-dioxide (racemate of 3aR,10aR and 3aS,10aS) | A (0.1) | A |
| E24 | tert-butyl 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide (racemate of 3aS,10aS and 3aR,10aR) | A (0.1) | — |
| E25 | (3aR,10aS)-N-(3,4-difluorophenyl)-7-methyl-2,3,3a,4,10,10a-hexahydro-1H,7H-dipyrrolo[3,4-b:3',2'-f][1,4,5]oxathiazocine-8-carboxamide 5,5-dioxide | B (0.1) | — |
| E26 | (3aR,10aS)-N8-(3,4-difluorophenyl)-N1,7-dimethyl-2,3,3a,4,10,10a-hexahydro-1H,7H-dipyrrolo[3,4-b:3',2'-f][1,4,5]oxathiazocine-1,8-dicarboxamide 5,5-dioxide | B (0.1) | — |
| E27 | ethyl (3aR,10aS)-8-((3,4-difluorophenyl)carbamoyl)-7-methyl-2,3,3a,4,10,10a-hexahydro-1H,7H-dipyrrolo[3,4-b:3',2'-f][1,4,5]oxathiazocine-1-carboxylate 5,5-dioxide | B (0.1) | — |
| E28 | cis-2-methyl-N-(3,4,5-trifluorophenyl)-5a,6,7,8,8a,9-hexahydro-2H,5H-cyclopenta[f]pyrrolo[3,4-b][1,4,5]oxathiazocine-1-carboxamide 4,4-dioxide | A (0.1) | A |
| E29 | N-(3,4-difluorophenyl)-2,8a-dimethyl-5a,6,7,8,8a,9-hexahydro-2H,5H-cyclopenta[f]pyrrolo[3,4-b][1,4,5]oxathiazocine-1-carboxamide 4,4-dioxide | B (0.1) | — |

TABLE 2-continued

Antiviral activity of the compounds of the invention

| Example | Compound Name | Anti HBV Activity (conc μM) | HBV inh EC$_{50}$ (μM) |
|---|---|---|---|
| E30 | cis-N-(3,4-difluorophenyl)-8a-hydroxy-2-methyl-5a,6,7,8,8a,9-hexahydro-2H,5H-cyclopenta[f]pyrrolo[3,4-b][1,4,5]oxathiazocine-1-carboxamide 4,4-dioxide | B (0.5) | — |
| E31 | ethyl 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide (Chiral 3aR,10aR or 3aS,10aS - Stereochemistry unknown) | B (0.1) | — |
| E32 | ethyl 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide (Chiral 3aR,10aR or 3aS,10aS - Stereochemistry unknown) | A (0.1) | A |
| E33 | tert-butyl 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | B (0.1) | — |
| E34 | N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide (Chiral 5aS,8aR or 5aR,8aS - Stereochemistry unknown) | B (0.1) | — |
| E35 | N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide (Chiral 5aS,8aR or 5aR,8aS - Stereochemistry unknown) | A (0.1) | A |
| E36 | 7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide (Chiral 3aS,10aS or 3aR,10aR - Stereochemistry unknown) | B (0.1) | — |
| E37 | Ethyl 8-((3,4-difluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | A (0.05) | — |
| E38 | Ethyl 8-((3,4-difluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | B (0.1) | — |
| E39 | Ethyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | A (0.05) | A |
| E40 | Ethyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | B (0.1) | — |
| E41 | Ethyl 8-((3-chloro-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | A (0.05) | A |
| E42 | Ethyl 8-((3-chloro-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | B (0.1) | — |
| E43 | Ethyl 8-((3-(difluoromethyl)-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | A (0.05) | A |
| E44 | Ethyl 8-((3-(difluoromethyl)-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | B (0.1) | — |
| E45 | Ethyl 8-((3-cyano-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | A (0.05) | — |
| E46 | Ethyl 8-((3-cyano-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | B (0.1) | — |
| E47 | cis-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide | A (0.05) | A |
| E48 | cis-N-(4-fluoro-3-methylphenyl)-7-methyl-2-(pyridin-3-yl)-2,3,3a,4,10,10a-hexahydro-1H,7H-dipyrrolo[3,4-b:3',4'-f][1,4,5]oxathiazocine-8-carboxamide 5,5-dioxide | — | A |

TABLE 2-continued

Antiviral activity of the compounds of the invention

| Example | Compound Name | Anti HBV Activity (conc μM) | HBV inh $EC_{50}$ (μM) |
|---|---|---|---|
| E49 | cis-N-(4-fluoro-3-methylphenyl)-7-methyl-2-(1,3,4-oxadiazol-2-yl)-2,3,3a,4,10,10a-hexahydro-1H,7H-dipyrrolo[3,4-b:3',4'-f][1,4,5]oxathiazocine-8-carboxamide 5,5-dioxide | — | A |
| E50 | cis-7-methyl-2-(oxazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A (0.05) | A |
| E51 | cis-7-methyl-2-(5-methyl-1,3,4-oxadiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A (0.05) | A |
| E52 | cis-N-(4-fluoro-3-methylphenyl)-7-methyl-2-(5-methylisoxazole-3-carbonyl)-2,3,3a,4,10,10a-hexahydro-1H,7H-dipyrrolo[3,4-b:3',4'-f][1,4,5]oxathiazocine-8-carboxamide 5,5-dioxide | A (0.05) | A |
| E53 | cis-N-(4-fluoro-3-methylphenyl)-2-(6-hydroxynicotinoyl)-7-methyl-2,3,3a,4,10,10a-hexahydro-1H,7H-dipyrrolo[3,4-b:3',4'-f][1,4,5]oxathiazocine-8-carboxamide 5,5-dioxide | B (0.1) | — |
| E54 | cis-N-(4-fluoro-3-methylphenyl)-7-methyl-2-nicotinoyl-2,3,3a,4,10,10a-hexahydro-1H,7H-dipyrrolo[3,4-b:3',4'-f][1,4,5]oxathiazocine-8-carboxamide 5,5-dioxide | A (0.1) | — |
| E55 | cis-N-(4-fluoro-3-methylphenyl)-2-isonicotinoyl-7-methyl-2,3,3a,4,10,10a-hexahydro-1H,7H-dipyrrolo[3,4-b:3',4'-f][1,4,5]oxathiazocine-8-carboxamide 5,5-dioxide | A (0.1) | — |
| E56 | cis-7-methyl-2-(5-oxo-4,5-dihydropyrazine-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | B (0.1) | — |
| E57 | cis-7-methyl-2-(1-methyl-1H-pyrazole-4-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | B (0.1) | — |
| E58 | cis-7-methyl-2-(thiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A (0.05) | A |
| E59 | cis-7-methyl-2-(6-oxo-1,6-dihydropyrimidin-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | — | B |
| E60 | cis-2-(4-amino-1,2,5-oxadiazole-3-carbonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | — | A |
| E61 | cis-2-(4-amino-1,2,5-oxadiazole-3-carbonyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide | — | A |
| E62 | cis-N-(4-fluoro-3-methylphenyl)-7-methyl-2-(5-methyl-1,3,4-thiadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E63 | cis-N-(4-fluoro-3-methylphenyl)-7-methyl-2-(1,2,4-oxadiazole-3-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E64 | cis-7-methyl-2-(oxazole-5-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | — | A |
| E65 | cis-7-methyl-2-(oxazole-4-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | — | A |
| E66 | cis-N-(4-fluoro-3-methylphenyl)-7-methyl-2-(3-methyloxetane-3-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E67 | cis-2-(L-alanyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | B (0.1) | — |

TABLE 2-continued

Antiviral activity of the compounds of the invention

| Example | Compound Name | Anti HBV Activity (conc μM) | HBV inh EC$_{50}$ (μM) |
|---|---|---|---|
| E68 | cis-2-(L-seryl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | B (0.1) | — |
| E69 | cis-2-(L-threonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | B (0.1) | — |
| E70 | cis-2-(7-methyl-5,5-dioxido-8-((3,4,5-trifluorophenyl)carbamoyl)-3a,4,10,10a-tetrahydro-1H,7H-dipyrrolo[3,4-b:3',4'-f][1,4,5]oxathiazocin-2(3H)-yl)-2-oxoethyl acetate | B (0.1) | — |
| E71 | cis-2-(2-hydroxyacetyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | B (0.1) | — |
| E72 | cis-2-(7-methyl-5,5-dioxido-8-((3,4,5-trifluorophenyl)carbamoyl)-3a,4,10,10a-tetrahydro-1H,7H-dipyrrolo[3,4-b:3',4'-f][1,4,5]oxathiazocin-2(3H)-yl)-2-oxoethyl dihydrogen phosphate | B (0.1) | — |
| E73 | cis-7-methyl-2-(2,2,2-trifluoroethyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A (0.1) | — |
| E74 | cis-2-(cyanomethyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A (0.05) | A |
| E75 | cis-2-(5-fluoropyrimidin-2-yl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A (0.05) | A |
| E76 | cis-2-(2-chloropyridin-4-yl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide | A (0.05) | A |
| E77 | ethyl (3R,6R)-10-methyl-9-((3,4,5-trifluorophenyl)carbamoyl)-3,4,6,7-tetrahydro-10H-3,6-methanopyrrolo[3,4-b][1,4,5,8]oxathiadiazecine-5(2H)-carboxylate 1,1-dioxide | — | A |
| E78 | cis-7-methyl-2-(5-methyl-1,3,4-oxadiazol-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A (0.05) | A |
| E79 | cis-2-(cyanomethyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide | A (0.05) | A |
| E80 | cis-N-(4-fluoro-3-methylphenyl)-7-methyl-2-(2,2,2-trifluoroethyl)-2,3,3a,4,10,10a-hexahydro-1H,7H-dipyrrolo[3,4-b:3',4'-f][1,4,5]oxathiazocine-8-carboxamide 5,5-dioxide | A (0.1) | — |
| E81 | cis-7-methyl-2-(pyridin-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A (0.1) | — |
| E82 | cis-7-methyl-2-(pyrazin-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A (0.1) | — |
| E83 | cis-7-methyl-2-(3-methyl-1,2,4-oxadiazol-5-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A (0.1) | A |
| E84 | cis-2-(5-hydroxypyrimidin-2-yl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | — | A |
| E85 | cis-(3aR,10aR)-7-methyl-2-(5-methyl-1,3,4-oxadiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | A (0.05) | — |
| E86 | cis-N-(4-fluoro-3-methylphenyl)-7,10a-dimethyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E87 | cis-N-(4-fluoro-3-methylphenyl)-7,10a-dimethyl-2-(5-methyloxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |

TABLE 2-continued

Antiviral activity of the compounds of the invention

| Example | Compound Name | Anti HBV Activity (conc μM) | HBV inh EC$_{50}$ (μM) |
|---|---|---|---|
| E88 | cis-N-(4-fluoro-3-methylphenyl)-7,10a-dimethyl-2-(2-methyltetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E89 | cis-N-(4-fluoro-3-methylphenyl)-7,10a-dimethyl-2-(3-methyloxetane-3-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E90 | cis-2-(2-oxabicyclo[2.1.1]hexane-1-carbonyl)-N-(4-fluoro-3-methylphenyl)-7,10a-dimethyl-2,3,3a,4,10,10a-hexahydro-1H,7H-dipyrrolo[3,4-b:3',4'-f][1,4,5]oxathiazocine-8-carboxamide 5,5-dioxide | — | A |
| E91 | Ethyl 7,10a-dimethyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | — | A |
| E92 | Ethyl 7,10a-dimethyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | — | A |
| E93 | Ethyl 8-((4-fluoro-3-methylphenyl)carbamoyl)-7,10a-dimethyl-3a,4,10,10a-tetrahydro-1H,7H-dipyrrolo[3,4-b:3',4'-f][1,4,5]oxathiazocine-2(3H)-carboxylate 5,5-dioxide (Chiral 3aS,10aS or 3aR,10aR - Stereochemistry unknown) | — | A |
| E94 | Ethyl 8-((4-fluoro-3-methylphenyl)carbamoyl)-7,10a-dimethyl-3a,4,10,10a-tetrahydro-1H,7H-dipyrrolo[3,4-b:3',4'-f][1,4,5]oxathiazocine-2(3H)-carboxylate 5,5-dioxide(Chiral 3aS,10aS or 3aR,10aR - Stereochemistry unknown) | — | A |
| E95 | N-(4-fluoro-3-methylphenyl)-7,10a-dimethyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide (Chiral 3aS,10aS or 3aR,10aR - Stereochemistry unknown) | — | A |
| E96 | N-(4-fluoro-3-methylphenyl)-7,10a-dimethyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide (Chiral 3aS,10aS or 3aR,10aR - Stereochemistry unknown) | — | A |
| E97 | (3aR,10aR)-7-methyl-2-(5-methyl-1,3,4-oxadiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | — | A |
| E98 | (3aR,10aR)-N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E99 | (3aR,10aR)-N-(3-chloro-4-fluorophenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E100 | (3aR,10aR)-N-(4-fluoro-3-methylphenyl)-7-methyl-2-((R)-tetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E101 | (3aR,10aR)-N-(4-fluoro-3-methylphenyl)-7-methyl-2-((S)-tetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E102 | (3aR,10aR)-2-(5-amino-1,3,4-oxadiazole-2-carbonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | — | A |
| E103 | (3aR,10aR)-N-(4-fluoro-3-methylphenyl)-7-methyl-2-(3-methyl-1,2,4-oxadiazole-5-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E104 | (3aR,10aR)-N-(4-fluoro-3-methylphenyl)-7-methyl-2-(oxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E105 | (3aR,10aR)-N-(4-fluoro-3-methylphenyl)-7-methyl-2-(1,2,5-oxadiazole-3-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |

TABLE 2-continued

Antiviral activity of the compounds of the invention

| Example | Compound Name | Anti HBV Activity (conc μM) | HBV inh EC$_{50}$ (μM) |
|---|---|---|---|
| E106 | (3aR,10aR)-7-methyl-2-(oxazole-4-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | — | A |
| E107 | (3aR,10aR)-N-(4-fluoro-3-methylphenyl)-7-methyl-2-(5-methyl-1,3,4-thiadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E108 | (3aR,10aR)-N-(4-fluoro-3-methylphenyl)-7-methyl-2-(oxetane-3-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E109 | (3aR,10aR)-2-(2-oxabicyclo[2.1.1]hexane-1-carbonyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide | — | A |
| E110 | (3aR,10aR)-N-(4-fluoro-3-methylphenyl)-7-methyl-2-(oxetane-2-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E111 | (3aR,10aR)-N-(4-fluoro-3-methylphenyl)-7-methyl-2-(2-methyltetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E112 | (3aR,10aR)-N-(4-fluoro-3-methylphenyl)-7-methyl-2-(2-methyloxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E113 | (3aR,10aR)-N-(4-fluoro-3-methylphenyl)-7-methyl-2-(5-methyloxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E114 | (3aR,10aR)-2-(2,5-dimethyloxazole-4-carbonyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide | — | A |
| E115 | (3aR,10aR)-N-(4-fluoro-3-methylphenyl)-7-methyl-2-(3-methyl-1,2,4-oxadiazol-5-yl)-2,3,3a,4,10,10a-hexahydro-1H,7H-dipyrrolo[3,4-b:3',4'-f][1,4,5]oxathiazocine-8-carboxamide 5,5-dioxide | — | A |
| E116 | (3aR,10aR)-N-(3-chloro-4-fluorophenyl)-7-methyl-2-(3-methyl-1,2,4-oxadiazol-5-yl)-2,3,3a,4,10,10a-hexahydro-1H,7H-dipyrrolo[3,4-b:3',4'-f][1,4,5]oxathiazocine-8-carboxamide 5,5-dioxide | — | A |
| E117 | (3aR,10aR)-7-methyl-2-(3-methyl-1,2,4-oxadiazol-5-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | — | A |
| E118 | (3aR,10aR)-N-(4-fluoro-3-methylphenyl)-7-methyl-2-(5-methyl-1,3,4-oxadiazol-2-yl)-2,3,3a,4,10,10a-hexahydro-1H,7H-dipyrrolo[3,4-b:3',4'-f][1,4,5]oxathiazocine-8-carboxamide 5,5-dioxide | — | A |
| E119 | (3aR,10aR)-N-(3-chloro-4-fluorophenyl)-7-methyl-2-(5-methyl-1,3,4-oxadiazol-2-yl)-2,3,3a,4,10,10a-hexahydro-1H,7H-dipyrrolo[3,4-b:3',4'-f][1,4,5]oxathiazocine-8-carboxamide 5,5-dioxide | — | A |
| E120 | (3aR,10aR)-7-methyl-2-(5-methyl-1,3,4-oxadiazol-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide | — | A |
| E121 | Ethyl (3aR,10aR)-8-((4-fluoro-3-methylphenyl)carbamoyl)-7-methyl-3a,4,10,10a-tetrahydro-1H,7H-dipyrrolo[3,4-c:3',4'-g][1,6,2]dithiazocine-2(3H)-carboxylate 5,5-dioxide | — | A |
| E122 | Ethyl (3aR,10aR)-8-((4-fluoro-3-methylphenyl)carbamoyl)-7-methyl-3a,4,10,10a-tetrahydro-1H,7H-dipyrrolo[3,4-c:3',4'-g][1,6,2]dithiazocine-2(3H)-carboxylate 5,5,9-trioxide | — | A |
| E123 | Ethyl (3aR,10aR)-8-((4-fluoro-3-methylphenyl)carbamoyl)-7-methyl-3a,4,10,10a-tetrahydro-1H,7H-dipyrrolo[3,4-c:3',4'-g][1,6,2]dithiazocine-2(3H)-carboxylate 5,5,9,9-tetraoxide | — | A |
| E124 | (3aR,10aR)-N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-c:3',4'-g][1,6,2]dithiazocine-8-carboxamide 5,5-dioxide | — | A |

TABLE 2-continued

Antiviral activity of the compounds of the invention

| Example | Compound Name | Anti HBV Activity (conc μM) | HBV inh $EC_{50}$ (μM) |
|---|---|---|---|
| E125 | Cis-N-(4-fluoro-3-methylphenyl)-2-methyl-8-(5-methyl-1,3,4-oxadiazole-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide | — | A |
| E126 | Cis-N-(4-fluoro-3-methylphenyl)-2-methyl-8-(3-methyloxetane-3-carbonyl)-5,5a,6,7,8,9,9a,10-octahydro-2H-pyrido[4,3-f]pyrrolo[3,4-b][1,4,5]oxathiazocine-1-carboxamide 4,4-dioxide | — | A |
| E127 | Cis-N-(4-fluoro-3-methylphenyl)-2-methyl-8-(2-methyltetrahydrofuran-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide | — | A |
| E128 | Cis-8-(2-oxabicyclo[2.1.1]hexane-1-carbonyl)-N-(4-fluoro-3-methylphenyl)-2-methyl-5,5a,6,7,8,9,9a,10-octahydro-2H-pyrido[4,3-f]pyrrolo[3,4-b][1,4,5]oxathiazocine-1-carboxamide 4,4-dioxide | — | A |
| E129 | Cis-(4-fluoro-3-methylphenyl)-2-methyl-8-(5-methyloxazole-4-carbonyl)-5,5a,6,7,8,9,9a,10-octahydro-2H-pyrido[4,3-f]pyrrolo[3,4-b][1,4,5]oxathiazocine-1-carboxamide 4,4-dioxide | — | A |
| E130 | Trans-N-(4-fluoro-3-methylphenyl)-2-methyl-8-(5-methyl-1,3,4-oxadiazole-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide | — | A |
| E131 | Trans-N-(4-fluoro-3-methylphenyl)-2-methyl-8-(3-methyloxetane-3-carbonyl)-5,5a,6,7,8,9,9a,10-octahydro-2H-pyrido[4,3-f]pyrrolo[3,4-b][1,4,5]oxathiazocine-1-carboxamide 4,4-dioxide | — | A |
| E132 | Trans-N-(4-fluoro-3-methylphenyl)-2-methyl-8-(2-methyltetrahydrofuran-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide | — | A |
| E133 | Trans-8-(2-oxabicyclo[2.1.1]hexane-1-carbonyl)-N-(4-fluoro-3-methylphenyl)-2-methyl-5,5a,6,7,8,9,9a,10-octahydro-2H-pyrido[4,3-f]pyrrolo[3,4-b][1,4,5]oxathiazocine-1-carboxamide 4,4-dioxide | — | A |
| E134 | Trans-N-(4-fluoro-3-methylphenyl)-2-methyl-8-(5-methyloxazole-4-carbonyl)-5,5a,6,7,8,9,9a,10-octahydro-2H-pyrido[4,3-f]pyrrolo[3,4-b][1,4,5]oxathiazocine-1-carboxamide 4,4-dioxide | — | A |
| E135 | Cis-N-(4-fluoro-3-methylphenyl)-2-methyl-7-(5-methyl-1,3,4-oxadiazole-2-carbonyl)-5,5a,6,7,8,9,9a,10-octahydro-2H-pyrido[3,4-f]pyrrolo[3,4-b][1,4,5]oxathiazocine-1-carboxamide 4,4-dioxide | — | A |
| E136 | Cis-N-(4-fluoro-3-methylphenyl)-2-methyl-7-(3-methyloxetane-3-carbonyl)-5,5a,6,7,8,9,9a,10-octahydro-2H-pyrido[3,4-f]pyrrolo[3,4-b][1,4,5]oxathiazocine-1-carboxamide 4,4-dioxide | — | A |
| E137 | Cis-N-(4-fluoro-3-methylphenyl)-2-methyl-8-(2-methyltetrahydrofuran-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide | — | A |
| E138 | Cis-7-(2-oxabicyclo[2.1.1]hexane-1-carbonyl)-N-(4-fluoro-3-methylphenyl)-2-methyl-5,5a,6,7,8,9,9a,10-octahydro-2H-pyrido[3,4-f]pyrrolo[3,4-b][1,4,5]oxathiazocine-1-carboxamide 4,4-dioxide | — | A |
| E139 | Cis-N-(4-fluoro-3-methylphenyl)-2-methyl-7-(5-methyloxazole-4-carbonyl)-5,5a,6,7,8,9,9a,10-octahydro-2H-pyrido[3,4-f]pyrrolo[3,4-b][1,4,5]oxathiazocine-1-carboxamide 4,4-dioxide | — | A |
| E140 | Trans-N-(4-fluoro-3-methylphenyl)-2-methyl-7-(5-methyl-1,3,4-oxadiazole-2-carbonyl)-5,5a,6,7,8,9,9a,10-octahydro-2H-pyrido[3,4-f]pyrrolo[3,4-b][1,4,5]oxathiazocine-1-carboxamide 4,4-dioxide | — | A |
| E141 | Trans-N-(4-fluoro-3-methylphenyl)-2-methyl-7-(3-methyloxetane-3-carbonyl)-5,5a,6,7,8,9,9a,10-octahydro-2H-pyrido[3,4-f]pyrrolo[3,4-b][1,4,5]oxathiazocine-1-carboxamide 4,4-dioxide | — | A |
| E142 | Trans-N-(4-fluoro-3-methylphenyl)-2-methyl-8-(2-methyltetrahydrofuran-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide | — | A |

TABLE 2-continued

Antiviral activity of the compounds of the invention

| Example | Compound Name | Anti HBV Activity (conc μM) | HBV inh EC$_{50}$ (μM) |
|---|---|---|---|
| E143 | Trans-7-(2-oxabicyclo[2.1.1]hexane-1-carbonyl)-N-(4-fluoro-3-methylphenyl)-2-methyl-5,5a,6,7,8,9,9a,10-octahydro-2H-pyrido[3,4-f]pyrrolo[3,4-b][1,4,5]oxathiazocine-1-carboxamide 4,4-dioxide | — | A |
| E144 | Trans-N-(4-fluoro-3-methylphenyl)-2-methyl-7-(5-methyloxazole-4-carbonyl)-5,5a,6,7,8,9,9a,10-octahydro-2H-pyrido[3,4-f]pyrrolo[3,4-b][1,4,5]oxathiazocine-1-carboxamide 4,4-dioxide | — | A |
| E145 | Trans-tert-butyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide | — | A |
| E146 | Trans-N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E147 | Trans-N-(4-fluoro-3-methylphenyl)-7-methyl-2-(5-methyloxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E148 | Trans-N-(4-fluoro-3-methylphenyl)-7-methyl-2-(2-methyltetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E149 | Trans-N-(4-fluoro-3-methylphenyl)-7-methyl-2-(3-methyloxetane-3-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E150 | Trans-2-(2-oxabicyclo[2.1.1]hexane-1-carbonyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide | — | A |
| E151 | tert-butyl (3aS,10aR)-8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide | — | A |
| E152 | tert-butyl (3aR,10aS)-8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide | — | A |
| E153 | (3aS,10aR)-N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E154 | (3aR,10aS)-N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide | — | A |
| E155 | Cis 2-benzyl-N-(4-fluoro-3-methylphenyl)-7-methyl-3-oxo-2,3,3a,4,10,10a-hexahydro-1H,7H-dipyrrolo[3,4-b:3',4'-f][1,4,5]oxathiazocine-8-carboxamide 5,5-dioxide | — | A |
| E156 | Cis/Trans ethyl 7-methyl-8-((3,4,5-trifluorophenyl)carbamoyl)-1,3a,4,10,11,11a-hexahydro-7H-dipyrrolo[3,4-b:3',4'-f][1,4,5]oxathiazonine-2(3H)-carboxylate 5,5-dioxide | — | A |
| E157 | Cis ethyl 8-((4-fluoro-3-methylphenyl)carbamoyl)-7-methyl-3a,4,7,9,10,10a-hexahydro-1H-dipyrrolo[3,4-c:3',4'-g][1,2,6]thiadiazocine-2(3H)-carboxylate 5,5-dioxide | — | B |

Results in Table 2 clearly indicate that the compounds of the invention display anti-HBV activity at a very low concentration. The tricyclic structure offers the possibility to introduce on the core scaffold functional groups able to optimize the potency and the physicochemical properties of the moieties. The authors of the invention thus obtained nanomolar inhibitors further characterized by optimal in vitro and in vivo pharmacokinetic properties and a positive liver to plasma ratio (data not shown).

The invention claimed is:

1. A compound of general formula (I):

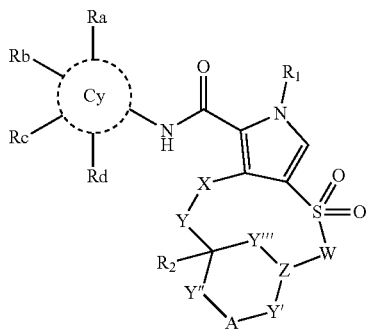

wherein:
Cy is aryl or heteroaryl;
X is O, NH, N—$C_{1-6}$ alkyl, S, SO or $SO_2$;
Y, Y', Y'' and Y''' are each independently a single bond or $C_{1-6}$alkanediyl optionally substituted with one or more $R_3$;
Z is $CR_4$ or N;
W is a single bond or $NR_5$, wherein if W is a single bond, Z is N, and if W is $NR_5$, Z is $CR_4$;
A is $NR_6$, O, S or $C_{1-6}$ alkanediyl optionally substituted with one or more $R_3$;
$R_1$ is H or $C_{1-6}$alkyl;
$R_2$ is selected from H, OH and $C_{1-6}$alkyl;
$R_3$ is selected from H, OH, $C_{1-6}$ alkyl, $C_{3-8}$cycloalkyl and halogen or two geminal $R_3$ form together with the atom to which they are attached a spiro-$C_{3-8}$-cycloalkyl or a spiro-$C_{3-8}$heterocycloalkyl or $R_3$ is O forming together with the carbon atom to with it is bonded a C=O;
$R_4$ is H or $C_{1-6}$alkyl;
or when W is $NR_5$ and Z is $CR_4$, $R_2$ and $R_4$ may optionally form a $C_{1-6}$alkanediyl bridge;
$R_5$ is selected from H, $C_{1-6}$alkyl, $C_{1-6}$alkylaryl, $C_{1-6}$alkylheteroaryl and $C_{1-6}$alkyl-$C_{3-8}$cycloalkyl wherein each of said $C_{1-6}$ alkyl, $C_{1-6}$alkylaryl, $C_{1-6}$alkylheteroaryl or $C_{1-6}$-alkyl-$C_{3-8}$cycloalkyl is optionally substituted with one or more substituents each independently selected from: OH, halogen, halo$C_{1-6}$ alkyl, cyano and $NH_2$;

$R_6$ is selected from:
hydrogen;
OH;
$C(O)R_7$;
$C(O)OR_7$;
$C(O)NHR_7$;
$C(O)N(R_7)_2$;
$SO_2R_7$;
$SO_2NH(R_7)$;
$SO_2N(R_7)_2$;
$C_{1-6}$ alkyl optionally substituted with one or more substituents each independently selected from the group consisting of: OH, halogen, CN, $NH_2$, $NH(R_7)$, $N(R_7)_2$, aryl, heteroaryl, 3-7 membered saturated ring and 5-7 membered unsaturated ring, each of said saturated or unsaturated ring optionally containing one or more heteroatoms selected from the group consisting of 0, N and S and each of said aryl, heteroaryl, 3-7 membered saturated or 5-7 membered unsaturated ring being optionally substituted with one or more substituents each independently selected from OH, halogen, halo$C_{1-6}$ alkyl, CN, halo$C_{1-6}$alkoxy and $C_{1-6}$alkoxy;
aryl or heteroaryl ring, each of said aryl or heteroaryl ring being optionally substituted with one or more substituents each independently selected from: OH, halogen, halo$C_{1-6}$ alkyl, CN, halo$C_{1-6}$ alkoxy, $C_{1-6}$ alkoxy, $C_{1-6}$ alkyl, and $NH_2$; and
a 3-8 membered saturated or partially unsaturated cyclic or bicyclic ring optionally containing one or more heteroatoms each independently selected from the group consisting of: O, S and N, the 3-8 membered saturated or partially unsaturated cyclic or bicyclic ring being optionally substituted with one, two or more substituents each independently selected from the group consisting of: OH, halogen, CN, $C_{1-6}$ alkyl, hydroxy$C_{1-6}$alkyl, C(O)OR$_7$, C(O)R$_7$, halo$C_{1-6}$ alkyl, halo$C_{1-6}$alkoxy and $C_{1-6}$alkoxy;

R$_7$ is selected from the group consisting of: $C_{1-9}$alkyl, $C_{3-8}$cycloalkyl, aryl, heteroaryl and 3-8 membered saturated or partially saturated heterocyclic ring, wherein each of said $C_{1-9}$alkyl, $C_{3-8}$cycloalkyl, aryl, heteroaryl or 3-8 membered saturated or partially saturated heterocyclic ring is optionally substituted with one or more substituents each independently selected from the group consisting of: OH, halogen, CN, $C_{1-6}$alkyl, hydroxy$C_{1-6}$alkyl, halo$C_{1-6}$alkyl, halo$C_{1-6}$alkoxy, $C_{1-6}$alkoxy, NH$_2$, OC(=O)$C_{1-6}$alkyl, OP(=O)(OH)$_2$, aryl, heteroaryl and NHC(=O)$C_{1-6}$alkyl; Ra, Rb, Rc and Rd are each independently selected from the group consisting of: hydrogen, halogen, CN, $C_{1-6}$alkyl, $C_{1-6}$alkoxy, halo$C_{1-6}$alkyl and halo$C_{1-6}$alkoxy; and pharmaceutically acceptable salts, tautomers, stereoisomers thereof.

2. The compound according to claim 1 having general formula (Ia):

(Ia)

wherein Cy, Y, Y', Y", A, R$_1$, R$_2$, Ra, Rb, Rc and Rd are as defined in claim 1 and X is O, S, NH or N—$C_{1-6}$alkyl; and pharmaceutically acceptable salts, tautomers, stereoisomers thereof.

3. The compound according to claim 1, wherein: Cy is phenyl, X is O, NH or S, A is CH$_2$, R$_1$ is CH$_3$, R$_2$ and R$_3$ are hydrogen, and pharmaceutically acceptable salts, tautomers, stereoisomers thereof.

4. The compound according to claim 1 having general formula (Ib):

(Ib)

wherein Cy, Y, Y', Y", A, R$_1$, R$_2$, R$_4$, R$_5$, Ra, Rb, Rc and Rd are as defined in claim 1 and X is O, S, NH or N—$C_{1-6}$alkyl; and pharmaceutically acceptable salts, tautomers, stereoisomers thereof.

5. The compound according to claim 1 wherein: Cy is phenyl, X is O, NH or S, Y is CH$_2$, Y' is CH$_2$, Y" is CH$_2$ and A is CH$_2$, O or NR$_6$, and pharmaceutically acceptable salts, tautomers, stereoisomers thereof.

6. The compound according to claim 1, wherein: A is NR$_6$, O or $C_{1-4}$ alkanediyl; R$_6$ is selected from the group consisting of: hydrogen, C(O)R$_7$, C(O)OR$_7$, C(O)NHR$_7$, SO$_2$R$_7$, SO$_2$NH(R$_7$), aryl, heteroaryl, $C_{1-6}$alkyl, said $C_{1-6}$ alkyl being optionally substituted with one or more substituents each independently selected from the group consisting of: halogen, CN and phenyl; R$_7$ is $C_{1-6}$ alkyl, $C_{3-8}$ cycloalkyl, aryl, heteroaryl or a 3-8 membered saturated heterocyclic ring and R$_7$ is optionally substituted with one or more substituents each independently selected from the group consisting of: OP(=O)(OH)$_2$, NH$_2$, OC(=O)CH$_3$, methyl, OH, aryl, heteroaryl, NHC(=O)$C_{1-6}$alkyl and halogen and pharmaceutically acceptable salts, tautomers, stereoisomers thereof.

7. The compound according to claim 1, wherein A is NR$_6$, R$_6$ is C(O)R$_7$ and R$_7$ is selected from the group consisting of: $C_{1-6}$alkyl, $C_{3-8}$ cycloalkyl, aryl, heteroaryl and 3-8 membered saturated or partially saturated heterocyclic ring, wherein each of said $C_{1-6}$alkyl, $C_{3-8}$cycloalkyl, aryl, heteroaryl or 3-8 membered saturated or partially saturated heterocyclic ring is optionally substituted with one or more substituents each independently selected from the group consisting of: OH, halogen, CN, $C_{1-6}$alkyl, hydroxy $C_{1-6}$ alkyl, halo$C_{1-6}$alkyl, halo$C_{1-6}$alkoxy, $C_{1-6}$alkoxy, NH$_2$, aryl, heteroaryl and pharmaceutically acceptable salts, tautomers, stereoisomers thereof.

8. A compound according to claim 1 selected from the group consisting of:
  N-(3,4-difluorophenyl)-2-methyl-6,7,8,9,9a,10-hexahydro-2H-pyrido[1,2-e]pyrrolo[3,4-b][1,4,5]oxathiazepine-1-carboxamide 4,4-dioxide;
  N-(3,4-difluorophenyl)-2-methyl-2,6,7,8,9,9a,10,11-octahydropyrido[1,2-b]pyrrolo[3,4-f][1,2,5]thiadiazepine-1-carboxamide 4,4-dioxide;
  N-(3,4-difluorophenyl)-2-methyl-6,7,7a,8-tetrahydro-2H-azeto[1,2-e]pyrrolo[3,4-b][1,4,5]oxathiazepine-1-carboxamide 4,4-dioxide;
  trans-N-(3,4-difluorophenyl)-7-methyl-1,3a,4,9a-tetrahydro-3H,7H-furo[3,4-f]pyrrolo[3,4-b][1,4,5]oxathiazepine-8-carboxamide 5,5-dioxide;
  cis-N-(3,4-difluorophenyl)-9-methyl-3,4,5,6-tetrahydro-2H,9H-3,5-methanopyrrolo[3,4-b][1,4,5]oxathiazonine-8-carboxamide 1,1-dioxide;
  cis-N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide;
  trans-7-methyl-N-(3,4,5-trifluorophenyl)-1,3a,4,9a-tetrahydro-3H,7H-furo[3,4-f]pyrrolo[3,4-b][1,4,5]oxathiazepine-8-carboxamide 5,5-dioxide;
  (5aR,8aR)—N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide;
  (5aS,8aS)—N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide;
  cis-Ethyl 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;
  cis-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2,7-dimethyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-Ethyl 8-((3,4-difluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

cis-Ethyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

cis-Ethyl 8-((3-chloro-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

cis-Ethyl 8-((3-(difluoromethyl)-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

cis-Ethyl 8-((3-cyano-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

cis-2-(isopropyl sulfonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(methylsulfonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(cyclopropylsulfonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(N-isopropylsulfamoyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-(3R,3aS,6aR)-hexahydrofuro[2,3-b]furan-3-yl 7-methyl-8-((3,4,5-trifluorophenyl) carbamoyl)-3a,4,10,10a-tetrahydro-1H,7H-dipyrrolo[3,4-b:3',4'-f][1,4,5]oxathiazocine-2(3H)-carboxylate 5,5-dioxide;

$N^2$,7-dimethyl-$N^8$-(3,4,5-trifluorophenyl)-3a,4,10,10a-tetrahydro-1H,7H-dipyrrolo[3,4-b:3',4'-f][1,4,5]oxathiazocine-2,8(3H)-dicarboxamide 5,5-dioxide;

tert-butyl 7-methyl-84(3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;

(3aR,10aS)—N-(3,4-difluorophenyl)-7-methyl-2,3,3a,4,10,10a-hexahydro-1H,7H-dipyrrolo[3,4-b:3',2'-f][1,4,5]oxathiazocine-8-carboxamide 5,5-dioxide;

(3aR,10aS)—N8-(3,4-difluorophenyl)-N1,7-dimethyl-2,3,3a,4,10,10a-hexahydro-1H,7H-dipyrrolo[3,4-b:3',2'-f][1,4,5]oxathiazocine-1,8-dicarboxamide 5,5-dioxide;

ethyl (3aR,10aS)-8-((3,4-difluorophenyl)carbamoyl)-7-methyl-2,3,3a,4,10,10a-hexahydro-1H,7H-dipyrrolo[3,4-b:3',2'-f][1,4,5]oxathiazocine-1-carboxylate 5,5-dioxide;

cis-2-methyl-N-(3,4,5-trifluorophenyl)-5a,6,7,8,8a,9-hexahydro-2H,5H-cyclopenta[f]pyrrolo[3,4-b][1,4,5]oxathiazocine-1-carboxamide 4,4-dioxide;

N-(3,4-difluorophenyl)-2,8a-dimethyl-5a,6,7,8,8a,9-hexahydro-2H,5H-cyclopenta[f]pyrrolo[3,4-b][1,4,5]oxathiazocine-1-carboxamide 4,4-dioxide;

cis-N-(3,4-difluorophenyl)-8a-hydroxy-2-methyl-5a,6,7,8,8a,9-hexahydro-2H,5H-cyclopenta[f]pyrrolo[3,4-b][1,4,5]oxathiazocine-1-carboxamide 4,4-dioxide;

(3aS,10aS)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

ethyl (3aR,10aR)-7-methyl-84(3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;

ethyl (3aS,10aS)-7-methyl-84(3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;

tert-butyl (3aS,10aS)-7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;

tert-butyl (3aR,10aR)-7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;

(5aS,8aR) N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide;

(5aR,8aS) N-(3,4-difluorophenyl)-2-methyl-5a,6,7,8,8a,9-hexahydro-2H,5H-cyclopenta[f]pyrrolo[3,4-b][1,4,5]oxathiazocine-1-carboxamide 4,4-dioxide;

(3a S,10aS) ethyl 8-((3,4-difluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3aR,10aR) ethyl 8-((3,4-difluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3a S,10aS) ethyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3aR,10aR) ethyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3a S,10aS) ethyl 8-((3-chloro-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3aR,10aR) ethyl 8-((3-chloro-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3a S,10aS) ethyl 8-((3-(difluoromethyl)-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3aR,10aR) ethyl 8-((3-(difluoromethyl)-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3a S,10aS) ethyl 8-((3-cyano-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

(3aR,10aR) ethyl 8-((3-cyano-4-fluorophenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

cis-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7-methyl-2-(pyridin-3-yl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7-methyl-2-(1,3,4-oxadiazol-2-yl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(oxazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(5-methyl-1,3,4-oxadiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7-methyl-2-(5-methylisoxazole-3-carbonyl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-2-(6-hydroxynicotinoyl)-7-methyl-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7-methyl-2-nicotinoyl-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-2isonicotinoyl-7-methyl-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(5-oxo-4,5-dihydropyrazine-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(1-methyl-1H-pyrazole-4-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(thiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(6-oxo-1,6-dihydropyrimidin-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(4-amino-1,2,5-oxadiazole-3-carbonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(4-amino-1,2,5-oxadiazole-3-carbonyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7-methyl-2-(5-methyl-1,3,4-thiadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7-methyl-2-(1,2,4-oxadiazole-3-carbonyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(oxazole-5-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(oxazole-4-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7-methyl-2-(3-methyloxetane-3-carbonyl)-2,3,3a,4,10,10a-hexahydro-1H,7H-dipyrrolo[3,4-b:3',4'-f][1,4,5]oxathiazocine-8-carboxamide 5,5-dioxide;

cis-2-(L-alanyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(L-seryl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(L-threonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(7-methyl-5,5-dioxido-8-((3,4,5-trifluorophenyl)carbamoyl)-3a,4,10,10a-tetrahydro-1H,7H-dipyrrolo[3,4-b:3',4'-f][1,4,5]oxathiazocin-2(3H)-yl)-2-oxoethyl acetate;

cis-2-(2-hydroxyacetyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(7-methyl-5,5-dioxido-8-((3,4,5-trifluorophenyl)carbamoyl)-3a,4,10,10a-tetrahydro-1H,7H-dipyrrolo[3,4-b:3',4'-f][1,4,5]oxathiazocin-2(3H)-yl)-2-oxoethyl dihydrogen phosphate;

cis-7-methyl-2-(2,2,2-trifluoroethyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(cyanomethyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(5-fluoropyrimidin-2-yl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(2-chloropyridin-4-yl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide;

ethyl (3R,6R)-10-methyl-94(3,4,5-trifluorophenyl)carbamoyl)-3,4,6,7-tetrahydro-10H-3,6-methanopyrrolo[3,4-b][1,4,5,8]oxathiadiazecine-5(2H)-carboxylate 1,1-dioxide;

cis-7-methyl-2-(5-methyl-1,3,4-oxadiazol-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(cyanomethyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7-methyl-2-(2,2,2-trifluoroethyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(pyridin-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(pyrazin-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-7-methyl-2-(3-methyl-1,2,4-oxadiazol-5-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-2-(5-hydroxypyrimidin-2-yl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-(3aR,10aR)-7-methyl-2-(5-methyl-1,3,4-oxadiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7,10a-dimethyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7,10a-dimethyl-2-(5-methyloxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7,10a-dimethyl-2-(2-methyltetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide;

cis-N-(4-fluoro-3-methylphenyl)-7,10a-dimethyl-2-(3-methyloxetane-3-carbonyl)-2,3,3a,4,10,10a-hexahydro-1H,7H-dipyrrolo[3,4-b:3',4'-f][1,4,5]oxathiazocine-8-carboxamide 5,5-dioxide;

cis-2-(2-oxabicyclo[2.1.1]hexane-1-carbonyl)-N-(4-fluoro-3-methylphenyl)-7,10a-dimethyl-2,3,3a,4,10,10a-hexahydro-1H,7H-dipyrrolo[3,4-b:3',4'-f][1,4,5]oxathiazocine-8-carboxamide 5,5-dioxide;

(3aS,10aS) ethyl 7,10a-dimethyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;

(3aR,10aR) ethyl 7,10a-dimethyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;

(3aS,10aS) ethyl 8-((4-fluoro-3-methylphenyl)carbamoyl)-7,10a-dimethyl-3a,4,10,10a-tetrahydro-1H,7H-dipyrrolo[3,4-b:3',4'-f][1,4,5]oxathiazocine-2(3H)-carboxylate 5,5-dioxide;

(3aR,10aR) ethyl 8-((4-fluoro-3-methylphenyl)carbamoyl)-7,10a-dimethyl-3a,4,10,10a-tetrahydro-1H,7H-dipyrrolo[3,4-b:3',4'-f][1,4,5]oxathiazocine-2(3H)-carboxylate 5,5-dioxide;

(3a S,10aS)N-(4-fluoro-3-methylphenyl)-7,10a-dimethyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)N-(4-fluoro-3-methylphenyl)-7,10a-dimethyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)-7-methyl-2-(5-methyl-1,3,4-oxadiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(3-chloro-4-fluorophenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-((R)-tetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-((S)-tetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)-2-(5-amino-1,3,4-oxadiazole-2-carbonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(3-methyl-1,2,4-oxadiazole-5-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(oxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(1,2,5-oxadiazole-3-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)-7-methyl-2-(oxazole-4-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(5-methyl-1,3,4-thiadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(oxetane-3-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)-2-(2-oxabicyclo[2.1.1]hexane-1-carbonyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(oxetane-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(2-methyltetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(2-methyloxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(5-methyloxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)-2-(2,5-dimethyloxazole-4-carbonyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(3-methyl-1,2,4-oxadiazol-5-yl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(3-chloro-4-fluorophenyl)-7-methyl-2-(3-methyl-1,2,4-oxadiazol-5-yl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)-7-methyl-2-(3-methyl-1,2,4-oxadiazol-5-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(4-fluoro-3-methylphenyl)-7-methyl-2-(5-methyl-1,3,4-oxadiazol-2-yl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)—N-(3-chloro-4-fluorophenyl)-7-methyl-2-(5-methyl-1,3,4-oxadiazol-2-yl)-2,3,3a,4,10,10a-hexahydro-1H,7H-dipyrrolo[3,4-b:3',4'-f][1,4,5]oxathiazocine-8-carboxamide 5,5-dioxide;

(3aR,10aR)-7-methyl-2-(5-methyl-1,3,4-oxadiazol-2-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;

ethyl (3aR,10aR)-8-((4-fluoro-3-methylphenyl)carbamoyl)-7-methyl-3a,4,10,10a-tetrahydro-1H,7H-dipyrrolo[3,4-c:3',4'-g][1,6,2]dithiazocine-2(3H)-carboxylate 5,5-dioxide;

ethyl (3aR,10aR)-8-((4-fluoro-3-methylphenyl)carbamoyl)-7-methyl-3a,4,10,10a-tetrahydro-1H,7H-dipyrrolo[3,4-c:3',4'-g][1,6,2]dithiazocine-2(3H)-carboxylate 5,5,9-trioxide;

ethyl (3aR,10aR)-8-((4-fluoro-3-methylphenyl)carbamoyl)-7-methyl-3a,4,10,10a-tetrahydro-1H,7H-dipyrrolo[3,4-c:3',4'-g][1,6,2]dithiazocine-2(3H)-carboxylate 5,5,9,9-tetraoxide;

(3aR,10aR)—N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-c:3',4'-g][1,6,2]dithiazocine-8-carboxamide 5,5-dioxide;

cis-N-(4-fluoro-3-methylphenyl)-2-methyl-8-(5-methyl-1,3,4-oxadiazole-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

cis-N-(4-fluoro-3-methylphenyl)-2-methyl-8-(3-methyloxetane-3-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

cis-N-(4-fluoro-3-methylphenyl)-2-methyl-8-(2-methyltetrahydrofuran-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

cis-8-(2-oxabicyclo[2.1.1]hexane-1-carbonyl)-N-(4-fluoro-3-methylphenyl)-2-methyl-5,5a,6,7,8,9,9a,10-octahydro-2H-pyrido[4,3-f]pyrrolo[3,4-b][1,4,5]oxathiazocine-1-carboxamide 4,4-dioxide;

cis-N-(4-fluoro-3-methylphenyl)-2-methyl-8-(5-methyloxazole-4-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

trans-N-(4-fluoro-3-methylphenyl)-2-methyl-8-(5-methyl-1,3,4-oxadiazole-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

trans-N-(4-fluoro-3-methylphenyl)-2-methyl-8-(3-methyloxetane-3-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

trans-N-(4-fluoro-3-methylphenyl)-2-methyl-8-(2-methyltetrahydrofuran-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

trans-8-(2-oxabicyclo[2.1.1]hexane-1-carbonyl)-N-(4-fluoro-3-methylphenyl)-2-methyl-5,5a,6,7,8,9,9a,10-octahydro-2H-pyrido[4,3-f]pyrrolo[3,4-b][1,4,5]oxathiazocine-1-carboxamide 4,4-dioxide;

trans-N-(4-fluoro-3-methylphenyl)-2-methyl-8-(5-methyloxazole-4-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

cis-N-(4-fluoro-3-methylphenyl)-2-methyl-7-(5-methyl-1,3,4-oxadiazole-2-carbonyl)-5,5a,6,7,8,9,9a,10-octahydro-2H-pyrido[3,4-f]pyrrolo[3,4-b][1,4,5]oxathiazocine-1-carboxamide 4,4-dioxide;

cis-N-(4-fluoro-3-methylphenyl)-2-methyl-7-(3-methyloxetane-3-carbonyl)-5,5a,6,7,8,9,9a,10-octahydro-2H-pyrido[3,4-f]pyrrolo[3,4-b][1,4,5]oxathiazocine-1-carboxamide 4,4-dioxide;

cis-N-(4-fluoro-3-methylphenyl)-2-methyl-8-(2-methyltetrahydrofuran-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide;

cis-7-(2-oxabicyclo[2.1.1]hexane-1-carbonyl)-N-(4-fluoro-3-methylphenyl)-2-methyl-5,5a,6,7,8,9,9a,10-octahydro-2H-pyrido[3,4-f]pyrrolo[3,4-b][1,4,5]oxathiazocine-1-carboxamide 4,4-dioxide;

cis-N-(4-fluoro-3-methylphenyl)-2-methyl-7-(5-methyloxazole-4-carbonyl)-5,5a,6,7,8,9,9a,10-octahydro-2H-pyrido[3,4-f]pyrrolo[3,4-b][1,4,5]oxathiazocine-1-carboxamide 4,4-dioxide;

trans-N-(4-fluoro-3-methylphenyl)-2-methyl-7-(5-methyl-1,3,4-oxadiazole-2-carbonyl)-5,5a,6,7,8,9,9a,10-octahydro-2H-pyrido[3,4-f]pyrrolo[3,4-b][1,4,5]oxathiazocine-1-carboxamide 4,4-dioxide;

trans-N-(4-fluoro-3-methylphenyl)-2-methyl-7-(3-methyloxetane-3-carbonyl)-5,5a,6,7,8,9,9a,10-octahydro-2H-pyrido[3,4-f]pyrrolo[3,4-b][1,4,5]oxathiazocine-1-carboxamide 4,4-dioxide;

trans-N-(4-fluoro-3-methylphenyl)-2-methyl-8-(2-methyltetrahydrofuran-2-carbonyl)-5,5a,6,7,8,9,9a,10-octahydro-2H-pyrido[3,4-f]pyrrolo[3,4-b][1,4,5]oxathiazocine-1-carboxamide 4,4-dioxide;

trans-7-(2-oxabicyclo[2.1.1]hexane-1-carbonyl)-N-(4-fluoro-3-methylphenyl)-2-methyl-5,5a,6,7,8,9,9a,10-octahydro-2H-pyrido[3,4-f]pyrrolo[3,4-b][1,4,5]oxathiazocine-1-carboxamide 4,4-dioxide;

trans-N-(4-fluoro-3-methylphenyl)-2-methyl-7-(5-methyloxazole-4-carbonyl)-5,5a,6,7,8,9,9a,10-octahydro-2H-pyrido[3,4-f]pyrrolo[3,4-b][1,4,5]oxathiazocine-1-carboxamide 4,4-dioxide;

trans-tert-butyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;

trans-N-(4-fluoro-3-methylphenyl)-7-methyl-2-(5-methyl-1,3,4-oxadiazole-2-carbonyl)-2,3,3a,4,10,10a- hexahydro-1H,7H-dipyrrolo[3,4-b:3',4'-f][1,4,5]oxathiazocine-8-carboxamide 5,5-dioxide;
trans-N-(4-fluoro-3-methylphenyl)-7-methyl-2-(5-methyloxazole-4-carbonyl)-2,3,3a,4,10,10a-hexahydro-1H,7H-dipyrrolo[3,4-b:3',4'-f][1,4,5]oxathiazocine-8-carboxamide 5,5-dioxide;
trans-N-(4-fluoro-3-methylphenyl)-7-methyl-2-(2-methyltetrahydrofuran-2-carbonyl)-2,3,3a,4,10,10a-hexahydro-1H,7H-dipyrrolo[3,4-b:3',4'-f][1,4,5]oxathiazocine-8-carboxamide 5,5-dioxide;
trans-N-(4-fluoro-3-methylphenyl)-7-methyl-2-(3-methyloxetane-3-carbonyl)-2,3,3a,4,10,10a-hexahydro-1H,7H-dipyrrolo[3,4-b:3',4'-f][1,4,5]oxathiazocine-8-carboxamide 5,5-dioxide;
trans-2-(2-oxabicyclo[2.1.1]hexane-1-carbonyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide;
tert-butyl (3aS,10aR)-8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;
tert-butyl (3aR,10aS)-8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-dioxide;
(3a S,10aR)—N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;
(3aR,10aS)—N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;
cis 2-benzyl-N-(4-fluoro-3-methylphenyl)-7-methyl-3-oxo-2,3,3a,4,10,10a-hexahydro-1H,7H-dipyrrolo[3,4-b:3',4'-f][1,4,5]oxathiazocine-8-carboxamide 5,5-dioxide;
cis/trans ethyl 7-methyl-8-(3,4,5-trifluorophenyl)carbamoyl)-1,3a,4,10,11,11a-hexahydro-7H-dipyrrolo[3,4-b:3',4'-f][1,4,5]oxathiazonine-2(3H)-carboxylate 5,5-dioxide;
cis ethyl 8-((4-fluoro-3-methylphenyl)carbamoyl)-7-methyl-3a,4,7,9,10,10a-hexahydro-1H-dipyrrolo[3,4-c:3',4'-g][1,2,6]thiadiazocine-2(3H)-carboxylate 5,5-dioxide; and
pharmaceutically acceptable salts, tautomers, stereoisomers thereof.

9. A compound according to claim 1 selected from the group consisting of:
cis-7-methyl-2-(5-methyl-1,3,4-oxadiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;
cis-N-(4-fluoro-3-methylphenyl)-7,10a-dimethyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;
(3aR,10aR)-7-methyl-2-(5-methyl-1,3,4-oxadiazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;
(3aR,10aR)—N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;
(3aS,10aR)—N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;
(3aR,10aR)—N-(3-chloro-4-fluorophenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;
(3aR,10aR)-2-(5-amino-1,3,4-oxadiazole-2-carbonyl)-7-methyl-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;
(3aR,10aR)—N-(4-fluoro-3-methylphenyl)-7-methyl-2-(3-methyl-1,2,4-oxadiazole-5-carbonyl)-2,3,3a,4,10,10a-hexahydro-1H,7H-dipyrrolo[3,4-b:3',4'-f][1,4,5]oxathiazocine-8-carboxamide 5,5-dioxide;
(3aR,10aR)—N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-c:3',4'-g][1,6,2]dithiazocine-8-carboxamide 5,5-dioxide;
cis-N-(4-fluoro-3-methylphenyl)-2-methyl-8-(5-methyl-1,3,4-oxadiazole-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide;
trans-N-(4-fluoro-3-methylphenyl)-2-methyl-8-(5-methyl-1,3,4-oxadiazole-2-carbonyl)-5,5a,6,7,8,9,9a,10-octahydro-2H-pyrido[4,3-f]pyrrolo[3,4-b][1,4,5]oxathiazocine-1-carboxamide 4,4-dioxide;
cis-N-(4-fluoro-3-methylphenyl)-2-methyl-7-(5-methyl-1,3,4-oxadiazole-2-carbonyl)-5,5a,6,7,8,9,9a,10-octahydro-2H-pyrido[3,4-f]pyrrolo[3,4-b][1,4,5]oxathiazocine-1-carboxamide 4,4-dioxide;
trans-N-(4-fluoro-3-methylphenyl)-2-methyl-7-(5-methyl-1,3,4-oxadiazole-2-carbonyl)-5,5a,6,7,8,9,9a,10-octahydro-2H-pyrido[3,4-f]pyrrolo[3,4-b][1,4,5]oxathiazocine-1-carboxamide 4,4-dioxide;
trans-N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;
(3aR,10aS)—N-(4-fluoro-3-methylphenyl)-7-methyl-2-(5-methyl-1,3,4-oxadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;
(3aR,10aR)—N-(4-fluoro-3-methylphenyl)-7-methyl-2-(1,2,5-oxadiazole-3-carbonyl)-2,3,3a,4,10,10a-hexahydro-1H,7H-dipyrrolo[3,4-b:3',4'-f][1,4,5]oxathiazocine-8-carboxamide 5,5-dioxide;
cis-N-(4-fluoro-3-methylphenyl)-7-methyl-2-(1,3,4-oxadiazol-2-yl)-2,3,3a,4,10,10a-hexahydro-1H,7H-dipyrrolo[3,4-b:3',4'-f][1,4,5]oxathiazocine-8-carboxamide 5,5-dioxide
and pharmaceutically acceptable salts, tautomers, stereoisomers thereof.

10. A compound according to claim 1 selected from the group consisting of:
cis-7-methyl-2-(oxazole-2-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;
cis-N-(4-fluoro-3-methylphenyl)-7-methyl-2-(5-methylisoxazole-3-carbonyl)-2,3,3a,4,10,10a-hexahydro-1H,7H-dipyrrolo[3,4-b:3',4'-f][1,4,5]oxathiazocine-8-carboxamide 5,5-dioxide;
cis-N-(4-fluoro-3-methylphenyl)-7-methyl-2-(5-methyl-1,3,4-thiadiazole-2-carbonyl)-2,3,3a,4,10,10a-hexahydro-1H,7H-dipyrrolo[3,4-b:3',4'-f][1,4,5]oxathiazo-cine-8-carboxamide 5,5-dioxide;
(3aR,10aR)—N-(4-fluoro-3-methylphenyl)-7-methyl-2-(5-methyl-1,3,4-thiadiazole-2-carbonyl)-2,3,3a,4,10,10a-hexahydro-1H,7H-dipyrrolo[3,4-b:3',4'-f][1,4,5]oxathiazocine-8-carboxamide 5,5-dioxide;
cis-N-(4-fluoro-3-methylphenyl)-7-methyl-2-(1,2,4-oxa-diazole-3-carbonyl)-2,3,3a,4,10,10a-hexahydro-1H,7H-dipyrrolo[3,4-b:3',4'-f][1,4,5]oxathiazocine-8-car-boxamide 5,5-dioxide;
cis-7-methyl-2-(oxazole-5-carbonyl)-N-(3,4,5-trifluoro-phenyl)-2,3,3a,4,10,10a-hexahydro-1H,7H-dipyrrolo[3,4-b:3',4'-f][1,4,5]oxathiazocine-8-carboxamide 5,5-dioxide;
cis-7-methyl-2-(oxazole-4-carbonyl)-N-(3,4,5-trifluoro-phenyl)-2,3,3a,4,10,10a-hexahydro-1H,7H-dipyrrolo[3,4-b:3',4'-f][1,4,5]oxathiazocine-8-carboxamide 5,5-dioxide;
cis-2-(5-fluoropyrimidin-2-yl)-7-methyl-N-(3,4,5-trifluo-rophenyl)-2,3,3a,4,10,10a-hexahydro-1H,7H-dipyrrolo[3,4-b:3',4'-f][1,4,5]oxathiazocine-8-carboxamide 5,5-dioxide;
cis-2-(2-chloropyridin-4-yl)-N-(4-fluoro-3-methylphe-nyl)-7-methyl-2,3,3a,4,10,10a-hexahydro-1H,7H-dipyrrolo[3,4-b:3',4'-f][1,4,5]oxathiazocine-8-carbox-amide 5,5-dioxide;
cis-N-(4-fluoro-3-methylphenyl)-7,10a-dimethyl-2-(5-methyloxazole-4-carbonyl)-2,3,3a, 4,10,10a-hexa-hydro-1H,7H-dipyrrolo[3,4-b:3',4'-f][1,4,5]oxathiazo-cine-8-carboxamide 5,5-dioxide;
(3aR,10aR)—N-(4-fluoro-3-methylphenyl)-7-methyl-2-(oxazole-4-carbonyl)-2,3,3a,4,10,10a-hexahydro-1H,7H-dipyrrolo[3,4-b:3',4'-f][1,4,5]oxathiazocine-8-car-boxamide 5,5-dioxide;
(3aR,10aR)-7-methyl-2-(oxazole-4-carbonyl)-N-(3,4,5-trifluorophenyl)-2,3,3a,4,10,10a-hexahydro-1H,7H-dipyrrolo[3,4-b:3',4'-f][1,4,5]oxathiazocine-8-carbox-amide 5,5-dioxide;
(3aR,10aR)—N-(4-fluoro-3-methylphenyl)-7-methyl-2-(2-methyloxazole-4-carbonyl)-2,3,3a, 4,10,10a-hexa-hydro-1H,7H-dipyrrolo[3,4-b:3',4'-f][1,4,5]oxathiazo-cine-8-carboxamide 5,5-dioxide;
(3aR,10aR)—N-(4-fluoro-3-methylphenyl)-7-methyl-2-(5-methyloxazole-4-carbonyl)-2,3,3a, 4,10,10a-hexa-hydro-1H,7H-dipyrrolo[3,4-b:3',4'-f][1,4,5]oxathiazo-cine-8-carboxamide 5,5-dioxide;
(3aR,10aR)-2-(2,5-dimethyloxazole-4-carbonyl)-N-(4-fluoro-3-methylphenyl)-7-methyl-2,3,3a,4,10,10a-hexahydro-1H,7H-dipyrrolo[3,4-b:3',4'-f][1,4,5]ox-athiazocine-8-carboxamide 5,5-dioxide;
cis-N-(4-fluoro-3-methylphenyl)-2-methyl-7-(5-methyl-oxazole-4-carbonyl)-5,5a,6,7,8,9,9a,10-octahydro-2H-pyrido[3,4-f]pyrrolo[3,4-b][1,4,5]oxathiazocine-1-car-boxamide 4,4-dioxide;
trans-N-(4-fluoro-3-methylphenyl)-2-methyl-7-(5-meth-yloxazole-4-carbonyl)-5,5a,6,7,8,9,9a,10-octahydro-2H-pyrido[3,4-f]pyrrolo[3,4-b][1,4,5]oxathiazocine-1-carboxamide 4,4-dioxide;
trans-N-(4-fluoro-3-methylphenyl)-7-methyl-2-(5-meth-yloxazole-4-carbonyl)-2,3,3a,4,10,10a-hexahydro-1H,7H-dipyrrolo[3,4-b:3',4'-f][1,4,5]oxathiazocine-8-car-boxamide 5,5-dioxide;
and pharmaceutically acceptable salts, tautomers, stereoiso-mers thereof.

11. A compound according to claim 1 selected from the group consisting of:
cis-Ethyl 7-methyl-8-((3,4,5-trifluorophenyl)carbamoyl)-3a,4,10,10a-tetrahydro-1H,7H-dipyrrolo[3,4-b:3',4'-f][1,4,5]oxathiazocine-2(3H)-carboxylate 5,5-dioxide;
cis-Ethyl 8-((4-fluoro-3-methylphenyl)carbamoyl)-7-methyl-3a,4,10,10a-tetrahydro-1H,7H-dipyrrolo[3,4-b:3',4'-f][1,4,5]oxathiazocine-2(3H)-carboxylate 5,5-di-oxide;
cis-Ethyl 8-((3-(difluoromethyl)-4-fluorophenyl)carbam-oyl)-7-methyl-3a,4,10,10a-tetrahydro-1H,7H-dipyr-rolo[3,4-b:3',4'-f][1,4,5]oxathiazocine-2(3H)-carboxy-late 5,5-dioxide:
cis-7-methyl-2-(thiazole-2-carbonyl)-N-(3,4,5-trifluoro-phenyl)-2,3,3a,4,10,10a-hexahydro-1H,7H-dipyrrolo[3,4-b:3',4'-f][1,4,5]oxathiazocine-8-carboxamide 5,5-dioxide;
cis-7-methyl-2-(3-methyl-1,2,4-oxadiazol-5-yl)-N-(3,4,5-trifluorophenyl)-2,3,3a,4,10,10a-hexahydro-1H,7H-dipyrrolo[3,4-b:3',4'-f][1,4,5]oxathiazocine-8-carbox-amide 5,5-dioxide;
(3aR,10aR)-7-methyl-2-(3-methyl-1,2,4-oxadiazol-5-yl)-N-(3,4,5-trifluorophenyl)-2,3,3a,4,10,10a-hexahydro-1H,7H-dipyrrolo[3,4-b:3',4'-f][1,4,5]oxathiazocine-8-carboxamide 5,5-dioxide;
cis-N-(4-fluoro-3-methylphenyl)-7-methyl-2-(pyridin-3-yl)-2,3,3a,4,10,10a-hexahydro-1H,7H-dipyrrolo[3,4-b:3',4'-f][1,4,5]oxathiazocine-8-carboxamide 5,5-diox-ide;
(3aR,10aR)-2-(2-oxabicyclo[2.1.1]hexane-1-carbonyl)-N-(4-fluoro-3-methylphenyl)-7-methyl-2,3,3a,4,10,10a-hexahydro-1H,7H-dipyrrolo[3,4-b:3',4'-f][1,4,5]oxathiazocine-8-carboxamide 5,5-dioxide;
cis-2-(2-oxabicyclo[2.1.1]hexane-1-carbonyl)-N-(4-fluoro-3-methylphenyl)-7,10a-dimethyl-2,3,3a,4,10,10a-hexahydro-1H,7H-dipyrrolo[3,4-b:3',4'-f][1,4,5]oxathiazocine-8-carboxamide 5,5-dioxide;
and pharmaceutically acceptable salts, tautomers, stereoiso-mers thereof.

12. A pharmaceutical composition comprising the com-pound or the pharmaceutically acceptable salt, tautomer, stereoisomer thereof as defined in claim 1, alone or in combination with at least one further therapeutic agent, and at least one pharmaceutically acceptable excipient.

13. The pharmaceutical composition according to claim 12, wherein the at least one further therapeutic agent is selected from the group consisting of: a therapeutic vaccine; an RNA interference therapeutic/antisense oligonucleotide; an immunomodulator; a STING agonist; a RIG-I modulator; a NKT modulator; an IL agonist; an interleukin or another immune acting protein; a therapeutic and prophylactic vac-cine; an immune checkpoint modulator/inhibitor; an HBV entry inhibitor; a cccDNA modulator; an inhibitor of HBV protein expression; an agent targeting HBV RNA; a capsid assembly inhibitor/modulator; a core or X protein targeting agent; a nucleotide analogue; a nucleoside analogue; an interferon or a modified interferon; an HBV antiviral of distinct or unknown mechanism; a cyclophilin inhibitor; a sAg release inhibitor; an HBV polymerase inhibitor; a dinucleotide; a SMAC inhibitor; a HDV targeting agent; a viral maturation inhibitor; a reverse transcriptase inhibitor and an HBV RNA destabilizer or another small-molecule inhibitor of HBV protein expression; or a combination thereof.

14. A method for the treatment and/or prevention of an HBV infection and/or a condition related to an HBV infec-tion, comprising administering a compound or a pharmaceutically acceptable salt, tautomer, stereoisomer thereof according to claim 1 to a patient in needed thereof, wherein said method is in treating, eradicating, reducing, slowing or inhibiting an HBV infection in an individual in need thereof, and/or in reducing the viral load associated with an HBV infection in an individual in need thereof, and/or in reducing reoccurrence of an HBV infection in an individual in need thereof, and/or in inducing remission of hepatic injury from an HBV infection in an individual in need thereof, and/or in prophylactically treating an HBV infection in an individual afflicted with a latent HBV infection.

15. A process for the synthesis of the compound of formula I or the pharmaceutically acceptable salt, tautomer, solvate, or stereoisomer thereof as defined in claim 1, said process comprising at least one of the following steps:

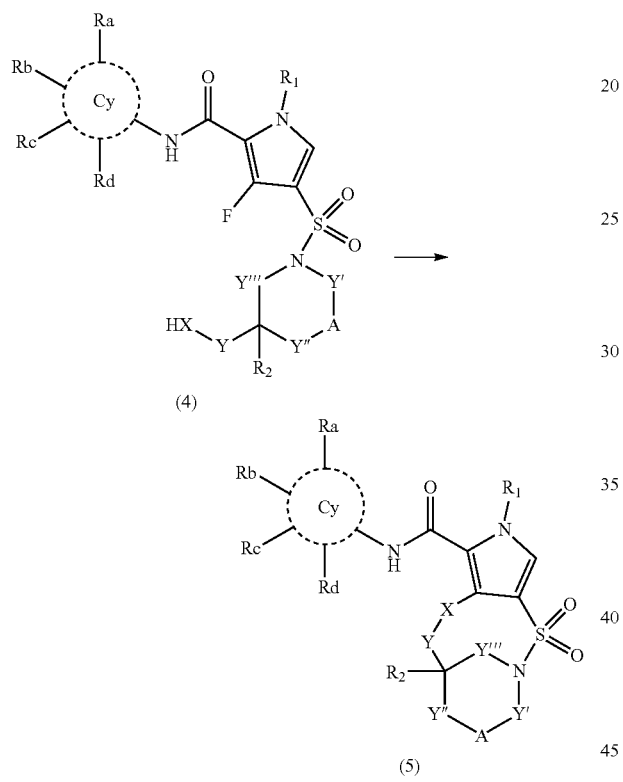

cyclisation of a compound of formula (4) in the presence of an appropriate base to obtain a compound of formula (5), wherein Cy, X, Y, Y', Y", Y''', A, $R_1$, $R_2$, Ra, Rb, Rc and Rd are as defined in any one of claim 1; or

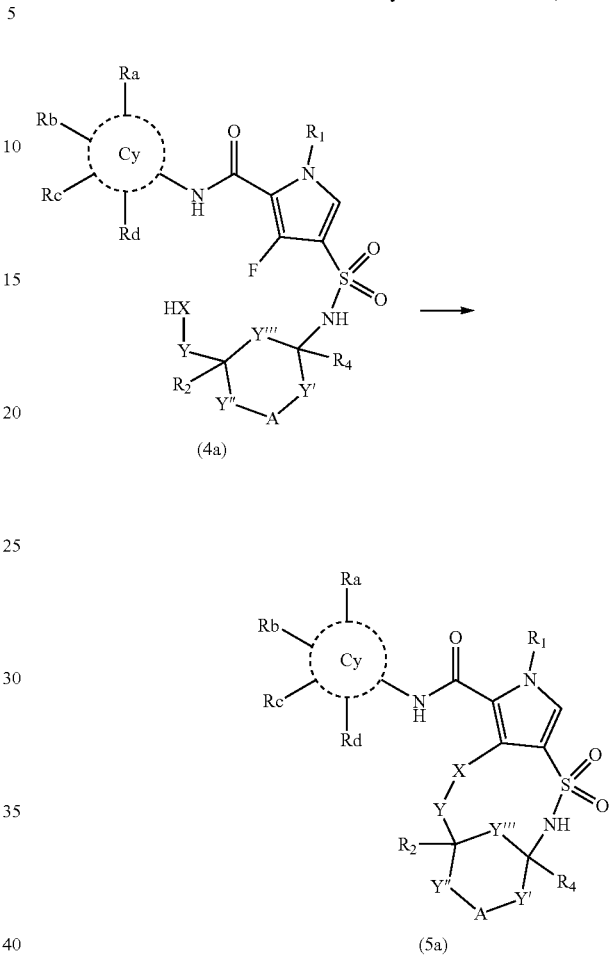

cyclisation of a compound of formula (4a) in the presence of an appropriate base to obtain a compound of formula (5a), wherein Cy, X, Y, Y', Y", Y''', A, $R_1$, $R_2$, $R_4$, Ra, Rb, Rc and Rd are as defined in claim 1.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: synthetic primer

<400> SEQUENCE: 1
atttgttcag tggttcgtag gg                                            22

<210> SEQ ID NO 2
<211> LENGTH: 22
<212> TYPE: DNA
<213> ORGANISM: Artificial Sequence
<220> FEATURE:
<223> OTHER INFORMATION: synthetic primer

<400> SEQUENCE: 2
cggtaaaaag ggactcaaga tg                                            22